(12) United States Patent
Ando et al.

(10) Patent No.: US 11,730,764 B2
(45) Date of Patent: *Aug. 22, 2023

(54) COMPOSITIONS AND METHODS FOR TREATING HER2 POSITIVE CANCERS

(71) Applicant: A2 Biotherapeutics, Inc., Agoura Hills, CA (US)

(72) Inventors: Yuta Ando, Agoura Hills, CA (US); Julyun Oh, Agoura Hills, CA (US); Han Xu, Agoura Hills, CA (US); Carl Alexander Kamb, Agoura Hills, CA (US)

(73) Assignee: A2 Biotherapeutics, Inc., Agoura Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/809,409

(22) Filed: Jun. 28, 2022

(65) Prior Publication Data

US 2022/0339194 A1 Oct. 27, 2022

Related U.S. Application Data

(63) Continuation of application No. PCT/US2022/016582, filed on Feb. 16, 2022.

(60) Provisional application No. 63/149,952, filed on Feb. 16, 2021.

(51) Int. Cl.
| | | |
|---|---|---|
| *A61K 35/17* | (2015.01) | |
| *C07K 14/725* | (2006.01) | |
| *C07K 16/28* | (2006.01) | |
| *C07K 16/30* | (2006.01) | |
| *A61K 39/00* | (2006.01) | |

(52) U.S. Cl.
CPC .......... *A61K 35/17* (2013.01); *C07K 14/7051* (2013.01); *C07K 16/2809* (2013.01); *C07K 16/2833* (2013.01); *C07K 16/2863* (2013.01); *C07K 16/30* (2013.01); *A61K 2039/507* (2013.01); *C07K 2317/622* (2013.01); *C07K 2319/03* (2013.01)

(58) Field of Classification Search
CPC ..................... A61K 35/17; C07K 14/7051
See application file for complete search history.

(56) References Cited

U.S. PATENT DOCUMENTS

| | | | |
|---|---|---|---|
| 4,690,915 A | 9/1987 | Rosenberg | |
| 5,350,674 A | 9/1994 | Boenisch et al. | |
| 5,585,362 A | 12/1996 | Wilson et al. | |
| 5,858,358 A | 1/1999 | June et al. | |
| 5,883,223 A | 3/1999 | Gray | |
| 6,326,193 B1 | 12/2001 | Liu et al. | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 10,040,846 B2 | 8/2018 | Frigault et al. | |
| 11,254,726 B2 * | 2/2022 | Kamb ................... | A61K 35/17 |
| 2003/0170238 A1 | 9/2003 | Gruenberg et al. | |
| 2004/0101519 A1 | 5/2004 | June et al. | |
| 2005/0244858 A1 | 11/2005 | Rossi et al. | |
| 2006/0034810 A1 | 2/2006 | Riley et al. | |
| 2006/0121005 A1 | 6/2006 | Berenson et al. | |
| 2014/0068797 A1 | 3/2014 | Doudna et al. | |
| 2015/0376296 A1 | 12/2015 | Fedorov et al. | |
| 2016/0289293 A1 | 10/2016 | Pulé et al. | |
| 2019/0185849 A1 | 6/2019 | Lundberg et al. | |
| 2019/0290691 A1 | 9/2019 | Jäckel et al. | |

(Continued)

FOREIGN PATENT DOCUMENTS

| | | | | |
|---|---|---|---|---|
| CN | 110484507 A | * | 11/2019 | ............. A61K 35/17 |
| WO | 0129058 A1 | | 4/2001 | |
| WO | 0196584 A2 | | 12/2001 | |

(Continued)

OTHER PUBLICATIONS

Sadelain et al., Cancer Disc 3:388-98 (Year: 2013).*
Hamburger et al., Mol. Immunol 128:298-310 (Year: 2020).*
Almagro et al., Front. Immunol., 8:1751, doi: 10.3389/fimmu.2017.01751 (Year: 2018).*
Rudikoff et al., Proc. Nat'l Acad. Sci. USA 1982; 79:1979-83 (Year: 1982).*
Brown et al., J. Immunol. 1996; 156(9):3285-91 (Year: 1996).*
Geneseq entry BGY93055, first entry Jan. 9, 2020 (Year: 2020).*
MO2R1_HUMAN, Cell surface glycoprotein CD200 receptor 1 • *Homo sapiens* (Human) • Gene: CD200R1 (CD200R, CRTR2, MOX2R, OX2R) • 325 amino acids • Evidence at protein level., Uniprot ref. Q8TD46, 8 pages, Release date Feb. 2022.

(Continued)

*Primary Examiner* — Jessica H Roark
(74) *Attorney, Agent, or Firm* — Mintz, Levin, Cohn, Ferris, Glovsky and Popeo, P.C.

(57) ABSTRACT

The disclosure relates to immune cells comprising a dual receptor system responsive to loss of heterozygosity in a target cell, and methods of making and using same. The first receptor comprises activator receptor specific to a HER2 antigen, and the second receptor comprises an inhibitory receptor specific to an antigen lost in cancer but not wild type cells, that inhibits activation of the immune cells by the first receptor.

22 Claims, 28 Drawing Sheets
(22 of 28 Drawing Sheet(s) Filed in Color)
Specification includes a Sequence Listing.

(56) References Cited

U.S. PATENT DOCUMENTS

| | | | |
|---|---|---|---|
| 2020/0316120 A1 | 10/2020 | Gross et al. | |
| 2022/0162287 A1* | 5/2022 | Kamb | A61K 35/17 |

FOREIGN PATENT DOCUMENTS

| | | | |
|---|---|---|---|
| WO | 2019068007 | A1 | 4/2019 |
| WO | 2020206248 | A1 | 10/2020 |
| WO | 2021030149 | A1 | 2/2021 |
| WO | 2021030153 | A2 | 2/2021 |
| WO | 2021035093 | A1 | 2/2021 |
| WO | 2021096868 | A1 | 5/2021 |
| WO | 2021119489 | A1 | 6/2021 |
| WO | 2021222576 | A1 | 11/2021 |

OTHER PUBLICATIONS

Altschul et al. (Oct. 5, 1990) "Basic Local Alignment Search Tool", Journal of Molecular Biology, 215 (3):403-410.

Altschul et al. (Sep. 1, 1997) "Gapped BLAST and PSI-BLAST: A New Generation of Protein Database Search Programs", Nucleic Acids Research, 25(17):3389-3402.

Arseneault et al. (Mar. 23, 2017) "Loss of Chromosome Y Leads to Down Regulation of KDM5D and KDM6C Epigenetic Modifiers in Clear Cell Renal Cell Carcinoma", Scientific Reports, Article No. 44876, 7:8 pages.

Berge et al. (Dec. 1998) "Selective Expansion of a Peripheral Blood Cd8+ Memory T Cell Subset Expressing Both Granzyme B and L-selectin During Primary Viral Infection in Renal Allograft Recipients", Transplantation Proceedings, 30(8):3975-3977.

Cong et al. (Feb. 15, 2013) "Multiplex Genome Engineering Using CRISPR/Cas Systems", Science, 339 (6121):819-823 (9 pages).

Database Genbank,"Collectin-12 [*Homo sapiens*]", NCBI Reference Sequence: NP_569057.2, 3 pages, May 22, 2022.

Database Genbank (Sep. 1, 2020) "C-X-C Motif Chemokine 16 Precursor [*Homo sapiens*]", NCBI Reference Sequence: NP_001094282. 1, 3 pages.

Database Genbank (Nov. 22, 2021) "*Homo sapiens* Chromosome 15, GRCh38.p14 Primary Assembly", NCBI Reference Sequence: NC_000015.10, 3 pages.

Doench et al. (Jan. 18, 2016) "Optimized sgRNA Design to Maximize Activity and Minimize Off-target Effects of CRISPR-Cas9", Nature Biotechnology, 34:184-191.

El-Naggar et al. (Jan. 2016) "Genotypic Analysis of Primary Head and Neck Squamous Carcinoma by Combined Fluorescence In Situ Hybridization and DNA Flow Cytometry", American Journal of Clinical Pathology, 105(1):102-108.

Garland et al. (Jul. 30, 1999) "The Use of Teflon Cell Culture Bags to Expand Functionally Active CD8+ Cytotoxic T Lymphocytes", Journal of Immunological Methods, 227(1-2):53-63.

GENBANK (May 22, 2022) "B2M beta-2-microglobulin [ *Homo sapiens* (human) ]", Gene ID: 567, 12 pages.

GENBANK (Jul. 3, 2022) "HLA-A major histocompatibility complex, class I, A [ *Homo sapiens* (human) ]", Gene ID: 3105, 15 pages.

GENBANK (Jul. 3, 2022) "HLA-B major histocompatibility complex, class I, B [ *Homo sapiens* (human) ]", Gene ID: 3106, 14 pages.

GENBANK (Jul. 3, 2022) "HLA-C Major Histocompatibility Complex, Class I, C [ *Homo sapiens* (human) ]", Gene ID: 3107, 13 pages.

Haanen et al. (Nov. 1, 1999) "Selective Expansion of Cross-Reactive Cd8+ Memory T Cells by Viral Variants", Journal of Experimental Medicine, 190(9):1319-1328.

Hofmann et al. (1993) "TMbase—A database of membrane spanning proteins segments", Journal of Biological Chemistry, 347:166(2 pages).

Kagoya et al. (Feb. 5, 2018) "A Novel Chimeric Antigen Receptor Containing a JAK-STAT Signaling Domain Mediates Superior Antitumor Effects", Nature medicine, 24(3):352-359.

Karlin et al. (Jun. 1993) "Applications and Statistics for Multiple High-Scoring Segments in Molecular Sequences", Proceedings of the National Academy of Sciences, 90(12):5873-5877.

Karlin et al. (Mar. 1990) "Methods for Assessing the Statistical Significance of Molecular Sequence Features by Using General Scoring Schemes", Proceedings of the National Academy of Sciences of the United States of America, 87(6):2264-2268.

Krogh et al. (Jan. 19, 2001) "Predicting Transmembrane Protein Topology with a Hidden Markov Model Application to Complete Genomes", Journal of Molecular Biology, 305(3):567-580.

Papathanasiou et al. (Nov. 2020) "Autologous CAR T-cell Therapies Supply Chain: Challenges and Opportunities?", Cancer Gene Therapy, 27(10-11):799-809.

Passerini et al. (Mar. 2008) "STAT5-signaling Cytokines Regulate the Expression of FOXP3 in CD4+CD25+ Regulatory T Cells and CD4+CD25-Effector T cells", International Immunology, 20(3):421-431.

Pennisi, Elizabeth (Aug. 23, 2013) "The CRISPR Craze", Science, 341(6148):833-836.

Ren et al. (May 1, 2017) "Multiplex Genome Editing to Generate Universal Car T Cells Resistant to PD1 Inhibition", Clinical Cancer Research, 23(9):2255-2266 (21 pages).

Saal et al. (1993) "Cytogenetic Differences Between Intestinal and Diffuse Types of Human Gastric Carcinoma", Virchows Archiv. B, Cell Pathology including Molecular Pathology, 64(3):145-150.

Tsai et al. (Jun. 2014) "Dimeric CRISPR RNA-Guided FokI Nucleases for Highly Specific Genome Editing", Nature Biotechnology, 32(6):569-576 (22 pages).

Ui-Tei et al. (2000) "Sensitive Assay of RNA Interference in *Drosophila* and Chinese Hamster Cultured Cells Using Firefly Luciferase Gene as Target", FEBS Letters, 479:79-82.

Wong et al. (Dec. 29, 2015) "TMSB4Y is a Candidate Tumor Suppressor on the Y Chromosome and is Deleted in Male Breast Cancer", Oncotarget, 6(42):44927-44940.

Zhang et al. (2021) "Targeting Loss of Heterozygosity: A Novel Paradigm for Cancer Therapy", Pharmaceuticals, 14 (1):57.

Wang et al. (Oct. 2015) "Targeted Disruption of the 32-Microglobulin Gene Minimizes the Immunogenicity of Human Embryonic Stem Cells", Stem Cells Translational Medicine, 4(10):1234-1245.

Alcover et al. (Apr. 26, 2018) "Cell Biology of T Cell Receptor Expression and Regulation", Annual Review of Immunology, 36:103-125.

Campoli et al. (Oct. 6, 2008) "HLA Antigen Changes in Malignant Cells: Epigenetic Mechanisms and Biologic Significance", Oncogene, 27(45):5869-5885.

Chen et al. (Mar. 21, 2012) "Structural and Functional Distinctiveness of HLA-A2 Allelic Variants", Immunologic Research, 53:182-190.

Ellis et al. (Mar. 2000) "Frequencies of HLA-A2 alleles in five U.S. population groups: Predominance of A?02011 and identification of HLA-A?0231", Human Immunology, 61(3):334-340.

Harrer et al. (May 2018) "Chimeric Antigen Receptors in Different Cell Types: New Vehicles Join the Race", Human Gene Therapy, 29(5):547-558.

Maleno et al. (2002) "Multiple mechanisms generate HLA class I altered phenotypes in laryngeal carcinomas: high frequency of HLA haplotype loss associated with loss of heterozygosity in chromosome region 6p21", Cancer Immunology, Immunotherapy, 51(7):389-396.

McEvoy et al. (2002) "Frequency and Genetic Basis of MHC, beta-2-microglobulin and MEMO-1 Loss of Heterozygosity in Sporadic Breast Cancer", Tissue Antigens, 60(3):235-243.

Morgan et al. (Apr. 2010) "Case Report of a Serious Adverse Event Following the Administration of T Cells Transduced With a Chimeric Antigen Receptor Recognizing ERBB2", Molecular Therapy, 18(4):843-851.

Natali et al. (Sep. 1, 1989) Selective Changes in Expression of HLA Class I Polymorphic Determinants in Human Solid Tumors, Proceedings of the National Academy of Sciences of the United States of America, 86 (17):6719-6723.

Norell et al. (Jun. 15, 2006) "Frequent Loss of HLA-A2 Expression in Metastasizing Ovarian Carcinomas Associated with Genomic

(56) References Cited

OTHER PUBLICATIONS

Haplotype Loss and HLA-A2-Restricted HER-2/neu-Specific Immunity", Cancer Research, 66(12):6387-6394.
Skuljec et al. (Sep. 12, 2017) "Chimeric Antigen Receptor-Redirected Regulatory T Cells Suppress Experimental Allergic Airway Inflammation, a Model of Asthma", Frontiers in Immunology, Article 1125, 8:12 pages.
Sun et al. (Jun. 11, 2014) "Construction and Evaluation of a Novel Humanized HER2-Specific Chimeric Receptor", Breast Cancer Research, R61 16(3):10 pages.
Dong et al. (Jul. 9, 2020) "Rewired signaling network in T cells expressing the chimeric antigen receptor (CAR)", The EMBO Journal, 39(16):e104730.
Hudecek et al. (Feb. 2015) "The Nonsignaling Extracellular Spacer Domain of Chimeric Antigen Receptors is Decisive for in Vivo Antitumor Activity", Cancer Immunology Research, 3(2):125-135.
MacDonald et al. (Mar. 21, 2016) "Alloantigen-specific Regulatory T Cells Generated with a Chimeric Antigen Receptor", Journal of Clinical Investigation, 126(4):1413-1424.
Saverino et al. (Oct. 1, 2000) "The CD85/LIR-1/ILT2 Inhibitory Receptor Is Expressed by All Human T Lymphocytes and Down-Regulates Their Functions", Journal of Immunology, 165(7):3742-3755.
Sergeeva et al. (Nov. 16, 2008) "Direct Visualization of PR1/HLA-A2 on the Membrane of HLAA2+ CD13 +CD33+ Myeloid Leukemia Blasts by a Novel Monoclonal Antibody", Blood, 112(11):2545(2 pages).
Staub et al. (May 2004) "Systematic Identification of Immunoreceptor Tyrosine-based Inhibitory Motifs in the Human Proteome", Cellular Signalling, 16(4):435-456.
Stein et al. (May 1994) "The Cytoplasmic Domain of CD28 is Both Necessary and Sufficient for Costimulation of Interleukin-2 Secretion and Association With Phosphatidylinositol 3'-kinase", Molecular and Cellular Biology, 14(5):3392-3402.
Tao et al. (Sep. 13, 2020) "CD19-CAR-T Cells Bearing a KIR/PD-1-Based Inhibitory CAR Eradicate CD19 +HLA-C1—Malignant B Cells While Sparing CD19+HLA-C1+ Healthy B Cells", Cancer Immunology, 12:2612, 18 pages.

\* cited by examiner

FIG. 1

| CAR | Constructs | Binding Domain | Binding Domain Format | Hinge | Transmembrane Domain | First Intracellular Domain | Second Intracellular Domain | Third Intracellular Domain | Activity |
|---|---|---|---|---|---|---|---|---|---|
| CAR1 | CT292 | 4D5* | VL-VH | CD8 | CD8 | CD28 | 4-1BB | CD3z | yes |
| CAR4 | CT298 | 4D5 | VL-VH | Linker | CD8 | 4-1BB | - | CD3z | low |
| CAR3 | CT299 | 4D5 | VL-VH | IgG4(EQ) | CD8 | 4-1BB | - | CD3z | yes |
| CAR2 | CT297 | FRP5 | VH-VL | CD28 | CD28 | CD28 | - | CD3z | no |
|  | CT1094 | FRP5 | VH-VL | IgG1 | CD28 | CD28 | - | CD3z | yes |
|  | CT1095 | FRP5* | VH-VL | IgG1 | CD28 | CD28 | - | CD3z | yes |

FIG. 13

| | HeLa | | HCT.116 | | MS751 | |
|---|---|---|---|---|---|---|
| | Antigen density | A:B ratio | Antigen density | A:B ratio | Antigen density | A:B ratio |
| HLA-A02 | 842,273 | | 44,173 | | 45,013 | |
| HER2 | 21,198 | 1:40 | 9,517 | 1:4 | 19,965 | 1:2 |
| EGFR | 53,080 | 1:15 | 22,321 | 1:2 | 247,051 | 5:1 |

COMPOSITIONS AND METHODS FOR TREATING HER2 POSITIVE CANCERS

CROSS REFERENCE TO RELATED APPLICATIONS

This application is a continuation of and claims priority to the International Patent Application No. PCT/US2022/016582, filed Feb. 16, 2022 and entitled "Compositions and Methods for Treating HER2 Positive Cancers," which claims priority to and benefit of U.S. Provisional Application No. 63/149,952, filed on Feb. 16, 2021, the content of which are incorporated herein by reference in their entireties.

INCORPORATION BY REFERENCE OF SEQUENCE LISTING

The present application is being filed with a Sequence Listing in electronic format. The Sequence Listing is provided as a file entitled A2BI_035_01WO_Seq_List_ST25.txt, created on Feb. 16, 2022, and is 5,413,164 bytes in size. The information in electronic format of the Sequence Listing is incorporated by reference in its entirety.

BACKGROUND

Cell therapy is a powerful tool for the treatment of various diseases, particularly cancers. In conventional adoptive cell therapies, immune cells are engineered to express specific receptors, for example chimeric antigen receptors (CARs) or T cell receptors (TCRs), which direct the activity of the immune cells to cellular targets via interaction of the receptor with a ligand expressed by the target cell. Identification of suitable target molecules remains challenging, as many targets are expressed in normal tissues. One example of such as target is erb-b2 receptor tyrosine kinase 2 (ERBB2, or HER2), which is expressed on the surface of many solid tumors, as well as normal epithelial cells. This expression can lead to toxicity when the transplanted cells target normal tissues expressing HER2 target molecules. Clinical trials with HER2 CAR have shown serious adverse effects, and the only current antibody treatments that target HER2 are only effect for breast cancers with very high HER2 levels. There is thus a need in the art for compositions and methods useful in the treatment of disease, particularly cancers, by adoptive cell therapy.

SUMMARY

The disclosure provides an immune cell responsive to loss of heterozygosity in a cancer cell, comprising: (a) an activator receptor comprising an extracellular ligand binding domain specific to an erb-b2 receptor tyrosine kinase 2 (HER2) antigen; and (b) an inhibitory receptor comprising an extracellular ligand binding domain specific to a non-target antigen that is not expressed by the cancer cell due to a loss of heterozygosity in the cancer cell.

In some embodiments of the immune cells of the disclosure, the non-target antigen is an HLA class I allele or a minor histocompatibility antigen (MiHA). In some embodiments, the HLA class I allele comprises HLA-A, HLA-B, HLA-C or HLA-E. In some embodiments, the HLA class I allele is HLA-A*02.

In some embodiments of the immune cells of the disclosure, the target antigen is HER2 or a peptide antigen of HER2 in a complex with a major histocompatibility class I complex (MHC I).

In some embodiments of the immune cells of the disclosure, the cancer cell expresses HER2. In some embodiments, the cancer cell is a breast cancer cell, bladder cancer cell, ovarian cancer cell, gastric cancer cell, a salivary duct carcinoma cell, a non-small cell lung cancer cell, a pancreatic cancer cell, or a colon cancer cell. In some embodiments, the cancer cell is a breast cancer cell or gastric cancer cell.

In some embodiments of the immune cells of the disclosure, the HLA-A*02 non-target antigen is expressed by healthy cells of a subject. In some embodiments, healthy cells of the subject express both the target antigen and the HLA-A*02 non-target antigen. In some embodiments, the activator receptor and the inhibitory receptor together specifically activate the immune cell in the presence of the cancer cell.

In some embodiments of the immune cells of the disclosure, the immune cell is a T cell. In some embodiments, the T cell is a CD8+ CD4− T cell.

In some embodiments of the immune cells of the disclosure, the HER2 antigen comprises a sequence or subsequence at least 95% identical to a sequence or subsequence of any one of SEQ ID NOs: 2-29.

In some embodiments of the immune cells of the disclosure, the activator receptor is a T cell receptor (TCR) or a chimeric antigen receptor (CAR). In some embodiments, the extracellular ligand binding domain of the activator receptor comprises an antibody fragment, a single chain Fv antibody fragment (scFv), a β chain variable domain (Vβ), or a TCR α chain variable domain and a TCR β chain variable domain. In some embodiments, the extracellular ligand binding domain of the activator receptor comprises a heavy chain variable (VH) region and a light chain variable (VL) region. In some embodiments, the VH and VL regions comprise complement determining regions (CDRs) selected from the group consisting of SEQ ID NOS: 30-42. In some embodiments, the VH region comprises one or more CDR sequences selected from the group consisting of GFNIKDTYIH (SEQ ID NO: 36), ARIYPTNGYTRYADSVKG (SEQ ID NO: 38), and SRWGGDGFYAMD[Y/V] (SEQ ID NO: 40) or (SEQ ID NO: 41); and the VL region comprises one or more CDR sequences selected from the group consisting of RASQDVNTAVA (SEQ ID NO: 30), SASFLY (SEQ ID NO: 32), and QQHYTTPP (SEQ ID NO: 34). In some embodiments, the VH region comprises one or more CDR sequences selected from the group consisting of NYGMN (SEQ ID NO: 37), WINTSTGESTFADDFKG (SEQ ID NO: 39) and WEVYHGYVPY (SEQ ID NO: 42); and the VL region comprises one or more CDR sequences selected from the group consisting of KASQDVYNAVA (SEQ ID NO: 31), SASSRYT (SEQ ID NO: 33), and QQHFRTPFT (SEQ ID NO: 35). In some embodiments, the VH region comprises CDR sequences of GFNIKDTYIH (SEQ ID NO: 36), ARIYPTNGYTRYADSVKG (SEQ ID NO: 38), and SRWGGDGFYAMD[Y/V] (SEQ ID NO: 40) or (SEQ ID NO: 41); and the VL region comprises CDR sequences of RASQDVNTAVA (SEQ ID NO: 30), SASFLY (SEQ ID NO: 32) and QQHYTTPP (SEQ ID NO: 34). In some embodiments, the VH region comprises CDR sequences of NYGMN (SEQ ID NO: 37), WINTSTGESTFADDFKG (SEQ ID NO: 39) and WEVYHGYVPY (SEQ ID NO: 42); and the VL region comprises CDR sequences of KASQDVYNAVA (SEQ ID NO: 31), SASSRYT (SEQ ID NO: 33), and QQHFRTPFT (SEQ ID NO: 35). In some embodiments, the VH region comprises CDR sequences of DTYIH (SEQ ID NO: 313), RIYPTNGYTRYADSVKG (SEQ ID NO: 314), and WGGDGFYAMDV (SEQ ID NO: 315); and the VL region comprises CDR sequences of RASQDVNTAVA (SEQ ID NO: 30), SASFLYS (SEQ ID NO: 311), QQHYTTPPT (SEQ ID NO: 312), and DTYIH (SEQ ID NO: 313). In some embodiments, the scFv comprises a sequence having at least 85%, at least 90%, at least 95%, at least 97%, at least 99% identity or is identical to a sequence selected from the group consisting of SEQ ID NOS: 51, 53, 55, 57. 59 and 61.

In some embodiments of the immune cells of the disclosure, the CAR comprises a hinge sequence isolated or derived from CD8, CD28, IgG1, or IgG4, or a synthetic hinge. In some embodiments, the CAR comprises a transmembrane domain isolated or derived from CD8 or CD28. In some embodiments, the CAR comprises an intracellular domain isolated or derived from CD28, 4-1BB or CD3z, or a combination thereof.

In some embodiments of the immune cells of the disclosure, the inhibitory receptor comprises a TCR or CAR. In some embodiments, the extracellular ligand binding domain of the inhibitory receptor comprises an antibody fragment, a single chain Fv antibody fragment (scFv), a β chain variable domain (Vβ), or a TCR α chain variable domain and a TCR β chain variable domain. In some embodiments, the extracellular ligand binding domain of the inhibitory receptor comprises a heavy chain variable (VH) region and a light chain variable (VL) region. In some embodiments, the VH and VL regions comprise CDRs selected from the group consisting of SEQ ID NOS: 87-102. In some embodiments, the VH region comprises one or more CDRs selected from the group consisting of ASGYTFTSYHIH (SEQ ID NO: 95), WIYPGNVNTEYNEKFKGK (SEQ ID NO: 98) and EEITYAMDY (SEQ ID NO: 101), and the VL region comprises one or more CDRs selected from the group consisting of RSSQSIVHSNGNTYLE (SEQ ID NO: 87), KVSNRFSGVP[D/A]R (SEQ ID NO: 90) OR (SEQ ID NO: 91), and FQGSHVPRT (SEQ ID NO: 92). In some embodiments, the VH region comprises one or more CDRs selected from the group consisting of SGYTFTSYHMH (SEQ ID NO: 97), WIYPGDGSTQYNEKFKG (SEQ ID NO: 100) and EGTYYAMDY (SEQ ID NO: 102); and the VL region comprises one or more CDRs selected from the group consisting of RSSQSIVHSNGNTYLD (SEQ ID NO: 89), KVSNRFSGVP[D/A]R (SEQ ID NO: 90) OR (SEQ ID NO: 91) and MQGSHVPRT (SEQ ID NO: 94). In some embodiments, the scFv comprises a sequence having at least 85%, at least 90%, at least 95%, at least 97%, at least 99% identity or is identical to a sequence selected from the group consisting of SEQ ID NOS: 63-74, 207, 209 and 211. In some embodiments, the VH region comprises CDR sequences of SYHIH (SEQ ID NO: 566), WIYPGNVNTEYNEKFKG (SEQ ID NO: 567), and EEITYAMDY (SEQ ID NO: 101); and the VL region comprises CDR sequences of RSSQSIVHSNGNTYLE (SEQ ID NO: 87), KVSNRFS (SEQ ID NO: 565), and FQGSHVPRT (SEQ ID NO: 92).

In some embodiments of the immune cells of the disclosure, the inhibitory receptor comprises a LILRB1 intracellular domain or a functional variant thereof. In some embodiments, the inhibitory receptor comprises LILRB1 hinge and transmembrane domains, or functional variants thereof. In some embodiments, the inhibitory receptor comprises a sequence having at least 85%, at least 90%, at least 95%, at least 97%, at least 99% identity or is identical to (SEQ ID NO: 254)
YGSQSSKPYLLTHPSDPLELVVSGPSGGPSSPTTGPTSTSGPEDQPLTP -continued

TGSDPQSGLGRHLGVVIGILVAVILLLLLLLLLFLILRHRRQGKHWTST

QRKADFQHPAGAVGPEPTDRGLQWRSSPAADAQEENLYAAVKHTQPEDG

VEMDTRSPHDEDPQAVTYAEVKHSRPRREMASPPSPLSGEFLDTKDRQA

EEDRQMDTEAAASEAPQDVTYAQLHSLTLRREATEPPPSQEGPSPAVPS

IYATLAIH.

The disclosure provides a pharmaceutical composition, comprising a therapeutically effective amount of the immune cells of the disclosure. In some embodiments, the pharmaceutical composition further comprises a pharmaceutically acceptable carrier, diluent or excipient.

The disclosure provides a pharmaceutical composition comprising the immune cells of the disclosure, for use as a medicament in the treatment of cancer.

The disclosure provides a polynucleotide system, comprising one or more polynucleotides comprising polynucleotide sequences encoding: (a) an activator receptor comprising an extracellular ligand binding domain specific to an erb-b2 receptor tyrosine kinase 2 (HER2) antigen; and (b) an inhibitory receptor comprising an extracellular ligand binding domain specific to a non-target antigen that is not expressed by the cancer cell due to a loss of heterozygosity in the cancer cell.

The disclosure provides a vector, comprising the polynucleotide system of the disclosure.

The disclosure provides a method of treating a HER2+ cancer in a subject identified as having or suspected of having a loss of heterozygosity at an allele encoding a non-target antigen in the HER2+ cancer, comprising administering to the subject the immune cells or pharmaceutical composition of the disclosure.

The disclosure provides a method of making an immune cell therapy, comprising transforming immune cells with the polynucleotide system or vector of the disclosure.

The disclosure provides a kit comprising the immune cells or pharmaceutical compositions of the disclosure. In some embodiments, the kit further comprises instructions for use.

The disclosure also provides a method of selectively killing HER2-positive tumor cells having loss of heterozygosity at an allele encoding a non-target antigen in the HER2-positive cancer, comprising contacting the HER2-positive tumor cells with a composition or an immune cell the tumor cell is in a mixed culture. In some embodiments, the non-target antigen is selected from the group consisting of HLA-A*02, HLA-A*01, HLA-A*03, HLA-A*11, HLA-B*07, and HLA-C*07.

The disclosure also provides an immune cell comprising (a) an activator receptor comprising an extracellular ligand binding domain specific to an erb-b2 receptor tyrosine kinase 2 (HER2) antigen, wherein the extracellular ligand binding domain of the activator receptor comprises (i) a VH region comprising CDR sequences of DTYIH (SEQ ID NO: 313), RIYPTNGYTRYADSVKG (SEQ ID NO: 314), and WGGDGFYAMDV (SEQ ID NO: 315); and (ii) a VL region comprising CDR sequences of RASQDVNTAVA (SEQ ID NO: 30), SASFLYS (SEQ ID NO: 311), QQHYTTPPT (SEQ ID NO: 312), and DTYIH (SEQ ID NO: 313) region and a light chain variable (VL) region; and (b) an inhibitory receptor comprising an extracellular ligand binding domain specific to a non-target antigen that is not expressed by the cancer cell due to a loss of heterozygosity in the cancer cell, wherein the extracellular ligand binding domain of the inhibitory receptor comprises (i) a heavy chain variable (VH) region comprising CDR sequences of SYHIH (SEQ ID NO: 566), WIYPGNVNTEYNEKFKG (SEQ ID NO: 567), and EEITYAMDY (SEQ ID NO: 101); and (ii) a light chain variable (VL) region comprising of RSSQSIVHSNGNTYLE (SEQ ID NO: 87), KVSNRFS (SEQ ID NO: 565), and FQGSHVPRT (SEQ ID NO: 92).

The disclosure also provides an immune cell comprising (a) an activator receptor comprising an extracellular ligand binding domain specific to an erb-b2 receptor tyrosine kinase 2 (HER2) antigen, wherein the extracellular ligand binding domain of the activator receptor is an scFv comprising the sequence of SEQ ID NO: 51; and (b) an inhibitory receptor comprising an extracellular ligand binding domain specific to a non-target antigen that is not expressed by the cancer cell due to a loss of heterozygosity in the cancer cell, wherein the extracellular ligand binding domain of the inhibitory receptor is an scFv comprising the sequence of SEQ ID NO: 209.

The disclosure also provides a method of treating a HER2+ cancer in a subject identified as having or suspected of having loss of heterozygosity at an allele encoding HLA-A*02, comprising administering to the subject an immune cell comprising (a) an activator receptor comprising an extracellular ligand binding domain specific to an erb-b2 receptor tyrosine kinase 2 (HER2) antigen, wherein the extracellular ligand binding domain of the activator receptor comprises (i) a VH region comprising CDR sequences of DTYIH (SEQ ID NO: 313), RIYPTNGYTRYADSVKG (SEQ ID NO: 314), and WGGDGFYAMDV (SEQ ID NO: 315); and (ii) a VL region comprising CDR sequences of RASQDVNTAVA (SEQ ID NO: 30), SASFLYS (SEQ ID NO: 311), QQHYTTPPT (SEQ ID NO: 312), and DTYIH (SEQ ID NO: 313) region and a light chain variable (VL) region; and (b) an inhibitory receptor comprising an extracellular ligand binding domain specific to a non-target antigen that is not expressed by the cancer cell due to a loss of heterozygosity in the cancer cell, wherein the extracellular ligand binding domain of the inhibitory receptor comprises (i) a heavy chain variable (VH) region comprising CDR sequences of SYHIH (SEQ ID NO: 566), WIYPGNVNTEYNEKFKG (SEQ ID NO: 567), and EEITYAMDY (SEQ ID NO: 101); and (ii) a light chain variable (VL) region comprising of RSSQSIVHSNGNTYLE (SEQ ID NO: 87), KVSNRFS (SEQ ID NO: 565), and FQGSHVPRT (SEQ ID NO: 92).

The disclosure also provides a method of treating a HER2+ cancer in a subject identified as having or suspected of having loss of heterozygosity at an allele encoding HLA-A*02, comprising administering to the subject an immune cell comprising (a) an activator receptor comprising an extracellular ligand binding domain specific to an erb-b2 receptor tyrosine kinase 2 (HER2) antigen, wherein the extracellular ligand binding domain of the activator receptor is an scFv comprising the sequence of SEQ ID NO: 51; and (b) an inhibitory receptor comprising an extracellular ligand binding domain specific to a non-target antigen that is not expressed by the cancer cell due to a loss of heterozygosity in the cancer cell, wherein the extracellular ligand binding domain of the inhibitory receptor is an scFv comprising the sequence of SEQ ID NO: 209.

The disclosure also provides a method of selectively killing HER2-positive tumor cells having loss of heterozygosity at an allele encoding HLA-A*02, comprising contacting the HER2-positive tumor cells with an immune cell comprising an immune cell comprising (a) an activator receptor comprising an extracellular ligand binding domain specific to an erb-b2 receptor tyrosine kinase 2 (HER2) antigen, wherein the extracellular ligand binding domain of the activator receptor comprises (i) a VH region comprising CDR sequences of DTYIH (SEQ ID NO: 313), RIYPTNGYTRYADSVKG (SEQ ID NO: 314), and WGGDGFYAMDV (SEQ ID NO: 315); and (ii) a VL region comprising CDR sequences of RASQDVNTAVA (SEQ ID NO: 30), SASFLYS (SEQ ID NO: 311), QQHYTTPPT (SEQ ID NO: 312), and DTYIH (SEQ ID NO: 313) region and a light chain variable (VL) region; and (b) an inhibitory receptor comprising an extracellular ligand binding domain specific to a non-target antigen that is not expressed by the cancer cell due to a loss of heterozygosity in the cancer cell, wherein the extracellular ligand binding domain of the inhibitory receptor comprises (i) a heavy chain variable (VH) region comprising CDR sequences of SYHIH (SEQ ID NO: 566), WIYPGNVNTEYNEKFKG (SEQ ID NO: 567), and EEITYAMDY (SEQ ID NO: 101); and (ii) a light chain variable (VL) region comprising of RSSQSIVHSNGNTYLE (SEQ ID NO: 87), KVSNRFS (SEQ ID NO: 565), and FQGSHVPRT (SEQ ID NO: 92).

The disclosure also provides a method of selectively killing HER2-positive tumor cells having loss of heterozygosity at an allele encoding HLA-A*02, comprising contacting the HER2-positive tumor cells with an immune cell comprising an immune cell comprising (a) an activator receptor comprising an extracellular ligand binding domain specific to an erb-b2 receptor tyrosine kinase 2 (HER2) antigen, wherein the extracellular ligand binding domain of the activator receptor is an scFv comprising the sequence of SEQ ID NO: 51; and (b) an inhibitory receptor comprising an extracellular ligand binding domain specific to a non-target antigen that is not expressed by the cancer cell due to a loss of heterozygosity in the cancer cell, wherein the extracellular ligand binding domain of the inhibitory receptor is an scFv comprising the sequence of SEQ ID NO: 209.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the features and advantages of the present invention will be obtained by reference to the following detailed description that sets forth illustrative embodiments, in which the principles of the invention are utilized, and the accompanying drawings of which:

FIG. 1 is a table comparing the activity of different chimeric antigen receptors with that target HER2. FRP5* and 4D5* each have a single amino acid change in the VH domain compared to FRP5 and 4D5, respectively. IgG4 (EQ) has a mutated CH2 region to avoid Fc receptor binding. Linker sequence: GGGSSGGGSG (SEQ ID NO: 1).

FIG. 13 is a table summarizing the antigen density, and ratio of activator to blocker antigen, on HeLa, HCT.116 and MS751 target cells. Cell surface antigens were quantified using the Agilent QIFI Kit.

DETAILED DESCRIPTION

Figure 2A:
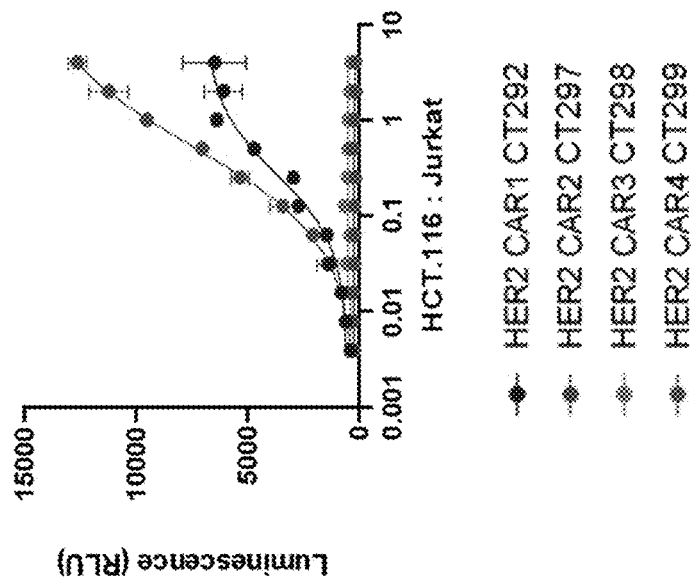
FIG. 2A is a plot showing HER2 activator EC50 in Jurkat cells, as measured by antigen titration on a solid substrate. HER2 CAR2 showed no activity.

The present disclosure describes engineered receptors, such as chimeric antigen receptors (CARs) and engineered T cell receptors (TCRs), adoptive cell therapies, and methods of use thereof. The engineered receptors can target the HER2 antigen and activate immune cells genetically altered to express the HER2 targeting receptor. Immune cells expressing the HER2 targeting activator receptors can be used in compositions as part of cell adoptive therapies in the treatment, for example, of cancers that are HER2 positive. The immune cells expressing the HER2 targeting activator receptors are also contemplated to further comprise a second inhibitory receptor. The second inhibitory receptor can prevent or inhibit the activation of an immune cell mediated by the activator receptor. For example, an immune cell expressing an activator receptor targeting HER2 and an inhibitory receptor that specifically binds a separate antigen, e.g. an MHC Class I antigen, will be activated in the presence of a cell expressing HER2, but will not be activated in the presence of a cell expressing both HER2 and the HLA Class I antigen that is the target of the inhibitory receptor. Selective activation and inhibition of the immune cell expressing both an activating and inhibitory receptors is useful for reducing toxicity in adoptive cell therapies. The inventors have found that this strategy can be employed using the HER2-targeting activator receptors and inhibitory receptors described herein. Both activating and inhibitory receptors can be, for example, chimeric antigen receptors (CARs) or T cell receptors (TCRs).

The term "chimeric antigen receptors" or "CARs" as used herein, may refer to artificial T-cell receptors, chimeric T-cell receptors, or chimeric immunoreceptors, for example, and encompass engineered receptors that graft an artificial specificity onto a particular immune effector cell, such as a helper T cell (CD4+), cytotoxic T cell (CD8+) or NK cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen such as a HER2 antigen. In some embodiments, CARs comprise an intracellular signaling domain, a transmembrane domain, and an extracellular domain comprising an antigen-binding region. In some embodiments, CARs comprise fusions of single-chain variable fragments (scFvs) or scFabs derived from monoclonal antibodies, fused to a transmembrane domain and intracellular signaling domain(s). The fusion may also comprise a hinge. Either heavy-light (H-L) and light-heavy (L-H) scFvs may be used. The specificity of CAR designs may be derived from ligands of receptors (e.g., peptides). Depending on the type of intracellular domain, a CAR can be an activator receptor or an inhibitory receptor. In some embodiments, for example when the CAR is an activator receptor, the CAR comprises domains for additional co-stimulatory signaling, such as CD3, FcR, CD27, CD28, CD137, DAP10, and/or OX40. In some embodiments, molecules can be co-expressed with the CAR, including co-stimulatory molecules, reporter genes for imaging (e.g., for positron emission tomography), gene products that conditionally ablate the T cells upon addition of a pro-drug, homing receptors, cytokines, and cytokine receptors. As used herein, characteristics attributed to a chimeric antigen receptor may be understood to refer to the receptor itself or to a host cell comprising the receptor.

As used herein, a "TCR", sometimes also called a "TCR complex" or "TCR/CD3 complex" refers to a protein complex comprising a TCR alpha chain, a TCR beta chain, and one or more of the invariant CD3 chains (zeta, gamma, delta and epsilon), sometimes referred to as subunits. The TCR alpha and beta chains can be disulfide-linked to function as a heterodimer to bind to peptide-MHC complexes. Once the TCR alpha/beta heterodimer engages peptide-MHC, conformational changes in the TCR complex in the associated invariant CD3 subunits are induced, which leads to their phosphorylation and association with downstream proteins, thereby transducing a primary stimulatory signal. In an exemplary TCR complex, the TCR alpha and TCR beta polypeptides form a heterodimer, CD3 epsilon and CD3 delta form a heterodimer, CD3 epsilon and CD3 gamma for a heterodimer, and two CD3 zeta form a homodimer.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" refers to a molecule or portion thereof that, when natively expressed by a T-cell, provides the primary cytoplasmic signaling sequence(s) that regulate activation of the TCR complex in a stimulatory way for at least some aspect of the T-cell signaling pathway. TCR alpha and/or TCR beta chains of wild type TCR complexes do not contain stimulatory domains and require association with CD3 subunits such as CD3 zeta to initiate signaling. In one aspect, the primary stimulatory signal is initiated by, for instance, binding of a TCR/CD3 complex with an a major histocompatibility complex (MHC) bound to peptide, and which leads to mediation of a T-cell response, including, but not limited to, proliferation, activation, differentiation, and the like. One or more stimulatory domains, as described herein, can be fused to the intracellular portion of any one or more subunits of the TCR complex, including TCR alpha, TCR beta, CD3 delta, CD3 gamma and CD3 epsilon.

As used herein, a "domain capable of providing a stimulatory signal" refers to any domain that, either directly or indirectly, can provide a stimulatory signal that enhances or increases the effectiveness of signaling mediated by the TCR complex to enhance at least some aspect of T-cell signaling. The domain capable of providing a stimulatory signal can provide this signal directly, for example with the domain capable of providing the stimulatory signal is a primary stimulatory domain or co-stimulatory domain. Alternatively, or in addition, the domain capable of providing the stimulatory signal can act indirectly. For example, the domain can be a scaffold that recruits stimulatory proteins to the TCR, or provide an enzymatic activity, such as kinase activity, that acts through downstream targets to provide a stimulatory signal.

As used herein, a "domain capable of providing an inhibitory signal" refers to any domain that, either directly or indirectly, can provide an inhibitory signal that inhibits or decreases the effectiveness signaling mediated by the TCR complex. The domain capable of providing an inhibitory signal can reduce, or block, totally or partially, at least some aspect of T-cell signaling or function. The domain capable of providing an inhibitory signal can provide this signal directly, for example with the domain capable of providing the inhibitory signal provides a primary inhibitory signal. Alternatively, or in addition, the domain capable of providing the stimulatory signal can act indirectly. For example, the domain can recruit additional inhibitory proteins to the TCR, or can provide an enzymatic activity that acts through downstream targets to provide an inhibitory signal.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

In general, "sequence identity" or "sequence homology" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

As used herein, a "subsequence" refers to a length of contiguous amino acids or nucleotides that form a part of a sequence described herein. A subsequence may be identical to a part of a full length sequence when aligned to the full length sequence, or less than 100% identical to the part of the full length sequence to which it aligns (e.g., 90% identical to 50% of the full sequence, or the like).

The term "exogenous" is used herein to refer to any molecule, including nucleic acids, protein or peptides, small molecular compounds, and the like that originate from outside the organism. In contrast, the term "endogenous" refers to any molecule that originates from inside the organism (i.e., naturally produced by the organism).

A polynucleotide is "operably linked" to another polynucleotide when it is placed into a functional relationship with the other polynucleotide. For example, a promoter or enhancer is operably linked to a coding sequence if it affects the transcription of the sequence. A peptide is "operably linked" to another peptide when the polynucleotides encoding them are operably linked, preferably they are in the same open reading frame.

A "promoter" is a sequence of DNA needed to turn a gene on or off. Promoters are located immediately upstream and/or overlapping the transcription start site, and are usually between about one hundred to several hundred base pairs in length.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%.

Antigens

The activator receptors disclosed can specifically bind to an erb-b2 receptor tyrosine kinase 2 (HER2) antigen. The HER2 antigen, also known as Neu, ErbB2, and other aliases, is a receptor tyrosine kinase that, upon activation, forms homo- or heterodimers with other ErbB family members to promote intracellular signaling resulting in survival signals and proliferation. HER2 is overexpressed or has differential expression of splice variants and isoforms that contribute to the mechanisms driving various cancers, such as breast, lung, and other cancers.

In some embodiments, the target antigen is a peptide antigen of HER2 in a complex with a major histocompatibility class I complex (MHC I) or major histocompatibility class II complex (MHC II). In some embodiments, the HER2 peptide bound to MHC I comprises KIFGSLAFL (SEQ ID NO: 309). In some embodiments, the HER2 peptide bound to MHC II comprises GSPYVSRLLGICL (SEQ ID NO: 310). In some embodiments, the HER2 antigen comprises a sequence or subsequence at least 80%, at least 85%, at least 90%, at least 95%, at least 97%, at least 99% or is identical to a sequence or a subsequence of any one of SEQ ID NOs: 2-29. However, all HER2 isoforms, and sequences and subsequences thereof that act as HER2 antigens are envisaged as within the scope of the disclosure. In some embodiments, A HER2 antigen comprises a protein comprising a sequence any one of SEQ ID NOS: 2-29, or a peptide fragment of any one of SEQ ID NOS: 2-29. In some embodiments, the HER2 antigen comprises a peptide fragment of any one of SEQ ID NOS: 2-29 in a complex with a major histocompatibility class I complex (MHC-I).

Any cancer comprising a cancer cell that expresses a HER2 antigen is a HER2 positive (HER2+) cancer. In some embodiments, the cancer cell is a breast cancer cell, bladder cancer cell, ovarian cancer cell, gastric cancer cell, a salivary duct carcinoma cell, a non-small cell lung cancer cell, a pancreatic cancer cell, or a colon cancer cell. In some embodiments, the cancer cell is a breast cancer cell or gastric cancer cell.

Engineered Receptors

The disclosure provides an activator receptor and an inhibitory receptor, comprising an extracellular region, the extracellular region comprising a first ligand binding domain capable of specifically binding a first ligand that activates or promotes activation of the receptor, which promotes activation of effector cells expressing the receptor. The disclosure further provides an inhibitory receptor comprising a second ligand binding domain capable of binding a second ligand, wherein binding of the second ligand by the second ligand binding domain inhibits, reduces, or prevents activation of effector cells even in the presence of the first receptor bound to the first ligand. The first ligand may also be referred to as activator ligand. The second ligand may also be referred to as inhibitor ligand. The activator and inhibitory receptors that bind to these ligands may also be referred to generally herein as engineered receptors. Engineered receptors can refer to either chimeric antigen receptors (CARs) and T cell receptors (TCRs) described in the disclosure. Engineered receptor may also refer to any receptor designed using the binding domains, hinge regions, transmembrane domains, and/or cytoplasmic domains described herein. Engineered receptors are sometimes referred to herein as fusion proteins.

Activator Ligands

The disclosure provides a first ligand, an activator, and a first engineered receptor comprising the first ligand binding domain that binds to the first activator ligand. In some embodiments, the first engineered receptor is an activator receptor. In some embodiments, the activator receptor is a T cell receptor (TCR) or a chimeric antigen receptor (CAR). In some embodiments, the first activator ligand is a HER2 antigen. In some embodiments, the HER2 antigen comprises a sequence or subsequence that shares at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or is identical to a sequence or a subsequence of any one of SEQ ID NOs: 2-29. An Illustrative HER2 sequences is shown in Table 1.

TABLE 1

Illustrative HER2 sequence

| HER2 Antigen | Sequence |
|---|---|
| HER2 Isoform a | MELAALCRWGLLLALLPPGAASTQVCTGTDMKLRLPASPETHLDMLRHL YQGCQVVQGNLELTYLPTNASLSFLQDIQEVQGYVLIAHNQVRQVPLQRL RIVRGTQLFEDNYALAVLDNGDPLNNTTPVTGASPGGLRELQLRSLTEILK GGVLIQRNPQLCYQDTILWKDIFHKNNQLALTLIDTNRSRACHPCSPMCK GSRCWGESSEDCQSLTRTVCAGGCARCKGPLPTDCCHEQCAAGCTGPKH SDCLACLHFNHSGICELHCPALVTYNTDTFESMPNPEGRYTFGASCVTACP YNYLSTDVGSCTLVCPLHNQEVTAEDGTQRCEKCSKPCARVCYGLGMEH LREVRAVTSANIQEFAGCKKIFGSLAFLPESFDGDPASNTAPLQPEQLQVFE TLEEITGYLYISAWPDSLPDLSVFQNLQVIRGRILHNGAYSLTLQGLGISWL GLRSLRELGSGLALIHHNTHLCFVHTVPWDQLFRNPHQALLHTANRPEDE CVGEGLACHQLCARGHCWGPGPTQCVNCSQFLRGQECVEECRVLQGLPR EYVNARHCLPCHPECQPQNGSVTCFGPEADQCVACAHYKDPPFCVARCPS GVKPDLSYMPIWKFPDEEGACQPCPINCTHSCVDLDDKGCPAEQRASPLT SIISAVVGILLVVVLGVVFGILIKRRQQKIRKYTMRRLLQETELVEPLTPSG AMPNQAQMRILKETELRKVKVLGSGAFGTVYKGIWIPDGENVKIPVAIKV LRENTSPKANKEILDEAVVMAGVGSPYVSRLLGICLTSTVQLVTQLMPYG CLLDHVRENRGRLGSQDLLNWCMQIAKGMSYLEDVRLVHRDLAARNVL VKSPNHVKITDFGLARLLDIDETEYHADGGKVPIKWMALESILRRRFTHQS DVWSYGVTVWELMTFGAKPYDGIPAREIPDLLEKGERLPQPPICTIDVYMI MVKCWMIDSECRPRFRELVSEFSRMARDPQRFVVIQNEDLGPASPLDSTF YRSLLEDDDMGDLVDAEEYLVPQQGFFCPDPAPGAGGMVHHRHRSSSTR SGGGDLTLGLEPSEEEAPRSPLAPSEGAGSDVFDGDLGMGAAKGLQSLPT HDPSPLQRYSEDPTVPLPSETDGYVAPLTCSPQPEYVNQPDVRPQPPSPRE GPLPAARPAGATLERPKTLSPGKNGVVKDVFAFGGAVENPEYLTPQGGAA PQPHPPPAFSPAFDNLYYWDQDPPERGAPPSTFKGTPTAENPEYLGLDVPV (SEQ ID NO: 2) |

In some embodiments, the activator antigen is a peptide antigen of HER2 in a complex with a major histocompatibility class I complex (MHC I). In some embodiments, the activator antigen is a peptide antigen of HER2 that is not in a complex with a major histocompatibility class I complex (MHC I).

As used herein, an "activator" or "activator ligand" refers to a first ligand that binds to a first, activator ligand binding domain (LBD) of an engineered receptor of the disclosure, such as a CAR or TCR, thereby mediating activation of a T cell expressing the activator receptor. The activator ligand is expressed by target cells, for example cancer cells, and may also be expressed more broadly than just the target cells. For example the activator can be expressed on some, or all types of normal, non-target cells such as epithelial cells.

In some embodiments, the activator ligand is expressed by target cells and is not expressed by non-target cells (i.e. normal cells not targeted by the adoptive cell therapy). In some embodiments, the target cells are cancer cells and the non-target cells are non-cancerous cells.

In some embodiments, the activator ligand has high cell surface expression on the target cells. This high cell surface expression confers the ability to deliver large activation signals. Methods of measuring cell surface expression will be known to the person of ordinary skill in the art and include, but are not limited to, immunohistochemistry using an appropriate antibody against the activator ligand, followed by microscopy or fluorescence activated cell sorting (FACS).

The activator ligand is present on all target cells. In some embodiments, the target cells are cancer cells—such as HER2+ cancer cells, e.g., in HER2+ breast cancer.

In some embodiments, the activator ligand is present on a plurality of target cells. In some embodiments, the target cells are cancer cells. In some embodiments, the activator ligand is present on at least 50%, at least 60%, at least 70%, at least 80%, at least 85%, at least 90%, at least 95%, at least 96%, at least 97%, at least 98%, at least 99%, at least 99.5% or at least 99.9% of target cells. In some embodiments, the activator ligand is present on at least 95% target cells. In some embodiments, the activator ligand is present on at least 99% target cells.

In some embodiments, the first, activator ligand is expressed by a plurality of target cells and a plurality of non-target cells. In some embodiments, the plurality of non-target cells expresses both the first, activator ligand and the second inhibitor ligand.

In some embodiments, and the first, activator ligand and second, inhibitor ligand are present on the plurality of non-target target cells at a ratio of about 1:100 to about 100:1 of the first ligand to the second ligand. In some embodiments, and the first, activator ligand and second, inhibitor ligand are present on the plurality of non-target target cells at a ratio of about 1:50 to about 50:1 of the first ligand to the second ligand. In some embodiments, and the first, activator ligand and second, inhibitor ligand are present on the plurality of non-target target cells at a ratio of about 1:40 to about 40:1 of the first ligand to the second ligand. In some embodiments, and the first, activator ligand and second, inhibitor ligand are present on the plurality of non-target target cells at a ratio of about 1:30 to about 30:1 of the first ligand to the second ligand. In some embodiments, and the first, activator ligand and second, inhibitor ligand are present on the plurality of non-target target cells at a ratio of about 1:20 to about 2:1 of the first ligand to the second ligand. In some embodiments, and the first, activator ligand and second, inhibitor ligand are present on the plurality of non-target target cells at a ratio of about 1:10 to about 10:1 of the first ligand to the second ligand. In some embodiments, and the first, activator ligand and second, inhibitor ligand are present on the plurality of non-target target cells at a ratio of about 1:5 to about 5:1 of the first ligand to the second ligand. In some embodiments, and the first, activator ligand and second, inhibitor ligand are present on the plurality of non-target target cells at a ratio of about 1:3 to about 3:1 of the first ligand to the second ligand. In some embodiments, and the first, activator ligand and second, inhibitor ligand are present on the plurality of non-target target cells at a ratio of about 1:2 to about 2:1 of the first ligand to the second ligand. In some embodiments, and the first, activator ligand and second, inhibitor ligand are present on the plurality of non-target target cells at a ratio of about 1:1.

Extracellular Ligand Binding Domains

The disclosure provides chimeric antigen receptors (CARs) comprising a polypeptide. In some embodiments, the polypeptide comprises a ligand binding domain, such as an antigen-binding domain. Suitable antigen-binding domains include, but are not limited to antigen-binding domains from antibodies, antibody fragments, scFv, antigen-binding domains derived from T cell receptors, and the like. All forms of antigen-binding domains known in the art are envisaged as within the scope of the disclosure.

An "extracellular domain", as used herein, refers to the extracellular portion of a protein. For example, the TCR alpha and beta chains each comprise an extracellular domain, which comprise a constant and a variable region involved in peptide-MHC recognition. The "extracellular domain" can also comprise a fusion domain, for example of fusions between additional domains capable of binding to and targeting a specific antigen and the endogenous extracellular domain of the TCR subunit.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen-binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')2, and Fv fragments, single-chain (sc)Fv ("scFv") antibody fragments, linear antibodies, single domain antibodies (abbreviated "sdAb") (either VL or VH), camelid VHH domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "VH" (or, in the case of single domain antibodies, e.g., nanobodies, "VHH") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the VL and VH variable regions in either order, e.g., with respect to the N-terminal and C-terminal ends of the polypeptide, the scFv may comprise VL-linker-VH or may comprise VH-linker-VL.

The term "antibody light chain," refers to the smaller of the two types of polypeptide chains present in antibody molecules in their naturally occurring conformations. Kappa ("κ") and lambda ("λ") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

In some embodiments, for example those embodiments wherein the receptor comprises a first and a second polypeptide, the antigen-binding domain is isolated or derived from a T cell receptor (TCR) extracellular domain or an antibody.

In some embodiments, the extracellular ligand binding domain of the activator receptor comprises an antibody fragment, a single chain Fv antibody fragment (scFv), a β chain variable domain (Vβ), or a TCR α chain variable domain and a TCR β chain variable domain. In some embodiments, the extracellular ligand binding domain of the activator receptor comprises a heavy chain variable (VH) region and a light chain variable (VL) region. In some embodiments, the VH and VL regions comprise complement determining regions (CDRs) selected from the group of CDRs disclosed in Table 2.

In some embodiments, the VH region comprises CDR sequences of GFNIKDTYIH (SEQ ID NO: 36), ARIYPTNGYTRYADSVKG (SEQ ID NO: 38), and SRWGGDGFYAMDY (SEQ ID NO: 40) or SRWGGDGFYAMDV (SEQ ID NO: 41); and the VL region comprises CDR sequences of RASQDVNTAVA (SEQ ID NO: 30), SASFLY (SEQ ID NO: 32) and QQHYTTPP (SEQ ID NO: 34).

In some embodiments, the VH region comprises CDR sequences of NYGMN (SEQ ID NO: 37), WINTSTGESTFADDFKG (SEQ ID NO: 39) and WEVYHGYVPY (SEQ ID NO: 42); and the VL region comprises CDR sequences of KASQDVYNAVA (SEQ ID NO: 31), SASSRYT (SEQ ID NO: 33), and QQHFRTPFT (SEQ ID NO: 35).

In some embodiments, the VH region comprises CDR sequences DTYIH (SEQ ID NO: 313), RIYPTNGYTRYADSVKG (SEQ ID NO: 314), and WGGDGFYAMDV (SEQ ID NO: 315); and the VL region comprises CDR sequences of RASQDVNTAVA (SEQ ID NO: 30), SASFLYS (SEQ ID NO: 311), and QQHYTTPPT (SEQ ID NO: 312).

In some embodiments, the full length VH and VL regions comprise the sequences disclosed in Table 3. In some embodiments, the binding domain comprises the full length

TABLE 2

HER2 antigen binding domain complement determining regions (CDRs)

| CDR-L1 | CDR-L2 | CDR-L3 | CDR-H1 | CDR-H2 | CDR-H3 |
| --- | --- | --- | --- | --- | --- |
| RASQDVNTAVA (SEQ ID NO: 30) | SASFLY (SEQ ID NO: 32) | QQHYTTPP (SEQ ID NO: 34) | GFNIKDTYIH (SEQ ID NO: 36) | ARIYPTNGYTRYADSVKG (SEQ ID NO: 38) | SRWGGDGFYAMDY (SEQ ID NO: 40) |
| RASQDVNTAVA (SEQ ID NO: 30) | SASFLY (SEQ ID NO: 32) | QQHYTTPP (SEQ ID NO: 34) | GFNIKDTYIH (SEQ ID NO: 36) | ARIYPTNGYTRYADSVKG (SEQ ID NO: 38) | SRWGGDGFYAMDV (SEQ ID NO: 41) |
| KASQDVYNAVA (SEQ ID NO: 31) | SASSRYT (SEQ ID NO: 33) | QQHFRTPFT (SEQ ID NO: 35) | NYGMN (SEQ ID NO: 37) | WINTSTGESTFADDFKG (SEQ ID NO: 39) | WEVYHGYVPY (SEQ ID NO: 42) |
| RASQDVNTAVA (SEQ ID NO: 30) | SASFLYS (SEQ ID NO: 311) | QQHYTTPPT (SEQ ID NO: 312) | DTYIH (SEQ ID NO: 313) | RIYPTNGYTRYADSVKG (SEQ ID NO: 314) | WGGDGFYAMDV (SEQ ID NO: 315) |

In some embodiments, the VH region comprises one or more CDR sequences selected from the group consisting of GFNIKDTYIH (SEQ ID NO: 36), ARIYPTNGYTRYADSVKG (SEQ ID NO: 38), and SRWGGDGFYAMD[Y/V] (SEQ ID NO: 40) or (SEQ ID NO: 41); and the VL region comprises one or more CDR sequences selected from the group consisting of RASQDVNTAVA (SEQ ID NO: 30), SASFLY (SEQ ID NO: 32), and QQHYTTPP (SEQ ID NO: 34).

In some embodiments, the VH region comprises one or more CDR sequences selected from the group consisting of NYGMN (SEQ ID NO: 37), WINTSTGESTFADDFKG (SEQ ID NO: 39) and WEVYHGYVPY (SEQ ID NO: 42); and the VL region comprises one or more CDR sequences selected from the group consisting of KASQDVYNAVA (SEQ ID NO: 31), SASSRYT (SEQ ID NO: 33), and QQHFRTPFT (SEQ ID NO: 35).

VH region and VL regions on a single polypeptide. In some embodiments, the polypeptide comprises from N-terminal to C-terminal the full length VH regions and the full length VL region. In some embodiments, the polypeptide comprises from N-terminal to C-terminal the full length VL region and the full length VH region. In some embodiments, the full length VH and VL comprises the sequence selected from Table 3. In some embodiments, the binding domain comprises SEQ ID NO: 43 and SEQ ID NO: 44. In some embodiments, the binding domain comprises SEQ ID NO: 45 and SEQ ID NO: 46. In some embodiments, the binding domain comprises SEQ ID NO: 47 and SEQ ID NO: 48. In some embodiments, the binding domain comprises SEQ ID NO: 45 and SEQ ID NO: 49. In some embodiments, the binding domain comprises SEQ ID NO: 50 and SEQ ID NO: 49.

TABLE 3

VH and VL Domains for HER2 CAR Constructs

| Construct and Orientation | VH Full Length | VL Full Length |
|---|---|---|
| CT-292 (VL-VH) | EVQLVESGGGLVQPGGSLRLSCA ASGFNIKDTYIHWVRQAPGKGLE WVARIYPTNGYTRYADSVKGRF TISADTSKNTAYLQMNSLRAEDT AVYYCSRWGGDGFYAMDVWG QGTLVTVSSAAA (SEQ ID NO: 43) | DIQMTQSPSSLSASVGDRVTITCR ASQDVNTAVAWYQQKPGKAPK LLIYSASFLYSGVPSRFSGSRSGT DFTLTISSLQPEDFATYYCQQHY TTPPTFGQGTKVEIKRT (SEQ ID NO: 44) |
| CT-297 (VH-VL) | QVQLQQSGPELKKPGETVKISCK ASGYPFTNYGMNWVKQAPGQG LKWMGWINTSTGESTFADDFKG RFDFSLETSANTAYLQINNLKSE DSATYFCARWEVYHGYVPYWG QGTTVTVSS (SEQ ID NO: 45) | DIQLTQSHKFLSTSVGDRVSITCK ASQDVYNAVAWYQQKPGQSPK LLIYSASSRYTGVPSRFTGSGSGP DFTFTISSVQAEDLAVYFCQQHF RTPFTFGSGTKLEIK (SEQ ID NO: 49) |
| CT-298 (VL-VH) | EVQLVESGGGLVQPGGSLRLSCA ASGFNIKDTYIHWVRQAPGKGLE WVARIYPTNGYTRYADSVKGRF TISADTSKNTAYLQMNSLRAEDT AVYYCSRWGGDGFYAMDYWG QGTLVTVSS (SEQ ID NO: 47) | DIQMTQSPSSLSASVGDRVTITCR ASQDVNTAVAWYQQKPGKAPK LLIYSASFLYSGVPSRFSGSRSGT DFTLTISSLQPEDFATYYCQQHY TTPPTFGQGTKVEIK (SEQ ID NO: 48) |
| CT-299 (VL-VH) | EVQLVESGGGLVQPGGSLRLSCA ASGFNIKDTYIHWVRQAPGKGLE WVARIYPTNGYTRYADSVKGRF TISADTSKNTAYLQMNSLRAEDT AVYYCSRWGGDGFYAMDYWG QGTLVTVSS (SEQ ID NO: 47) | DIQMTQSPSSLSASVGDRVTITCR ASQDVNTAVAWYQQKPGKAPK LLIYSASFLYSGVPSRFSGSRSGT DFTLTISSLQPEDFATYYCQQHY TTPPTFGQGTKVEIK (SEQ ID NO: 48) |
| CT-1094 (VH-VL) | QVQLQQSGPELKKPGETVKISCK ASGYPFTNYGMNWVKQAPGQG LKWMGWINTSTGESTFADDFKG RFDFSLETSANTAYLQINNLKSE DSATYFCARWEVYHGYVPYWG QGTTVTVSS (SEQ ID NO: 45) | DIQLTQSHKFLSTSVGDRVSITCK ASQDVYNAVAWYQQKPGQSPK LLIYSASSRYTGVPSRFTGSGSGP DFTFTISSVQAEDLAVYFCQQHF RTPFTFGSGTKLEIK (SEQ ID NO: 49) |
| CT-1095 VH-VL | QVQLQQSGPELKKPGETVKISCK ASGYPFTNYGMNWVKQAPGQG LKWMGWINTSTGESTFADDFKG RFDFSLETSANTAYLQINNLKSE DMATYFCARWEVYHGYVPYWG QGTTVTVSS (SEQ ID NO: 50) | DIQLTQSHKFLSTSVGDRVSITCK ASQDVYNAVAWYQQKPGQSPK LLIYSASSRYTGVPSRFTGSGSGP DFTFTISSVQAEDLAVYFCQQHF RTPFTFGSGTKLEIK (SEQ ID NO: 49) |

In some embodiments, the binding domain is a HER2 scFv domain. In some embodiments, the HER2 scFv domain is selected from a sequence listed in Table 4. In some embodiments, the HER2 scFv domain comprises a polypeptide comprising SEQ ID NO: 51. In some embodiments, the HER2 scFv domain is encoded by a polynucleotide sequence comprising SEQ ID NO: 52. In some embodiments, the HER2 scFv domain comprises a polypeptide comprising SEQ ID NO: 53. In some embodiments, the HER2 scFv domain is encoded by a polynucleotide sequence comprising SEQ ID NO: 54. In some embodiments, the HER2 scFv domain comprises a polypeptide comprising SEQ ID NO: 55. In some embodiments, the HER2 scFv domain is encoded by a polynucleotide sequence comprising SEQ ID NO: 56. In some embodiments, the HER2 scFv domain comprises a polypeptide comprising SEQ ID NO: 57. In some embodiments, the HER2 scFv domain is encoded by a polynucleotide sequence comprising SEQ ID NO: 58. In some embodiments, the HER2 scFv domain comprises a polypeptide comprising SEQ ID NO: 59. In some embodiments, the HER2 scFv domain is encoded by a polynucleotide sequence comprising SEQ ID NO: 60. In some embodiments, the HER2 scFv domain comprises a polypeptide comprising SEQ ID NO: 61. In some embodiments, the HER2 scFv domain is encoded by a polynucleotide sequence comprising SEQ ID NO: 62. In some embodiments, the HER2 scFv domain is encoded by a polynucleotide sequence comprising SEQ ID NO: 21803.

TABLE 4

HER2 ScFv Domains for HER2 CAR Constructs

| HER2 CAR | Protein Sequence | DNA Sequence |
|---|---|---|
| CT292 (VL-VH) | MDFQVQIFSFLLI SASVIMSRGDIQ MTQSPSSLSASV | ATGGATTTTCAGGTGCAGATTTTCAGCTTCCTGCT AATCAGTGCCTCAGTCATAATGTCCAGAGGAGAT ATCCAGATGACCCAGTCCCCGAGCTCCCTGTCCGC |

TABLE 4-continued

HER2 ScFv Domains for HER2 CAR Constructs

| HER2 CAR | Protein Sequence | DNA Sequence |
|---|---|---|
| | GDRVTITC<u>RASQ</u> <u>DVNTAVA</u>WYQQ KPGKAPKLLIY<u>S</u> <u>ASFLYS</u>GVPSRFS GSRSGTDFTLTIS SLQPEDFATYYC <u>QQHYTTPPT</u>FGQ GTKVEIKRTGST SGSGKPGSGEGS EVQLVESGGGLV QPGGSLRLSCAA SGFNIK<u>DTYIH</u>W VRQAPGKGLEW VA<u>RIYPTNGYTR</u> <u>YADSVKG</u>RFTIS ADTSKNTAYLQ MNSLRAEDTAV YYCSR<u>WGGDGF</u> <u>YAMDV</u>WGQGTL VTVSSAAA (SEQ ID NO: 51) | CTCTGTGGGCGATAGGGTCACCATCACCTGCCGTG CCAGTCAGGATGTGAATACTGCTGTAGCCTGGTAT CAACAGAAACCAGGAAAAGCTCCGAAACTACTGA TTTACTCGGCATCCTTCCTTTATTCTGGAGTCCCTT CTCGCTTCTCTGGATCTAGATCTGGGACGGATTTC ACTCTGACCATCAGCAGTCTGCAGCCGGAAGACT TCGCAACTTATTACTGTCAGCAACATTATACTACT CCTCCCACGTTCGGACAGGGTACCAAGGTGGAGA TCAAACGCACTGGGTCTACATCTGGATCTGGGAA GCCGGGTTCTGGTGAGGGTTCTGAGGTTCAGCTG GTGGAGTCTGGCGGTGGCCTGGTGCAGCCAGGGG GCTCACTCCGTTGTCCTGTGCAGCTTCTGGCTTC AACATTAAAGACACCTATATACACTGGGTGCGTC AGGCCCCGGGTAAGGGCCTGGAATGGGTTGCAAG GATTTATCCTACGAATGGTTATACTAGATATGCCG ATAGCGTCAAGGGCCGTTTCACTATAAGCGCAGA CACATCCAAAAACACAGCCTACCTGCAGATGAAC AGCCTGCGTGCTGAGGACACTGCCGTCTATTATTG TTCTAGATGGGGAGGGGACGGCTTCTATGCTATG GACGTGTGGGGTCAAGGAACCCTGGTCACCGTCT CCTCGGCGGCCGCA (SEQ ID NO: 52) |
| CT297 (VH-VL) | MDMRVPAQLLG LLLLWLRGARC QVQLQQSGPELK KPGETVKISCKA SGYPFT<u>NYGMN</u> WVKQAPGQGLK WMGW<u>INTSTGE</u> <u>STFADDFKGR</u>FD FSLETSANTAYL QINNLKSEDSAT YFCAR<u>WEVYHG</u> <u>YVPY</u>WGQGTTV TVSSGGGGSGGG GSGGGGSDIQLT QSHKFLSTSVGD RVSITC<u>KASQDV</u> <u>YNAVA</u>WYQQKP GQSPKLLIY<u>SASS</u> <u>RYT</u>GVPSRFTGS GSGPDFTFTISSV QAEDLAVYFCQ <u>QHFRTPFT</u>FGSG TKLEIK (SEQ ID NO: 53) | ATGGACATGAGGGTCCCCGCTCAGCTCCTGGGGC TCCTGCTACTCTGGCTCCGAGGTGCCAGATGTCAG GTACAACTGCAGCAGTCAGGACCTGAACTGAAGA AGCCTGGAGAGACAGTCAAGATCTCCTGCAAGGC CTCTGGGTATCCTTTCACAAACTATGGAATGAACT GGGTGAAGCAGGCTCCAGGACAGGGTTTAAAGTG GATGGGCTGGATTAACACCTCCACTGGAGAGTCA ACATTTGCTGATGACTTCAAGGGACGGTTTGACTT CTCTTTGGAAACCTCTGCCAACACTGCCTATTTGC AGATCAACAACTCAAAAGTGAAGACTCGGCTAC ATATTTCTGTGCAAGATGGGAGGTTTACCACGGCT ACGTTCCTTACTGGGGCCAAGGGACCACGGTCAC CGTTTCCTCTGGCGGTGGCGGTTCTGGTGGCGGTG GCTCCGGCGGTGGCGGTTCTGACATCCAGCTGAC CCAGTCTCACAAATTCCTGTCCACTTCAGTAGGAG ACAGGGTCAGCATCACCTGCAAGGCCAGTCAGGA TGTGTATAATGCTGTTGCCTGGTATCAACAGAAAC CAGGACAATCTCCTAAACTTCTGATTTACTCGGCA TCCTCCCGGTACACTGGAGTCCCTTCTCGCTTCAC TGGCAGTGGCTCTGGGCCGGATTTCACTTTCACCA TCAGCAGTGTGCAGGCTGAAGACCTGGCAGTTTA TTTCTGTCAGCAACATTTTCGTACTCCATTCACGTT CGGCTCGGGGACAAAATTGGAGATCAAA (SEQ ID NO: 54) |
| CT298 (VL-VH) | MLLLVTSLLLCE LPHPAFLLIPDIQ MTQSPSSLSASV GDRVTITC<u>RASQ</u> <u>DVNTAVA</u>WYQQ KPGKAPKLLIY<u>S</u> <u>ASFLYS</u>GVPSRFS GSRSGTDFTLTIS SLQPEDFATYYC <u>QQHYTTPPT</u>FGQ GTKVEIKGSTSG GGSGGGSGGGG SSEVQLVESGGG LVQPGGSLRLSC AAS<u>GFNIKDTYI</u> <u>H</u>WVRQAPGKGL EWVA<u>RIYPTNGY</u> <u>TRYADSVKG</u>RFT ISADTSKNTAYL QMNSLRAEDTA VYYC<u>SRWGGDG</u> <u>FYAMDY</u>WGQGT LVTVSS (SEQ ID NO: 55) | ATGCTGCTACTGGTCACCAGTCTACTGCTGTGCGA ACTGCCACATCCGGCCTTCCTGCTAATACCGGATA TCCAGATGACCCAGTCCCCGAGCTCCCTGTCCGCC TCTGTGGGCGATAGGGTCACCATCACCTGCCGTGC CAGTCAGGATGTGAATACTGCTGTAGCCTGGTATC AACAGAAACCAGGAAAAGCTCCGAAACTACTGAT TTACTCGGCATCCTTCCTTTATTCTGGAGTCCCTTC TCGCTTCTCTGGATCTAGATCTGGGACGGATTTCA CTCTGACCATCAGCAGTCTGCAGCCGGAAGACTT CGCAACTTATTACTGTCAGCAACATTATACTACTC CTCCCACGTTCGGACAGGGTACCAAGGTGGAGAT CAAAGGGTCTACATCTGGCTGGCTCTGGTGGC GGTTCCGGCGGTGGCGGTTCTTCCGAGGTTCAGCT GGTGGAGTCTGGCGGTGGCCTGGTGCAGCCAGGG GGCTCACTCCGTTTGTCCTGTGCAGCTTCTGGCTT CAACATTAAAGACACCTATATACACTGGGTGCGT CAGGCCCCGGGTAAGGGCCTGGAATGGGTTGCAA GGATTTATCCTACGAATGGTTATACTAGATATGCC GATAGCGTCAAGGGCCGTTTCACTATAAGCGCAG ACACATCCAAAAACACAGCCTACCTGCAGATGAA CAGCCTGCGTGCTGAGGACACTGCCGTCTATTATT GTTCTAGATGGGGAGGGGACGGCTTCTATGCTAT GGACTATTGGGGTCAAGGAACCCTGGTCACCGTC TCCTCG (SEQ ID NO: 56) |
| CT299 (VL-VH) | MLLLVTSLLLCE LPHPAFLLIPDIQ MTQSPSSLSASV | ATGCTGCTACTGGTCACCAGTCTACTGCTGTGCGA ACTGCCACATCCGGCCTTCCTGCTAATACCGGATA TCCAGATGACCCAGTCCCCGAGCTCCCTGTCCGCC |

TABLE 4-continued

HER2 ScFv Domains for HER2 CAR Constructs

| HER2 CAR | Protein Sequence | DNA Sequence |
|---|---|---|
| | GDRVTITCRASQ DVNTAVAWYQQ KPGKAPKLLIYS ASFLYSGVPSRFS GSRSGTDFTLTIS SLQPEDFATYYC QQHYTTPPTFGQ GTKVEIKGSTSG GGSGGGSGGGG SSEVQLVESGGG LVQPGGSLRLSC AASGFNIKDTYI HWVRQAPGKGL EWVARIYPTNGY TRYADSVKGRFT ISADTSKNTAYL QMNSLRAEDTA VYYCSRWGGDG FYAMDYWGQGT LVTVSS (SEQ ID NO: 57) | TCTGTGGGCGATAGGGTCACCATCACCTGCCGTGC CAGTCAGGATGTGAATACTGCTGTAGCCTGGTATC AACAGAAACCAGGAAAAGCTCCGAAACTACTGAT TTACTCGGCATCCTTCCTTTATTCTGGAGTCCCTTC TCGCTTCTCTGGATCTAGATCTGGGACGGATTTCA CTCTGACCATCAGCAGTCTGCAGCCGGAAGACTT CGCAACTTATTACTGTCAGCAACATTATACTACTC CTCCCACGTTCGGACAGGGTACCAAGGTGGAGAT CAAAGGGTCTACATCTGGCGGTGGCTCTGGTGGC GGTTCCGGCGGTGGCGGTTCTTCCGAGGTTCAGCT GGTGGAGTCTGGCGGTGGCCTGGTGCAGCCAGGG GGCTCACTCCGTTTGTCCTGTGCAGCTTCTGGCTT CAACATTAAAGACACCTATATACACTGGGTGCGT CAGGCCCCGGGTAAGGGCCTGGAATGGGTTGCAA GGATTTATCCTACGAATGGTTATACTAGATATGCC GATAGCGTCAAGGGCCGTTTCACTATAAGCGCAG ACACATCCAAAAACACAGCCTACCTGCAGATGAA CAGCCTGCGTGCTGAGGACACTGCCGTCTATTATT GTTCTAGATGGGGAGGGGACGGCTTCTATGCTAT GGACTATTGGGGTCAAGGAACCCTGGTCACCGTC TCCTCG (SEQ ID NO: 58) |
| CT1094 (VH-VL) | MDMRVPAQLLG LLLLWLRGARC QVQLQQSGPELK KPGETVKISCKA SGYPFTNYGMN WVKQAPGQGLK WMGWINTSTGE STFADDFKGRFD FSLETSANTAYL QINNLKSEDSAT YFCARWEVYHG YVPYWGQGTTV TVSSGGGGSGGG GSGGGGSDIQLT QSHKFLSTSVGD RVSITCKASQDV YNAVAWYQQKP GQSPKLLIYSASS RYTGVPSRFTGS GSGPDFTFTISSV QAEDLAVYFCQ QHFRTPFTFGSG TKLEIK (SEQ ID NO: 59) | ATGGACATGAGGGTCCCCGCTCAGCTCCTGGGGC TCCTGCTACTCTGGCTCCGAGGTGCCAGATGTCAG GTACAACTGCAGCAGTCAGGACCTGAACTGAAGA AGCCTGGAGAGACAGTCAAGATCTCCTGCAAGGC CTCTGGGTATCCTTTCACAAACTATGGAATGAACT GGGTGAAGCAGGCTCCAGGACAGGGTTTAAAGTG GATGGGCTGGATTAACACCTCCACTGGAGAGTCA ACATTTGCTGATGACTTCAAGGGACGGTTTGACTT CTCTTTGGAAACCTCTGCCAACACTGCCTATTTGC AGATCAACAACCTCAAAAGTGAAGACTCGGCTAC ATATTTCTGTGCAAGATGGGAGGTTTACCACGGCT ACGTTCCTTACTGGGGCCAAGGGACCACGGTCAC CGTTTCCTCTGGCGGTGGCGGTTCTGGTGGCGGTG GCTCCGGCGGTGGCGGTTCTGACATCCAGCTGAC CCAGTCTCACAAATTCCTGTCCACTTCAGTAGGAG ACAGGGTCAGCATCACCTGCAAGGCCAGTCAGGA TGTGTATAATGCTGTTGCCTGGTATCAACAGAAAC CAGGACAATCTCCTAAACTTCTGATTTACTCGGCA TCCTCCCGGTACACTGGAGTCCCTTCTCGCTTCAC TGGCAGTGGCTCTGGGCCGGATTTCACTTTCACCA TCAGCAGTGTGCAGGCTGAAGACCTGGCAGTTTA TTTCTGTCAGCAACATTTTCGTACTCCATTCACGTT CGGCTCGGGGACAAAATTGGAGATCAAA (SEQ ID NO: 60) |
| CT1095 (VH-VL) | MDMRVPAQLLG LLLLWLRGARC QVQLQQSGPELK KPGETVKISCKA SGYPFTNYGMN WVKQAPGQGLK WMGWINTSTGE STFADDFKGRFD FSLETSANTAYL QINNLKSEDMAT YFCARWEVYHG YVPYWGQGTTV TVSSGGGGSGGG GSGGGGSDIQLT QSHKFLSTSVGD RVSITCKASQDV YNAVAWYQQKP GQSPKLLIYSASS RYTGVPSRFTGS GSGPDFTFTISSV QAEDLAVYFCQ QHFRTPFTFGSG TKLEIK (SEQ ID NO: 61) | ATGGACATGAGGGTCCCCGCTCAGCTCCTGGGGC TCCTGCTACTCTGGCTCCGAGGTGCCAGATGTCAG GTACAACTGCAGCAGTCAGGACCTGAACTGAAGA AGCCTGGAGAGACAGTCAAGATCTCCTGCAAGGC CTCTGGGTATCCTTTCACAAACTATGGAATGAACT GGGTGAAGCAGGCTCCAGGACAGGGTTTAAAGTG GATGGGCTGGATTAACACCTCCACTGGAGAGTCA ACATTTGCTGATGACTTCAAGGGACGGTTTGACTT CTCTTTGGAAACCTCTGCCAACACTGCCTATTTGC AGATCAACAACCTCAAAAGTGAAGACATGGCTAC ATATTTCTGTGCAAGATGGGAGGTTTACCACGGCT ACGTTCCTTACTGGGGCCAAGGGACCACGGTCAC CGTTTCCTCTGGCGGTGGCGGTTCTGGTGGCGGTG GCTCCGGCGGTGGCGGTTCTGACATCCAGCTGAC CCAGTCTCACAAATTCCTGTCCACTTCAGTAGGAG ACAGGGTCAGCATCACCTGCAAGGCCAGTCAGGA TGTGTATAATGCTGTTGCCTGGTATCAACAGAAAC CAGGACAATCTCCTAAACTTCTGATTTACTCGGCA TCCTCCCGGTACACTGGAGTCCCTTCTCGCTTCAC TGGCAGTGGCTCTGGGCCGGATTTCACTTTCACCA TCAGCAGTGTGCAGGCTGAAGACCTGGCAGTTTA TTTCTGTCAGCAACATTTTCGTACTCCATTCACGTT CGGCTCGGGGACAAAATTGGAGATCAAA (SEQ ID NO: 62) |

In some embodiments, the HER2 scFv domain comprises a sequence of any one of SEQ ID NOS: 51, 53, 55, 57, 59 or 61, or a sequence having at least 90%, at least 95%, at least 97%, at least 99% or is identical thereto.

Inhibitory Receptors

The disclosure provides a second ligand, an inhibitor, and a second inhibitory receptor comprising a second ligand binding domain that binds to the inhibitor ligand. In some embodiments, the second, inhibitory ligand is an antigen, and the second inhibitory receptor comprises an antigen binding domain that specifically recognizes the second, inhibitory antigen.

The disclosure provides a second inhibitory receptor comprising an extracellular region, the extracellular region comprising a second ligand binding domain capable of specifically binding to a second ligand that inhibits activation of effector cells expressing the first and second receptors, wherein the effector cells are activated by binding of the first ligand to the first activator receptor.

As used herein an "inhibitor" or "inhibitor ligand" refers to a second ligand that binds to a second, ligand binding domain (inhibitor LBD) of an engineered receptor of the disclosure, but inhibits activation of an immune cell expressing the engineered receptor. The inhibitor is not expressed by the target cells. The inhibitor ligand is also expressed in a plurality of normal, non-target cells, including normal, non-target cells that express the activator ligand, thereby protecting these cells from the cytotoxic effects of the adoptive cell therapy. Without wishing to be bound by theory, inhibitor ligands can block activation of the effector cells through a variety of mechanisms. For example, binding of the inhibitor ligand to the inhibitor LBD can block transmission of a signal that occurs upon binding of the activator ligand to the activator LBD that would, in the absence of the inhibitor, lead to activation of the immune cell expressing the engineered receptors described herein.

Alternatively, or in addition, binding of the inhibitor ligand to the second engineered receptor can cause loss of cell surface expression the first, activator receptor from the surface of the immune cells comprising the two receptor system described herein. Without wishing to be bound by theory, it is thought that immune cell engagement of activator and inhibitor ligands on normal cells causes the inhibitory receptor to cause removal of nearby activator receptor molecules from the immune cell surface. This process locally desensitizes the immune cell, reversibly raising its activation threshold. Immune cells that engage only the activator ligand on a target cell cause local activation signals which are unimpeded by signals from the second, inhibitory receptor. This local activation increases until release of cytotoxic granules leads to target cell selective cell death. However, modulation of surface receptor expression levels may not be the only mechanism by which inhibitory receptors inhibit activation of immune cells by the first activator receptor. Without wishing to be bound by theory, other mechanisms may come into play, including, but not limited to, cross-talk between activator and inhibitory receptor signaling pathways.

In some embodiments, the second ligand is not expressed by the target cells, and is expressed by the non-target cells. In some embodiments, the target cells are cancer cells and the non-target cells are non-cancerous cells.

In some embodiments, the second, inhibitor ligand is an antigen and the second ligand binding domain comprises an scFv domain.

In some embodiments, the second, inhibitor ligand binding domain comprises a Vβ-only ligand binding domain.

In some embodiments, the second, inhibitor ligand binding domain comprises an antigen binding domain isolated or derived from a T cell receptor (TCR). For example, the second, inhibitor ligand binding domain comprises TCR α and β chain variable domains.

In some embodiments, the second, inhibitor ligand binding domain is an antigen binding domain. Suitable antigen-binding domains include, but are not limited to antigen-binding domains from antibodies, antibody fragments, scFv, antigen-binding domains derived from T cell receptors, and the like.

Inhibitor Targets

The disclosure provides an inhibitory receptor. In some embodiments, the inhibitory receptor comprises an extracellular ligand binding domain specific to a non-target antigen that is not expressed by the cancer cell due to a loss of heterozygosity in the cancer cell. In some embodiments, the non-target antigen is an HLA class I allele or a minor histocompatibility antigen (MiHA). In some embodiments, the HLA Class I allele comprises HLA-A, HLA-B, HLA-C, or HLA-E. In some embodiments, the HLA class I allele is HLA-A*02. In some embodiments, the HLA-A*02 non-target antigen is expressed by healthy cells of a subject.

In some embodiments, the inhibitory receptor comprises an extracellular antigen binding domain specific to a non-target antigen that is not expressed by the cancer cell due to a loss of heterozygosity in the cancer cell.

Alternatively, or in addition, expression of activator and inhibitor targets may be correlated, i.e. the two are expressed at similar levels on non-target cells.

In some embodiments, the second, inhibitor ligand is a peptide ligand. In some embodiments, the second, inhibitor ligand is a peptide antigen complexed with a major histocompatibility (MHC) class I complex (peptide MHC, or pMHC). Inhibitor ligands comprising peptide antigens complexed with pMHC comprising any of HLA-A, HLA-B, HLA-C, or HLA-E are envisaged as within the scope of the disclosure.

In some embodiment, the inhibitor ligand is encoded by a gene that is absent or polymorphic in many tumors.

Methods of distinguishing the differential expression of inhibitor ligands between target and non-target cells will be readily apparent to the person or ordinary skill in the art. For example, the presence or absence of inhibitor ligands in non-target and target cells can be assayed by immunohistochemistry with an antibody that binds to the inhibitor ligand, followed by microscopy or FACS, RNA expression profiling of target cells and non-target cells, or DNA sequencing of non-target and target cells to determine if the genomic locus of the inhibitor ligand comprises mutations in either the target or non-target cells.

Alleles Lost Due to Loss of Heterozygosity (LOH)

Homozygous deletions in primary tumors are rare and small, and therefore unlikely to yield target B candidates. For example, in an analysis of 2218 primary tumors across 21 human cancer types, the top four candidates were cyclin dependent kinase inhibitor 2A (CDKN2A), RB transcriptional corepressor 1 (RB1), phosphatase and tensin homolog (PTEN) and N3PB2. However, CDKN2A (P16) was deleted in only 5% homozygous deletion across all cancers. Homozygous HLA-A deletions were found in less than 0.2% of cancers (Cheng et al., Nature Comm. 8:1221 (2017)). In contrast, deletion of a single copy of a gene in cancer cells due to loss of hemizygosity occurs far more frequently.

In some embodiments, the second, inhibitor ligand comprises an allele of a gene that is lost in target cells due to loss of heterozygosity. In some embodiments, the target cells comprises cancer cells. Cancer cells undergo frequent genome rearrangements, including duplication and deletions. These deletions can lead to the deletion of one copy of one or more genes in the cancer cells.

As used herein, "loss of heterozygosity (LOH)" refers to a genetic change that occurs at high frequency in cancers, whereby one of the two alleles is deleted, leaving a single mono-allelic (hemizygous) locus.

HLA Class I Alleles

In some embodiments, the second, inhibitor ligand comprises an HLA class I allele. The major histocompatibility complex (MHC) class I is a protein complex that displays antigens to cells of the immune system, triggering immune response. The Human Leukocyte Antigens (HLAs) corresponding to MHC class I are HLA-A, HLA-B, HLA-C, and HLA-E.

In some embodiments, the second, inhibitor ligand comprises an HLA class I allele. In some embodiments, the second, inhibitor ligand comprises an allele of HLA class I that is lost in a target cell through LOH. HLA-A is a group of human leukocyte antigens (HLA) of the major histocompatibility complex (MHC) that are encoded by the HLA-A locus. HLA-A is one of three major types of human MHC class I cell surface receptors. The receptor is a heterodimer comprising a heavy a chain and smaller β chain. The α chain is encoded by a variant of HLA-A, while the β chain (β2-microglobulin) is invariant. There are several thousand HLA-A variants, all of which fall within the scope of the instant disclosure.

In some embodiments, the second, inhibitor ligand comprises an HLA-B allele. The HLA-B gene has many possible variations (alleles). Hundreds of versions (alleles) of the HLA-B gene are known, each of which is given a particular number (such as HLA-B27).

In some embodiments, the second, inhibitor ligand comprises an HLA-C allele. HLA-C belongs to the HLA class I heavy chain paralogues. This class I molecule is a heterodimer consisting of a heavy chain and a light chain (beta-2 microglobulin). Over one hundred HLA-C alleles have been described.

In some embodiments, the HLA class I allele has broad or ubiquitous RNA expression.

In some embodiments, the HLA class I allele has a known, or generally high minor allele frequency.

In some embodiments, the HLA class I allele does not require a peptide-MHC antigen, for example when the HLA class I allele is recognized by a pan-HLA ligand binding domain.

In some embodiments, the second inhibitor ligand comprises an HLA-A allele. In some embodiments the HLA-A allele comprises HLA-A*02. Various single variable domains known in the art or disclosed herein that bind to and recognize HLA-A*02 are suitable for use in embodiments. Such scFvs include, for example and without limitation, the following mouse and humanized scFv antibodies that bind HLA-A*02 in a peptide-independent way shown in Table 5 and Table 6 below (complementarity determining regions underlined):

TABLE 5

HLA-A*02 ScFv Sequences and Inhibitory receptor Constructs

| Construct | Protein Sequence | DNA Sequence |
|---|---|---|
| C-1765 (PA2.1, VL-VH) | MDMRVPAQLLGL LLLWLRGARCDV LMTQTPLSLPVSL GDQASISC<u>RSSQSI VHSNGNTYLE</u>WY LQKPGQSPKLLIY <u>KVSNRFS</u>GVPDRF SGSGSGTDFTLKI SRVEAEDLGVYY C<u>FQGSHVPRT</u>SGG GTKLEIKGGGGSG GGGSGGGGSGGQ VQLQQSGPELVK PGASVRISCK<u>ASG YTFTSYHIH</u>WVK QRPGQGLEWIG<u>W IYPGNVNTEYNEK FKGK</u>ATLTADKS SSTAYMHLSSLTS EDSAVYFCA<u>REEI TYAMDY</u>WGQGT SVTVSS (SEQ ID NO: 207) | ATGGACATGAGGGTCCCCGCTCAGCTCCTGGGGCTC CTGCTACTCTGGCTCCGAGGTGCCAGATGTGATGTT TTGATGACCCAAACTCCACTCTCCCTGCCTGTCAGT CTTGGAGATCAAGCCTCCATCTCTTGCAGATCTAGT CAGAGCATTGTACATAGTAATGGAAACACCTATTTA GAATGGTACCTGCAGAAACCAGGCCAGTCTCCAAA GCTCCTGATCTACAAAGTTTCCAACCGATTTTCTGG GGTCCCAGACAGGTTCAGTGGCAGTGGATCAGGGA CAGATTTCACACTCAAGATCAGTAGAGTGGAGGCT GAGGATCTGGGAGTTTATTACTGCTTTCAAGGTTCA CATGTTCCTCGGACGTCCGGTGGAGGCACCAAGCTG GAAATCAAAGGCGGAGGTGGAAGCGGAGGGGGAG GATCTGGCGGCGGAGGAAGCGGAGGCCAGGTCCAG CTGCAGCAGTCTGGACCTGAGCTGGTGAAGCCTGG GGCTTCAGTGAGGATATCCTGCAAGGCTTCTGGCTA CACCTTCACAAGTTACCATATACATTGGGTGAAGCA GAGGCCTGGACAGGGACTTGAGTGGATTGGATGGA TTTATCCTGGAAATGTTAATACTGAGTACAATGAGA AGTTCAAGGGCAAGGCCACACTGACTGCAGACAAA TCGTCCAGCACAGCCTACATGCACCTCAGCAGCCTG ACCTCTGAGGACTCTGCGGTCTATTTCTGTGCCAGA GAGGAGATTACCTATGCTATGGACTACTGGGGTCA AGGAACCTCAGTCACCGTGTCCTCA (SEQ ID NO: 208) |
| C-2162 (huPA2.1, VH-VL) | MDMRVPAQLLGL LLLWLRGARCQV QLVQSGAEVKKP GSSVKVSCK<u>ASG YTFTSYHIH</u>WVR QAPGQGLEWIG<u>W IYPGNVNTEYNEK FKGK</u>ATITADEST NTAYMELSSLRSE DTAVYYCA<u>REEIT YAMDY</u>WGQGTL VTVSSGGGGSGG GGSGGGGSGGDI QMTQSPSTLSASV GDRVTITC<u>RSSQSI VHSNGNTYLE</u>WY | ATGGACATGAGGGTCCCCGCTCAGCTCCTGGGGCTC CTGCTACTCTGGCTCCGAGGTGCCAGATGTCAGGTG CAGCTGGTGCAGTCTGGGGCTGAGGTGAAGAAGCC TGGGTCCTCAGTGAAGGTTTCCTGCAAGGCTTCTGG ATACACCTTCACTAGCTATCATATACATTGGGTGCG CCAGGCCCCCGGACAAGGGCTTGAGTGGATCGGAT GGATCTACCCTGGCAATGTTAACACAGAATATAATG AGAAGTTCAAGGGCAAAGCCACCATTACCGCGGAC GAATCCACGAACACAGCCTACATGGAGCTGAGCAG CCTGAGATCTGAAGACACGGCTGTGTATTACTGTGC GAGGGAGGAAATTACCTACGCTATGGACTACTGGG GCCAGGGAACCCTGGTCACCGTGTCCTCAGGCGGA GGTGGAAGCGGAGGGGGAGGATCTGGCGGCGGAG GAAGCGGAGGCGACATTCAAATGACCCAGAGCCCA TCCACCCTGAGCGCATCTGTAGGTGACCGGGTCACC ATCACTTGTAGATCCAGTCAGAGTATTGTACACAGT |

TABLE 5-continued

HLA-A*02 ScFv Sequences and Inhibitory receptor Constructs

| Construct | Protein Sequence | DNA Sequence |
|---|---|---|
|  | QQKPGKAPKLLIY<br>KVSNRFSGVPARF<br>SGSGSGTEFTLTIS<br>SLQPDDFATYYCF<br>QGSHVPRTFGQG<br>TKVEVK (SEQ ID<br>NO: 209) | AATGGGAACACCTATTTGGAATGGTATCAGCAGAA<br>ACCAGGTAAAGCCCCAAAATTGCTCATCTACAAAG<br>TCTCTAACAGATTTAGTGGTGTACCAGCCAGGTTCA<br>GCGGTTCCGGAAGTGGTACTGAATTCACCCTCACGA<br>TCTCCTCTCTCCAGCCAGATGATTTCGCCACTTATTA<br>CTGTTTTCAAGGTTCACATGTGCCGCGCACATTCGG<br>TCAGGGTACTAAAGTAGAAGTCAAA (SEQ ID NO:<br>210) |
| C-2163<br>(huPA2.1,<br>VH-VL) | MDMRVPAQLLGL<br>LLLWLRGARCQV<br>QLVQSGAEVKKP<br>GSSVKVSCKASG<br>YTFTSYHMHWVR<br>QAPGQGLEWIGYI<br>YPGNVNTEYNEK<br>FKGKATLTADKS<br>TNTAYMELSSLRS<br>EDTAVYFCAREEI<br>TYAMDYWGQGT<br>LVTVSSGGGGSG<br>GGGSGGGGSGGD<br>VQMTQSPSTLSAS<br>VGDRVTITCSSSQ<br>SIVHSNGNTYME<br>WYQQKPGKAPKL<br>LIYKVSNRFSGVP<br>DRFSGSGSGTEFT<br>LTISSLQPDDFAT<br>YYCHQGSHVPRT<br>FGQGTKVEVK<br>(SEQ ID NO: 211) | ATGGACATGAGGGTCCCCGCTCAGCTCCTGGGGCTC<br>CTGCTACTCTGGCTCCGAGGTGCCAGATGTCAGGTG<br>CAGCTGGTGCAGTCTGGGGCTGAGGTGAAGAAGCC<br>TGGGTCCTCAGTGAAGGTTTCCTGCAAGGCTTCTGG<br>ATACACCTTCACTAGCTATCATATGCATTGGGTGCG<br>CCAGGCCCCCGGACAAGGGCTTGAGTGGATCGGAT<br>ACATCTACCCTGGCAATGTTAACACAGAATATAATG<br>AGAAGTTCAAGGGCAAAGCCACCCTTACCGCGGAC<br>AAATCCACGAACACAGCCTACATGGAGCTGAGCAG<br>CCTGAGATCTGAAGACACGGCTGTGTATTTCTGTGC<br>GAGGGAGGAAATTACCTACGCTATGGACTACTGGG<br>GCCAGGGAACCCTGGTCACCGTGTCCTCAGGCGGA<br>GGTGGAAGCGGAGGGGGAGGATCTGGCGGCGGAG<br>GAAGCGGAGGCGACGTTCAAATGACCCAGAGCCCA<br>TCCACCCTGAGCGCATCTGTAGGTGACCGGGTCACC<br>ATCACTTGTAGCTCCAGTCAGAGTATTGTACACAGT<br>AATGGGAACACCTATATGGAATGGTATCAGCAGAA<br>ACCAGGTAAAGCCCCAAAATTGCTCATCTACAAAG<br>TCTCTAACAGATTTAGTGGTGTACCAGACAGGTTCA<br>GCGGTTCCGGAAGTGGTACTGAATTCACCCTCACGA<br>TCTCCTCTCTCCAGCCAGATGATTTCGCCACTTATTA<br>CTGTCATCAAGGTTCACATGTGCCGCGCACATTCGG<br>TCAGGGTACTAAAGTAGAAGTCAAA (SEQ ID NO:<br>212) |

In some embodiments, the second antigen binding domain comprises an scFv domain that binds to HLA-A*02 antigen. In some embodiments, the scFv domain comprises a sequence of SEQ ID NO: 207, 209 or 211, or sequences having at least 90%, at least 95%, at least 97%, at least 99% or is identical thereto. In some embodiments, the scFv domain comprises a sequence of SEQ ID NO: 207, 209 or 211.

TABLE 6

Additional HLA-A*02 scFv binding domains

HLA-A*02 antigen binding domains derived from PA2.1 mAb

C-001765 PA2.1 scFv (mouse):
DVLMTQTPLSLPVSLGDQASISCRSSQSIVHSNGNTYLEWYLQKPG
QSPKWYKVSNRFSGVPDRFSGSGSGTDFTLKISRVEAEDLGVYYC
FQGSHVPRTSGGGTKLEIKGGGGSGGGGSGGGGSGGQVQLQQSGP
ELVKPGASVRISCKASGYTFTSYHIHWVKQRPGQGLEWIGWIYPGN
VNTEYNEKFKGKATLTADKSSSTAYMHLSSLTSEDSAVYFCAREEI
TYAMDYWGQGTSVTVSS (SEQ ID NO: 63)

C-001765 PA2.1
scFv (mouse)
DNA Sequence:
SEQ ID NO: 75

C-002159 PA2.1.8 scFv (humanized):
QVQLVQSGAEVKKPGSSVKVSCKASGYTFTSYHIHWVRQAPGQGL
EWMGWIYPGNVNTEYNEKFKGKATITADKSTSTAYMELSSLRSED
TAVYYCAREEITYAMDYWGQGTTVTVSSGGGGSGGGGSGGGGSG
GEIVLTQSPGTLSLSPGERATLSCRSSQSIVHSNGNTYLEWYQQKPG
QAPRLLIYKVSNRFSGIPDRFSGSGSGTDFTLTISRLEPEDFAVYYCF
QGSHVPRTFGGGTKVEIK (SEQ ID NO: 64)

C-002159 PA2.1.8
scFv (humanized)
DNA Sequence:
SEQ ID NO: 76

C-002160 PA2.1.9 scFv (humanized):
QVQLVQSGAEVKKPGSSVKVSCKASGYTFTSYHIHWVRQAPGQGL
EWMGWIYPGNVNTEYNEKFKGKATITADKSTSTAYMELSSLRSED
TAVYYCAREEITYAMDYWGQGTTVTVSSGGGGSGGGGSGGGGSG
GDIVMTQTPLSLPVTPGEPASISCRSSQSIVHSNGNTYLEWYLQKPG
QSPQLLIYKVSNRFSGVPDRFSGSGSGTDFTLKISRVEAEDVGVYYC
FQGSHVPRTFGGGTKVEIK
(SEQ ID NO: 65)

C-002160 PA2.1.9
scFv (humanized)
DNA Sequence:
SEQ ID NO: 77

C-002161 PA2.1.10 scFv (humanized):
EVQLVESGGGLVKPGGSLRLSCAASGYTFTSYHIHWVRQAPGKGL
EWVGWIYPGNVNTEYNEKFKGRFTISRDDSKNTLYLQMNSLKTED C-002161
PA2.1.10 scFv
(humanized) DNA TABLE 6-continued Additional HLA-A*02 scFv binding domains TAVYYCAR<u>EEITYAMDY</u>WGQGTTVTVSSGGGGSGGGGSGGGGSG
GDIQMTQSPSSLSASVGDRVTITC<u>RSSQSIVHSNGNTYLE</u>WYQQKP
GKAPKLLIY<u>KVSNRFSGVPSR</u>FSGSGSGTDFTLTISSLQPEDFATYY
C<u>FQGSHVPRT</u>FGGGTKVEIK
(SEQ ID NO: 66)

Sequence: SEQ ID NO: 78

C-002162 PA2.1.14 scFv (humanized):
QVQLVQSGAEVKKPGSSVKVSCKA<u>SGYTFTSYHIH</u>WVRQAPGQGL
EWIG<u>WIYPGNVNTEYNEKFKG</u>KATITADESTNTAYMELSSLRSEDT
AVYYCAR<u>EEITYAMDY</u>WGQGTLVTVSSGGGGSGGGGSGGGGSGG
DIQMTQSPSTLSASVGDRVTITC<u>RSSQSIVHSNGNTYLE</u>WYQQKPG
KAPKLLIY<u>KVSNRFSGVPAR</u>FSGSGSGTEFTLTISSLQPDDFATYYC
<u>FQGSHVPRT</u>FGQGTKVEVK (SEQ ID NO: 67)

C-002162 PA2.1.14 scFv (humanized) DNA Sequence: SEQ ID NO: 79

C-002163 PA2.1.18 scFv (humanized):
QVQLVQSGAEVKKPGSSVKVSCKA<u>SGYTFTSYHMH</u>WVRQAPGQG
LEWIG<u>YIYPGNVNTEYNEKFKG</u>KATLTADKSTNTAYMELSSLRSE
DTAVYFCAR<u>EEITYAMDY</u>WGQGTLVTVSSGGGGSGGGGSGGGGS
GGDVQMTQSPSTLSASVGDRVTITC<u>SSSQSIVHSNGNTYME</u>WYQQ
KPGKAPKLLIY<u>KVSNRFSGVPDR</u>FSGSGSGTEFTLTISSLQPDDFAT
YYC<u>HQGSHVPRT</u>FGQGTKVEVK (SEQ ID NO: 68)

C-002163 PA2.1.18 scFv (humanized) DNA Sequence: SEQ ID NO: 80

HLA-A*02 antigen binding domains derived from BB7.2 mAb

C-002164 BB7.2 scFv (mouse):
QVQLQQSGPELVKPGASVKMSCKA<u>SGYTFTSYHIQ</u>WVKQRPGQG
LEWIG<u>WIYPGDGSTQYNEKFKG</u>KTTLTADKSSSTAYMLLSSLTSED
SAIYFCAR<u>EGTYYAMDY</u>WGQGTSVTVSSGGGGSGGGGSGGGGSG
GDVLMTQTPLSLPVSLGDQVSISC<u>RSSQSIVHSNGNTYLE</u>WYLQKP
GQSPKLLIY<u>KVSNRFSGVPDR</u>FSGSGSGTDFTLKISRVEAEDLGVYY
C<u>FQGSHVPRT</u>FGGGTKLEIK (SEQ ID NO: 69)

C-002164 BB7.2 scFv (mouse) DNA Sequence: SEQ ID NO: 81

C-002165 BB7.2.1 scFv (humanized):
QLQLQESGPGLVKPSETLSLTCTV<u>SGYTFTSYHIQ</u>WIRQPPGKGLE
WIG<u>WIYPGDGSTQYNEKFKG</u>RATISVDTSKNQFSLNLDSVSAADTA
IYYCA<u>REGTYYAMDY</u>WGKGSTVTVSSGGGGSGGGGSGGGGSGG
DIQMTQSPSSLSASVGDRVTITC<u>RSSQSIVHSNGNTYLE</u>WYQQKPG
KAPKLLIY<u>KVSNRFSGVPSR</u>FSGSGSGTDFTFTISSLQPEDIATYYC<u>F</u>
<u>QGSHVPRT</u>FGPGTKVDIK (SEQ ID NO: 70)

C-002165 BB7.2.1 scFv (humanized) DNA Sequence: SEQ ID NO: 82

C-002166 BB7.2.2 scFv (humanized):
EVQLVQSGAELKKPGSSVKVSCKA<u>SGYTFTSYHIQ</u>WVKQAPGQGL
EWIG<u>WIYPGDGSTQYNEKFKG</u>KATLTVDKSTNTAYMELSSLRSED
TAVYYCAR<u>EGTYYAMDY</u>WGQGTLVTVSSGGGGSGGGGSGGGGS
GGDIQMTQSPSTLSASVGDRVTITC<u>RSSQSIVHSNGNTYLE</u>WYQQK
PGKAPKLLIY<u>KVSNRFSGVPSR</u>FSGSGSGTDFTLTISSLQPDDFATY
YC<u>FQGSHVPRT</u>FGQGTKVEVK (SEQ ID NO: 71)

C-002166 BB7.2.2 scFv (humanized) DNA Sequence: SEQ ID NO: 83

C-002167 BB7.2.3 scFv (humanized):
QVQLVQSGAEVKKPGSSVKVSCKA<u>SGYTFTSYHIQ</u>WVRQAPGQGL
EWMG<u>WIYPGDGSTQYNEKFKG</u>RVTITADKSTSTAYMELSSLRSED
TAVYYCAR<u>EGTYYAMDY</u>WGQGTTVTVSSGGGGSGGGGSGGGGS
GGEIVLTQSPGTLSLSPGERATLSC<u>RSSQSIVHSNGNTYLE</u>WYQQKP
GQAPRLLIY<u>KVSNRFSGIPDR</u>FSGSGSGTDFTLTISRLEPEDFAVYYC
<u>FQGSHVPRT</u>FGGGTKVEIK (SEQ ID NO: 72)

C-002167 BB7.2.3 scFv (humanized) DNA Sequence: SEQ ID NO: 84

C-002168 BB7.2.5 scFv (humanized):
QVTLKQSGAEVKKPGSSVKVSCTA<u>SGYTFTSYHVS</u>WVRQAPGQGL
EWLG<u>RIYPGDGSTQYNEKFKG</u>KVTITADKSMDTSFMELTSLTSEDT
AVYYCAR<u>EGTYYAMDL</u>WGQGTLVTVSSGGGGSGGGGSGGGGSG
GEIVLTQSPGTLSLSPGERATLSC<u>RSSQSIVHSNGNTYLA</u>WYQQKPG
QAPRLLIS<u>KVSNRFSGVPDR</u>FSGSGSGTDFTLTISRLEPEDFAVYYC
<u>QQGSHVPRT</u>FGGGTKVEIK (SEQ ID NO: 73)

C-002168 BB7.2.5 scFv (humanized) DNA Sequence: SEQ ID NO: 85

C-002169 BB7.2.6 scFv (humanized):
QVQLVQSGAEVKKPGASVKVSCKA<u>SGYTFTSYHMH</u>WVRQAPGQ
RLEWMG<u>WIYPGDGSTQYNEKFKG</u>KVTITRDTSASTAYMELSSLRS
EDTAVYYCAR<u>EGTYYAMDY</u>WGQGTLVTVSSGGGGSGGGGSGGG
GSGGDIVMTQTPLSLPVTPGEPASISC<u>RSSQSIVHSNGNTYLDW</u>YLQ
KPGQSPQLLIY<u>KVSNRFSGVPDR</u>FSGSGSGTDFTLKISRVEAEDVGV
YYC<u>MQGSHVPRT</u>FGGGTKVEIK (SEQ ID NO: 74)

C-002169 BB7.2.6 scFv (humanized) DNA Sequence: SEQ ID NO: 86

In some embodiments, the non-target antigen comprises HLA-B*07. Various single variable domains known in the art or disclosed herein that bind to and recognize HLA-B*07 are suitable for use in embodiments.

In some embodiments, the non-target antigen comprises HLA-A*11. Various single variable domains known in the art or disclosed herein that bind to and recognize HLA-A*11 are suitable for use in embodiments.

In some embodiments, the non-target antigen comprises HLA-A*01. Various single variable domains known in the art or disclosed herein that bind to and recognize HLA-A*01 are suitable for use in embodiments.

In some embodiments, the non-target antigen comprises HLA-A*03. Various single variable domains known in the art or disclosed herein that bind to and recognize HLA-A*03 are suitable for use in embodiments.

In some embodiments, the non-target antigen comprises HLA-C*07. Various single variable domains known in the art or disclosed herein that bind to and recognize HLA-C*07 are suitable for use in embodiments.

Such scFvs include, for example and without limitation, the following mouse and humanized scFv antibodies that bind non-target antigens (e.g. HLA-A*02, HLA-A*01, HLA-A*03, HLA-A*11, HLA-B*07, or HLA-C*07) in a peptide-independent way shown in Table 7 below (where indicated, complementarity determining regions underlined):

TABLE 7

Exemplary HLA-A*02, HLA-A 01, HLA-A*03, HLA-A*11, HLA-B*07, or HLA-C*07 Binding Domains

| | HLA-B*07 antigen binding domains |
|---|---|
| BB7.1.10_ scFv | QVQLQESGPGLVKPSQTLSLTCTVSGYSITSGYSWHWIRQPPGKGLEWIG YIHFSGSTHYHPSLKSRVTISVDTSKNQFSLKLSSVTAADTAVYYCARGG VVSHYAMDCWGQGTTVTVSSGGGGSGGGGSGGGGSGGDIQMTQSPSS LSASVGDRVTITCRASENIYSNLAWYQQKPGKAPKLLIYAATYLPDGVP SRFSGSGSGTDFTLTISSLQPEDFATYYCQHFWVTPYTFGGGTKVEIK (SEQ ID NO: 330) |
| BB 7.1.9_ scFv | EVQLVESGGGLVKPGGSLRLSCAASGYSITSGYSWHWVRQAPGKGLEW VSYIHFSGSTHYHPSLKSRFTISRDNAKNSLYLQMNSLRAEDTAVYYCA RGGVVSHYAMDCWGQGTTVTVSSGGGGSGGGGSGGGGSGGDIQMTQS PSSVSASVGDRVTITCRASENIYSNLAWYQQKPGKAPKLLIYAATYLPDG VPSRFSGSGSGTDFTLTISSLQPEDFATYYCQHFWVTPYTFGGGTKVEIK (SEQ ID NO: 331) |
| BB7.1.8_ scFv | EVQLVESGGGLVKPGGSLRLSCAASGYSITSGYSWHWVRQAPGKGLEW VGYIHFSGSTHYHPSLKSRFTISRDDSKNTLYLQMNSLKTEDTAVYYCA RGGVVSHYAMDCWGQGTTVTVSSGGGGSGGGGSGGGGSGGEIVLTQS PATLSLSPGERATLSCRASENIYSNLAWYQQKPGQAPRLLIYAATYLPDG IPARFSGSGSGTDFTLTISSLEPEDFAVYYCQHFWVTPYTFGGGTKVEIK (SEQ ID NO: 332) |
| BB7.1.7_ scFv | QVQLQQSGPGLVKPSQTLSLTCAISGYSITSGYSWHWIRQSPSRGLEWLG YIHFSGSTHYHPSLKSRITINPDTSKNQFSLQLNSVTPEDTAVYYCARGG VVSHYAMDCWGQGTTVTVSSGGGGSGGGGSGGGGSGGEIVLTQSPATL SLSPGERATLSCRASENIYSNLAWYQQKPGQAPRLLIYAATYLPDGIPAR FSGSGSGTDFTLTISRLEPEDFAVYYCQHFWVTPYTFGGGTKVEIK (SEQ ID NO: 333) |
| BB7.1.6_ scFv | EVQLVESGGGLVKPGGSLRLSCAASGYSITSGYSWHWVRQAPGKGLEW VGYIHFSGSTHYHPSLKSRFTISRDDSKNTLYLQMNSLKTEDTAVYYCA RGGVVSHYAMDCWGQGTTVTVSSGGGGSGGGGSGGGGSGGDIQMTQS PSSVSASVGDRVTITCRASENIYSNLAWYQQKPGKAPKLLIYAATYLPDG VPSRFSGSGSGTDFTLTISSLQPEDFATYYCQHFWVTPYTFGGGTKVEIK (SEQ ID NO: 334) |
| BB7.1.5_ scFv | EVQLVESGGGLVQPGGSLRLSCAASGYSITSGYSWHWVRQAPGKGLEW VSYIHFSGSTHYHPSLKSRFTISRDNSKNTLYLQMNSLRAEDTAVYYCAR GGVVSHYAMDCWGQGTTVTVSSGGGGSGGGGSGGGGSGGDIQMTQSP SSLSASVGDRVTITCRASENIYSNLAWYQQKPGKAPKLLIYAATYLPDG VPSRFSGSGSGTDFTLTISSLQPEDFATYYCQHFWVTPYTFGGGTKVEIK (SEQ ID NO: 335) |
| BB 7.1.4_ scFv | EVQLVESGGGLVKPGGSLRLSCAASGYSITSGYSWHWVRQAPGKGLEW VGYIHFSGSTHYHPSLKSRFTISRDDSKNTLYLQMNSLKTEDTAVYYCA RGGVVSHYAMDCWGQGTTVTVSSGGGGSGGGGSGGGGSGGDIQMTQS PSSLSASVGDRVTITCRASENIYSNLAWYQQKPGKAPKLLIYAATYLPDG VPSRFSGSGSGTDFTLTISSLQPEDFATYYCQHFWVTPYTFGGGTKVEIK (SEQ ID NO: 336) |
| BB7.1.3_ scFv | QVQLQQWGAGLLKPSETLSLTCAVYGYSITSGYSWHWIRQPPGKGLEWI GYIHFSGSTHYHPSLKSRVTISVDTSKNQFSLKLSSVTAADTAVYYCARG GVVSHYAMDCWGQGTTVTVSSGGGGSGGGGSGGGGSGGDIQMTQSPS SLSASVGDRVTITCRASENIYSNLAWYQQKPGKAPKLLIYAATYLPDGV PSRFSGSGSGTDFTLTISSLQPEDFATYYCQHFWVTPYTFGGGTKVEIK (SEQ ID NO: 337) |
| BB 7.1.2_ scFv | QVQLQESGPGLVKPSQTLSLTCTVSGYSITSGYSWHWIRQHPGKGLEWI GYIHFSGSTHYHPSLKSRVTISVDTSKNQFSLKLSSVTAADTAVYYCARG GVVSHYAMDCWGQGTTVTVSSGGGGSGGGGSGGGGSGGDIQMTQSPS SLSASVGDRVTITCRASENIYSNLAWYQQKPGKAPKLLIYAATYLPDGV PSRFSGSGSGTDFTLTISSLQPEDFATYYCQHFWVTPYTFGGGTKVEIK (SEQ ID NO: 338) |

TABLE 7-continued

Exemplary HLA-A*02, HLA-A 01, HLA-A*03, HLA-A*11, HLA-B*07, or HLA-C*07 Binding Domains

| | |
|---|---|
| BB7.1.1_<br>scFv | QVQLQQSGPGLVKPSQTLSLTCAISGYSITSGYSWHWIRQSPSRGLEWLG<br>YIHFSGSTHYHPSLKSRITINPDTSKNQFSLQLNSVTPEDTAVYYCARGG<br>VVSHYAMDCWGQGTTVTVSSGGGGSGGGGSGGGGSGGDIQMTQSPSS<br>LSASVGDRVTITCRASENIYSNLAWYQQKPGKAPKLLIYAATYLPDGVP<br>SRFSGSGSGTDFTLTISSLQPEDFATYYCQHFWVTPYTFGGGTKVEIK<br>(SEQ ID NO: 339) |
| BB7.1<br>scFv | VQLQESGPDLVKPSQSLSLTCTVTGYSITSGYSWHWIRQFPRNKLEWMG<br>YIHFSGSTHYHPSLKSRISITRDTSKNQFFLQLNSVTTEDTATYYCARGGV<br>VSHYAMDCWGQGTSVTVSSGGGGSGGGGSGGGGSGGDIQMTQSPASL<br>SVSVGETVTITCRASENIYSNLAWYQQKQGKSPHLLVYAATYLPDGVPS<br>RFSGSGSGTQYSLKINSLQSEDFGSYYCQHFWVTPYTFGGGTKVEIK<br>(SEQ ID NO: 21806) |

HLA-A*11 antigen binding domains

| | |
|---|---|
| 9 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARH<br>YYYYSMDVWGKGTTVTVSSGGGGSGGGGSGGGGSGGDIQMTQSPSSLS<br>ASVGDRVTITCRASQSISSYLNWYQQKPGKAPKLLIYAASSLQSGVPSRF<br>SGSGSGTDFTLTISSLQPEDFATYYCQQSYSTPLTFGGGTKVEIK (SEQ ID<br>NO: 340) |
| 8 | QITLKESGPTLVKPTQTLTLTCTFSGFSLSTSGVGVGWIRQPPGKALEWL<br>ALIYWNDDKRYSPSLKSRLTITKDTSKNQVVLTMTNMDPVDTATYYCA<br>HRHMRLSCFDYWGQGTLVTVSSGGGGSGGGGSGGGGSGGDIQMTQSPS<br>SLSASVGDRVTITCRASQSISSYLNWYQQKPGKAPKLLIYAASSLQSGVP<br>SRFSGSGSGTDFTLTISSLQPEDFATYYCQQSYSTPLTFGGGTKVEIK<br>(SEQ ID NO: 341) |
| 7 | QVQLVQSGAEVKKPGASVKVSCKASGYTFTSYAMHWVRQAPGQRLEW<br>MGWINAGNGNTKYSQKFQGRVTITRDTSASTAYMELSSLRSEDTAVYY<br>CAREGNGANPDAFDIWGQGTMVTVSSGGGGSGGGGSGGGGSGGDIQM<br>TQSPSSLSASVGDRVTITCRASQSISSYLNWYQQKPGKAPKLLIYAASSL<br>QSGVPSRFSGSGSGTDFTLTISSLQPEDFATYYCQQSYSTPLTFGGGTKVE<br>IK (SEQ ID NO: 342) |
| 6 | EVQLVESGGGLVQPGGSLRLSCAASGFTFSSYDMHWVRQATGKGLEW<br>VSAIGTAGDTYYPGSVKGRFTISRENAKNSLYLQMNSLRAGDTAVYYC<br>ARDLPGSYWYFDLWGRGTLVTVSSGGGGSGGGGSGGGGSGGDIQMTQ<br>SPSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 343) |
| 5 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARH<br>YYYYYLDVWGKGTTVTVSSGGGGSGGGGSGGGGSGGDIQMTQSPSSLS<br>ASVGDRVTITCRASQSISSYLNWYQQKPGKAPKLLIYAASSLQSGVPSRF<br>SGSGSGTDFTLTISSLQPEDFATYYCQQSYSTPLTFGGGTKVEIK (SEQ ID<br>NO: 344) |
| 4 | EVQLVESGGGLVQPGGSLRLSCAASGFTFSSYWMHWVRQAPGKGLVW<br>VSRINSDGSSTSYADSVKGRFTISRDNAKNTLYLQMNSLRAEDTAVYYC<br>CLGVLLYNWFDPWGQGTLVTVSSGGGGSGGGGSGGGGSGGDIQMTQS<br>PSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 345) |
| 3 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARH<br>YYYYMDVWGKGTTVTVSSGGGGSGGGGSGGGGSGGDIQMTQSPSSLS<br>ASVGDRVTITCRASQSISSYLNWYQQKPGKAPKLLIYAASSLQSGVPSRF<br>SGSGSGTDFTLTISSLQPEDFATYYCQQSYSTPLTFGGGTKVEIK (SEQ ID<br>NO: 346) |
| 2 | QITLKESGPTLVKPTQTLTLTCTFSGFSLSTSGVGVGWIRQPPGKALEWL<br>ALIYWNDDKRYSPSLKSRLTITKDTSKNQVVLTMTNMDPVDTATYYCA<br>HKTTSFYFDYWGQGTLVTVSSGGGGSGGGGSGGGGSGGDIQMTQSPSS<br>LSASVGDRVTITCRASQSISSYLNWYQQKPGKAPKLLIYAASSLQSGVPS<br>RFSGSGSGTDFTLTISSLQPEDFATYYCQQSYSTPLTFGGGTKVEIK (SEQ<br>ID NO: 347) |
| 1 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARH<br>YYYYMDVWGKGTTVTVSSGGGGSGGGGSGGGGSGGDIQMTQSPSSL<br>SASVGDRVTITCRASQSISSYLNWYQQKPGKAPKLLIYAASSLQSGVPSR |

TABLE 7-continued

Exemplary HLA-A*02, HLA-A 01, HLA-A*03, HLA-A*11, HLA-B*07, or HLA-C*07 Binding Domains

FSGSGSGTDFTLTISSLQPEDFATYYCQQSYSTPLTFGGGTKVEIK (SEQ
ID NO: 348)

HLA-C*07 antigen binding domains

C7-45
EVQLLESGGGLVQPGGSLRLSCAASGFTFSSYAMSWVRQAPGKGLEWV
SAISGSGGSTYYADSVKGRFTISRDNSKNTLYLQMNSLRAEDTAVYYCA
VSFDWFDPWGQGTLVTVSSGGGGSGGGGSGGGGSGGDIQMTQSPSSLS
ASVGDRVTITCRASQSISSYLNWYQQKPGKAPKLLIYAASSLQSGVPSRF
SGSGSGTDFTLTISSLQPEDFATYYCQQSYSTPLTFGGGTKVEIK (SEQ ID
NO: 349)

C7-44
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARE
RSISPYYYYYMDVWGKGTTVTVSSGGGGSGGGGSGGGGSGGDIQMTQS
PSSLSASVGDRVTITCRASQSISSYLNWYQQKPGKAPKLLIYAASSLQSG
VPSRFSGSGSGTDFTLTISSLQPEDFATYYCQQSYSTPLTFGGGTKVEIK
(SEQ ID NO: 350)

C7-43
QLQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARD
SVIWYWFDPWGQGTLVTVSSGGGGSGGGGSGGGGSGGQSVLTQPPSAS
GTPGQRVTISCSGSSSNIGSNTVNWYQQLPGTAPKLLIYSNNQRPSGVPD
RFSGSKSGTSASLAISGLQSEDEADYYCAAWDDSLNGWVFGGGTKLTV
L (SEQ ID NO: 351)

C7-42
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARE
EILPRLSYYYYMDVWGKGTTVTVSSGGGGSGGGGSGGGGSGGDIQMTQ
SPSSLSASVGDRVTITCRASQSISSYLNWYQQKPGKAPKLLIYAASSLQSG
VPSRFSGSGSGTDFTLTISSLQPEDFATYYCQQSYSTPLTFGGGTKVEIK
(SEQ ID NO: 352)

C7-41
QVQLVQSGSELKKPGASVKVSCKASGYTFTSYAMNWVRQAPGQGLEW
MGWINTNTGNPTYAQGFTGRFVFSFDTSVSTAYLQICSLKAEDTAVYYC
ARGGRAHSSWYFDLWGRGTLVTVSSGGGGSGGGGSGGGGSGGDIQMT
QSPSSLSASVGDRVTITCRASQSISSYLNWYQQKPGKAPKLLIYAASSLQS
GVPSRFSGSGSGTDFTLTISSLQPEDFATYYCQQSYSTPLTFGGGTKVEIK
(SEQ ID NO: 353)

C7-40
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARD
RIKILPRLGYYYYMDVWGKGTTVTVSSGGGGSGGGGSGGGGSGGDIQM
TQSPSSLSASVGDRVTITCRASQSISSYLNWYQQKPGKAPKLLIYAASSL
QSGVPSRFSGSGSGTDFTLTISSLQPEDFATYYCQQSYSTPLTFGGGTKVE
IK (SEQ ID NO: 354)

C7-39
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARD
TVIHYYYYMDVWGKGTTVTVSSGGGGSGGGGSGGGGSGGDIQMTQSP
SSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIK
(SEQ ID NO: 355)

C7-38
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARD
VIVEVFLSYYYYMDVWGKGTTVTVSSGGGGSGGGGSGGGGSGGDIQM
TQSPSSLSASVGDRVTITCRASQSISSYLNWYQQKPGKAPKLLIYAASSL
QSGVPSRFSGSGSGTDFTLTISSLQPEDFATYYCQQSYSTPLTFGGGTKVE
IK (SEQ ID NO: 356)

C7-37
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARD
IFIHYYYYMDVWGKGTTVTVSSGGGGSGGGGSGGGGSGGDIQMTQSPS
SLSASVGDRVTITCRASQSISSYLNWYQQKPGKAPKLLIYAASSLQSGVP
SRFSGSGSGTDFTLTISSLQPEDFATYYCQQSYSTPLTFGGGTKVEIK
(SEQ ID NO: 357)

C7-36
EVQLVESGGGLVQPGGSLRLSCAASGFTFSSYSMNWVRQAPGKGLEWV
SYISSSSSTIYYADSVKGRFTISRDNAKNSLYLQMNSLRAEDTAVYYCAR
DGTFYSYSPYYFDYWGQGTLVTVSSGGGGSGGGGSGGGGSGGDIQMTQ
SPSSLSASVGDRVTITCRASQSISSYLNWYQQKPGKAPKLLIYAASSLQSG
VPSRFSGSGSGTDFTLTISSLQPEDFATYYCQQSYSTPLTFGGGTKVEIK
(SEQ ID NO: 358)

C7-35
QVQLQESGPGLVKPSQTLSLTCTVSGGSISSGGYYWSWIRQPPGKGLEWI
GYIYYSGSTYYNPSLKSRVTISVDTSKNQFSLKLSSVTAADTAVYYCARE
WIKILPRLGYYYYMDVWGKGTTVTVSSGGGGSGGGGSGGGGSGGDIQ

TABLE 7-continued

Exemplary HLA-A*02, HLA-A 01, HLA-A*03, HLA-A*11, HLA-B*07, or HLA-C*07 Binding Domains

| | |
|---|---|
| | MTQSPSSLSASVGDRVTITCRASQSISSYLNWYQQKPGKAPKLLIYAASS<br>LQSGVPSRFSGSGSGTDFTLTISSLQPEDFATYYCQQSYSTPLTFGGGTKV<br>EIK (SEQ ID NO: 359) |
| C7-34 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>RSLYYYYYMDVWGKGTTVTVSSGGGGSGGGGSGGGGSGGDIQMTQSP<br>SSLSASVGDRVTITCRASQSISSYLNWYQQKPGKAPKLLIYAASSLQSGV<br>PSRFSGSGSGTDFTLTISSLQPEDFATYYCQQSYSTPLTFGGGTKVEIK<br>(SEQ ID NO: 360) |
| C7-33 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>KILAPNYYYYYMDVWGKGTTVTVSSGGGGSGGGGSGGGGSGGDIQMTQ<br>SPSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 361) |
| C7-32 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>KSWKYFYYYYYMDVWGKGTTVTVSSGGGGSGGGGSGGGGSGGDIQ<br>MTQSPSSLSASVGDRVTITCRASQSISSYLNWYQQKPGKAPKLLIYAASS<br>LQSGVPSRFSGSGSGTDFTLTISSLQPEDFATYYCQQSYSTPLTFGGGTKV<br>EIK (SEQ ID NO: 362) |
| C7-31 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>NTSTIPYYYYYMDVWGKGTTVTVSSGGGGSGGGGSGGGGSGGDIQMT<br>QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGGGTKVEIK<br>(SEQ ID NO: 363) |
| C7-30 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>DVDKNTSTIYYYYYYMDVWGKGTTVTVSSGGGGSGGGGSGGGGSGGD<br>IQMTQSPSSLSASVGDRVTITCRASQSISSYLNWYQQKPGKAPKLLIYAA<br>SSLQSGVPSRFSGSGSGTDFTLTISSLQPEDFATYYCQQSYSTPLTFGGGT<br>KVEIK (SEQ ID NO: 364) |
| C7-29 | QVQLVESGGGLVKPGGSLRLSCAASGFTFSDYYMSWIRQAPGKGLEWV<br>SYISSSSGSTIYYADSVKGRFTISRDNAKNSLYLQMNSLRAEDTAVYYCAR<br>DGGDIVSSSAIYWYFDLWGRGTLVTVSSGGGGSGGGGSGGGGSGGAIQ<br>LTQSPSSLSASVGDRVTITCRASQGISSALAWYQQKPGKAPKLLIYDASS<br>LESGVPSRFSGSGSGTDFTLTISSLQPEDFATYYCQQFNSYPLTFGGGTKV<br>EIK (SEQ ID NO: 365) |
| C7-28 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>LILPPYYYYYMDVWGKGTTVTVSSGGGGSGGGGSGGGGSGGDIQMTQS<br>PSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 366) |
| C7-27 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>TWIKILPRYYYYYYMDVWGKGTTVTVSSGGGGSGGGGSGGGGSGGD<br>IQMTQSPSSLSASVGDRVTITCRASQSISSYLNWYQQKPGKAPKLLIYAA<br>SSLQSGVPSRFSGSGSGTDFTLTISSLQPEDFATYYCQQSYSTPLTFGGGT<br>KVEIK (SEQ ID NO: 367) |
| C7-26 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>LSRYYYYYMDVWGKGTTVTVSSGGGGSGGGGSGGGGSGGDIQMTQSP<br>SSLSASVGDRVTITCRASQSISSYLNWYQQKPGKAPKLLIYAASSLQSGV<br>PSRFSGSGSGTDFTLTISSLQPEDFATYYCQQSYSTPLTFGGGTKVEIK<br>(SEQ ID NO: 368) |
| C7-25 | EVQLVESGGGLVQPGGSLRLSCAASGFTFSSYSMNWVRQAPGKGLEWV<br>SYISSSSSTIYYADSVKGRFTISRDNAKNSLYLQMNSLRAEDTAVYYCAR<br>EHIVLCFDYWGQGTLVTVSSGGGGSGGGGSGGGGSGGDIQMTQSPSSLS<br>ASVGDRVTITCRASQGISSWLAWYQQKPEKAPKSLIYAASSLQSGVPSRF<br>SGSGSGTDFTLTISSLQPEDFATYYCQQYNSYPLTFGGGTKVEIK (SEQ ID<br>NO: 369) |
| C7-24 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>KILPRPYYYYYMDVWGKGTTVTVSSGGGGSGGGGSGGGGSGGDIQMT |

TABLE 7-continued

Exemplary HLA-A*02, HLA-A 01, HLA-A*03, HLA-A*11, HLA-B*07, or HLA-C*07 Binding Domains

| | |
|---|---|
| | QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGGGTKVEIK<br>(SEQ ID NO: 370) |
| C7-23 | QVQLVQSGAEVKKPGASVKVSCKASGYTFTSYGISWVRQAPGQGLEW<br>MGWISAYNGNTNYAQKLQGRVTMTTDTSTSTAYMELRSLRSDDTAVY<br>YCARGSNEYFQHWGQGTLVTVSSGGGGSGGGGSGGGGSGGQSALTQPP<br>SASGSPGQSVTISCTGTSSDVGGYNYVSWYQQHPGKAPKLMIYEVSKRP<br>SGVPDRFSGSKSGNTASLTVSGLQAEDEADYYCSSYAGSNNWVFGGGT<br>KLTVL (SEQ ID NO: 371) |
| C7-22 | QVQLVQSGSELKKPGASVKVSCKASGYTFTSYAMNWVRQAPGQGLEW<br>MGWINTNTGNPTYAQGFTGRFVFSFDTSVSTAYLQICSLKAEDTAVYYC<br>ARGTSYWYFDLWGRGTLVTVSSGGGGSGGGGSGGGGSGGDIQMTQSPS<br>SLSASVGDRVTITCRASQSISSYLNWYQQKPGKAPKLLIYAASSLQSGVP<br>SRFSGSGSGTDFTLTISSLQPEDFATYYCQQSYSTPLTFGGGTKVEIK<br>(SEQ ID NO: 372) |
| C7-21 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>EIVEVFYYYYMDVWGKGTTVTVSSGGGGSGGGGSGGGGSGGDIQMTQ<br>SPSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 373) |
| C7-20 | EVQLLESGGGLVQPGGSLRLSCAASGFTFSSYAMSWVRQAPGKGLEWV<br>SAISGSGGSTYYADSVKGRFTISRDNSKNTLYLQMNSLRAEDTAVYYCA<br>KVDDYYFDYWGQGTLVTVSSGGGGSGGGGSGGGGSGGDIQMTQSPSSL<br>SASVGDRVTITCRASQSISSYLNWYQQKPGKAPKLLIYAASSLQSGVPSR<br>FSGSGSGTDFTLTISSLQPEDFATYYCQQSYSTPLTFGGGTKVEIK (SEQ<br>ID NO: 374) |
| C7-19 | EVQLVESGGGLVQPGGSLRLSCAASGFTFSSYWMHWVRQAPGKGLVW<br>VSRINSDGSSTSYADSVKGRFTISRDNAKNTLYLQMNSLRAEDTAVYYC<br>AWSTNILLSYTKAFDIWGQGTMVTVSSGGGGSGGGGSGGGGSGGDIQM<br>TQSPSSLSASVGDRVTITCRASQSISSYLNWYQQKPGKAPKLLIYAASSL<br>QSGVPSRFSGSGSGTDFTLTISSLQPEDFATYYCQQSYSTPLTFGGGTKVE<br>IK (SEQ ID NO: 375) |
| C7-18 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>KTYYYYYYMDVWGKGTTVTVSSGGGGSGGGGSGGGGSGGDIQMTQSP<br>SSLSASVGDRVTITCRASQSISSYLNWYQQKPGKAPKLLIYAASSLQSGV<br>PSRFSGSGSGTDFTLTISSLQPEDFATYYCQQSYSTPLTFGGGTKVEIK<br>(SEQ ID NO: 376) |
| C7-17 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>KYFHDKYFHDYYYYYMDVWGKGTTVTVSSGGGGSGGGGSGGGGSGG<br>DIQMTQSPSSLSASVGDRVTITCRASQSISSYLNWYQQKPGKAPKLLIYA<br>ASSLQSGVPSRFSGSGSGTDFTLTISSLQPEDFATYYCQQSYSTPLTFGGG<br>TKVEIK (SEQ ID NO: 377) |
| C7-16 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>TSVYYYYYMDVWGKGTTVTVSSGGGGSGGGGSGGGGSGGDIQMTQSP<br>SSLSASVGDRVTITCRASQSISSYLNWYQQKPGKAPKLLIYAASSLQSGV<br>PSRFSGSGSGTDFTLTISSLQPEDFATYYCQQSYSTPLTFGGGTKVEIK<br>(SEQ ID NO: 378) |
| C7-15 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>KILPYYYYYYMDVWGKGTTVTVSSGGGGSGGGGSGGGGSGGDIQMTQ<br>SPSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 379) |
| C7-14 | EVQLVESGGGLVQPGGSLRLSCAASGFTFSSYSMNWVRQAPGKGLEWV<br>SYISSSSSTIYYADSVKGRFTISRDNAKNSLYLQMNSLRAEDTAVYYCAI<br>QWIYIYINPRGFIFLHDAFDIWGQGTMVTVSSGGGGSGGGGSGGGGSGG<br>QSVLTQPPSASGTPGQRVTISCSGSSSNIGSNTVNWYQQLPGTAPKLLIYS<br>NNQRPSGVPDRFSGSKSGTSASLAISGLQSEDEADYYCAAWDDSLNGW<br>VFGGGTKLTVL (SEQ ID NO: 380) |
| C7-13 | QVQLQQSGPGLVKPSQTLSLTCAISGDSVSSNSAAWNWIRQSPSRGLEW<br>LGRTYYRSKWYNDYAVSVKSRITINPDTSKNQFSLQLNSVTPEDTAVYY<br>CAKEDVDFHHDAFDIWGQGTMVTVSSGGGGSGGGGSGGGGSGGDIQM |

TABLE 7-continued

Exemplary HLA-A*02, HLA-A 01, HLA-A*03, HLA-A*11, HLA-B*07, or HLA-C*07 Binding Domains

| | |
|---|---|
| | TQSPSSLSASVGDRVTITCRASQSISSYLNWYQQKPGKAPKLLIYAASSL<br>QSGVPSRFSGSGSGTDFTLTISSLQPEDFATYYCQQSYSTPLTFGGGTKVE<br>IK (SEQ ID NO: 381) |
| C7-12 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>GVDKNTSTIYYYYYMDVWGKGTTVTVSSGGGGSGGGGSGGGGSGGD<br>IQMTQSPSSLSASVGDRVTITCRASQSISSYLNWYQQKPGKAPKLLIYAA<br>SSLQSGVPSRFSGSGSGTDFTLTISSLQPEDFATYYCQQSYSTPLTFGGGT<br>KVEIK (SEQ ID NO: 382) |
| C7-11 | EVQLVESGGGLVQPGGSLRLSCAASGFTFSSYSMNWVRQAPGKGLEWV<br>SYISSSSSTIYYADSVKGRFTISRDNAKNSLYLQMNSLRAEDTAVYYCAR<br>DRRGYFDLWGRGTLVTVSSGGGGSGGGGSGGGGSGGDIQMTQSPSSLS<br>ASVGDRVTITCRASQGISSWLAWYQQKPEKAPKSLIYAASSLQSGVPSRF<br>SGSGSGTDFTLTISSLQPEDFATYYCQQYNSYPLTFGGGTKVEIK (SEQ ID<br>NO: 383) |
| C7-10 | EVQLVQSGAEVKKPGATVKISCKVSGYTFTDYYMHWVQQAPGKGLEW<br>MGLVDPEDGETIYAEKFQGRVTITADTSTDTAYMELSSLRSEDTAVYYC<br>ATGIHVDIRSMEDWFDPWGQGTLVTVSSGGGGSGGGGSGGGGSGGDIQ<br>MTQSPSSLSASVGDRVTITCRASQSISSYLNWYQQKPGKAPKLLIYAASS<br>LQSGVPSRFSGSGSGTDFTLTISSLQPEDFATYYCQQSYSTPLTFGGGTKV<br>EIK (SEQ ID NO: 384) |
| C7-9 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>IGTSYYYYMDVWGKGTTVTVSSGGGGSGGGGSGGGGSGGDIQMTQSPS<br>SLSASVGDRVTITCRASQSISSYLNWYQQKPGKAPKLLIYAASSLQSGVP<br>SRFSGSGSGTDFTLTISSLQPEDFATYYCQQSYSTPLTFGGGTKVEIK<br>(SEQ ID NO: 385) |
| C7-8 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>VVEVFLYYYYYMDVWGKGTTVTVSSGGGGSGGGGSGGGGSGGDIQMT<br>QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGGGTKVEIK<br>(SEQ ID NO: 386) |
| C7-7 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>LYYYYYYYMDVWGKGTTVTVSSGGGGSGGGGSGGGGSGGDIQMTQSP<br>SSLSASVGDRVTITCRASQSISSYLNWYQQKPGKAPKLLIYAASSLQSGV<br>PSRFSGSGSGTDFTLTISSLQPEDFATYYCQQSYSTPLTFGGGTKVEIK<br>(SEQ ID NO: 387) |
| C7-6 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>SWKYFYPRGSIFIHYYYYMDVWGKGTTVTVSSGGGGSGGGGSGGGGSG<br>GDIQMTQSPSSLSASVGDRVTITCRASQSISSYLNWYQQKPGKAPKLLIY<br>AASSLQSGVPSRFSGSGSGTDFTLTISSLQPEDFATYYCQQSYSTPLTFGG<br>GTKVEIK (SEQ ID NO: 388) |
| C7-5 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>RIVEVFYYYYMDVWGKGTTVTVSSGGGGSGGGGSGGGGSGGDIQMTQ<br>SPSSLSASVGDRVTITCRASQSISSYLNWYQQKPGKAPKLLIYAASSLQSG<br>VPSRFSGSGSGTDFTLTISSLQPEDFATYYCQQSYSTPLTFGGGTKVEIK<br>(SEQ ID NO: 389) |
| C7-4 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>KYFHDWLYYYYYMDVWGKGTTVTVSSGGGGSGGGGSGGGGSGGDIQ<br>MTQSPSSLSASVGDRVTITCRASQSISSYLNWYQQKPGKAPKLLIYAASS<br>LQSGVPSRFSGSGSGTDFTLTISSLQPEDFATYYCQQSYSTPLTFGGGTKV<br>EIK (SEQ ID NO: 390) |
| C7-3 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>LVDKNTSYYYYYMDVWGKGTTVTVSSGGGGSGGGGSGGGGSGGDIQ<br>MTQSPSSLSASVGDRVTITCRASQSISSYLNWYQQKPGKAPKLLIYAASS<br>LQSGVPSRFSGSGSGTDFTLTISSLQPEDFATYYCQQSYSTPLTFGGGTKV<br>EIK (SEQ ID NO: 391) |
| C7-2 | QVQLVQSGAEVKKPGASVKVSCKASGYTFTSYGISWVRQAPGQGLEW<br>MGWISAYNGNTNYAQKLQGRVTMTTDTSTSTAYMELRSLRSDDTAVY<br>YCARVQNEYFQHWGQGTLVTVSSGGGGSGGGGSGGGGSGGQSALTQP |

TABLE 7-continued

Exemplary HLA-A*02, HLA-A 01, HLA-A*03, HLA-A*11, HLA-B*07, or HLA-C*07 Binding Domains

| | |
|---|---|
| | PSASGSPGQSVTISCTGTSSDVGGYNYVSWYQQHPGKAPKLMIYEVSKR PSGVPDRFSGSKSGNTASLTVSGLQAEDEADYYCSSYAGSNNWVFGGG TKLTVL (SEQ ID NO: 392) |
| C7-1 | QVQLVESGGGLVKPGGSLRLSCAASGFTFSDYYMSWIRQAPGKGLEWV SYISSSGSTIYYADSVKGRFTISRDNAKNSLYLQMNSLRAEDTAVYYCAT ANWFDPWGQGTLVTVSSGGGGSGGGGSGGGGSGGDIQMTQSPSSVSAS VGDRVTITCRASQGISSWLAWYQQKPGKAPKLLIYAASSLQSGVPSRFS GSGSGTDFTLTISSLQPEDFATYYCQQANSFPLTFGGGTKVEIK (SEQ ID NO: 393) |

HLA-A*03 scFv Sequences

| | |
|---|---|
| 15 | QVQLVQSGAEVKKPGASVKVSCKASGYTFTSYGISWVRQAPGQGLEW MGWISAYNGNTNYAQKLQGRVTMTTDTSTSTAYMELRSLRSDDTAVY YCARERVSQRGAFDIWGQGTMVTVSSGGGGSGGGGSGGGGSGGDIQM TQSPSSLSASVGDRVTITCRASQSISSYLNWYQQKPGKAPKLLIYAASSL QSGVPSRFSGSGSGTDFTLTISSLQPEDFATYYCQQSYSTPLTFGGGTKVE IK (SEQ ID NO: 394) |
| 16 | EVQLVESGGGLVQPGGSLRLSCAASGFTFSSYSMNWVRQAPGKGLEWV SYISSSSSTIYYADSVKGRFTISRDNAKNSLYLQMNSLRAEDTAVYYCAR GNPDKDPFDYWGQGTLVTVSSGGGGSGGGGSGGGGSGGDIQMTQSPSS LSASVGDRVTITCRASQSISSYLNWYQQKPGKAPKLLIYAASSLQSGVPS RFSGSGSGTDFTLTISSLQPEDFATYYCQQSYSTPLTFGGGTKVEIK (SEQ ID NO: 395) |
| 17 | QVQLQESGPGLVKPSETLSLTCTVSGGSVSSGSYYWSWIRQPPGKGLEW IGYIYYSGSTNYNPSLKSRVTISVDTSKNQFSLKLSSVTAADTAVYYCAR DFYCTNWYFDLWGRGTLVTVSSGGGGSGGGGSGGGGSGGDIQMTQSPS SLSASVGDRVTITCRASQSISSYLNWYQQKPGKAPKLLIYAASSLQSGVP SRFSGSGSGTDFTLTISSLQPEDFATYYCQQSYSTPLTFGGGTKVEIK (SEQ ID NO: 396) |
| 18 | QVQLQESGPGLVKPSETLSLTCTVSGGSISSYYWSWIRQPPGKGLEWIGY IYYSGSTNYNPSLKSRVTISVDTSKNQFSLKLSSVTAADTAVYYCARESS SGSYWYFDLWGRGTLVTVSSGGGGSGGGGSGGGGSGGDIQMTQSPSSL SASVGDRVTITCRASQSISSYLNWYQQKPGKAPKLLIYAASSLQSGVPSR FSGSGSGTDFTLTISSLQPEDFATYYCQQSYSTPLTFGGGTKVEIK (SEQ ID NO: 397) |
| 19 | EVQLVQSGAEVKKPGESLKISCKGSGYSFTSYWIGWVRQMPGKGLEWM GIIYPGDSDTRYSPSFQGQVTISADKSISTAYLQWSSLKASDTAMYYCAR DSGYKYNLYYYYYYMDVWGKGTTVTVSSGGGGSGGGGSGGGGSGGD IQMTQSPSSLSASVGDRVTITCRASQSISSYLNWYQQKPGKAPKLLIYAA SSLQSGVPSRFSGSGSGTDFTLTISSLQPEDFATYYCQQSYSTPLTFGGGT KVEIK (SEQ ID NO: 398) |
| 20 | QVQLVQSGAEVKKPGASVKVSCKASGYTFTSYGISWVRQAPGQGLEW MGWISAYNGNTNYAQKLQGRVTMTTDTSTSTAYMELRSLRSDDTAVY YCARGGDLSHYYYYMDVWGKGTTVTVSSGGGGSGGGGSGGGGSGGQ TVVTQEPSLTVSPGGTVTLTCASSTGAVTSGYYPNWFQQKPGQAPRALI YSTSNKHSWTPARFSGSLLGGKAALTLSGVQPEDEAEYYCLLYYGGAQ WVFGGGTKLTVL (SEQ ID NO: 399) |
| 21 | QVQLVQSGAEVKKPGASVKVSCKASGYTFTSYGISWVRQAPGQGLEW MGWISAYNGNTNYAQKLQGRVTMTTDTSTSTAYMELRSLRSDDTAVY YCARENRRYNSCYYFDYWGQGTLVTVSSGGGGSGGGGSGGGGSGGDI QMTQSPSSLSASVGDRVTITCRASQSISSYLNWYQQKPGKAPKLLIYAAS SLQSGVPSRFSGSGSGTDFTLTISSLQPEDFATYYCQQSYSTPLTFGGGTK VEIK (SEQ ID NO: 400) |
| 22 | QVQLVQSGAEVKKPGASVKVSCKASGYTFTSYGISWVRQAPGQGLEW MGWISAYNGNTNYAQKLQGRVTMTTDTSTSTAYMELRSLRSDDTAVY YCARGGDLSHYYYYLDVWGKGTTVTVSSGGGGSGGGGSGGGGSGGQT VVTQEPSLTVSPGGTVTLTCASSTGAVTSGYYPNWFQQKPGQAPRALIY STSNKHSWTPARFSGSLLGGKAALTLSGVQPEDEAEYYCLLYYGGAQW VFGGGTKLTVL (SEQ ID NO: 401) |
| 23 | EVQLVESGGGLVQPGGSLRLSCAASGFTVSSNYMSWVRQAPGKGLEWV SVIYSGGSTYYADSVKGRFTISRDNSKNTLYLQMNSLRAEDTAVYYCAR ATLLSLSYDAFDIWGQGTMVTVSSGGGGSGGGGSGGGGSGGDIQMTQS PSSLSASVGDRVTITCRASQSISSYLNWYQQKPGKAPKLLIYAASSLQSG VPSRFSGSGSGTDFTLTISSLQPEDFATYYCQQSYSTPLTFGGGTKVEIK (SEQ ID NO: 402) |

TABLE 7-continued

Exemplary HLA-A*02, HLA-A 01, HLA-A*03, HLA-A*11, HLA-B*07, or HLA-C*07 Binding Domains

| | |
|---|---|
| 24 | QVQLVQSGAEVKKPGASVKVSCKASGYTFTSYGISWVRQAPGQGLEW<br>MGWISAYNGNTNYAQKLQGRVTMTTDTSTSTAYMELRSLRSDDTAVY<br>YCARGGDLSHYYYMDVWGKGTTVTVSSGGGGSGGGGSGGGGSGGQT<br>VVTQEPSLTVSPGGTVTLTCASSTGAVTSGYYPNWFQQKPGQAPRALIY<br>STSNKHSWTPARFSGSLLGGKAALTLSGVQPEDEAEYYCLLYYGGAQW<br>VFGGGTKLTVL(SEQ ID NO: 403) |
| 25 | EVQLVQSGAEVKKPGESLKISCKGSGYSFTSYWIGWVRQMPGKGLEWM<br>GIIYPGDSDTRYSPSFQGQVTISADKSISTAYLQWSSLKASDTAMYYCAR<br>ERDRWFDPWGQGTLVTVSSGGGGSGGGGSGGGGSGGDIQMTQSPSSLS<br>ASVGDRVTITCRASQSISSYLNWYQQKPGKAPKLLIYAASSLQSGVPSRF<br>SGSGSGTDFTLTISSLQPEDFATYYCQQSYSTPLTFGGGTKVEIK (SEQ ID<br>NO: 404) |
| 26 | QVQLVQSGAEVKKPGASVKVSCKASGYTFTSYGISWVRQAPGQGLEW<br>MGWISAYNGNTNYAQKLQGRVTMTTDTSTSTAYMELRSLRSDDTAVY<br>YCARETPPSLGAFDIWGQGTMVTVSSGGGGSGGGGSGGGGSGGQSALT<br>QPPSASGSPGQSVTISCTGTSSDVGGYNYVSWYQQHPGKAPKLMIYEVS<br>KRPSGVPDRFSGSKSGNTASLTVSGLQAEDEADYYCSSYAGSNNWVFG<br>GGTKLTVL (SEQ ID NO: 405) |
| 27 | QLQLQESGPGLVKPSETLSLTCTVSGGSISSSSYYWGWIRQPPGKGLEWI<br>GSIYYSGSTYYNPSLKSRVTISVDTSKNQFSLKLSSVTAADTAVYYCARE<br>AYCLSDSYWYFDLWGRGTLVTVSSGGGGSGGGGSGGGGSGGQSVLTQ<br>PPSASGTPGQRVTISCSGSSSNIGSNTVNWYQQLPGTAPKLLIYSNNQRPS<br>GVPDRFSGSKSGTSASLAISGLQSEDEADYYCAAWDDSLNGWVFGGGT<br>KLTVL (SEQ ID NO: 406) |
| 28 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARE<br>SWKYFYPRGYMDVWGKGTTVTVSSGGGGSGGGGSGGGGSGGDIQMT<br>QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGGGTKVEIK<br>(SEQ ID NO: 407) |
| HLA-A*01 scFv Sequences | |
| A1-9 | QVQLVQSGAEVKKPGASVKVSCKASGYTFTSYGISWVRQAPGQGLEW<br>MGWISAYNGNTNYAQKLQGRVTMTTDTSTSTAYMELRSLRSDDTAVY<br>YCARGGWTAWYYYMDVWGKGTTVTVSSGGGGSGGGGSGGGGSGGQ<br>TVVTQEPSLTVSPGGTVTLTCASSTGAVTSGYYPNWFQQKPGQAPRALI<br>YSTSNKHSWTPARFSGSLLGGKAALTLSGVQPEDEAEYYCLLYYGGAQ<br>WVFGGGTKLTVL (SEQ ID NO: 408) |
| A1-8 | EVQLVESGGGLVQPGGSLRLSCAASGFTFSSYSMNWVRQAPGKGLEWV<br>SYISSSSSTIYYADSVKGRFTISRDNAKNSLYLQMNSLRAEDTAVYYCAR<br>AKYYYMDVWGKGTTVTVSSGGGGSGGGGSGGGGSGGQSVLTQPPSAS<br>GTPGQRVTISCSGSSSNIGSNTVNWYQQLPGTAPKLLIYSNNQRPSGVPD<br>RFSGSKSGTSASLAISGLQSEDEADYYCAAWDDSLNGWVFGGGTKLTV<br>L (SEQ ID NO: 409) |
| A1-7 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>QVDKNTYYYYMDVWGKGTTVTVSSGGGGSGGGGSGGGGSGGDIQMT<br>QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGGGTKVEIK<br>(SEQ ID NO: 410) |
| A1-6 | QVQLVESGGGLVKPGGSLRLSCAASGFTFSDYYMSWIRQAPGKGLEWV<br>SYISSSGSTIYYADSVKGRFTISRDNAKNSLYLQMNSLRAEDTAVYYCAR<br>ACQLAEYFQHWGQGTLVTVSSGGGGSGGGGSGGGGSGGDIQMTQSPSS<br>VSASVGDRVTITCRASQGISSWLAWYQQKPGKAPKLLIYAASSLQSGVP<br>SRFSGSGSGTDFTLTISSLQPEDFATYYCQQANSFPLTFGGGTKVEIK<br>(SEQ ID NO: 411) |
| A1-5 | QVQLQESGPGLVKPSQTLSLTCTVSGGSISSGGYYWSWIRQPPGKGLEWI<br>GYIYYSGSTYYNPSLKSRVTISVDTSKNQFSLKLSSVTAADTAVYYCARD<br>RVDKNTSYYYMDVWGKGTTVTVSSGGGGSGGGGSGGGGSGGDIQMT<br>QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGGGTKVEIK<br>(SEQ ID NO: 412) |
| A1-4 | QVQLQESGPGLVKPSDTLSLTCAVSGYSISSSNWWGWIRQPPGKGLEWI<br>GYIYYSGSTYYNPSLKSRVTMSVDTSKNQFSLKLSSVTAVDTAVYYCAR<br>RVQLKLVHWFDPWGQGTLVTVSSGGGGSGGGGSGGGGSGGDIQMTQS<br>PSSLSASVGDRVTITCRASQSISSYLNWYQQKPGKAPKLLIYAASSLQSG |

TABLE 7-continued

Exemplary HLA-A*02, HLA-A 01, HLA-A*03, HLA-A*11, HLA-B*07, or HLA-C*07 Binding Domains

|  | |
|---|---|
| | VPSRFSGSGSGTDFTLTISSLQPEDFATYYCQQSYSTPLTFGGGTKVEIK (SEQ ID NO: 413) |
| A1-3 | QVQLVQSGAEVKKPGASVKVSCKASGYTFTSYDINWVRQATGQGLEW MGWMNPNSGNTGYAQKFQGRVTMTRNTSISTAYMELSSLRSEDTAVY YCATYYDYVTVPYFQHWGQGTLVTVSSGGGGSGGGGSGGGGSGGDIQ MTQSPSSLSASVGDRVTITCRASQSISSYLNWYQQKPGKAPKLLIYAASS LQSGVPSRFSGSGSGTDFTLTISSLQPEDFATYYCQQSYSTPLTFGGGTKV EIK (SEQ ID NO: 414) |
| A1-2 | QLQLQESGSGLVKPSQTLSLTCAVSGGSISSGGYSWSWIRQPPGKGLEWI GYIYHSGSTYYNPSLKSRVTISVDRSKNQFSLKLSSVTAADTAVYYCARE SYPSFYAFDIWGQGTMVTVSSGGGGSGGGGSGGGGSGGDIQMTQSPSSL SASVGDRVTITCRASQSISSYLNWYQQKPGKAPKLLIYAASSLQSGVPSR FSGSGSGTDFTLTISSLQPEDFATYYCQQSYSTPLTFGGGTKVEIK (SEQ ID NO: 415) |
| A1-1 | QITLKESGPTLVKPTQTLTLTCTFSGFSLSTSGVGVGWIRQPPGKALEWL ALIYWNDDKRYSPSLKSRLTITKDTSKNQVVLTMTNMDPVDTATYYCA HSNMWSYSLNDYYFDYWGQGTLVTVSSGGGGSGGGGSGGGGSGGDIQ MTQSPSSLSASVGDRVTITCRASQSISSYLNWYQQKPGKAPKLLIYAASS LQSGVPSRFSGSGSGTDFTLTISSLQPEDFATYYCQQSYSTPLTFGGGTKV EIK (SEQ ID NO: 416) |

Exemplary heavy chain and light chain CDRs (CDR-H1, CDR-H2 and CDR-H3, or CDR-L1, CDR-L2 and CDR-L3, respectively) for HLA-A*02 antigen binding domains are shown in Table 8 below.

TABLE 8

HLA-A*02 CDR Sequences

| CDR-L1 | CDR-L2 | CDR-L3 | CDR-H1 | CDR-H2 | CDR-H3 |
|---|---|---|---|---|---|
| RSSQSIVHSNGNTYLE (SEQ ID NO: 87) | KVSNRFSGVPDR (SEQ ID NO: 90) | FQGSHVPRT (SEQ ID NO: 92) | ASGYTFTSYHIH (SEQ ID NO: 95) | WIYPGNVNTEYNEKFKGK (SEQ ID NO: 98) | EEITYAMDY (SEQ ID NO: 101) |
| RSSQSIVHSNGNTYLE (SEQ ID NO: 87) | KVSNRFSGVPAR (SEQ ID NO: 91) | FQGSHVPRT (SEQ ID NO: 92) | ASGYTFTSYHIH (SEQ ID NO: 95) | WIYPGNVNTEYNEKFKGK (SEQ ID NO: 98) | EEITYAMDY (SEQ ID NO: 101) |
| SSSQSIVHSNGNTYME (SEQ ID NO: 88) | KVSNRFSGVPDR (SEQ ID NO: 90) | HQGSHVPRT (SEQ ID NO: 93) | ASGYTFTSYHMH (SEQ ID NO: 96) | YIYPGNVNTEYNEKFKGK (SEQ ID NO: 99) | EEITYAMDY (SEQ ID NO: 101) |
| RSSQSIVHSNGNTYLD (SEQ ID NO: 89) | KVSNRFSGVPDR (SEQ ID NO: 90) | MQGSHVPRT (SEQ ID NO: 94) | SGYTFTSYHMH (SEQ ID NO: 97) | WIYPGDGSTQYNEKFKG (SEQ ID NO: 100) | EGTYYAMDY (SEQ ID NO: 102) |
| RSSQSIVHSNGNTYLE (SEQ ID NO: 87 | KVSNRFS (SEQ ID NO: 565) | FQGSHVPRT (SEQ ID NO: 92) | SYHIH (SEQ ID NO: 566) | WIYPGNVNTEYNEKFKG (SEQ ID NO: 567) | EEITYAMDY (SEQ ID NO: 101) |

In some embodiments, the scFv comprises the complementarity determined regions (CDRs) of any one of SEQ ID NOS: 87-102. In some embodiments, the scFv comprises a sequence at least 95% identical to any one of SEQ ID NOS: 87-102. In some embodiments, the scFv comprises a sequence identical to any one of SEQ ID NOS: 87-102. In some embodiments, the heavy chain of the antibody comprises the heavy chain CDRs of any one of SEQ ID NOS: 95-102, and wherein the light chain of the antibody comprises the light chain CDRs of any one of SEQ ID NOS: 87-94. In some embodiments, the heavy chain of the antibody comprises a sequence at least 95% identical to the heavy chain portion of any one of SEQ ID NOS: 95-102, and wherein the light chain of the antibody comprises a sequence at least 95% identical to the light chain portion of any one of SEQ ID NOS: 87-94.

Additional exemplary heavy chain and light chain CDRs (CDR-H1, CDR-H2 and CDR-H3, or CDR-L1, CDR-L2 and CDR-L3, respectively) for HLA-A*03, HLA-B*07, HLA-A*11, HLA-C*07 and HLA-A*01 Ligand Binding Domains binding domains are shown in Table 9 below.

TABLE 9

CDRs Of HLA-A*03, HLA-B*07, HLA-A*11, HLA-C*07 and HLA-A*01 Ligand Binding Domains

| CDR-L1 | CDR-L2 | CDR-L3 | CDR-H1 | CDR-H2 | CDR-H3 |
|---|---|---|---|---|---|
| HLA-A*03 CDRs | | | | | |
| RASQSISSYLN (SEQ ID NO: 417) | AASSLQS (SEQ ID NO: 424) | QQSYSTPLT (SEQ ID NO: 430) | SYGIS (SEQ ID NO: 438) | WISAYNGNTNYAQKLQG (SEQ ID NO: 459) | ERVSQRGAFDI (SEQ ID NO: 478) |
| RASQSISSYLN (SEQ ID NO: 417) | AASSLQS (SEQ ID NO: 424) | QQSYSTPLT (SEQ ID NO: 430) | SYSMN (SEQ ID NO: 439) | YISSSSSTIYYADSVKG (SEQ ID NO: 460) | GNPDKDPFDY (SEQ ID NO: 479) |
| RASQSISSYLN (SEQ ID NO: 417) | AASSLQS (SEQ ID NO: 424) | QQSYSTPLT (SEQ ID NO: 430) | SGSYYWS (SEQ ID NO: 440) | YIYYSGSTNYNPSLKS (SEQ ID NO: 461) | DFYCTNWYFDL (SEQ ID NO: 480) |
| RASQSISSYLN (SEQ ID NO: 417) | AASSLQS (SEQ ID NO: 424) | QQSYSTPLT (SEQ ID NO: 430) | SYYWS (SEQ ID NO: 441) | YIYYSGSTNYNPSLKS (SEQ ID NO: 461) | ESSSGSYWYFDL (SEQ ID NO: 481) |
| RASQSISSYLN (SEQ ID NO: 417) | AASSLQS (SEQ ID NO: 424) | QQSYSTPLT (SEQ ID NO: 430) | SYWIG (SEQ ID NO: 442) | IIYPGDSDTRYSPSFQG (SEQ ID NO: 462) | DSGYKYNLYYYYYMDV (SEQ ID NO: 482) |
| ASSTGAVTSGYYPN (SEQ ID NO: 418) | STSNKHS (SEQ ID NO: 425) | LLYYGAQWV (SEQ ID NO: 431) | SYGIS (SEQ ID NO: 438) | WISAYNGNTNYAQKLQG (SEQ ID NO: 459) | GGDLSHYYYYMDV (SEQ ID NO: 483) |
| RASQSISSYLN (SEQ ID NO: 417) | AASSLQS (SEQ ID NO: 424) | QQSYSTPLT (SEQ ID NO: 430) | SYGIS (SEQ ID NO: 438) | WISAYNGNTNYAQKLQG (SEQ ID NO: 459) | ENRRYNSCYYFDY (SEQ ID NO: 484) |
| ASSTGAVTSGYYPN (SEQ ID NO: 418) | STSNKHS (SEQ ID NO: 425) | LLYYGAQWV (SEQ ID NO: 431) | SYGIS (SEQ ID NO: 438) | WISAYNGNTNYAQKLQG (SEQ ID NO: 459) | GGDLSHYYYLDV (SEQ ID NO: 485) |
| RASQSISSYLN (SEQ ID NO: 417) | AASSLQS (SEQ ID NO: 424) | QQSYSTPLT (SEQ ID NO: 430) | SNYMS (SEQ ID NO: 443) | VIYSGGSTYYADSVKG (SEQ ID NO: 463) | ATLLSLSYDAFDI (SEQ ID NO: 486) |
| ASSTGAVTSGYYPN (SEQ ID NO: 418) | STSNKHS (SEQ ID NO: 425) | LLYYGAQWV (SEQ ID NO: 431) | SYGIS (SEQ ID NO: 438) | WISAYNGNTNYAQKLQG (SEQ ID NO: 459) | GGDLSHYYYMDV (SEQ ID NO: 487) |
| RASQSISSYLN (SEQ ID NO: 417) | AASSLQS (SEQ ID NO: 424) | QQSYSTPLT (SEQ ID NO: 430) | SYWIG (SEQ ID NO: 442) | IIYPGDSDTRYSPSFQG (SEQ ID NO: 462) | ERDRWFDP (SEQ ID NO: 488) |
| TGTSSDVGGYNYVS (SEQ ID NO: 419) | EVSKRPS (SEQ ID NO: 426) | SSYAGSNNWV (SEQ ID NO: 432) | SYGIS (SEQ ID NO: 438) | WISAYNGNTNYAQKLQG (SEQ ID NO: 459) | ETPPSLGAFDI (SEQ ID NO: 489) |
| SGSSSNIGSNTVN (SEQ ID NO: 420) | SNNQRPS (SEQ ID NO: 427) | AAWDDSLNGWV (SEQ ID NO: 433) | SSSYYWG (SEQ ID NO: 444) | SIYYSGSTYYNPSLKS (SEQ ID NO: 464) | EAYCLSDSYWYFDL (SEQ ID NO: 490) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | ESWKYFYPRGYMDV (SEQ ID NO: 491) |

TABLE 9-continued

CDRs Of HLA-A*03, HLA-B*07, HLA-A*11, HLA-C*07 and HLA-A*01 Ligand Binding Domains

| CDR-L1 | CDR-L2 | CDR-L3 | CDR-H1 | CDR-H2 | CDR-H3 |
|---|---|---|---|---|---|
| HLA-B*07 CDRs | | | | | |
| RASENIYSNLA (SEQ ID NO: 421) | AATYLPD (SEQ ID NO: 428) | QHFWVTPYT (SEQ ID NO: 434) | SGYSWH (SEQ ID NO: 446) | YIHFSGSTHYHPSLKS (SEQ ID NO: 466) | GGVVSHYAMDC (SEQ ID NO: 492) |
| HLA-A*11 CDRs | | | | | |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | HYYYYYMDV (SEQ ID NO: 493) |
| RASQSISSYLN (SEQ ID NO: 417) | AASSLQS (SEQ ID NO: 424) | QQSYSTPLT (SEQ ID NO: 430) | TSGVGVG (SEQ ID NO: 447) | LIYWNDDKRYSPSLKS (SEQ ID NO: 467) | KTTSFYFDY (SEQ ID NO: 494) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | HYYYYMDV (SEQ ID NO: 495) |
| RASQSISSYLN (SEQ ID NO: 417) | AASSLQS (SEQ ID NO: 424) | QQSYSTPLT (SEQ ID NO: 430) | SYWMH (SEQ ID NO: 448) | RINSDGSSTSYADSVKG (SEQ ID NO: 468) | GVLLYNWFDP (SEQ ID NO: 496) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | HYYYYYLDV (SEQ ID NO: 497) |
| RASQSISSYLN (SEQ ID NO: 417) | AASSLQS (SEQ ID NO: 424) | QQSYSTPLT (SEQ ID NO: 430) | SYDMH (SEQ ID NO: 449) | AIGTAGDTYYPGSVKG (SEQ ID NO: 469) | DLPGSYWYFDL (SEQ ID NO: 498) |
| RASQSISSYLN (SEQ ID NO: 417) | AASSLQS (SEQ ID NO: 424) | QQSYSTPLT (SEQ ID NO: 430) | SYAMH (SEQ ID NO: 450) | WINAGNGNTKYSQKFQG (SEQ ID NO: 470) | EGNGANPDAFDI (SEQ ID NO: 499) |
| RASQSISSYLN (SEQ ID NO: 417) | AASSLQS (SEQ ID NO: 424) | QQSYSTPLT (SEQ ID NO: 430) | TSGVGVG (SEQ ID NO: 447) | LIYWNDDKRYSPSLKS (SEQ ID NO: 467) | RHMRLSCFDY (SEQ ID NO: 500) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | HYYYYSMDV (SEQ ID NO: 501) |
| HLA-C*07 CDRs | | | | | |
| RASQSISSYLN (SEQ ID NO: 417) | AASSLQS (SEQ ID NO: 424) | QQSYSTPLT (SEQ ID NO: 430) | SYAMS (SEQ ID NO: 451) | AISGSGGSTYYADSVKG (SEQ ID NO: 471) | SFDWFDP (SEQ ID NO: 502) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | ERSISPYYYYYMDV (SEQ ID NO: 503) |
| SGSSSNIGSNTVN (SEQ ID NO: 420) | SNNQRPS (SEQ ID NO: 427) | AAWDDSLNGWV (SEQ ID NO: 433) | SSSYYWG (SEQ ID NO: 444) | SIYYSGSTYYNPSLKS (SEQ ID NO: 464) | DSVIWYWFDP (SEQ ID NO: 504) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EEILPRLSYYYYMDV (SEQ ID NO: 505) |
| RASQSISSYLN (SEQ ID NO: 417) | AASSLQS (SEQ ID NO: 424) | QQSYSTPLT (SEQ ID NO: 430) | SYAMN (SEQ ID NO: 452) | WINTNTGNPTYAQGFTG (SEQ ID NO: 472) | GGRAHSSWYFDL (SEQ ID NO: 506) |

TABLE 9-continued

CDRs Of HLA-A*03, HLA-B*07, HLA-A*11, HLA-C*07 and HLA-A*01 Ligand Binding Domains

| CDR-L1 | CDR-L2 | CDR-L3 | CDR-H1 | CDR-H2 | CDR-H3 |
|---|---|---|---|---|---|
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DRIKILPRLGYYYYMDV (SEQ ID NO: 507) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DTVIHYYYYMDV (SEQ ID NO: 508) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DVIVEVFLSYYYYMDV (SEQ ID NO: 509) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DIFIHYYYYMDV (SEQ ID NO: 510) |
| RASQSISSYLN (SEQ ID NO: 417) | AASSLQS (SEQ ID NO: 424) | QQSYSTPLT (SEQ ID NO: 430) | SYSMN (SEQ ID NO: 439) | YISSSSSTIYYADSVKG (SEQ ID NO: 460) | DGTFYSYSPYYFDY (SEQ ID NO: 511) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EWIKILPRLGYYYYMDV (SEQ ID NO: 512) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DRSLYYYYMDV (SEQ ID NO: 513) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DKILAPNYYYYMDV (SEQ ID NO: 514) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EKSWKYFYYYYYMDV (SEQ ID NO: 515) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | ENTSTIPYYYYYMDV (SEQ ID NO: 516) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EDVDKNTSTIYYYYYMDV (SEQ ID NO: 517) |
| RASQGISSALA (SEQ ID NO: 422) | DASSLES (SEQ ID NO: 429) | QQFNSYPLT (SEQ ID NO: 435) | DYYMS (SEQ ID NO: 453) | YISSSGSTIYYADSVKG (SEQ ID NO: 473) | DGGDIVSSSAIYWYFDL (SEQ ID NO: 518) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DLILPPYYYYMDV (SEQ ID NO: 519) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | ETWIKILPRYYYYYYMDV (SEQ ID NO: 520) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DLSRYYYYMDV (SEQ ID NO: 521) |
| RASQGISSWLA (SEQ ID NO: 423) | AASSLQS (SEQ ID NO: 424) | QQYNSYPLT (SEQ ID NO: 436) | SYSMN (SEQ ID NO: 439) | YISSSSSTIYYADSVKG (SEQ ID NO: 460) | EHIVLCFDY (SEQ ID NO: 522) |

TABLE 9-continued

CDRs Of HLA-A*03, HLA-B*07, HLA-A*11, HLA-C*07 and HLA-A*01 Ligand Binding Domains

| CDR-L1 | CDR-L2 | CDR-L3 | CDR-H1 | CDR-H2 | CDR-H3 |
| --- | --- | --- | --- | --- | --- |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DKILPRPYYYYYMDV (SEQ ID NO: 523) |
| TGTSSDVGGYNYVS (SEQ ID NO: 419) | EVSKRPS (SEQ ID NO: 426) | SSYAGSNNWV (SEQ ID NO: 432) | SYGIS (SEQ ID NO: 438) | WISAYNGNTNYAQKLQG (SEQ ID NO: 459) | GSNEYFQH (SEQ ID NO: 524) |
| RASQSISSYLN (SEQ ID NO: 417) | AASSLQS (SEQ ID NO: 424) | QQSYSTPLT (SEQ ID NO: 430) | SYAMN (SEQ ID NO: 452) | WINTNTGNPTYAQGFTG (SEQ ID NO: 472) | GTSYWYFDL (SEQ ID NO: 525) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EEIVEVFYYYYMDV (SEQ ID NO: 526) |
| RASQSISSYLN (SEQ ID NO: 417) | AASSLQS (SEQ ID NO: 424) | QQSYSTPLT (SEQ ID NO: 430) | SYAMS (SEQ ID NO: 451) | AISGSGGSTYYADSVKG (SEQ ID NO: 471) | VDDYYFDY (SEQ ID NO: 527) |
| RASQSISSYLN (SEQ ID NO: 417) | AASSLQS (SEQ ID NO: 424) | QQSYSTPLT (SEQ ID NO: 430) | SYWMH (SEQ ID NO: 44) | RINSDGSSTSYADSVKG (SEQ ID NO: 468) | STNILLSYTKAFDI (SEQ ID NO: 528) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DKTYYYYYYMDV (SEQ ID NO: 529) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EKYFHDKYFHDYYYYYMDV (SEQ ID NO: 530) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DTSVYYYYYMDV (SEQ ID NO: 531) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EKILPYYYYYYMDV (SEQ ID NO: 532) |
| SGSSSNIGSNTVN (SEQ ID NO: 420) | SNNQRPS (SEQ ID NO: 427) | AAWDDSLNGWV (SEQ ID NO: 433) | SYSMN (SEQ ID NO: 439) | YISSSSSTIYYADSVKG (SEQ ID NO: 460) | QWIYIYINPRGFIFLHDAFDI (SEQ ID NO: 533) |
| RASQSISSYLN (SEQ ID NO: 417) | AASSLQS (SEQ ID NO: 424) | QQSYSTPLT (SEQ ID NO: 430) | SNSAAWN (SEQ ID NO: 454) | RTYYRSKWYNDYAVSVKS (SEQ ID NO: 474) | EDVDFHHDAFDI (SEQ ID NO: 534) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EGVDKNTSTIYYYYYMDV (SEQ ID NO: 535) |
| RASQGISSWLA (SEQ ID NO: 423) | AASSLQS (SEQ ID NO: 424) | QQYNSYPLT (SEQ ID NO: 436) | SYSMN (SEQ ID NO: 439) | YISSSSSTIYYADSVKG (SEQ ID NO: 460) | DRRGYFDL (SEQ ID NO: 536) |
| RASQSISSYLN (SEQ ID NO: 417) | AASSLQS (SEQ ID NO: 424) | QQSYSTPLT (SEQ ID NO: 430) | DYYMH (SEQ ID NO: 455) | LVDPEDGETIYAEKFQG (SEQ ID NO: 475) | GIHVDIRSMEDWFDP (SEQ ID NO: 537) |

TABLE 9-continued

CDRs Of HLA-A*03, HLA-B*07, HLA-A*11, HLA-C*07 and HLA-A*01 Ligand Binding Domains

| CDR-L1 | CDR-L2 | CDR-L3 | CDR-H1 | CDR-H2 | CDR-H3 |
|---|---|---|---|---|---|
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DIGTSYYYYMDV (SEQ ID NO: 538) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EVVEVFLYYYYYMDV (SEQ ID NO: 539) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DLYYYYYYMDV (SEQ ID NO: 540) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | ESWKYFYPRGSIFIHYYYYMDV (SEQ ID NO: 541) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DRIVEVFYYYYMDV (SEQ ID NO: 542) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | EKYFHDWLYYYYYMDV (SEQ ID NO: 543) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DLVDKNTSYYYYYMDV (SEQ ID NO: 544) |
| TGTSSDVGGYNYVS (SEQ ID NO: 419) | EVSKRPS (SEQ ID NO: 426) | SSYAGSNNWV (SEQ ID NO: 432) | SYGIS (SEQ ID NO: 438) | WISAYNGNTNYAQKLQG (SEQ ID NO: 459) | VQNEYFQH (SEQ ID NO: 545) |
| RASQGISSWLA (SEQ ID NO: 423) | AASSLQS (SEQ ID NO: 424) | QQANSFPLT (SEQ ID NO: 437) | DYYMS (SEQ ID NO: 453) | YISSSGSTIYYADSVKG (SEQ ID NO: 473) | ANWFDP (SEQ ID NO: 546) |
| HLA-A*01 CDRs | | | | | |
| ASSTGAVTSGYYPN (SEQ ID NO: 418) | STSNKHS (SEQ ID NO: 425) | LLYYGAQWV (SEQ ID NO: 431) | SYGIS (SEQ ID NO: 438) | WISAYNGNTNYAQKLQG (SEQ ID NO: 459) | GGWTAWYYMDV (SEQ ID NO: 547) |
| SGSSSNIGSNTVN (SEQ ID NO: 420) | SNNQRPS (SEQ ID NO: 427) | AAWDDSLNGWV (SEQ ID NO: 433) | SYSMN (SEQ ID NO: 439) | YISSSSSTIYYADSVKG (SEQ ID NO: 460) | AKYYYMDV (SEQ ID NO: 548) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DQVDKNTYYYYMDV (SEQ ID NO: 549) |
| RASQGISSWLA (SEQ ID NO: 423) | AASSLQS (SEQ ID NO: 424) | QQANSFPLT (SEQ ID NO: 437) | DYYMS (SEQ ID NO: 453) | YISSSGSTIYYADSVKG (SEQ ID NO: 473) | ACQLAEYFQH (SEQ ID NO: 550) |
| RASQSISSYLN (SEQ ID NO: 417) | AASSLQS (SEQ ID NO: 424) | QQSYSTPLT (SEQ ID NO: 430) | SGGYYWS (SEQ ID NO: 445) | YIYYSGSTYYNPSLKS (SEQ ID NO: 465) | DRVDKNTSYYYMDV (SEQ ID NO: 551) |
| RASQSISSYLN (SEQ ID NO: 417) | AASSLQS (SEQ ID NO: 424) | QQSYSTPLT (SEQ ID NO: 430) | SSNWWG (SEQ ID NO: 456) | YIYYSGSTYYNPSLKS (SEQ ID NO: 465) | RVQLKLVHWFDP (SEQ ID NO: 552) |

TABLE 9-continued

CDRs Of HLA-A*03, HLA-B*07, HLA-A*11, HLA-C*07 and HLA-A*01 Ligand Binding Domains

| CDR-L1 | CDR-L2 | CDR-L3 | CDR-H1 | CDR-H2 | CDR-H3 |
| --- | --- | --- | --- | --- | --- |
| RASQSISSY LN (SEQ ID NO: 417) | AASSLQS (SEQ ID NO: 424) | QQSYSTPL T (SEQ ID NO: 430) | SYDIN (SEQ ID NO: 457) | WMNPNSGNT GYAQKFQG (SEQ ID NO: 476) | YYDYVTVFY FQH (SEQ ID NO: 553) |
| RASQSISSY LN (SEQ ID NO: 417) | AASSLQS (SEQ ID NO: 424) | QQSYSTPL T (SEQ ID NO: 430) | SGGYSW S (SEQ ID NO: 458) | YIYHSGSTYY NPSLKS (SEQ ID NO: 477) | ESYPSFYAF DI (SEQ ID NO: 554) |
| RASQSISSY LN (SEQ ID NO: 417) | AASSLQS (SEQ ID NO: 424) | QQSYSTPL T (SEQ ID NO: 430) | TSGVGV G (SEQ ID NO: 447) | LIYWNDDKR YSPSLKS (SEQ ID NO: 467) | SNMWSYSL NDYYFDY (SEQ ID NO: 555) |

In some embodiments, the second, inhibitory ligand is HLA-A*02, and the inhibitory ligand binding domain comprises an HLA-A*02 antigen binding domain. In some embodiments, the second antigen binding domain binds HLA-A*02 independent of the peptide in a pMHC complex comprising HLA-A*02. In some embodiments, the HLA-A*02 antigen binding domain comprises an scFv domain. In some embodiments, the HLA-A*02 antigen binding domain comprises a sequence of any one of SEQ ID NOs: 63-74, 207, 209 or 211. In some embodiments, the HLA-A*02 ligand binding domain comprises a sequence at least 90%, at least 95% or at least 99% identical to a sequence of any one of SEQ ID NOs: 63-74, 207, 209 or 211.

In some embodiments, the non-target antigen comprises HLA-B*07, and the ligand binding domain of the second receptor comprises an HLA-B*07 ligand binding domain. In some embodiments, the ligand binding domain binds HLA-B*07 independent of the peptide in a pMHC complex comprising HLA-B*07. In some embodiments, the HLA-B*07 ligand binding domain comprises an scFv domain. In some embodiments, the HLA-B*07 ligand binding domain comprises a sequence of any one of the indicated B7 binding domains in Table 7. In some embodiments, the HLA-B*07 ligand binding domain comprises a sequence at least 90%, at least 95% or at least 99% identical to a sequence of any one of the indicated HLA-B*07 binding domains in Table 7 Table 9. In some embodiments, the HLA-B*07 scFv comprises any one of the indicated HLA-B*07 complementarity determined regions (CDRs) in Table 9. In some embodiments, the scFv comprises a sequence at least 95% identical to any one of the indicated HLA-B*07 scFv sequences in Table 7. In some embodiments, the scFv comprises a sequence identical to any one of the indicated HLA-B*07 scFv sequences in Table 7.

In some embodiments, the non-target antigen comprises HLA-A*11, and the ligand binding domain of the second receptor comprises an HLA-A*11 ligand binding domain. In some embodiments, the ligand binding domain binds HLA-A*11 independent of the peptide in a pMHC complex comprising HLA-A*11. In some embodiments, the HLA-A*11 ligand binding domain comprises an scFv domain. In some embodiments, the HLA-A*11 ligand binding domain comprises a sequence of any one of the indicated HLA-A*11 binding domains in Table 7. In some embodiments, the HLA-A*11 ligand binding domain comprises a sequence at least 90%, at least 95% or at least 99% identical to a sequence of any one of the indicated HLA-A*11 binding domains in Table 7. In some embodiments, the HLA-A*11 scFv comprises any one of the indicated HLA-A*11 complementarity determined regions (CDRs) in Table 9. In some embodiments, the scFv comprises a sequence at least 95% identical to any one of the indicated HLA-A*11 scFv sequences in Table 7. In some embodiments, the scFv comprises a sequence identical to any one of the indicated HLA-A*11 scFv sequences in Table 7.

In some embodiments, the non-target antigen comprises HLA-A*01, and the ligand binding domain of the second receptor comprises an HLA-A*01 ligand binding domain. In some embodiments, the ligand binding domain binds HLA-A*01 independent of the peptide in a pMHC complex comprising HLA-A*01. In some embodiments, the HLA-A*01 ligand binding domain comprises an scFv domain. In some embodiments, the HLA-A*01 ligand binding domain comprises a sequence of any one of the indicated HLA-A*01 binding domains in Table 7. In some embodiments, the HLA-A*01 ligand binding domain comprises a sequence at least 90%, at least 95% or at least 99% identical to a sequence of any one of the indicated HLA-A*01 binding domains in Table 7. In some embodiments, the HLA-A*01 scFv comprises any one of the indicated HLA-A*01 complementarity determined regions (CDRs) in Table 9. In some embodiments, the scFv comprises a sequence at least 95% identical to any one of the indicated HLA-A*01 scFv sequences in Table 7. In some embodiments, the scFv comprises a sequence identical to any one of the indicated HLA-A*01 scFv sequences in Table 7.

In some embodiments, the non-target antigen comprises HLA-A*03, and the ligand binding domain of the second receptor comprises an HLA-A*03 ligand binding domain. In some embodiments, the ligand binding domain binds HLA-A*03 independent of the peptide in a pMHC complex comprising HLA-A*03. In some embodiments, the HLA-A*03 ligand binding domain comprises an scFv domain. In some embodiments, the HLA-A*03 ligand binding domain comprises a sequence of any one of the indicated HLA-A*03 binding domains in Table 7. In some embodiments, the HLA-A*03 ligand binding domain comprises a sequence at least 90%, at least 95% or at least 99% identical to a sequence of any one of the indicated HLA-A*03 binding domains in Table 7. In some embodiments, the HLA-A*03 scFv comprises any one of the indicated HLA-A*03 complementarity determined regions (CDRs) in Table 9. In some embodiments, the scFv comprises a sequence at least 95% identical to any one of the indicated HLA-A*03 scFv sequences in Table 7. In some embodiments, the scFv comprises a sequence identical to any one of the indicated HLA-A*03 scFv sequences in Table 7.

In some embodiments, the non-target antigen comprises HLA-C*07, and the ligand binding domain of the second receptor comprises an HLA-C*07 ligand binding domain. In some embodiments, the ligand binding domain binds HLA-C*07 independent of the peptide in a pMHC complex comprising HLA-C*07. In some embodiments, the HLA-C*07 ligand binding domain comprises an scFv domain. In some embodiments, the HLA-C*07 ligand binding domain comprises a sequence of any one of the indicated HLA-C*07 binding domains in Table 7. In some embodiments, the HLA-C*07 ligand binding domain comprises a sequence at least 90%, at least 95% or at least 99% identical to a sequence of any one of the indicated HLA-C*07 binding domains in Table 7. In some embodiments, the HLA-C*07 scFv comprises any one of the indicated HLA-C*07 complementarity determined regions (CDRs) in Table 9. In some embodiments, the scFv comprises a sequence at least 95% identical to any one of the indicated HLA-C*07 scFv sequences in Table 7. In some embodiments, the scFv comprises a sequence identical to any one of the indicated HLA-C*07 scFv sequences in Table 7.

Minor Histocompatibility Antigens

In some embodiments, the second, inhibitor ligand comprises a minor histocompatibility antigen (MiHA). In some embodiments, the second, inhibitor ligand comprises an allele of a MiHA that is lost in a target cell through LOH.

MiHAs are peptides derived from proteins that contain nonsynonymous differences between alleles and are displayed by common HLA alleles. The non-synonymous differences can arise from SNPs, deletions, frameshift mutations or insertions in the coding sequence of the gene encoding the MiHA. Exemplary MiHAs can be about 9-12 amino acids in length and can bind to MHC class I and MHC class II proteins. Binding of the TCR to the MHC complex displaying the MiHA can activate T cells. The genetic and immunological properties of MiHAs will be known to the person of ordinary skill in the art. Candidate MiHAs are known peptides presented by known HLA class I alleles, are known to elicit T cell responses in the clinic (for example, in graft versus host disease, or transplant rejection, and allow for patient selection by simple SNP genotyping.

In some embodiments, the MiHA has broad or ubiquitous RNA expression.

In some embodiments, the MiHA has high minor allele frequency.

In some embodiments, the MiHA comprises a peptide derived from a Y chromosome gene.

In some embodiments, the second inhibitor ligand comprises a MiHA selected from the group of MiHAs disclosed in Table 10 and Table 11.

Exemplary, but non-limiting, examples of MiHAs that are envisaged as within the scope of the instant invention are disclosed in Table 10 below. Columns in Table 10 indicate, from left to right, the name of the MiHA, the gene which from which it is derived, MHC class I variant which can display the MiHA and the sequences of the peptide variants [A/B variants indicated in brackets].

TABLE 10

HLA Class I Autosomal MiHAs

| MiHA | Gene | HLA | Peptide A/B |
|---|---|---|---|
| LB-CYBA-1Y | cytochrome b-245 alpha chain (CYBA) | A*01:01 | STMERWGQK[Y/H] (SEQ ID NO: 103) |
| LB-OAS1-1R | 2'-5'-oligoadenylate synthetase 1 (OAS1) | A*01:01 | ETDDPR[R/T]YQKY (SEQ ID NO: 104) |
| HA-1/A2 | Rho GTPase activating protein 45 (HMHA1) | A*02:01 | VL[HR]DDLLEA (SEQ ID NO: 105) |
| HA-2 | myosin IG (MYO1G) | A*02:01 | YIGEVLVS[V/M] (SEQ ID NO: 106) |
| HA-8 | pumilio RNA binding family member 3 (KIAA0020, PUM3) | A*02:01 | [R/P]TLDKVLEV (SEQ ID NO: 107) |
| HA-3 | A-kinase anchoring protein 13 (AKAP13) | A*01:01 | V[T/M]EPGTAQY (SEQ ID NO: 108) |
| HwA11-S | chromosome 19 open reading frame 48 (C19ORF48) | A*02:01 | CIPPD[S/T]LLFPA (SEQ ID NO: 109) |
| LB-ADIR-1F | torsin family 3 member A (TOR3A) | A*02:01 | SVAPALAL[F/S]PA (SEQ ID NO: 110) |
| LB-HIVEP1-1S | HIVEP zinc finger 1 (HIVEP1) | A*02:01 | SLPKH[S/N]VTI (SEQ ID NO: 111) |
| LB-NISCH-1A | nischarin (NISCH) | A*02:01 | ALAPAP[A/V]EV (SEQ ID NO: 112) |
| LB-SSR1-1S | signal sequence receptor subunit 1 (SSR1) | A*02:01 | [S/L]LAVAQDLT (SEQ ID NO: 113) |
| LB-WNK1-1I | WNK lysine deficient protein kinase 1 (WNK1) | A*02:01 | RTLSPE[I/M]ITV (SEQ ID NO: 114) |
| T4A | tripartite motif containing 4 (TRIM42) | A*02:01 | GLYTYWSAG[A/E] (SEQ ID NO: 115) |

TABLE 10-continued

HLA Class I Autosomal MiHAs

| MiHA | Gene | HLA | Peptide A/B |
|---|---|---|---|
| UTA2-1 | retroelement silencing factor 1 (KIAA1551) | A*02:01 | QL[L/P]NSVLTL (SEQ ID NO: 116) |
| LB-CLYBL-1Y | citramalyl-CoA lyase (CLYBL) | A*02:01 | SLAA[Y/D]IPRL (SEQ ID NO: 117) |
| TRIM22 | tripartite motif containing 22 (TRIM22) | A*02:01 | MAVPPC[C/R]IGV (SEQ ID NO: 118) |
| PARP10-1L | poly(ADP-ribose) polymerase family member 10 (PARP10) | A*02:01 | GL[L/P]GQEGLVEI (SEQ ID NO: 119) |
| FAM119A-1T | methyltransferase like 21A (FAM119A) | A*02:01 | AMLERQF[T/I] (SEQ ID NO: 120) |
| GLRX3-1S | glutaredoxin 3 (GLRX3) | A*02:01 | FL[S/P]SANEHL (SEQ ID NO: 121) |
| HNF4G-1M | hepatocyte nuclear factor 4 gamma (HNF4G) | A*02:01 | M[M/I]YKDILLL (SEQ ID NO: 122) |
| HMMR-1V | hyaluronan mediated motility receptor (HMMR) | A*02:01 | SLQEK[V/A]AKA (SEQ ID NO: 123) |
| BCL2A1 | BCL2 related protein A1 (BCL2A1) | A*02:01 | VLQ[N/K]VAFSV (SEQ ID NO: 124) |
| CDC26-1F | cell division cycle 26 (CDC26) | A*02:01 | [F/S]VAGTQEVFV (SEQ ID NO: 125) |
| APOBEC3F-1S/A | apolipoprotein B mRNA editing enzyme catalytic subunit 3F (APOBEC3F) | A*02:01 | FL[S/A]EHPNVTL (SEQ ID NO: 126) |
| LB-PRCP-1D | prolylcarboxypeptidase (PRCP) | A*02:01 | FMWDVAE[D/E] (9 mer) (SEQ ID NO: 127), FMWDVAE[D/E]LKA (11 mer) (SEQ ID NO: 128) |
| LB-CCL4-1T | C-C motif chemokine ligand 4 (CCL4) | A*02:01 | CADPSE[T/S]WV (SEQ ID NO: 129) |
| LB-NCAPD3-1Q | non-SMC condensin II complex subunit D (NCAPD3) | A*02:01 | WL[Q/R]GVVPVV (SEQ ID NO: 130) |
| LB-NDC80-1P | NDC80 kinetochore complex component (NDC80) | A*02:01 | HLEEQI[P/A]KV (SEQ ID NO: 131) |
| LB-TTK-1D | TTK protein kinase (TTK) | A*02:01 | RLH[D/E]GRVFV (SEQ ID NO: 132) |
| WDR27-1L | WD repeat domain 27 (WDR27) | A*02:01 | S[L/P]DDHVVAV (SEQ ID NO: 133) |
| MIIP | migration and invasion inhibitory protein (MIIP) | A*02:01 | SEESAVP[K/E]RSW (11 mer) (SEQ ID NO: 134), EESAVP[K/E]RSW (10 mer) (SEQ ID NO: 135) |
| HER-2/NEU | Eerb-b2 receptor tyrosine kinase 2 (RBB2) | A*02:01 | not reported |
| LB-DHX33-1C | DEAH-box helicase 33 (DHX33) | A*02:01, C*03:03 | YLYEGGIS[C/R] (SEQ ID NO: 136) |
| PANE1 | centromere protein M (CENPM) | A*03:01 | RVWDLPGVLK (SEQ ID NO: 137) |
| SP110 | SP110 nuclear body protein (SP110) | A*03:01 | SLP[R/G]GTSTPK (SEQ ID NO: 138) |
| ACC-1C/Y | BCL2 related protein A1 (BCL2A1) | A*24:02 | DYLQ[Y/C]VLQI (SEQ ID NO: 139) |

TABLE 10-continued

HLA Class I Autosomal MiHAs

| MiHA | Gene | HLA | Peptide A/B |
|---|---|---|---|
| P2RX7 | purinergic receptor P2X 7 (P2RX7) | A*29:02 | WFHHC[H/R]PKY (SEQ ID NO: 140) |
| ACC-4 | cathepsin H (CTSH) | A*31:01 | ATLPLLCA[R/G] (SEQ ID NO: 141) |
| ACC-5 | CTSH | A*33:03 | WATLPLLCA[R/G] (SEQ ID NO: 142) |
| AKAP13 | A-kinase anchoring protein 13 (AKAP13) | B*07:02 | APAGVREV[M/T] (SEQ ID NO: 143) |
| LB-APOBEC3B-1K | apolipoprotein B mRNA editing enzyme catalytic subunit 3B (APOBEC3B) | B*07:02, B*08:01 | [K/E]PQYHAEMCF (SEQ ID NO: 144) |
| APOBEC3H | apolipoprotein B mRNA editing enzyme catalytic subunit 3H (APOBEC3H) | B*07:02 | KPQQ[K/E]GLRL (SEQ ID NO: 145) |
| LB-ARHGDIB-1R | Rho GDP dissociation inhibitor beta (ARHGDIB) | B*07:02 | LPRACW[R/P]EA (SEQ ID NO: 146) |
| LB-BCAT2-1R | BCAT2-branched chain amino acid transaminase 2 (BCAT2) | B*07:02 | QP[R/T]RALLFVIL (SEQ ID NO: 147) |
| BFAR | bifunctional apoptosis regulator (BFAR) | B*07:02 | APNTGRANQQ[M/R] (SEQ ID NO: 148) |
| C14orf169 | ribosomal oxygenase 1 (C14orf169 or RIOX1) | B*07:02 | RPR[A/V]PTEELAL (SEQ ID NO: 149) |
| LB-C16ORF-1R | C16ORF | B*07:02 | [R/W]PCPSVGLSFL (SEQ ID NO: 150) |
| C18orf21 | chromosome 18 open reading frame 21 (C18orf21) | B*07:02 | NPATP[A/T]SKL (SEQ ID NO: 151) |
| LB-EBI3-1I | Epstein-Barr virus induced 3 (EBI3) | B*07:02 | RPRARYY[I/V]QV (SEQ ID NO: 152) |
| POP1 | POP1 homolog, ribonuclease P/MRP subunit (POP1) | B*07:02 | LPQKKS[N/K]AL (SEQ ID NO: 153) |
| SCRIB | scribble planar cell polarity protein (SCRIB) | B*07:02 | LPQQPP[L/P]SL (SEQ ID NO: 154) |
| MTRR | 5-methyltetrahydrofolate-homocysteine methyltransferase reductase (MTRR) | B*07:02 | SPAS[S/L]RTDL (SEQ ID NO: 155) |
| LLGL2 | LLGL scribble cell polarity complex component 2 (LLGL2) | B*07:02 | SPSL[R/H]ILAI (SEQ ID NO: 156) |
| LB-ECGF-1H | thymidine phosphorylase (TYMP) | B*07:02 | RP[H/R]AIRRPLAL (SEQ ID NO: 157) |
| LB-ERAP1-1R | endoplasmic reticulum aminopeptidase 1 (ERAP1) | B*07:02 | HP[R/P]QEQIALLA (11 mer) (SEQ ID NO: 158), HP[R/P]QEQIAL (9 mer) (SEQ ID NO: 159) |
| LB-FUCA2-1V | alpha-L-fucosidase 2 (FUCA2) | B*07:02 | RLRQ[V/M]GSWL (SEQ ID NO: 160) |
| LB-GEMIN4-1V | gem nuclear organelle associated protein 4 (GEMIN4) | B*07:02, B*08:01 | FPALRFVE[V/E] (SEQ ID NO: 161) |
| HDGF | heparin binding growth factor (HDGF) | B*07:02 | LPMEVEKNST[L/P] (SEQ ID NO: 162) |
| LB-PDCD11-1F | programmed cell death 11 (PDCD11) | B*07:02 | GPDSSKT[F/L]LCL (SEQ ID NO: 163) |

TABLE 10-continued

HLA Class I Autosomal MiHAs

| MiHA | Gene | HLA | Peptide A/B |
|---|---|---|---|
| LB-PFAS-1P | phosphoribosylformylglycinamidine synthase (PFAS) | B*07:02 | A[P/S]GHTRRKL (SEQ ID NO: 164) |
| LB-TEP1-1S | telomerase associated protein 1 (TEP1) | B*07:02 | APDGAKVA[S/P]L (SEQ ID NO: 165) |
| LB-TMEM8A-1I | post-glycosylphosphatidylinositol attachment to proteins 6 (TMEM8A or PGAP6) | B*07:02 | RPRSVT[I/V]QPLL (SEQ ID NO: 166) |
| LB-USP15-1I | ubiquitin specific peptidase 15 (USP15) | B*07:02 | MPSHLRN[I/T]LL (SEQ ID NO: 167) |
| LRH-1 | purinergic receptor P2X 5 (P2RX5) | B*07:02 | TPNQRQNVC (SEQ ID NO: 168) |
| LB-MOB3A-1C | MOB kinase activator 3A (MOB3A) | B*07:02 | [C/S]PRPGTWTC (SEQ ID NO: 169) |
| LB-ZDHHC6-1Y | zinc finger DHHC-type palmitoyltransferase 6 (ZDHHC6) | B*07:02 | RPR[Y/H]WILLVKI (SEQ ID NO: 170) |
| ZAPHIR | zinc finger protein 419 (ZNF419) | B*07:02 | IPRDSWWVEL (SEQ ID NO: 171) |
| HEATR1 | HEAT repeat containing 1 (HEATR1) | B*08:01 | ISKERA[E/G]AL (SEQ ID NO: 172) |
| LB-GSTP1-1V | glutathione S-transferase pi 1 (GSTP1) | B*08:01 | DLRCKY[V/I]SL (SEQ ID NO: 173) |
| HA-1/B60 | Rho GTPase activating protein 45 (HMHA1) | B*40:01 | KECVL[H/R] (SEQ ID NO: 174) |
| LB-SON-1R | SON DNA and RNA binding protein (SON) | B*40:01 | SETKQ[R/C]TVL (SEQ ID NO: 175) |
| LB-SWAP70-1Q | switching B cell complex subunit SWAP70 (SWAP70) | B*40:01 | MEQLE[Q/E]LEL (SEQ ID NO: 176) |
| LB-TRIP10-1EPC | thyroid hormone receptor interactor 10 (TRIP 10) | B*40:01 | G[E/G][P/S]QDL[C/G]TL (SEQ ID NO: 177) |
| LB-NUP133-1R | nucleoporin 133 (NUP133) | B*40:01 | SEDLILC[R/Q]L (SEQ ID NO: 178) |
| LB-ZNFX1-1Q | zinc finger NFX1-type containing 1 (ZNFX1) | B*40:01 | NEIEDVW[Q/H]LDL (SEQ ID NO: 179) |
| SLC1A5 | solute carrier family 1 member 5 (SLC1A5) | B*40:02 | AE[A/P]TANGGLAL (SEQ ID NO: 180) |
| ACC-2 | BCL2A1 | B*44:02, B*44:03 | KEFED[D/G]IINW (SEQ ID NO: 181) |
| ACC-6 | histocompatibility minor serpin domain containing (HMSD) | B*44:03 | MEIFIEVFSHF (SEQ ID NO: 182) |
| HB-1H/Y | histocompatibility minor HB-1 (HMHB1) | B*44:03 | EEKRGSL[H/Y] (SEQ ID NO: 183) |
| DPH1 | diphthamide biosynthesis 1 (DPH1) | B*57:01 | S[V/L]LPEVDVW (SEQ ID NO: 184) |
| UGT2B17/A02 | UDP glucuronosyltransferase family 2 member B17 (UGT2B17) | A*02:06 | CVATMIFMI (SEQ ID NO: 185) |
| UGT2B17/A29 | UGT2B17 | A*29:02 | AELLNIPFLY (SEQ ID NO: 186) |

TABLE 10-continued

HLA Class I Autosomal MiHAs

| MiHA | Gene | HLA | Peptide A/B |
|---|---|---|---|
| UGT2B17/B44 | UGT2B17 | B*44:03 | AELLNIPFLY (SEQ ID NO: 187) |

Exemplary, but non-limiting, examples of MiHAs that are envisaged as within the scope of the instant invention are disclosed in Table 11 below. Columns in Table 11 indicate, from left to right, the name of the MiHA, the gene which from which it is derived, MHC class I variant which can display the MiHA and the sequences of the peptide variants [A/B variants indicated in brackets).

TABLE 11

HLA Class I Y linked MiHAs

| MiHA | Gene | HLA | Peptide A/B |
|---|---|---|---|
| DFFRY | ubiquitin specific peptidase 9 Y-linked (DFFRY) | A*01:01 | IVD[C/S]LTEMY (SEQ ID NO: 188) |
| SMCY | lysine demethylase 5 (SMCY) | A*02:01 | FIDSYICQV (SEQ ID NO: 189) |
| TMSB4Y | thymosin beta 4 Y-linked (TMSB4Y) | A*33:03 | EVLLRPGLHFR (SEQ ID NO: 190) |
| SMCY | SMCY | B*07:02 | SP[S/A]VDKA[R/Q]AEL (SEQ ID NO: 191) |
| UTY | ubiquitously transcribed tetratricopeptide repeat containing, Y-linked (UTY) | B*08:01 | LPHN[H/R]T[D/N]L (SEQ ID NO: 192) |
| RPS4Y | ribosomal protein S4 Y-linked 1 (RPS4Y) | B*52:01 | TIRYPDP[V/L]I (*SEQ ID NO: 193*) |
| UTY | UTY | B*60:01 | [R/G]ESEE[E/A]S[V/P]SL (SEQ ID NO: 194) |

In some embodiments, the MiHA comprises HA-1. HA-1 is a peptide antigen having a sequence of VL[H/R]DDLLEA (SEQ ID NO: 105), and is derived from the Rho GTPase activating protein 45 (HA-1) gene.

Exemplary ligand binding domains that selectively bind to HA-1 variant H peptide (VLHDDLLEA (SEQ ID NO: 195)) are shown in Table 12 below. TCR alpha and TCR beta sequences are separated by a P2A self-cleaving polypeptide of sequence ATNFSLLKQAGDVEENPGP (SEQ ID NO: 196) with an N terminal GSG linker.

TABLE 12

Ftcr HA-1(H) Inhibitory receptor Sequences

| | |
|---|---|
| C-003754 KP7 HA-1H TCRalpha T48C P2A KP7 HA-1H TCRbeta S57C:<br>MVKIRQFLLAILWLQLSCVSAAKNEVEQSPQNLTAQEGEFITINCS<br>YSVGISALHWLQQHPGGGIVSLFMLSSGKKKHGRLIATINIQEKH<br>SSLHITASHPRDSAVYICAVRSVSGAGSYQLTFGKGTKLSVIPNIQ<br>NPDPAVYQLRDSKSSDKSVCLFTDFDSQTNVSQSKDSDVYITDKC<br>VLDMRSMDFKSNSAVAWSNKSDFACANAFNNSIIPEDTFFPSPES<br>SCDVKLVEKSFETDTNLNFQNLSVIGFRILLLKVAGFNLLMTLRL<br>WSSGSGATNFSLLKQAGDVEENPGPMGTSLLCWMALCLLGADH<br>ADTGVSQNPRHKITKRGQNVTFRCDPISEHNRLYWYRQTLGQGP<br>EFLTYFQNEAQLEKSRLLSDRFSAERPKGSFSTLEIQRTEQGDSAM<br>YLCASSIDSFNEQFFGPGTRLTVLEDLKNVFPPEVAVFEPSEAEISH<br>TQKATLVCLATGFYPDHVELSWWVNGKEVHSGVCTDPQPLKEQ<br>PALNDSRYCLSSRLRVSATFWQNPRNHFRCQVQFYGLSENDEWT | C-003754 KP7 HA-1H TCRalpha T48C P2A KP7 HA-1H TCRbeta S57C DNA Sequence: SEQ ID NO: 194 |

TABLE 12-continued

Ftcr HA-1(H) Inhibitory receptor Sequences

| | |
|---|---|
| QDRAKPVTQIVSAEAWGRADCGFTSESYQQGVLSATILYEILLGK<br>ATLYAVLVSALVLMAMVKRKDSRG (SEQ ID NO: 197) | |
| HA-1H TCR alpha:<br>MVKIRQFLLAILWLQLSCVSAAKNEVEQSPQNLTAQEGEFITINCS<br>YSVGISALHWLQQHPGGGIVSLFMLSSGKKKHGRLIATINIQEKH<br>SSLHITASHPRDSAVYICAVRSVSGAGSYQLTFGKGTKLSVIPNIQ<br>NPDPAVYQLRDSKSSDKSVCLFTDFDSQTNVSQSKDSDVYITDKC<br>VLDMRSMDFKSNSAVAWSNKSDFACANAFNNSIIPEDTFFPSPES<br>SCDVKLVEKSFETDTNLNFQNLS (SEQ ID: 198) | HA-1H<br>TCR alpha<br>DNA<br>Sequence:<br>SEQ ID<br>NO: 201 |
| HA-1(H) TCRbeta:<br>MGTSLLCWMALCLLGADHADTGVSQNPRHKITKRGQNVTFRCD<br>PISEHNRLYWYRQTLGQGPEFLTYFQNEAQLEKSRLLSDRFSAER<br>PKGSFSTLEIQRTEQGDSAMYLCASSIDSFNEQFFGPGTRLTVLED<br>LKNVFPPEVAVFEPSEAEISHTQKATLVCLATGFYPDHVELSWW<br>VNGKEVHSGVCTDPQPLKEQPALNDSRYCLSSRLRVSATFWQNP<br>RNHFRCQVQFYGLSENDEWTQDRAKPVTQIVSAEAWGRADCGF<br>TSESYQQGVLS (SEQ ID NO: 199) | HA-1H<br>TCRbeta<br>DNA<br>Sequence:<br>SEQ ID<br>NO: 202 |
| C-003755 KP7 HA-1H FTCRalpha LIR1 TICD:<br>MVKIRQFLLAILWLQLSCVSAAKNEVEQSPQNLTAQEGEFITINCS<br>YSVGISALHWLQQHPGGGIVSLFMLSSGKKKHGRLIATINIQEKH<br>SSLHITASHPRDSAVYICAVRSVSGAGSYQLTFGKGTKLSVIPNIQ<br>NPDPAVYQLRDSKSSDKSVCLFTDFDSQTNVSQSKDSDVYITDKC<br>VLDMRSMDFKSNSAVAWSNKSDFACANAFNNSIIPEDTFFPSPES<br>SCDVKLVEKSFETDTNLNFQNLSVVIGILVAVILLLLLLLLLFLILR<br>HRRQGKHWTSTQRKADFQHPAGAVGPEPTDRGLQWRSSPAADA<br>QEENLYAAVKHTQPEDGVEMDTRSPHDEDPQAVTYAEVKHSRP<br>RREMASPPSPLSGEFLDTKDRQAEEDRQMDTEAAASEAPQDVTY<br>AQLHSLTLRREATEPPPSQEGPSPAVPSIYATLAIH (SEQ ID NO:<br>200) | C-003755<br>KP7 HA-1H<br>FTCRalpha<br>LIR1 TICD<br>DNA<br>Sequence:<br>SEQ ID<br>NO: 196 |
| C-003756 KP7 HA-1H FTCRbeta LIR1 TICD:<br>MGTSLLCWMALCLLGADHADTGVSQNPRHKITKRGQNVTFRCD<br>PISEHNRLYWYRQTLGQGPEFLTYFQNEAQLEKSRLLSDRFSAER<br>PKGSFSTLEIQRTEQGDSAMYLCASSIDSFNEQFFGPGTRLTVLED<br>LKNVFPPEVAVFEPSEAEISHTQKATLVCLATGFYPDHVELSWW<br>VNGKEVHSGVCTDPQPLKEQPALNDSRYCLSSRLRVSATFWQNP<br>RNHFRCQVQFYGLSENDEWTQDRAKPVTQIVSAEAWGRADCGF<br>TSESYQQGVLSVVIGILVAVILLLLLLLLLFLILRHRRQGKHWTST<br>QRKADFQHPAGAVGPEPTDRGLQWRSSPAADAQEENLYAAVKH<br>TQPEDGVEMDTRSPHDEDPQAVTYAEVKHSRPRREMASPPSPLS<br>GEFLDTKDRQAEEDRQMDTEAAASEAPQDVTYAQLHSLTLRRE<br>ATEPPPSQEGPSPAVPSIYATLAIH (SEQ ID NO: 201) | C-003756<br>KP7 HA-1H<br>FTCRbeta<br>LIR1 TICD<br>DNA<br>Sequence:<br>SEQ ID<br>NO: 198 |

In some embodiments, the second, inhibitory ligand comprises HA-1(H). In some embodiments, the second, inhibitory ligand binding is isolated or derived from a TCR. In some embodiments, the second, inhibitory ligand binding domain comprises TCR alpha and TCR beta variable domains. In some embodiments, the TCR alpha and TCR beta variable domains are separated by a self-cleaving polypeptide sequence. In some embodiments, the TCR alpha and TCR beta variable domains separated by a self-cleaving polypeptide sequence comprise SEQ ID NO: 197. In some embodiments, the TCR alpha and TCR beta variable domains separated by a self-cleaving polypeptide sequence comprise SEQ ID NO: 197, or a sequence having at least 90%, at least 95%, or at least 99% identity thereto. In some embodiments, the TCR alpha and TCR beta variable domains are encoded by a sequence of SEQ ID NO: 202, or a sequence having at least 80% identity, at least 90%, at least 95%, or at least 99% identity thereto. In some embodiments, the TCR alpha variable domain comprises SEQ ID NO: 198 or a sequence having at least 90%, at least 95%, or at least 99% identity thereto. In some embodiments, the TCR beta variable domain comprises SEQ ID NO: 199 or a sequence having at least 90%, at least 95%, or at least 99% identity thereto.

Loss of Y Chromosome Antigens

In some embodiments, the second, inhibitor ligand comprises a Y chromosome gene, i.e. peptide encoded by a gene on the Y chromosome. In some embodiments, the second, inhibitor ligand comprises a peptide encoded by a Y chromosome gene that is lost in target cells through loss of Y chromosome (LoY). For example, about a third of the characterized MiHAs come from the Y chromosome. The Y chromosome contains over 200 protein coding genes, all of which are envisaged as within the scope of the instant disclosure.

As used herein, "loss of Y", or "LoY" refers a genetic change that occurs at high frequency in tumors whereby one copy of part or all of the Y chromosome is deleted, leading to a loss of Y chromosome encoded gene(s).

Loss of Y chromosome is known to occur in certain cancers. For example, there is a reported 40% somatic loss of Y chromosome in renal clear cell cancers (Arseneault et al., Sci. Rep. 7: 44876 (2017)). Similarly, clonal loss of the Y chromosome was reported in 5 out of 31 in male breast cancer subjects (Wong et al., Oncotarget 6(42):44927-40 (2015)). Loss of the Y chromosome in tumors from male patients has been described as a "consistent feature" of head and neck cancer patients (el-Naggar et al., Am J Clin Pathol 105(1):102-8 (1996)). Further, Y chromosome loss was associated with X chromosome disomy in four of seven male patients with gastric cancer (Saal et al., Virchows Arch B Cell Pathol (1993)). Thus, Y chromosome genes can be lost in a variety of cancers, and can be used as inhibitor ligands with the engineered receptors of the instant disclosure targeting cancer cells.

Chimeric Antigen Receptors (CARs)

In some embodiments, the either the first or the second engineered receptor is a chimeric antigen receptor (CAR). In some embodiments, the first and second engineered receptors are chimeric antigen receptors. All CAR architectures are envisaged as within the scope of the instant disclosure.

Extracellular Domains

In some embodiments, the extracellular domain of the CAR comprises the antigen binding domains described supra.

Hinge Region

In some embodiments, the CARs of the present disclosure comprise an extracellular hinge region. Incorporation of a hinge region can affect cytokine production from CAR-T cells and improve expansion of CAR-T cells in vivo. Exemplary hinges can be isolated or derived from IgG, CD28 or CD8, among others, for example IgG1. Exemplary hinge domains are provided in Table 13.

In some embodiments, the hinge is isolated or derived from CD8α or CD28. In some embodiments, the CD8α hinge comprises an amino acid sequence having at least 80% identity, at least 90% identity, at least 95% identity, at least 99% identity or is identical to a sequence of TTTPAPRPPT-PAPTIASQPLSLRPEACRPAAGGAVHTRGLDFACD (SEQ ID NO: 219). In some embodiments, the CD8α hinge comprises SEQ ID NO: 219. In some embodiments, the CD8α hinge consists essentially of SEQ ID NO: 219. In some embodiments, the CD8α hinge is encoded by a nucleotide sequence having at least 80% identity, at least 90% identity, at least 95% identity, at least 99% identity or is identical to a sequence of

```
                                      (SEQ ID NO: 220)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGAT.
```

In some embodiments, the CD8α hinge is encoded by SEQ ID NO: 220.

In some embodiments, the CD28 hinge comprises an amino acid sequence having at least 80% identity, at least 90% identity, at least 95% identity, at least 99% identity or is identical to a sequence of CTIEVMYPPPYLD-NEKSNGTIIHVKGKHLCPSPLFPGPSKP (SEQ ID NO: 221). In some embodiments, the CD28 hinge comprises or consists essentially of SEQ ID NO: 221. In some embodiments, the CD28 hinge is encoded by a nucleotide sequence having at least 80% identity, at least 90% identity, at least 95% identity, at least 99% identity or is identical to a sequence of:

```
                                      (SEQ ID NO: 222)
TGTACCATTGAAGTTATGTATCCTCCTCCTTACCTAGACAATGAGAAGAG

CAATGGAACCATTATCCATGTGAAAGGGAAACACCTTTGTCCAAGTCCCC

TATTTCCCGGACCTTCTAAGCCC.
```

In some embodiments, the CD28 hinge is encoded by SEQ ID NO: 222.

In some embodiments, the activator receptor comprises a hinge sequence isolated or derived from CD8, CD28, IgG1, or IgG4, or a synthetic hinge.

TABLE 13

Hinge Domain Sequences and Their Use in HER2 CAR Constructs

| CAR Construct | Hinge | Protein Sequence | DNA Sequence |
|---|---|---|---|
| CT-292 | CD8 | FVPVFLPAKPTT TPAPRPPTPAPTI ASQPLSLRPEAC RPAAGGAVHTR GLDFACD (SEQ ID NO 223) | TTCGTGCCGGTCTTCCTGCCAGCGAAGCCCA CCACGACGCCAGCGCCGCGACCACCAACAC CGGCGCCCACCATCGCGTCGCAGCCCCTGTC CCTGCGCCCAGAGGCGTGCCGGCCAGCGGC GGGGGGCGCAGTGCACACGAGGGGCTGGA CTTCGCCTGTGAT (SEQ ID NO 224) |
| CT-297 | CD28 | IEVMYPPPYLDN EKSNGTIIHVKG KHLCPSPLFPGP SKP (SEQ ID NO 225) | ATTGAAGTTATGTATCCTCCTCCTTACCTAG ACAATGAGAAGAGCAATGGAACCATTATCC ATGTGAAAGGGAAACACCTTTGTCCAAGTCC CCTATTTCCCGGACCTTCTAAGCCC (SEQ ID NO 226) |
| CT-298 | Short linker | GGGSSGGGSG (SEQ ID NO: 1) | GGTGGCGGTTCTTCCGGCGGTGGCTCTGGT (SEQ ID NO: 227) |
| CT-299 | IgG4 (EQ) | ESKYGPPCPSCP APEFEGGPSVFL FPPKPKDTLMIS RTPEVTCVVVD VSQEDPEVQFN WYVDGVEVHN AKTKPREEQFQ STYRVVSVLTV LHQDWLNGKE YKCKVSNKGLP SSIEKTISKAKG QPREPQVYTLPP | GAGTCCAAATATGGTCCCCCATGCCCATCAT GCCCAGCACCTGAGTTCGAGGGGGGACCAT CAGTCTTCCTGTTCCCCCCAAAACCCAAGGA CACTCTCATGATCTCCCGGACCCCTGAGGTC ACGTGCGTGGTGGTGGACGTGAGCCAGGAA GACCCCGAGGTCCAGTTCAACTGGTACGTGG ATGGCGTGGAGGTGCATAATGCCAAGACAA AGCCGCGGGAGGAGCAGTTCCAGAGCACGT ACCGTGTGGTCAGCGTCCTCACCGTCCTGCA CCAGGACTGGCTGAACGGCAAGGAGTACAA GTGCAAGGTCTCCAACAAAGGCCTCCCGTCC TCCATCGAGAAAACCATCTCCAAAGCCAAA |

TABLE 13-continued

Hinge Domain Sequences and Their Use in HER2 CAR Constructs

| CAR Construct | Hinge | Protein Sequence | DNA Sequence |
|---|---|---|---|
| | | SQEEMTKNQVS LTCLVKGFYPS DIAVEWESNGQ PENNYKTTPPVL DSDGSFFLYSRL TVDKSRWQEGN VFSCSVMHEAL HNHYTQKSLSL SLGK (SEQ ID NO: 228) | GGGCAGCCCCGAGAGCCACAGGTGTACACC CTGCCCCCATCCCAGGAGGAGATGACCAAG AACCAGGTCAGCCTGACCTGCCTGGTCAAA GGCTTCTACCCCAGCGACATCGCCGTGGAGT GGGAGAGCAATGGGCAGCCGGAGAACAACT ACAAGACCACGCCTCCCGTGCTGGACTCCGA CGGCTCCTTCTTCCTCTACAGCAGGCTCACC GTGGACAAGAGCAGGTGGCAGGAGGGGAAT GTCTTCTCATGCTCCGTGATGCATGAGGCTC TGCACAACCACTACACACAGAAGAGCCTCT CCCTGTCTCTGGGTAAA (SEQ ID NO: 229) |
| CT-1094, CT-1095 | IgG1 | AEPKSPDKTHT CPPCPKDPK (SEQ ID NO: 230) | GCCGAGCCCAAGTCCCCTGATAAAACTCAC ACCTGCCCACCCTGTCCTAAGGACCCGAAG (SEQ ID NO: 231) |

In some embodiments, for example those embodiments where the CAR is an activator receptor, the hinge comprises a sequence of SEQ ID NO: 1, 223, 225, 228, or 230, or a sequence having at least 80%, at least 85%, at least 90%, at least 95%, at least 97%, at least 99%, or that is identical thereto. In some embodiments, for example those embodiments where the CAR is an activator receptor, the hinge comprises a sequence of SEQ ID NO: 1, 223, 225, 228, or 230.

Transmembrane Domain

The CARs of the present disclosure can be designed to comprise a transmembrane domain that is fused to the extracellular domain of the CAR. In some embodiments, the transmembrane domain that naturally is associated with one of the domains in the CAR is used. For example, a CAR comprising a CD28 co-stimulatory domain might also use a CD28 transmembrane domain. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions may be isolated or derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In some embodiments of the CARs of the disclosure, the CARs comprise a CD28 transmembrane domain. In some embodiments, the CD28 transmembrane domain comprises an amino acid sequence having at least 80% identity, at least 90% identity, at least 95% identity, at least 99% identity or is identical to a sequence of FWVLVVVGGVLACYSLL-VTVAFIIFWV (SEQ ID NO: 232). In some embodiments, the CD28 transmembrane domain comprises or consists essentially of SEQ ID NO: 232. In some embodiments, the CD28 transmembrane domain is encoded by a nucleotide sequence having at least 80% identity, at least 90% identity, at least 95% identity, at least 99% identity or is identical to a sequence of (SEQ ID NO: 233)
TTCTGGGTGCTGGTCGTTGTGGGCGGCGTGCTGGCCTGCTACAGCCTGCT

GGTGACAGTGGCCTTCATCATCTTTTGGGTG.

In some embodiments, the CD28 transmembrane domain is encoded by SEQ ID NO: 233.

In some embodiments of the CARs of the disclosure, the CARs comprise an IL-2Rbeta transmembrane domain. In some embodiments, the IL-2Rbeta transmembrane domain comprises an amino acid sequence having at least 80% identity, at least 90% identity, at least 95% identity, at least 99% identity or is identical to a sequence of IPWLGHLL-VGLSGAFGFIILVYLLI (SEQ ID NO: 234). In some embodiments, the IL-2Rbeta transmembrane domain comprises or consists essentially of SEQ ID NO: 234. In some embodiments, the IL-2Rbeta transmembrane domain is encoded by a nucleotide sequence having at least 80% identity, at least 90% identity, at least 95% identity, at least 99% identity or is identical to a sequence of (SEQ ID NO: 235)
ATTCCGTGGCTCGGCCACCTCCTCGTGGGCCTCAGCGGGGCTTTTGGCTT

CATCATCTTAGTGTACTTGCTGATC.

In some embodiments, the IL-2Rbeta transmembrane domain is encoded by SEQ ID NO: 235.

In some embodiments, the CAR comprises a transmembrane domain isolated or derived from CD8 or CD28. In some embodiments, the CAR comprises a transmembrane domain sequence in Table 14. In some embodiments, the CAR comprises a transmembrane domain sequence of SEQ ID NO: 232 or SEQ ID NO: 236, or a sequence having at least 80% identity, at least 90% identity, at least 95% identity, at least 99% identity or is identical thereto. In some embodiments, the CAR comprises a transmembrane domain sequence of SEQ ID NO: 232 or SEQ ID NO: 236. In some embodiments, the CAR comprises a transmembrane domain sequence of SEQ ID NO: 561.

TABLE 14

Transmembrane Domain Sequences and their use in HER2 CAR Constructs

| CAR Construct | TM Domain | Protein Sequence | DNA Sequence |
|---|---|---|---|
| CT-298, CT-299 | CD8 | IYIWAPLAGTCGVL LLSLVIT (SEQ ID NO: 236) | ATCTACATCTGGGCGCCCTTGGCCG GGACTTGTGGGGTCCTTCTCCTGTC ACTGGTTATCACC (SEQ ID NO: 237) |
| CT-292 | CD8 | IYIWAPLAGTCGVL LLSLVITLYCNHRN (SEQ ID NO: 561) | ATCTACATCTGGGCGCCCTTGGCCG GGACTTGTGGGGTCCTTCTCCTGTC ACTGGTTATCACCCTTTACTGCAAC CACAGGAAC (SEQ ID NO: 562) |
| CT-297, CT-1094, CT1095 | CD28 | FWVLVVVGGVLAC YSLLVTVAFIIFWV (SEQ ID NO: 232) | TTCTGGGTGCTGGTCGTTGTGGGCG GCGTGCTGGCCTGCTACAGCCTGCT GGTGACAGTGGCCTTCATCATCTTT TGGGTG (SEQ ID NO: 233) |

Cytoplasmic Domain

The disclosure provides an activator receptor comprising an extracellular ligand binding domain specific to an erb-b2 receptor tyrosine kinase 2 (HER2) antigen. In some embodiments, the activator receptor is a T cell receptor (TCR) or a chimeric antigen receptor (CAR). In some embodiments, the CAR comprises an intracellular domain isolated or derived from CD28, 4-1BB or CD3z, or a combination thereof.

The cytoplasmic domain or otherwise the intracellular signaling domain of the CARs of the instant invention is responsible for activation of at least one of the normal effector functions of the immune cell in which the CAR has been placed. The term "effector function" refers to a specialized function of a cell. Effector functions of a regulatory T cell, for example, include the suppression or downregulation of induction or proliferation of effector T cells. Thus the term "intracellular signaling domain" refers to the portion of a protein which transduces the effector function signal and directs the cell to perform a specialized function. While usually the entire intracellular signaling domain can be employed, in many cases it is not necessary to use the entire domain. To the extent that a truncated portion of the intracellular signaling domain is used, such truncated portion may be used in place of the intact chain as long as it transduces the effector function signal. In some cases, multiple intracellular domains can be combined to achieve the desired functions of the CAR-T cells of the instant disclosure. The term intracellular signaling domain is thus meant to include any truncated portion of one or more intracellular signaling domains sufficient to transduce the effector function signal.

Examples of intracellular signaling domains for use in the CARs of the instant disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Accordingly, the intracellular domain of CARs of the instant disclosure comprises at least one cytoplasmic activation domain. In some embodiments, the intracellular activation domain ensures that there is T-cell receptor (TCR) signaling necessary to activate the effector functions of the CAR T-cell. In some embodiments, the at least one cytoplasmic activation is a CD247 molecule (CD3ζ) activation domain, a stimulatory killer immunoglobulin-like receptor (KIR) KIR2DS2 activation domain, or a DNAX-activating protein of 12 kDa (DAP12) activation domain. In some embodiments, the CD3ζ activation domain comprises an amino acid sequence having at least 80% identity, at least 90% identity, at least 95% identity, at least 99% identity or is identical to a sequence of (SEQ ID NO: 238)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

In some embodiments, the CD3ζ activation domain comprises or consists essentially of SEQ ID NO: 238. In some embodiments, the CD3ζ activation domain is encoded by a nucleotide sequence having at least 80% identity, at least 90% identity, at least 95% identity, at least 99% identity or is identical to a sequence of AGAGTGAAGTTCAGCAG-GAGCGCAGACGCCCCCGCGTA-CAAGCAGGGCCAGAA CCAGCTCTATAACGAGCT-CAATCTAGGACGAAGAGAGGAGTACGATGTTTTG GA CAAGCGTAGAGGCCGGGACCCT-GAGATGGGGGGAAAGCCGAGAAGGAAGAACC CTCAGGAAGGCCTGTACAATGAACTGCAGAAAGA-TAAGATGGCGGAGGCCTACA GTGAGATTGGGAT-GAAAGGCGAGCGCCGGAGGGGCAAGGGGCAC-GATGGCCTT TACCAGGGACTCAGTACAGCCACCAAGGACACC-TACGACGCCCTTCACATGCAG GCCCTGCCCCCTCGC (SEQ ID NO: 239). In some embodiments, the CD3ζ activation domain is encoded by SEQ ID NO: 239.

It is known that signals generated through the TCR alone are often insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. In some embodiments, the ITAM contains a tyrosine separated from a leucine or an isoleucine by any two other amino acids (YxxL) (SEQ ID NO: 240).

In some embodiments, the cytoplasmic domain contains 1, 2, or 3 ITAMs. In some embodiments, the cytoplasmic domain contains 1 ITAM. In some embodiments, the cytoplasmic domain contains 2 ITAMs. In some embodiments, the cytoplasmic domain contains 3 ITAMs. In some embodiments, the cytoplasmic domain contains 4 ITAMs. In some embodiments, the cytoplasmic domain contains 5 ITAMs.

In some embodiments, the cytoplasmic domain is a CD3ζ activation domain. In some embodiments, CD3ζ activation domain comprises a single ITAM. In some embodiments, CD3ζ activation domain comprises two ITAMs. In some embodiments, CD3ζ activation domain comprises three ITAMs.

In some embodiments, the CD3ζ activation domain comprising a single ITAM comprises an amino acid sequence having at least 80% identity, at least 90% identity, at least 95% identity, at least 99% identity or is identical to a sequence of (SEQ ID NO: 241)
RVKFSRSADAPAYQQGQNQLYNELNLGRREEYDVLHMQALPPR.

In some embodiments, the CD3ζ activation domain comprises SEQ ID NO: 241. In some embodiments, the CD3ζ activation domain comprising a single ITAM consists essentially of an amino acid sequence of (SEQ ID NO: 241)
RVKFSRSADAPAYQQGQNQLYNELNLGRREEYDVLHMQALPPR.

In some embodiments, the CD3ζ activation domain comprising a single ITAM is encoded by a nucleotide sequence having at least 80% identity, at least 90% identity, at least 95% identity, at least 99% identity or is identical to a sequence of AGAGTGAAGTTCAGCAGGAGCGCAGACGCCCCCGCGTACCAGCAGGGCCAGAACCAGCTCTATAACGAGCTCAATCTAGGACGAAGAGAGGAGTACGATGTTTTGCACATGCAGGCCCTGCCCCCTCGC (SEQ ID NO: 242). In some embodiments, the CD3ζ activation domain is encoded by SEQ ID NO: 242.

Further examples of ITAM containing primary cytoplasmic signaling sequences that can be used in the CARs of the instant disclosure include those derived from TCRζ, FcRγ, FcRβ, CD3γ, CD3δ, CD3ε, CD3ζ, CD5, CD22, CD79a, CD79b, and CD66d. It is particularly preferred that cytoplasmic signaling molecule in the CAR of the instant invention comprises a cytoplasmic signaling sequence derived from CD3.

Co-Stimulatory Domain

In some embodiments, the cytoplasmic domain of the CAR can be designed to comprise the CD3ζ signaling domain by itself or combined with any other desired cytoplasmic domain(s) useful in the context of the CAR of the instant disclosure. For example, the cytoplasmic domain of the CAR can comprise a CD3ζ chain portion and a co-stimulatory domain. The co-stimulatory domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include the co-stimulatory domain is selected from the group consisting of IL-2Rβ, Fc Receptor gamma (FcRγ), Fc Receptor beta (FcRβ), CD3g molecule gamma (CD3γ), CD3δ, CD3ε, CD5 molecule (CD5), CD22 molecule (CD22), CD79a molecule (CD79a), CD79b molecule (CD79b), carcinoembryonic antigen related cell adhesion molecule 3 (CD66d), CD27 molecule (CD27), CD28 molecule (CD28), TNF receptor superfamily member 9 (4-1BB), TNF receptor superfamily member 4 (OX40), TNF receptor superfamily member 8 (CD30), CD40 molecule (CD40), programmed cell death 1 (PD-1), inducible T cell costimulatory (ICOS), lymphocyte function-associated antigen-1 (LFA-1), CD2 molecule (CD2), CD7 molecule (CD7), TNF superfamily member 14 (LIGHT), killer cell lectin like receptor C2 (NKG2C) and CD276 molecule (B7-H3) c-stimulatory domains, or functional fragments thereof.

The cytoplasmic domains within the cytoplasmic signaling portion of the CARs of the instant disclosure may be linked to each other in a random or specified order. Optionally, a short oligo- or polypeptide linker, for example between 2 and 10 amino acids in length may form the linkage. A glycine-serine doublet provides an example of a suitable linker.

In some embodiments, the intracellular domains of CARs of the instant disclosure comprise at least one co-stimulatory domain. In some embodiments, the co-stimulatory domain is isolated or derived from CD28. In some embodiments, the CD28 co-stimulatory domain comprises an amino acid sequence having at least 80% identity, at least 90% identity, at least 95% identity, at least 99% identity or is identical to a sequence of (SEQ ID NO: 243)
RSKRSRLLHSDYMNMTPRRPGPTRKHYQPYAPPRDFAAYRS.

In some embodiments, the CD28 co-stimulatory domain comprises or consists essentially of SEQ ID NO: 243. In some embodiments, the CD28 co-stimulatory domain is encoded by a nucleotide sequence having at least 80% identity, at least 90% identity, at least 95% identity, at least 99% identity or is identical to a sequence of AGGAGCAAGCGGAGCAGACTGCTGCACAGCGACTACATGAACATGACCCCCCGG AGGCCTGGCCCCACCCGGAAGCACTACCAGCCCTACGCCCCTCCCAGGGATTTCGCCGCCTACCGGAGC (SEQ ID NO: 244). In some embodiments, the CD28 co-stimulatory domain is encoded by SEQ ID NO: 44.

In some embodiments, the intracellular domain of the CARs of the instant disclosure comprises an interleukin-2 receptor beta-chain (IL-2Rbeta or IL-2R-beta) cytoplasmic domain. In some embodiments, the IL-2Rbeta domain is truncated. In some embodiments, the IL-2Rbeta cytoplasmic domain comprises one or more STAT5-recruitment motifs. In some embodiments, the CAR comprises one or more STAT5-recruitment motifs outside the IL-2Rbeta cytoplasmic domain.

In some embodiments, the IL-2-Rbeta intracellular domain comprises an amino acid sequence having at least 80% identity, at least 90% identity, at least 95% identity, at least 99% identity or is identical to a sequence of NCRNTGPWLKKVLKCNTPDPSKFF-SQLSSEHGGDVQKWLSSPFPSSSFSPGGLAPEIS PLEVLERDKVTQLLPLNTDAYLSLQELQGQDPTHLV (SEQ ID NO: 245). In some embodiments, the IL2R-beta intracellular domain comprises or consists essentially of SEQ ID NO: 245. In some embodiments, the IL-2R-beta intracellular domain is encoded by a nucleotide sequence having at least 80% identity, at least 90% identity, at least 95% identity, at least 99% identity or is identical to a sequence of AACTGCAGGAACACCGGGCCATGGCTGAAGAAGGTCCTGAAGTGTAACACCCCAGACCCCTCGAAGTTCTTTTCCCAGCTGAGCTCAGAGCATGGAGGCGACGTCCAGAAGTGGCTCTCTTCGCCCTTCCCCTCATCGTCCTTCAGCCCTGGCGGCCTGGCACCTGAGATCTCGCCACTAGAAGTGCTGGAGAGGGACAAGGTGACGCAGCTGCTCCCCCTGAACACTGATGCCTACTTGTCTCTCCAAGAACTCCAGGGTCAGGACCCAACTCACTTGGTG (SEQ ID NO: 246). In some embodiments, the IL-2R-beta intracellular domain is encoded by SEQ ID NO: 246.

In an embodiment, the IL-2R-beta cytoplasmic domain comprises one or more STAT5-recruitment motifs. Exemplary STAT5-recruitment motifs are provided by Passerini et al. (2008) STAT5-signaling cytokines regulate the expression of FOXP3 in CD4+CD25+ regulatory T cells and CD4+CD25+ effector T cells. International Immunology, Vol. 20, No. 3, pp. 421-431, and by Kagoya et al. (2018) A novel chimeric antigen receptor containing a JAK-STAT signaling domain mediates superior antitumor effects. Nature Medicine doi:10.1038/nm.4478.

In some embodiments, the STAT5-recruitment motif(s) consists of the sequence Tyr-Leu-Ser-Leu (SEQ ID NO: 247).

In some embodiments, the CAR comprises an intracellular domain isolated or derived from CD28, 4-1BB and/or CD3z, or a combination thereof. Exemplary domains derived from CD28, 4-1BB and/or CD3z are shown in Table 15 below. In some embodiments, the CAR comprises an intracellular domain comprising a sequence of SEQ ID NOS: 248, 250 or 252, or a sequence having at least 80%, at least 85%, at least 90%, at least 95%, at least 97%, at least 99%, or that is identical thereto. In some embodiments, the CAR comprises an intracellular domain comprising a sequence of SEQ ID NOS: 248, 250 or 252. In some embodiments, the CAR intracellular domain is encoded by the sequence set forth in any one of SEQ ID NOs: 249, 251, 253, or 21804.

TABLE 15

Intracellular Domain Sequences and their use in HER2 CAR Constructs

| CAR Construct | IC Domain | Protein Sequence | DNA Sequence |
|---|---|---|---|
| CT-292 | CD28-4-1BB-CD3z | RSKRSRLLHS DYMNMTPRR PGPTRKHYQP YAPPRDFAA YRSRFSVVKR GRKKLLYIFK QPFMRPVQTT QEEDGCSCRF PEEEEGGCEL RVKFSRSADA PAYQQGQNQ LYNELNLGR REEYDVLDK RRGRDPEMG GKPRRKNPQ EGLYNELQK DKMAEAYSEI GMKGERRRG KGHDGLYQG LSTATKDTYD ALHMQALPP R (SEQ ID NO: 248) | AGGAGTAAGAGGAGCAGGCTCCTGCAC AGTGACTACATGAACATGACTCCCCGC CGCCCCGGGCCCACCCGCAAGCATTAC CAGCCCTATGCCCCACCACGCGACTTCG CAGCCTATCGCTCCCGTTTCTCTGTTGT TAAACGGGGCAGAAAGAAGCTCCTGTA TATATTCAAACAACCATTTATGAGACCA GTACAAACTACTCAAGAGGAAGATGGC TGTAGCTGCCGATTTCCAGAAGAAGAA GAAGGAGGATGTGAACTGAGAGTGAAG TTCAGCAGGAGCGCAGACGCCCCCGCG TACCAGCAGGGCCAGAACCAGCTCTAT AACGAGCTCAATCTAGGACGAAGAGAG GAGTACGATGTTTTGGACAAGAGACGT GGCCGGGACCCTGAGATGGGGGGAAAG CCGAGAAGGAAGAACCCTCAGGAAGGC CTGTACAATGAACTGCAGAAAGATAAG ATGGCGGAGGCCTACAGTGAGATTGGG ATGAAAGGCGAGCGCCGGAGGGGCAA GGGGCACGATGGCCTTTACCAGGGTCT CAGTACAGCCACCAAGGACACCTACGA CGCCCTTCACATGCAGGCCCTGCCCCCT CGCTAG (SEQ ID NO: 249) |
| CT-297, CT-1094, CT-1095 | CD28-CD3z | RSKRSRLLHS DYMNMTPRR PGPTRKHYQP YAPPRDFAA YRSRVKFSRS ADAPAYKQG QNQLYNELN LGRREEYDV LDKRRGRDP EMGGKPRRK NPQEGLYNEL QKDKMAEAY SEIGMKGERR RGKGHDGLY QGLSTATKDT YDALHMQAL PPR (SEQ ID NO: 250) | AGGAGCAAGCGGAGCAGACTGCTGCAC AGCGACTACATGAACATGACCCCCCGG AGGCCTGGCCCCACCCGGAAGCACTAC CAGCCCTACGCCCCTCCCAGGGATTTCG CCGCCTACCGGAGCAGAGTGAAGTTCA GCAGGAGCGCAGACGCCCCCGCGTACA AGCAGGGCCAGAACCAGCTCTATAACG AGCTCAATCTAGGACGAAGAGAGGAGT ACGATGTTTTGGACAAGCGTAGAGGCC GGGACCCTGAGATGGGGGGAAAGCCGA GAAGGAAGAACCCTCAGGAAGGCCTGT ACAATGAACTGCAGAAAGATAAGATGG CGGAGGCCTACAGTGAGATTGGGATGA AAGGCGAGCGCCGGAGGGGCAAGGGG CACGATGGCCTTTACCAGGGACTCAGT ACAGCCACCAAGGACACCTACGACGCC CTTCACATGCAGGCCCTGCCCCCTCGCT AG (SEQ ID NO: 251) |
| CT-298, CT-299 | 4-1BB-CD3z | KRGRKKLLYI FKQPFMRPV | AAACGGGGCAGAAAGAAGCTCCTGTAT ATATTCAAACAACCATTTATGAGACCA |

TABLE 15-continued

Intracellular Domain Sequences and their use in HER2 CAR Constructs

| CAR Construct IC Domain | Protein Sequence | DNA Sequence |
|---|---|---|
| | QTTQEEDGCS | GTACAAACTACTCAAGAGGAAGATGGC |
| | CRFPEEEEGG | TGTAGCTGCCGATTTCCAGAAGAAGAA |
| | CELGGGRVK | GAAGGAGGATGTGAACTGGGCGGTGGC |
| | FSRSADAPAY | AGAGTGAAGTTCAGCAGGAGCGCAGAC |
| | QQGQNQLYN | GCCCCCGCGTACCAGCAGGGCCAGAAC |
| | ELNLGRREEY | CAGCTCTATAACGAGCTCAATCTAGGA |
| | DVLDKRRGR | CGAAGAGAGGAGTACGATGTTTTGGAC |
| | DPEMGGKPR | AAGAGACGTGGCCGGGACCCTGAGATG |
| | RKNPQEGLY | GGGGGAAAGCCGAGAAGGAAGAACCC |
| | NELQKDKMA | TCAGGAAGGCCTGTACAATGAACTGCA |
| | EAYSEIGMKG | GAAAGATAAGATGGCGGAGGCCTACAG |
| | ERRRGKGHD | TGAGATTGGGATGAAAGGCGAGCGCCG |
| | GLYQGLSTAT | GAGGGGCAAGGGGCACGATGGCCTTTA |
| | KDTYDALHM | CCAGGGTCTCAGTACAGCCACCAAGGA |
| | QALPPR (SEQ ID NO: 252) | CACCTACGACGCCCTTCACATGCAGGC CCTGCCCCCTCGCTAG (SEQ ID NO: 253) |

T Cell Receptors (TCRs)

The disclosure provides a first, activator receptor and immune cells comprising same. In some embodiments, the first receptor is a T cell receptor (TCR). Exemplary TCRs comprising intracellular domains for use in the instant disclosure are described in PCT/US2020/045250 filed on Sep. 6, 2020, the contents of which are incorporated herein by reference.

As used herein, a "TCR", sometimes also called a "TCR complex" or "TCR/CD3 complex" refers to a protein complex comprising a TCR alpha chain, a TCR beta chain, and one or more of the invariant CD3 chains (zeta, gamma, delta and epsilon), sometimes referred to as subunits. The TCR alpha and beta chains can be disulfide-linked to function as a heterodimer to bind to peptide-MHC complexes. Once the TCR alpha/beta heterodimer engages peptide-MHC, conformational changes in the TCR complex in the associated invariant CD3 subunits are induced, which leads to their phosphorylation and association with downstream proteins, thereby transducing a primary stimulatory signal. In an exemplary TCR complex, the TCR alpha and TCR beta polypeptides form a heterodimer, CD3 epsilon and CD3 delta form a heterodimer, CD3 epsilon and CD3 gamma form a heterodimer, and two CD3 zeta form a homodimer.

Any suitable ligand binding domain may be fused to an extracellular domain, hinge domain or transmembrane of the TCRs described herein. For example, the ligand binding domain can be an antigen binding domain of an antibody or TCR, or comprise an antibody fragment, a Vβ only domain, a linear antibody, a single-chain variable fragment (scFv), or a single domain antibody (sdAb).

In some embodiments, the ligand binding domain is fused to one or more extracellular domains or transmembrane domains of one or more TCR subunits. The TCR subunit can be TCR alpha, TCR beta, CD3 delta, CD3 epsilon, CD3 gamma or CD3 zeta. For example, the ligand binding domain can be fused to TCR alpha, or TCR beta, or portions of the ligand binding can be fused to two subunits, for example portions of the ligand binding domain can be fused to both TCR alpha and TCR beta.

TCR subunits include TCR alpha, TCR beta, CD3 zeta, CD3 delta, CD3 gamma and CD3 epsilon. Any one or more of TCR alpha, TCR beta chain, CD3 gamma, CD3 delta, CD3 epsilon, or CD3 zeta, or fragments or derivative thereof, can be fused to one or more domains capable of providing a stimulatory signal of the disclosure, thereby enhancing TCR function and activity.

TCR transmembrane domains isolated or derived from any source are envisaged as within the scope of the disclosure. The transmembrane domain may be derived either from a natural or from a recombinant source. Where the source is natural, the domain may be derived from any membrane-bound or transmembrane protein.

In some embodiments, the transmembrane domain is capable of signaling to the intracellular domain(s) whenever the TCR complex has bound to a target. A transmembrane domain of particular use in this disclosure may include at least the transmembrane region(s) of e.g., the alpha, beta or zeta chain of the TCR, CD3 delta, CD3 epsilon or CD3 gamma, CD28, CD3 epsilon, CD45, CD4, CD5, CD8, CD9, CD16, CD22, CD33, CD37, CD64, CD80, CD86, CD134, CD137, CD154.

In some embodiments, the transmembrane domain can be attached to the extracellular region of a polypeptide of the TCR, e.g., the antigen binding domain of the TCR alpha or beta chain, via a hinge, e.g., a hinge from a human protein. For example, the hinge can be a human immunoglobulin (Ig) hinge, e.g., an IgG4 hinge, or a CD8α hinge. In some embodiments, the hinge is isolated or derived from CD8α or CD28.

In some embodiments, the extracellular ligand binding domain is attached to one or more transmembrane domains of the TCR. In some embodiments, the transmembrane domain comprises a TCR alpha transmembrane domain, a TCR beta transmembrane domain, or both. In some embodiments, the transmembrane comprises a CD3 zeta transmembrane domain.

A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region).

In some embodiments, the transmembrane domain can be selected or modified by amino acid substitution to avoid binding of such domains to the transmembrane domains of the same or different surface membrane proteins, e.g., to minimize interactions with other members of the receptor complex.

When present, the transmembrane domain may be a natural TCR transmembrane domain, a natural transmembrane domain from a heterologous membrane protein, or an artificial transmembrane domain. The transmembrane domain may be a membrane anchor domain. Without limitation, a natural or artificial transmembrane domain may comprise a hydrophobic a-helix of about 20 amino acids, often with positive charges flanking the transmembrane segment. The transmembrane domain may have one transmembrane segment or more than one transmembrane segment. Prediction of transmembrane domains/segments may be made using publicly available prediction tools (e.g. TMHMM, Krogh et al. Journal of Molecular Biology 2001; 305(3):567-580; or TMpred, Hofmann & Stoffel Biol. Chem. Hoppe-Seyler 1993; 347: 166). Non-limiting examples of membrane anchor systems include platelet derived growth factor receptor (PDGFR) transmembrane domain, glycosylphosphatidylinositol (GPI) anchor (added post-translationally to a signal sequence) and the like.

In some embodiments, the transmembrane domain comprises a TCR alpha transmembrane domain. In some embodiments, the TCR alpha transmembrane domain comprises an amino acid sequence having at least 85% identity, at least 90% identity, at least 95% identity, at least 96% identity, at least 97% identity, at least 98% identity, at least 99% identity or is identical to a sequence of: VIGFRILLLKVAGFNLLMTLRLW (SEQ ID NO: 316). In some embodiments, the TCR alpha transmembrane domain comprises, or consists essentially of, SEQ ID NO: 316. In some embodiments, the TCR alpha transmembrane domain is encoded by a sequence of

```
                                          (SEQ ID NO: 317)
GTGATTGGGTTCCGAATCCTCCTCCTGAAAGTGGCCGGGTTTAATCTGCT

CATGACGCTGCGGCTGTGG.
```

In some embodiments, the transmembrane domain comprises a TCR beta transmembrane domain. In some embodiments, the TCR beta transmembrane domain comprises an amino acid sequence having at least 85% identity, at least 90% identity, at least 95% identity, at least 96% identity, at least 97% identity, at least 98% identity, at least 99% identity or is identical to a sequence of: TILYEILLGKATLYAVLVSALVL (SEQ ID NO: 318). In some embodiments, the TCR beta transmembrane domain comprises, or consists essentially of, SEQ ID NO: 318. In some embodiments, the TCR beta transmembrane domain is encoded by a sequence of

```
                                          (SEQ ID NO: 319)
ACCATCCTCTATGAGATCTTGCTAGGGAAGGCCACCTTGTATGCCGTGCT

GGTCAGTGCCCTCGTGCTG.
```

TCRs of the disclosure can comprise one or more intracellular domains. In some embodiments, the intracellular domain comprises one or more domains capable of providing a stimulatory signal to a transmembrane domain. In some embodiments, the intracellular domain comprises a first intracellular domain capable of providing a stimulatory signal and a second intracellular domain capable of providing a stimulatory signal. In other embodiments, the intracellular domain comprises a first, second and third intracellular domain capable of providing a stimulatory signal. The intracellular domains capable of providing a stimulatory signal are selected from the group consisting of a CD28 molecule (CD28) domain, a LCK proto-oncogene, Src family tyrosine kinase (Lck) domain, a TNF receptor superfamily member 9 (4-1BB) domain, a TNF receptor superfamily member 18 (GITR) domain, a CD4 molecule (CD4) domain, a CD8α molecule (CD8a) domain, a FYN proto-oncogene, Src family tyrosine kinase (Fyn) domain, a zeta chain of T cell receptor associated protein kinase 70 (ZAP70) domain, a linker for activation of T cells (LAT) domain, lymphocyte cytosolic protein 2 (SLP76) domain, (TCR) alpha, TCR beta, CD3 delta, CD3 gamma and CD3 epsilon intracellular domains.

In some embodiments, an intracellular domain comprises at least one intracellular signaling domain. An intracellular signaling domain generates a signal that promotes a function a cell, for example an immune effector function of a TCR containing cell, e.g., a TCR-expressing T-cell. In some embodiments, the intracellular domain of the first receptor of the disclosure includes at least one intracellular signaling domain. For example, the intracellular domains of CD3 gamma, delta or epsilon comprise signaling domains.

In some embodiments, the extracellular domain, transmembrane domain and intracellular domain are isolated or derived from the same protein, for example T-cell receptor (TCR) alpha, TCR beta, CD3 delta, CD3 gamma, CD3 epsilon or CD3 zeta.

Examples of intracellular domains for use in activator receptors of the disclosure include the cytoplasmic sequences of the TCR alpha, TCR beta, CD3 zeta, and 4-1BB, and the intracellular signaling co-receptors that act in concert to initiate signal transduction following antigen receptor engagement, as well as any derivative or variant of these sequences and any recombinant sequence that has the same functional capability.

In some embodiments, the intracellular signaling domain comprises a primary intracellular signaling domain. Exemplary primary intracellular signaling domains include those derived from the proteins responsible for primary stimulation, or antigen dependent stimulation.

In some embodiments, the intracellular domain comprises a CD3 delta intracellular domain, a CD3 epsilon intracellular domain, a CD3 gamma intracellular domain, a CD3 zeta intracellular domain, a TCR alpha intracellular domain or a TCR beta intracellular domain.

In some embodiments, the intracellular domain comprises a TCR alpha intracellular domain. In some embodiments, a TCR alpha intracellular domain comprises Ser-Ser. In some embodiments, a TCR alpha intracellular domain is encoded by a sequence of TCCAGC.

In some embodiments, the intracellular domain comprises a TCR beta intracellular domain. In some embodiments, the TCR beta intracellular domain comprises an amino acid sequence having at least 80% identity, at least 90% identity, or is identical to a sequence of: MAMVKRKDSR (SEQ ID NO: 320). In some embodiments, the TCR beta intracellular domain comprises, or consists essentially of SEQ ID NO: 320. In some embodiments, the TCR beta intracellular domain is encoded by a sequence of

```
                                          (SEQ ID NO: 321)
                   ATGGCCATGGTCAAGAGAAAGGATTCCAGA.
```

In some embodiments, the intracellular signaling domain comprises at least one stimulatory intracellular domain. In some embodiments, the intracellular signaling domain comprises a primary intracellular signaling domain, such as a CD3 delta, CD3 gamma and CD3 epsilon intracellular domain, and one additional stimulatory intracellular domain, for example a co-stimulatory domain. In some embodiments, the intracellular signaling domain comprises a primary intracellular signaling domain, such as a CD3 delta, CD3 gamma and CD3 epsilon intracellular domain, and two additional stimulatory intracellular domains.

Exemplary co-stimulatory intracellular signaling domains include those derived from proteins responsible for co-stimulatory signals, or antigen independent stimulation. Co-stimulatory molecules include, but are not limited to an MHC class I molecule, BTLA, a Toll ligand receptor, as well as DAP10, DAP12, CD30, LIGHT, OX40, CD2, CD27, CDS, ICAM-1, LFA-1 (CD11a/CD18) 4-1BB (CD137, TNF receptor superfamily member 9), and CD28 molecule (CD28). A co-stimulatory protein can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, a ligand that specifically binds with CD83, CD4, and the like. The co-stimulatory domain can comprise the entire intracellular portion, or the entire native intracellular signaling domain, of the molecule from which it is derived, or a functional variant thereof.

In some embodiments, the stimulatory domain comprises a co-stimulatory domain. In some embodiments, the co-stimulatory domain comprises a CD28 or 4-1BB co-stimulatory domain. CD28 and 4-1BB are well characterized co-stimulatory molecules required for full T cell activation and known to enhance T cell effector function. For example, CD28 and 4-1BB have been utilized in chimeric antigen receptors (CARs) to boost cytokine release, cytolytic function, and persistence over the first-generation CAR containing only the CD3 zeta signaling domain. Likewise, inclusion of co-stimulatory domains, for example CD28 and 4-1BB domains, in TCRs can increase T cell effector function and specifically allow co-stimulation in the absence of co-stimulatory ligand, which is typically down-regulated on the surface of tumor cells. In some embodiments, the stimulatory domain comprises a CD28 intracellular domain or a 4-1BB intracellular domain.

Inhibitory Receptors

The disclosure provides a second receptor, comprising an extracellular ligand binding domain specific to a non-target antigen that has been lost in a cancer cell, such as an allelic variant of a gene. The non-target allelic variant can be lost in the cancer cell through any mechanism, such as, without limitation, epigenetic changes that effect non-target allelic variant expression, mutations to the gene encoding the non-target allelic variant, disruption of cellular signaling that regulates expression of the non-target allelic variant, chromosome loss, partial or complete deletion of the genomic locus, gene silencing through modification of nucleic acids or heterochromatin, or loss of expression through other mechanisms. In variations of the compositions and methods disclosed herein, the cells or subject treated may exhibit a loss of expression of the non-target allelic variant because of non-genetic changes. Accordingly the disclosure provides compositions and methods for killing cells and/or treating subject lacking expression of the non-target antigen from any cause, including but not limited to, loss of heterozygosity.

Exemplary inhibitory receptors are described in PCT/US2020/045228 filed on Sep. 6, 2020, PCT/US2020/064607, filed on Dec. 11, 2020, PCT/US2021/029907, filed on Apr. 29, 2021 and PCT/US2020/059856 filed on Nov. 10, 2020, the contents of each of which are incorporated herein by reference.

The term "inhibitory chimeric antigen receptor" or "inhibitory receptor" as used herein refers to an antigen-binding domain that is fused to an intracellular signaling domain capable of transducing an inhibitory signal that inhibits or suppresses the immune activity of an immune cell. Inhibitory receptors have immune cell inhibitory potential, and are distinct and distinguishable from CARs, which are receptors with immune cell activating potential. For example, CARs are activating receptors as they include intracellular stimulatory and/or co-stimulatory domains. Inhibitory receptors are inhibiting receptors that contain intracellular inhibitory domains.

As used herein "inhibitory signal" refers to signal transduction or changes in protein expression in an immune cell resulting in suppression of an immune response (e.g., decrease in cytokine production or reduction of immune cell activation). Inhibition or suppression of an immune cell can selective and/or reversible, or not selective and/or reversible. Inhibitory receptors are responsive to non-target antigens (e.g. HLA-A*02). For example, when a non-target antigen (e.g. HLA-A*02) binds to or contacts the inhibitory receptor, the inhibitory receptor is responsive and activates an inhibitory signal in the immune cell expressing the inhibitory receptor upon binding of the non-target antigen by the extracellular ligand binding domain of the inhibitory receptor.

The non-target antigen can be a non-target allelic variant. A "non-target allelic variant" as used herein refers to an allele (e.g. an allelic variant of an MHC Class I gene), whose expression is reduced or eliminated in a target cell (e.g. a cancer cell) due to loss of heterozygosity, or another mechanism of expression loss, but is expressed or detectably expressed in a normal or healthy cell. The non-target antigen can be a protein, or an antigen peptide thereof in a complex with a major histocompatibility complex class I (MHC-I), where the non-target antigen comprises a polymorphism. Because the non-target antigen is polymorphic, loss of a single copy of the gene encoding the non-target antigen, which may occur through loss of heterozygosity in a cancer cell, yields a cancer cell that retains the other polymorphic variant of gene, but has lost the non-target antigen. For example, a subject having HLA-A*02 and HLA-A*01 alleles at the HLA locus may have a cancer in which only the HLA-A*02 allele is lost. In such a subject, the HLA-A*01 protein remains present, but is not recognized by the inhibitory receptor of immune cells encountering the cancer cell, because the inhibitor receptor is designed to be specific to the HLA-A*02 (or other non-target antigen). In normal non-malignant cells, the HLA-A*02 (or other non-target antigen) is present and inhibits activation of the engineered immune cell. In cancer cells having loss of heterozygosity, the HLA-A*02 allelic variant (or other non-target antigen) is lost. Immune cells engineered to express the inhibitory receptor do not receive an inhibitory signal from the inhibitory receptor, as the inhibitory receptor only responds to the HLA-A*02 (or other non-target antigen), which is absent on cancer cells. By this mechanism, the immune cell is selectively activated, and selectively kills, cancer cells expressing HER2 but having lost HLA-A*02 (or another non-target antigen) due to loss-of-heterozygosity. HLA-A is used here as an example. Similar polymorphic variation occurs in the population at other MHC genes and in other non-MHC genes as well. Accordingly, in some embodiments, the non-target antigen comprises a polymorphic variant of COLEC12, APCDD1 or CXCL16, or HLA-A*02. In some embodiments, the non-target antigen is an HLA class I allele or a minor histocompatibility antigen (MiHA). In some embodiments, the HLA Class I allele comprises HLA-A, HLA-B, HLA-C, or HLA-E. In some embodiments, the HLA class I allele is HLA-A*02. In some embodiments, the HLA-A*02 non-target antigen is expressed by healthy cells of a subject. In some embodiments, the non-target antigen is a non-target allelic variant. In some embodiments, the non-target antigen is not expressed in a cancer cell of the subject. In some embodiments, the non-target antigen is not expressed in a fraction of the cells in a tumor in the subject. In some embodiments, a cancer cell in a subject has lost expression of the non-target antigen. Loss of expression or lack of expression of the non-target antigen in a cell can be by any mechanism, such as, without limitation, epigenetic changes that effect non-target gene expression, mutations to the gene encoding the non-target antigen, or disruption of cellular signaling that regulates expression of the non-target gene.

In some embodiments, the second receptor is an inhibitory chimeric antigen receptor (i.e. inhibitory receptor). In some embodiments, the second receptor is an inhibitory receptor. In some embodiments, the second receptor is humanized.

In some embodiments, the second receptor comprises SEQ ID NO: 323, or a sequence sharing at least 75%, at least 80%, at least 85%, at least 90%, at least 95%, or at least 98% identity thereto. In some embodiments, the second receptor comprises SEQ ID NO: 324 or a sequence sharing at least 75%, at least 80%, at least 85%, at least 90%, at least 95%, or at least 98% identity thereto.

The disclosure provides a second receptor, which is an inhibitory receptor, comprising an extracellular ligand binding that can discriminate between single amino-acid variant alleles of a non-target antigen. This ability to discriminate between allelic variants of a non-target antigen allows the second receptor to inhibit activation of immune cells comprising the second receptor in the presence of non-target cells that express that the allele recognized by the ligand binding domain. However, activation of immune cells is not inhibited in the presence of target cells that have lost the allele, for example cancer cells that have lost one allele of a gene through loss of heterozygosity.

The disclosure provides a second receptor, which is an inhibitory receptor, comprising an extracellular ligand binding that can discriminate between different levels of expression of a non-target antigen. This allows the second receptor to inhibit activation of immune cells comprising the second receptor in the presence of non-target cells that express the ligand for the second receptor, but to allow activation of immune cells in the presence of cancer cells that express low levels, or have no expression, of the ligand for the second receptor.

Inhibitor Ligands

In some embodiments, the non-target antigen is not expressed by the target cells, and is expressed by non-target cells. In some embodiments, the non-target antigen is expressed by healthy cells, i.e. cells that are not cancer cells. In some embodiments, the target cells are a plurality of cancer cells that have lost expression of the non-target antigen through loss of heterozygosity (LOH). In some embodiments, the non-target cells are a plurality of healthy cells (i.e., non-cancer, normal, or healthy cells), that express both the target and the non-target antigen.

Any cell surface molecule expressed by the non-target cells that is not expressed by target cells may be a suitable non-target antigen for the second receptor extracellular ligand binding domain. For example, a cell adhesion molecule, a cell-cell signaling molecule, an extracellular domain, a molecule involved in chemotaxis, a glycoprotein, a G protein-coupled receptor, a transmembrane, a receptor for a neurotransmitter or a voltage gated ion channel can be used as a non-target antigen.

In some embodiments, the target antigen is a peptide antigen of a cancer cell-specific antigen in a complex with a major histocompatibility complex class I (MHC-I).

In some embodiments, the non-target antigen is lost in the cancer cells due to loss of heterozygosity. Exemplary non-target antigens lost in cancer cells due to loss of heterozygosity include COLEC12, APCDD1, CXCL16 and HLA-A*02. In some embodiments, the non-target antigen is selected from the group consisting of a polymorphic variant of COLEC12, APCDD1 and CXCL166, or a peptide antigen thereof a complex with a major histocompatibility complex class I (MHC-I), or HLA-A*02. In some embodiments, the non-target antigen is an antigen peptide comprising a polymorphic residue of COLEC12, APCDD1 and CXCL16 in a complex with a major histocompatibility complex class I (MHC-I).

Non-target MHC-1 (MHC) antigens comprising any of HLA-A, HLA-B or HLA-C are envisaged as within the scope of the disclosure. In some embodiments, the non-target antigen comprises HLA-A. In some embodiments, the non-target antigen comprises a human leukocyte antigen A*02 allelic product (HLA-A*02). In some embodiments, the non-target antigen comprises human leukocyte antigen A*69. In some embodiments, the non-target antigen comprises HLA-B. In some embodiments, the non-target antigen comprises HLA-C.

In some embodiments, the non-target antigen comprises HLA-A*02.

In some embodiments, the non-target antigen comprises C-X-C motif chemokine ligand 16 (CXCL16) or an antigen peptide thereof in a complex with MHC-I. Human CXCL16 precursor is described in NCBI record number NP_001094282.1, the contents of which are incorporated by reference herein in their entirety. In some embodiments, CXCL16 comprises an amino acid sequence of:

```
                                          (SEQ ID NO: 325)
  1  MSGSQSEVAP  SPQSPRSPEM  GRDLRPGSRV  LLLLLLLLLV
     YLTQPGNGNE  GSVTGSCYCG

61  KRISSDSPPS  VQFMNRLRKH  LRAYHRCLYY  TRFQLLSWSV
     CGGNKDPWVQ  ELMSCLDLKE

121  CGHAYSGIVA  HQKHLLPTSP  PISQASEGAS  SDIHTPAQML
     LSTLQSTQRP  TLPVGSLSSD

181  KELTRPNETT  IHTAGHSLAA  GPEAGENQKQ  PEKNAGPTAR
     TSATVPVLCL  LAIIFILTAA

241  LSYVLCKRRR  GQSPQSSPDL  PVHYIPVAPD  SNT.
```

In some embodiments, the non-target antigen comprises a polymorphism of CXCL16. For example, the non-target antigen comprises a peptide derived from CXCL16 comprising a polymorphic residue of CXCL16. Polymorphic residues of CXCL16 include positions 142 and 200 of SEQ ID NO: 325. In some embodiments, the non-target antigen comprises a peptide of CXCL16 comprising amino acid 142 or 200 of SEQ ID NO: 325. In some embodiments, the non-target antigen comprises a peptide of CXCL16 comprising an A at amino acid 200 of SEQ ID NO: 325. In some embodiments, the non-target antigen comprises a peptide of CXCL16 comprising a V at amino acid 200 of SEQ ID NO: 325. In some embodiments, the non-target antigen comprises a peptide of CXCL16 comprising an I at amino acid 142 of SEQ ID NO: 325. In some embodiments, the non-target antigen comprises a peptide of CXCL16 comprising a T at amino acid 142 of SEQ ID NO: 325.

In some embodiments, the non-target antigen comprises a polymorphism of CXCL16. In some embodiments, the non-target antigen comprises a peptide of CXCL16 comprising an A at amino acid 200 of SEQ ID NO: 325, and the second receptor comprises a ligand binding domain with a higher affinity for a CXCL16 ligand with an A at position 200 of SEQ ID NO: 325 than for a CXCL16 ligand with a V at position 200 of SEQ ID NO: 325. In some embodiments, the non-target antigen comprises a peptide of CXCL16 comprising a V at amino acid 200 of SEQ ID NO: 325, and the second receptor comprises a ligand binding domain with a higher affinity for a CXCL16 ligand with a V at position 200 of SEQ ID NO: 325 than for a CXCL16 ligand with an A at position 200 of SEQ ID NO: 325. In some embodiments, the non-target antigen comprises a peptide of CXCL16 comprising an I at amino acid 142 of SEQ ID NO: 325, and the second receptor comprises a ligand binding domain with a higher affinity for a CXCL16 ligand with an I at position 142 of SEQ ID NO: 325 than for a CXCL16 ligand with a T at position 142 of SEQ ID NO: 325. In some embodiments, the non-target antigen comprises a peptide of CXCL16 comprising a T at amino acid 142 of SEQ ID NO: 325, and the second receptor comprises a ligand binding domain with a higher affinity for a CXCL16 ligand with a T at position 142 of SEQ ID NO: 325 than for a CXCL16 ligand with an I at position 142 of SEQ ID NO: 325.

In some embodiments, the non-target antigen comprises collectin subfamily member 12 (COLEC12) or an antigen peptide thereof in a complex with MHC-I. Human COLEC12 is described in NCBI record number NP_569057.2, the contents of which are incorporated by reference herein in their entirety. In some embodiments, COLEC12 comprises an amino acid sequence of:

```
                                        (SEQ ID NO: 326)
  1 MKDDFAEEEE VQSFGYKRFG IQEGTQCTKC KNNWALKFSI

ILLYILCALL TITVAILGYK

61 VVEKMDNVTG GMETSRQTYD DKLTAVESDL KKLGDQTGKK

AISTNSELST FRSDILDLRQ

121 QLREITEKTS KNKDTLEKLQ ASGDALVDRQ SQLKETLENN

SFLITTVNKT LQAYNGYVTN

181 LQQDTSVLQG NLQNQMYSHN VVIMNLNNLN LTQVQQRNLI

TNLQRSVDDT SQAIQRIKND

241 FQNLQQVFLQ AKKDTDWLKE KVQSLQTLAA NNSALAKANN

DTLEDMNSQL NSFTGQMENI
```

-continued

```
301 TTISQANEQN LKDLQDLHKD AENRTAIKFN QLEERFQLFE

TDIVNIISNI SYTAHHLRTL

361 TSNLNEVRTT CTDTLTKHTD DLTSLNNTLA NIRLDSVSLR

MQQDLMRSRL DTEVANLSVI

421 MEEMKLVDSK HGQLIKNFTI LQGPPGPRGP RGDRGSQGPP

GPTGNKGQKG EKGEPGPPGP

481 AGERGPIGPA GPPGERGGKG SKGSQGPKGS RGSPGKPGPQ

GSSGDPGPPG PPGKEGLPGP

541 QGPPGFQGLQ GTVGEPGVPG PRGLPGLPGV PGMPGPKGPP

GPPGPSGAVV PLALQNEPTP

601 APEDNGCPPH WKNFTDKCYY FSVEKEIFED AKLFCEDKSS

HLVFINTREE QQWIKKQMVG

661 RESHWIGLTD SERENEWKWL DGTSPDYKNW KAGQPDNWGH

GHGPGEDCAG LIYAGQWNDF

721 QCEDVNNFIC EKDRETVLSS AL.
```

In some embodiments, the non-target antigen comprises a polymorphism of COLEC12. For example, the non-target antigen comprises a peptide derived from COLEC12 comprising a polymorphic residue of COLEC12. Polymorphic residues of COLEC12 include position 522 of SEQ ID NO: 326. In some embodiments, the non-target antigen comprises a peptide of COLEC12 comprising amino acid 522 of SEQ ID NO: 326. In some embodiments, the non-target antigen comprises a peptide of COLEC12 comprising an S at amino acid 522 of SEQ ID NO: 326. In some embodiments, the non-target antigen comprises a peptide of COLEC12 comprising a P at amino acid 522 of SEQ ID NO: 326.

In some embodiments, the non-target antigen comprises APC down-regulated 1 (APCDD1) or an antigen peptide thereof in a complex with MHC-I. An exemplary human APCDD1 is described in UniProtKB record number Q8J025, the contents of which are incorporated by reference herein in their entirety. In some embodiments, APCDD1 comprises an amino acid sequence of:

```
                                        (SEQ ID NO: 327)
  1 MSWPRRLLLR YLFPALLLHG LGEGSALLHP DSRSHPRSLE

KSAWRAFKES QCHHMLKHLH

61 NGARITVQMP PTIEGHWVST GCEVRSGPEF ITRSYRFYHN

NTFKAYQFYY GSNRCTNPTY

121 TLIIRGKIRL RQASWIIRGG TEADYQLHNV QVICHTEAVA

EKLGQQVNRT CPGFLADGGP

181 WVQDVAYDLW REENGCECTK AVNFAMHELQ LIRVEKQYLH

HNLDHLVEEL FLGDIHTDAT

241 QRMFYRPSSY QPPLQNAKNH DHACIACRII YRSDEHHPPI

LPPKADLTIG LHGEWVSQRC

301 EVRPEVLFLT RHFIFHDNNN TWEGHYYHYS DPVCKHPTFS

IYARGRYSRG VLSSRVMGGT
```

```
361  EFVFKVNHMK  VTPMDAATAS  LLNVFNGNEC  GAEGSWQVGI

QQDVTHTNGC  VALGIKLPHT

421  EYEIFKMEQD  ARGRYLLFNG  QRPSDGSSPD  RPEKRATSYQ

MPLVQCASSS  PRAEDLAEDS

481  GSSLYGRAPG  RHTWSLLLAA  LACLVPLLHW  NIRR.
```

In some embodiments, the non-target antigen comprises a polymorphism of APCDD1. Exemplary polymorphisms of APCDD1 include rs3748415, which can be a V, I or L at position 150 of SEQ ID NO: 327. In some embodiments, the non-target antigen comprises a peptide of APCDD1 comprising amino acid 150 of SEQ ID NO: 327. In some embodiments, the non-target antigen comprises a peptide of APCDD1 comprising an V at amino acid 150 of SEQ ID NO: 327. In some embodiments, the non-target antigen comprises a peptide of APCDD1 comprising an I at amino acid 150 of SEQ ID NO: 327. In some embodiments, the non-target antigen comprises a peptide of APCDD1 comprising an L at amino acid 150 of SEQ ID NO: 327.

A further exemplary human APCDD1 is described in UniProtKB record number V9GY82, the contents of which are incorporated by reference herein in their entirety. In some embodiments, APCDD1 comprises an amino acid sequence of:

```
                                      (SEQ ID NO: 328)
  1  XDVAYDLWRE  ENGCECTKAV  NFAMHELQLI  RVEKQYLHHN

LDHLVEELFL  GDIHTDATQR

61  MFYRPSSYQP  PLQNAKCAAE  SSGSFQILPQ  DSSEKEQNGL

SHWCLSRPGH  QKDWALCAHA

121  GPATAGCPSC  LWPPAETGRK  AGRTSSKTVH  ACPGEAGTSS

FELFYFPNCW  SIETKLKISL

181  NAKLSFKPRA  SAPLETGHRV  KIETLSQLVF  LSFIQLCCEV

QSPLANK.
```

Exemplary polymorphisms of APCDD1 include rs1786683, which can be a Y or S at position 165 of SEQ ID NO: 328. In some embodiments, the non-target antigen comprises a peptide of APCDD1 comprising amino acid 165 of SEQ ID NO: 328. In some embodiments, the non-target antigen comprises a peptide of APCDD1 comprising a Y at amino acid 165 of SEQ ID NO: 328. In some embodiments, the non-target antigen comprises a peptide of APCDD1 comprising an S at amino acid 165 of SEQ ID NO: 328.

A further exemplary human APCDD1 is described in UniProt record number J3QSE3, the contents of which are incorporated by reference herein in their entirety. In some embodiments, APCDD1 comprises an amino acid sequence of:

```
                                      (SEQ ID NO: 329)
  1  PEDVLPALQL  PAPSAECQVE  MGFHHVGQDG  LQLPTSSDPP

ALASQSAGIT  GVSHRPPGRH

61  LSNDLRTTTM  PASPVGSSIG  QTSTTLPSCP  QRQT.
```

Exemplary polymorphisms of APCDD1 include rs9952598, which can be a Q or R at position 28 of SEQ ID NO: 329. In some embodiments, the non-target antigen comprises a peptide of APCDD1 comprising amino acid 28 of SEQ ID NO: 329. In some embodiments, the non-target antigen comprises a peptide of APCDD1 comprising a Q at amino acid 28 of SEQ ID NO: 329. In some embodiments, the non-target antigen comprises a peptide of APCDD1 comprising an R at amino acid 28 of SEQ ID NO: 329.

In some embodiments, APCDD1 comprises a sequence that shares at least 80%, at least 85%, at least 90%, at least 95%, at least 94%, at least 97%, at least 98%, or at least 99% identity to any one of SEQ ID NOs: 327-329. Polymorphic residues of APCDD1 are marked as bold and underlined in SEQ ID NOs: 327-329.

In some embodiments, the non-target antigen comprising HLA-A*02, and the ligand binding domain of the second receptor comprises an HLA-A*02 ligand binding domain. In some embodiments, the ligand binding domain binds HLA-A*02 independent of the peptide in a pMHC complex comprising HLA-A*02. In some embodiments, the HLA-A*02 ligand binding domain comprises an scFv domain. In some embodiments, the HLA-A*02 ligand binding domain comprises a sequence of any one of SEQ ID NOs: 63-74. In some embodiments, the HLA-A*02 ligand binding domain comprises a sequence at least 90%, at least 95% or at least 99% identical to a sequence of any one of SEQ ID NOs: 63-74.

In some embodiments, the HLA-A*02 scFv comprises the complementarity determined regions (CDRs) of any one of SEQ ID NOS: 87-102. In some embodiments, the scFv comprises a sequence at least 95% identical to any one of SEQ ID NOS: 87-102. In some embodiments, the scFv comprises a sequence identical to any one of SEQ ID NOS: 87-102. In some embodiments, the heavy chain of the antigen binding domain comprises the heavy chain CDRs of any one of SEQ ID NOS: 87-102, and wherein the light chain of the antigen binding domain comprises the light chain CDRs of any one of SEQ ID NOS: 87-102. In some embodiments, the HLA-A*02 antigen binding domain comprises a heavy chain and a light chain, and the heavy chain comprises CDRs selected from SEQ ID NOs: 95-102 and the light chain comprises CDRs selected from SEQ ID NOs: 87-94. In further embodiments of any of the ligand binding domains, each CDR sequence may have 1, 2, 3 or more substitutions, insertions, or deletions. CDR sequences may tolerate substitutions, deletions, or insertions. Using sequence alignment tools, routine experimentation, and known assays, those of skill in the art may generate and test variant sequences having 1, 2, 3, or more substitutions, insertions, or deletions in CDR sequences without undue experimentation.

In some embodiments, the HLA-A*02 antigen binding domain comprises a heavy chain and a light chain, and the heavy chain comprises a sequence at least 95% identical to the heavy chain portion of any one of SEQ ID NOS: 63-74, and the light chain comprises a sequence at least 95% identical to the light chain portion of any one of SEQ ID NOS: 63-74.

In some embodiments, the heavy chain comprises a sequence identical to the heavy chain portion of any one of SEQ ID NOS: 63-74, and wherein the light chain of comprises a sequence identical to the light chain portion of any one of SEQ ID NOS: 63-74.

In some embodiments, the non-target antigen comprises HLA-B*07, and the ligand binding domain of the second receptor comprises an HLA-B*07 ligand binding domain. In some embodiments, the ligand binding domain binds HLA-B*07 independent of the peptide in a pMHC complex comprising HLA-B*07. In some embodiments, the HLA- B*07 ligand binding domain comprises an scFv domain. In some embodiments, the HLA-B*07 ligand binding domain comprises a sequence of any one of the indicated B7 binding domains in Table 7. In some embodiments, the HLA-B*07 ligand binding domain comprises a sequence at least 90%, at least 95% or at least 99% identical to a sequence of any one of the indicated HLA-B*07 binding domains in Table 7. In some embodiments, the HLA-B*07 scFv comprises any one of the indicated HLA-B*07 complementarity determined regions (CDRs) in Table 9. In some embodiments, the scFv comprises a sequence at least 95% identical to any one of the indicated HLA-B*07 scFv sequences in Table 7. In some embodiments, the scFv comprises a sequence identical to any one of the indicated HLA-B*07 scFv sequences in Table 7.

In some embodiments, the non-target antigen comprises HLA-A*11, and the ligand binding domain of the second receptor comprises an HLA-A*11 ligand binding domain. In some embodiments, the ligand binding domain binds HLA-A*11 independent of the peptide in a pMHC complex comprising HLA-A*11. In some embodiments, the HLA-A*11 ligand binding domain comprises an scFv domain. In some embodiments, the HLA-A*11 ligand binding domain comprises a sequence of any one of the indicated HLA-A*11 binding domains in Table 7. In some embodiments, the HLA-A*11 ligand binding domain comprises a sequence at least 90%, at least 95% or at least 99% identical to a sequence of any one of the indicated HLA-A*11 binding domains in Table 7. In some embodiments, the HLA-A*11 scFv comprises any one of the indicated HLA-A*11 complementarity determined regions (CDRs) in Table 9. In some embodiments, the scFv comprises a sequence at least 95% identical to any one of the indicated HLA-A*11 scFv sequences in Table 7. In some embodiments, the scFv comprises a sequence identical to any one of the indicated HLA-A*11 scFv sequences in Table 7.

In some embodiments, the non-target antigen comprises HLA-A*01, and the ligand binding domain of the second receptor comprises an HLA-A*01 ligand binding domain. In some embodiments, the ligand binding domain binds HLA-A*01 independent of the peptide in a pMHC complex comprising HLA-A*01. In some embodiments, the HLA-A*01 ligand binding domain comprises an scFv domain. In some embodiments, the HLA-A*01 ligand binding domain comprises a sequence of any one of the indicated HLA-A*01 binding domains in Table 7. In some embodiments, the HLA-A*01 ligand binding domain comprises a sequence at least 90%, at least 95% or at least 99% identical to a sequence of any one of the indicated HLA-A*01 binding domains in Table 7. In some embodiments, the HLA-A*01 scFv comprises any one of the indicated HLA-A*01 complementarity determined regions (CDRs) in Table 9 In some embodiments, the scFv comprises a sequence at least 95% identical to any one of the indicated HLA-A*01 scFv sequences in Table 7. In some embodiments, the scFv comprises a sequence identical to any one of the indicated HLA-A*01 scFv sequences in Table 7.

In some embodiments, the non-target antigen comprises HLA-A*03, and the ligand binding domain of the second receptor comprises an HLA-A*03 ligand binding domain. In some embodiments, the ligand binding domain binds HLA-A*03 independent of the peptide in a pMHC complex comprising HLA-A*03. In some embodiments, the HLA-A*03 ligand binding domain comprises an scFv domain. In some embodiments, the HLA-A*03 ligand binding domain comprises a sequence of any one of the indicated HLA-A*03 binding domains in Table 7. In some embodiments, the HLA-A*03 ligand binding domain comprises a sequence at least 90%, at least 95% or at least 99% identical to a sequence of any one of the indicated HLA-A*03 binding domains in Table 7. In some embodiments, the HLA-A*03 scFv comprises any one of the indicated HLA-A*03 complementarity determined regions (CDRs) in Table 9. In some embodiments, the scFv comprises a sequence at least 95% identical to any one of the indicated HLA-A*03 scFv sequences in Table 7. In some embodiments, the scFv comprises a sequence identical to any one of the indicated HLA-A*03 scFv sequences in Table 7.

In some embodiments, the non-target antigen comprises HLA-C*07, and the ligand binding domain of the second receptor comprises an HLA-C*07 ligand binding domain. In some embodiments, the ligand binding domain binds HLA-C*07 independent of the peptide in a pMHC complex comprising HLA-C*07. In some embodiments, the HLA-C*07 ligand binding domain comprises an scFv domain. In some embodiments, the HLA-C*07 ligand binding domain comprises a sequence of any one of the indicated HLA-C*07 binding domains in Table 7. In some embodiments, the HLA-C*07 ligand binding domain comprises a sequence at least 90%, at least 95% or at least 99% identical to a sequence of any one of the indicated HLA-C*07 binding domains in Table 7. In some embodiments, the HLA-C*07 scFv comprises any one of the indicated HLA-C*07 complementarity determined regions (CDRs) in Table 9. In some embodiments, the scFv comprises a sequence at least 95% identical to any one of the indicated HLA-C*07 scFv sequences in Table 7. In some embodiments, the scFv comprises a sequence identical to any one of the indicated HLA-C*07 scFv sequences in Table 7.

Inhibitory receptors of the disclosure may comprise an extracellular ligand binding domain. Any type of ligand binding domain that can regulate the activity of a receptor in a ligand dependent manner is envisaged as within the scope of the instant disclosure.

In some embodiments, the ligand binding domain is an antigen binding domain. Exemplary antigen binding domains include, inter alia, scFv, SdAb, Vβ-only domains, and TCR antigen binding domains derived from the TCR α and β chain variable domains.

Any type of antigen binding domain is envisaged as within the scope of the instant disclosure.

In some embodiments, the extracellular ligand binding domain of the second receptor binds to and recognizes a polymorphic variant of COLEC12, APCDD1, CXCL16 or an antigen peptide thereof in a complex with a major histocompatibility complex class I (MHC-I), or HLA-A*02. In some embodiments, the extracellular ligand binding domain of the second receptor is an scFv.

In some embodiments, the extracellular ligand binding domain of the second receptor is fused to the extracellular domain of an inhibitory receptor.

In some embodiments, the inhibitory receptors of the present disclosure comprise an extracellular hinge region. Exemplary hinges can be isolated or derived from IgD and CD8 domains, for example IgG1. In some embodiments, the hinge is isolated or derived from CD8α or CD28.

The inhibitory receptors of the present disclosure can be designed to comprise a transmembrane domain that is fused to the extracellular domain of the inhibitory receptors. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions may be isolated or derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively, the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the intracellular domain of the inhibitory receptors. A glycine-serine doublet provides a particularly suitable linker.

The disclosure provides an inhibitory receptors comprising an intracellular domain. The intracellular domain of the inhibitory receptors of the instant disclosure is responsible for inhibiting activation of the immune cells comprising the inhibitory receptors, which would otherwise be activated in response to activation signals by the first receptor. In some embodiments, for example in the second inhibitory receptors of the disclosure which provide an inhibitory signal, the inhibitory signal is transmitted through the intracellular domain of the receptor. In some embodiments, the inhibitory receptor comprises an inhibitory intracellular domain. In some embodiments, the inhibitory engineered receptor is a CAR comprising an inhibitory intracellular domain (an inhibitory CAR).

In some embodiments, the inhibitory intracellular domain comprises an immunoreceptor tyrosine-based inhibitory motif (ITIM). In some embodiments, the inhibitory intracellular domain comprising an ITIM can be isolated or derived from an immune checkpoint inhibitor such as CTLA-4 and PD-1. CTLA-4 and PD-1 are immune inhibitory receptors expressed on the surface of T cells, and play a pivotal role in attenuating or terminating T cell responses.

Inhibitory domains can be isolated from human tumor necrosis factor related apoptosis inducing ligand (TRAIL) receptor and CD200 receptor 1. In some embodiments, the TRAIL receptor comprises TR10A, TR10B or TR10D.

In some embodiments, the inhibitory domain comprises an intracellular domain, a transmembrane or a combination thereof. In some embodiments, the inhibitory intracellular domain is isolated from phosphoprotein membrane anchor with glycosphingolipid microdomains 1 (PAG1). In some embodiments, the inhibitory intracellular domain is isolated from leukocyte immunoglobulin like receptor B1 (LILRB1). In some embodiments, the inhibitory domain is isolated or derived from a human protein, for example a human TRAIL receptor, CTLA-4, or PD-1, PAG1 or LILRB1 protein.

In some embodiments, the inhibitory domain comprises an intracellular domain, a transmembrane domain, a hinge region or a combination thereof. In some embodiments, the inhibitory domain comprises an immunoreceptor tyrosine-based inhibitory motif (ITIM). In some embodiments, the inhibitory domain comprising an ITIM can be isolated or derived from an immune checkpoint inhibitor such as CTLA-4 and PD-1. Exemplary hinge, transmembrane, and intracellular domains that may be used in inhibitory receptors described herein are shown in Table 16.

Inhibitory domains can be isolated from human tumor necrosis factor related apoptosis inducing ligand (TRAIL) receptor and CD200 receptor 1. In some embodiments, the inhibitory domain is isolated or derived from a human protein, for example a human TRAIL receptor, CTLA-4, or PD-1 protein. In some embodiments, the TRAIL receptor comprises TR10A, TR10B or TR10D.

Endogenous TRAIL is expressed as a 281-amino acid type II trans-membrane protein, which is anchored to the plasma membrane and presented on the cell surface. TRAIL is expressed by natural killer cells, which, following the establishment of cell-cell contacts, can induce TRAIL-dependent apoptosis in target cells. Physiologically, the TRAIL-signaling system was shown to be essential for immune surveillance, for shaping the immune system through regulating T-helper cell 1 versus T-helper cell 2 as well as "helpless" CD8+ T-cell numbers, and for the suppression of spontaneous tumor formation.

In some embodiments, the inhibitory domain comprises an intracellular domain isolated or derived from a CD200 receptor. The cell surface glycoprotein CD200 receptor 1 (Uniprot ref: Q8TD46) represents another example of an inhibitory intracellular domain of the present invention. This inhibitory receptor for the CD200/OX2 cell surface glycoprotein limits inflammation by inhibiting the expression of proinflammatory molecules including TNF-alpha, interferons, and inducible nitric oxide synthase (iNOS) in response to selected stimuli.

In some embodiments, the engineered receptor comprises an inhibitory domain isolated or derived from killer cell immunoglobulin like receptor, three Ig domains and long cytoplasmic tail 2 (KIR3DL2), killer cell immunoglobulin like receptor, three Ig domains and long cytoplasmic tail 3 (KIR3DL3), leukocyte immunoglobulin like receptor B1 (LIR1, also called LIR-1 and LILRB1), programmed cell death 1 (PD-1), Fc gamma receptor IIB (FcgRIIB), killer cell lectin like receptor K1 (NKG2D), CTLA-4, a domain containing a synthetic consensus ITIM, a ZAP70 SH2 domain (e.g., one or both of the N and C terminal SH2 domains), or ZAP70 KI_K369A (kinase inactive ZAP70).

In some embodiments, the inhibitory domain is isolated or derived from a human protein. In some embodiments, the second, inhibitory receptor comprises an inhibitory domain. In some embodiments, the second, inhibitory receptor comprises an inhibitory intracellular domain and/or an inhibitory domain and transmembrane domain. In some embodiments, the inhibitory intracellular domain is fused to an intracellular domain of an inhibitory receptors. In some embodiments, the inhibitory intracellular domain is fused to the transmembrane domain of an inhibitory receptors.

In some embodiments, the second, inhibitory receptor comprises a cytoplasmic domain and transmembrane domain isolated or derived from the same protein, for example an ITIM containing protein. In some embodiments, the second, inhibitory receptor comprises a cytoplasmic domain, a transmembrane domain, and an extracellular domain or a portion thereof isolated or derived isolated or derived from the same protein, for example an ITIM containing protein. In some embodiments, the second, inhibitory receptor comprises a hinge region isolated or derived from isolated or derived from the same protein as the intracellular domain and/or transmembrane domain, for example an ITIM containing protein. In some embodiments, the second, inhibitory receptor comprises an inhibitory domain. In some embodiments, the second, inhibitory receptor comprises an inhibitory intracellular domain and/or an inhibitory transmembrane domain. In some embodiments, the second engineered receptor is a CAR comprising an inhibitory domain (an inhibitory CAR). In some embodiments, the inhibitory intracellular domain is fused to the intracellular domain of a CAR. In some embodiments, the inhibitory intracellular domain is fused to the transmembrane domain of a CAR.

LILRB1 Inhibitory Receptors

The present disclosure provides a second inhibitory receptor comprising a LILRB1 inhibitory domain, and optionally, a LILRB1 transmembrane and/or hinge domain, or functional variants thereof. The inclusion of the LILRB1 transmembrane domain and/or the LILRB1 hinge domain in the inhibitory receptor may increase the inhibitory signal generated by the inhibitory receptor compared to a reference inhibitory receptor having another transmembrane domain or another hinge domains. The second, inhibitory receptor comprising the LILRB1 inhibitory domain may be a CAR or TCR, as described herein. Any suitable ligand binding domain, as described herein, may be fused to the LILRB1-based second, inhibitory receptors having one or more domains from Leukocyte immunoglobulin-like receptor subfamily B member 1 (LILRB1, or LIR1). In some embodiments, the inhibitory receptor comprises a LILRB1 intracellular domain or a functional variant thereof.

Leukocyte immunoglobulin-like receptor subfamily B member 1 (LILRB1), also known as Leukocyte immunoglobulin-like receptor B1, as well as ILT2, LIR1, MIR7, PIRB, CD85J, ILT-2 LIR-1, MIR-7 and PIR-B, is a member of the leukocyte immunoglobulin-like receptor (LIR) family. The LILRB1 protein belongs to the subfamily B class of LIR receptors. These receptors contain two to four extracellular immunoglobulin domains, a transmembrane domain, and two to four cytoplasmic immunoreceptor tyrosine-based inhibitory motifs (ITIMs). The LILRB1 receptor is expressed on immune cells, where it binds to MHC class I molecules on antigen-presenting cells and transduces a negative signal that inhibits stimulation of an immune response. LILRB1 is thought to regulate inflammatory responses, as well as cytotoxicity, and to play a role in limiting auto-reactivity. Multiple transcript variants encoding different isoforms of LILRB1 exist, all of which are contemplated as within the scope of the instant disclosure.

In some embodiments of the inhibitory receptors described herein, the inhibitory receptor comprises one or more domains isolated or derived from LILRB1. In some embodiments of the receptors having one or more domains isolated or derived from LILRB1, the one or more domains of LILRB1 comprise an amino acid sequence that is at least 80%, at least 90%, at least 95%, at least 96%, at least 97%, at least 98%, at least 99% or is identical to a sequence or subsequence of SEQ ID NO: 280. In some embodiments, the one or more domains of LILRB1 comprise an amino acid sequence that is identical to a sequence or subsequence of SEQ ID NO: 280. In some embodiments, the one or more domains of LILRB1 consist of an amino acid sequence that is at least 80%, at least 90%, at least 95%, at least 96%, at least 97%, at least 98%, at least 99% or is identical to a sequence or subsequence of SEQ ID NO: 280. In some embodiments, the one or more domains of LILRB1 consist of an amino acid sequence that is identical to a sequence or subsequence of SEQ ID NO: 280.

In some embodiments of the receptors having one or more domains isolated or derived from LILRB1, the one or more domains of LILRB1 are encoded by a polynucleotide sequence that is at least 80%, at least 90%, at least 95%, at least 96%, at least 97%, at least 98%, at least 99% or is identical to a sequence or subsequence of SEQ ID NO: 556.

In some embodiments of the receptors having one or more domains of LILRB1, the one or more domains of LILRB1 are encoded by a polynucleotide sequence that is identical to a sequence or subsequence of SEQ ID NO: 556. In various embodiments, a chimeric antigen receptor is provided, comprising a polypeptide, wherein the polypeptide comprises one or more of: an LILRB1 hinge domain or functional fragment or variant thereof; an LILRB1 transmembrane domain or a functional variant thereof; and an LILRB1 intracellular domain or an intracellular domain comprising at least one, or at least two immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

Intracellular Domain

The disclosure provides inhibitory receptors, the inhibitory receptors comprising a polypeptide. In some embodiments, the polypeptide comprises an intracellular domain. In some embodiments, the inhibitory receptor comprises a LILRB1 intracellular domain or a functional variant thereof.

As used herein, "intracellular domain" refers to the cytoplasmic or intracellular domain of a protein, such as a receptor, that interacts with the interior of the cell, and carries out a cytosolic function. As used herein, "cytosolic function" refers to a function of a protein or protein complex that is carried out in the cytosol of a cell. For example, intracellular signal transduction cascades are cytosolic functions.

As used herein an "immunoreceptor tyrosine-based inhibitory motif" or "ITIM" refers to a conserved sequence of amino acids with a consensus sequence of S/I/V/LxYxxI/V/L (SEQ ID NO: 260), or the like, that is found in the cytoplasmic tails of many inhibitory receptors of the immune system. After ITIM-possessing inhibitory receptors interact with their ligand, the ITIM motif is phosphorylated, allowing the inhibitory receptor to recruit other enzymes, such as the phosphotyrosine phosphatases SHP-1 and SHP-2, or the inositol-phosphatase called SHIP.

In some embodiments, the polypeptide comprises an intracellular domain comprising at least one immunoreceptor tyrosine-based inhibitory motif (ITIM), at least two ITIMs, at least 3 ITIMs, at least 4 ITIMs, at least 5 ITIMs or at least 6 ITIMs. In some embodiments, the intracellular domain has 1, 2, 3, 4, 5, or 6 ITIMs.

In some embodiments, the polypeptide comprises an intracellular domain comprising at least one ITIM selected from the group of ITIMs consisting of NLYAAV (SEQ ID NO: 256), VTYAEV (SEQ ID NO: 257), VTYAQL (SEQ ID NO: 258), and SIYATL (SEQ ID NO: 259).

In further particular embodiments, the polypeptide comprises an intracellular domain comprising at least two immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In some embodiments, the intracellular domain comprises both ITIMs NLYAAV (SEQ ID NO: 256) and VTYAEV (SEQ ID NO: 257). In some embodiments, the intracellular domain comprises a sequence at least 95% identical to SEQ ID NO: 260. In some embodiments, the intracellular domain comprises or consists essentially of a sequence identical to SEQ ID NO: 281.

In some embodiments, the intracellular domain comprises both ITIMs VTYAEV (SEQ ID NO: 257) and VTYAQL (SEQ ID NO: 258). In some embodiments, the intracellular domain comprises a sequence at least 95% identical to SEQ ID NO: 261. In some embodiments, the intracellular domain comprises or consists essentially of a sequence identical to SEQ ID NO: 261.

In some embodiments, the intracellular domain comprises both ITIMs VTYAQL (SEQ ID NO: 258) and SIYATL (SEQ ID NO: 259). In some embodiments, the intracellular domain comprises a sequence at least 95% identical to SEQ ID NO: 262. In some embodiments, the intracellular domain comprises or consists essentially of a sequence identical to SEQ ID NO: 262.

In some embodiments, the intracellular domain comprises the ITIMs NLYAAV (SEQ ID NO: 256), VTYAEV (SEQ ID NO: 257), and VTYAQL (SEQ ID NO: 258). In some embodiments, the intracellular domain comprises a sequence at least 95% identical to SEQ ID NO: 263. In some embodiments, the intracellular domain comprises or consists essentially of a sequence identical to SEQ ID NO: 263.

In some embodiments, the intracellular domain comprises the ITIMs VTYAEV (SEQ ID NO: 257), VTYAQL (SEQ ID NO: 258), and SIYATL (SEQ ID NO: 259). In some embodiments, the intracellular domain comprises a sequence at least 95% identical to SEQ ID NO: 264. In some embodiments, the intracellular domain comprises or consists essentially of a sequence identical to SEQ ID NO: 264.

In some embodiments, the intracellular domain comprises the ITIMs NLYAAV (SEQ ID NO: 256), VTYAEV (SEQ ID NO: 257), VTYAQL (SEQ ID NO: 258), and SIYATL (SEQ ID NO: 259). In embodiments, the intracellular domain comprises a sequence at least 95% identical to SEQ ID NO: 265. In some embodiments, the intracellular domain comprises or consists essentially of a sequence identical to SEQ ID NO: 265.

In some embodiments, the intracellular domain comprises a sequence at least 95% identical to the LILRB1 intracellular domain (SEQ ID NO: 266). In some embodiments, the intracellular domain comprises or consists essentially of a sequence identical to the LILRB1 intracellular domain (SEQ ID NO: 266).

LILRB1 intracellular domains or functional variants thereof of the disclosure can have at least 1, at least 2, at least 4, at least 4, at least 5, at least 6, at least 7, or at least 8 ITIMs. In some embodiments, the LILRB1 intracellular domain or functional variant thereof has 2, 3, 4, 5, or 6 ITIMs.

In particular embodiments, the polypeptide comprises an intracellular domain comprising two, three, four, five, or six immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In particular embodiments, the polypeptide comprises an intracellular domain comprising at least three immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In particular embodiments, the polypeptide comprises an intracellular domain comprising three immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In particular embodiments, the polypeptide comprises an intracellular domain comprising four immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In particular embodiments, the polypeptide comprises an intracellular domain comprising five immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In particular embodiments, the polypeptide comprises an intracellular domain comprising six immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In particular embodiments, the polypeptide comprises an intracellular domain comprising at least seven immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In some embodiments, the intracellular domain comprises a TCR alpha intracellular domain. In some embodiments, the intracellular domain comprises a TCR alpha intracellular domain and an LILRB1 intracellular domain, as described herein. In some embodiments, a TCR alpha intracellular domain comprises Ser-Ser. In some embodiments, a TCR alpha intracellular domain is encoded by a sequence of TCCAGC.

In some embodiments, the intracellular domain comprises a TCR beta intracellular domain. In some embodiments, the intracellular domain comprises a TCR beta intracellular domain and an LILRB1 intracellular domain, as described herein. In some embodiments, the TCR beta intracellular domain comprises an amino acid sequence having at least 80% identity, at least 90% identity, or is identical to a sequence of: MAMVKRKDSR (SEQ ID NO: 267). In some embodiments, the TCR beta intracellular domain comprises, or consists essentially of MAMVKRKDSR (SEQ ID NO: 267). In some embodiments, the TCR beta intracellular domain is encoded by a sequence of

```
                                    (SEQ ID NO: 268)
ATGGCCATGGTCAAGAGAAAGGATTCCAGA.
```

The LILRB1 protein has four immunoglobulin (Ig) like domains termed D1, D2, D3 and D4. In some embodiments, the LILRB1 hinge domain comprises an LILRB1 D3D4 domain or a functional variant thereof. In some embodiments, the LILRB1 D3D4 domain comprises a sequence at least 95%, at least 96%, at least 97%, at least 98%, at least 99% or identical to SEQ ID NO: 274. In some embodiments, the LILRB1 D3D4 domain comprises or consists essentially of SEQ ID NO: 274.

Transmembrane Domain

The disclosure provides inhibitory receptors the receptors comprising a polypeptide. In some embodiments, the polypeptide comprises a transmembrane domain. In some embodiments, the inhibitory receptor comprises a LILRB1 hinge domain, or a functional variant thereof. In some embodiments, the inhibitory receptor comprises a LILRBI transmembrane domain, or a functional variant thereof. In some embodiments, the inhibitory receptor comprises LILRB1 hinge and transmembrane domains, or functional variants thereof.

A "transmembrane domain", as used herein, refers to a domain of a protein that spans membrane of the cell.

Transmembrane domains typically consist predominantly of non-polar amino acids, and may traverse the lipid bilayer once or several times. Transmembrane domains usually comprise alpha helices, a configuration which maximizes internal hydrogen bonding.

Transmembrane domains isolated or derived from any source are envisaged as within the scope of the fusion proteins of the disclosure.

In particular embodiments, the polypeptide comprises an LILRB1 transmembrane domain or a functional variant thereof.

In some embodiments, the LILRB1 transmembrane domain or a functional variant thereof comprises a sequence at least 95% identical, at least 96% identical, at least 97% identical, at least 98% identical or at least 99% to SEQ ID NO: 269. In some embodiments, the LILRB1 transmembrane domain or a functional variant thereof comprises a sequence at least 95% identical to SEQ ID NO: 269. In some embodiments, the LILRB1 transmembrane domain comprises a sequence identical to SEQ ID NO: 269. In embodiments, the LILRB1 transmembrane domain consists essentially of a sequence identical to SEQ ID NO: 269.

In some embodiments of the chimeric antigen receptors of the disclosure, the transmembrane domain is not a LILRB1 transmembrane domain. In some embodiments, the transmembrane domain is one that is associated with one of the other domains of the fusion protein, or isolated or derived from the same protein as one of the other domains of the fusion protein.

The transmembrane domain may be derived either from a natural or from a recombinant source. Where the source is natural, the domain may be derived from any membrane-bound or transmembrane protein. Exemplary transmembrane domains may include at least the transmembrane region(s) of e.g., the alpha, beta or zeta chain of the TCR, CD3 delta, CD3 epsilon or CD3 gamma, CD28, CD3 epsilon, CD45, CD4, CD5, CD8, CD9, CD16, CD22, CD33, CD37, CD64, CD80, CD86, CD134, CD137, CD154.

In some embodiments, the transmembrane comprises a TCR alpha transmembrane domain. In some embodiments, the TCR alpha transmembrane domain comprises an amino acid sequence having at least 85% identity, at least 90% identity, at least 95% identity, at least 96% identity, at least 97% identity, at least 98% identity, at least 99% identity or is identical to a sequence of: VIGFRILLLKVAGFNLL-MTLRLW (SEQ ID NO: 270). In some embodiments, the TCR alpha transmembrane domain comprises, or consists essentially of, VIGFRILLLKVAGFNLLMTLRLW (SEQ ID NO: 270). In some embodiments, the TCR alpha transmembrane domain is encoded by a sequence of:

(SEQ ID NO: 271)
GTGATTGGGTTCCGAATCCTCCTCCTGAAAGTGGCCGGGTTTAATCTGCT

CATGACGCTGCGGCTGTGG.

In some embodiments, the transmembrane comprises a TCR beta transmembrane domain. In some embodiments, the TCR beta transmembrane domain comprises an amino acid sequence having at least 85% identity, at least 90% identity, at least 95% identity, at least 96% identity, at least 97% identity, at least 98% identity, at least 99% identity or is identical to a sequence of: TILYEILLGKAT-LYAVLVSALVL (SEQ ID NO: 272). In some embodiments, the TCR beta transmembrane domain comprises, or consists essentially of TILYEILLGKATLYAVLVSALVL (SEQ ID NO: 272). In some embodiments, the TCR beta transmembrane domain is encoded by a sequence of (SEQ ID NO: 273)
ACCATCCTCTATGAGATCTTGCTAGGGAAGGCCACCTTGTATGCCGTGCT

GGTCAGTGCCCTCGTGCTG.

In some embodiments, the TCR alpha and/or TCR beta transmembrane domain comprises one or more mutations that attenuate or abolish interaction of the TCR with the TCR CD3 subunit. In some embodiments, the TCR alpha transmembrane domain comprises a R253L mutation. In some embodiments, the TCR beta transmembrane domain comprises a K288L mutation.

In some embodiments the transmembrane domain comprise a CD28 transmembrane domain. In some embodiments, the CD28 transmembrane domain comprises an amino acid sequence having at least 80% identity, at least 90% identity, at least 95% identity, at least 99% identity or is identical to a sequence of FWVLVVVGGVLACYSLL-VTVAFIIFWV (SEQ ID NO: 232). In some embodiments, the CD28 transmembrane domain comprises or consists essentially of FWVLVVVGGVLACYSLLVTVAFIIFWV (SEQ ID NO: 232). In some embodiments, the CD28 transmembrane domain is encoded by a nucleotide sequence having at least 80% identity, at least 90% identity, at least 95% identity, at least 99% identity or is identical to a sequence of (SEQ ID NO: 233)
TTCTGGGTGCTGGTCGTTGTGGGCGGCGTGCTGGCCTGCTACAGCCTGCT

GGTGACAGTGGCCTTCATCATCTTTTGGGTG.

In some embodiments, the transmembrane domain can be attached to the extracellular region chimeric antigen receptor, e.g., the antigen-binding domain or ligand binding domain, via a hinge, e.g., a hinge from a human protein. For example, in some embodiments, the hinge can be a human immunoglobulin (Ig) hinge, e.g., an IgG4 hinge, a CD8α hinge or an LILRB1 hinge.

Hinge Domain

The disclosure provides inhibitory receptors, the receptors comprising a polypeptide. In some embodiments, the polypeptide comprises a hinge domain. In some embodiments, the hinge domain is a LILRB1 hinge domain or a functional variant thereof.

The LILRB1 protein has four immunoglobulin (Ig) like domains termed D1, D2, D3 and D4. In some embodiments, the LILRB1 hinge domain comprises an LILRB1 D3D4 domain or a functional variant thereof. In some embodiments, the LILRB1 D3D4 domain comprises a sequence at least 95%, at least 96%, at least 97%, at least 98%, at least 99% or identical to SEQ ID NO: 274. In some embodiments, the LILRB1 D3D4 domain comprises or consists essentially of SEQ ID NO: 274.

In some embodiments, the polypeptide comprises the LILRB1 hinge domain or functional fragment or variant thereof. In embodiments, the LILRB1 hinge domain or functional fragment or variant thereof comprises a sequence at least 95%, at least 96%, at least 97%, at least 98%, at least 99% identical or identical to SEQ ID NO: 275, SEQ ID NO: 274, or SEQ ID NO: 276. In embodiments, the LILRB1 hinge domain or functional fragment or variant thereof comprises a sequence at least 95% identical to SEQ ID NO: 275, SEQ ID NO: 274, or SEQ ID NO: 276.

In some embodiments, the LILRB1 hinge domain comprises a sequence identical to SEQ ID NO: 275, SEQ ID NO: 274, or SEQ ID NO: 276.

In some embodiments, the LILRB1 hinge domain consists essentially of a sequence identical to SEQ ID NO: 275, SEQ ID NO: 274, or SEQ ID NO: 276.

In some embodiments the chimeric antigen receptors of the disclosure, the polypeptide comprises a hinge that is not isolated or derived from LILRB1.

In some embodiments, the hinge is isolated or derived from CD8α or CD28. In some embodiments, the CD8α hinge comprises an amino acid sequence having at least 80% identity, at least 90% identity, at least 95% identity, at least 99% identity or is identical to a sequence of TTTPAPRPPT-PAPTIASQPLSLRPEACRPAAGGAVHTRGLDFACD (SEQ ID NO: 219). In some embodiments, the CD8α hinge comprises TTTPAPRPPTPAPTIASQPLSLRPEACR-PAAGGAVHTRGLDFACD (SEQ ID NO: 219).

In some embodiments, the CD8α hinge consists essentially of

```
                                         (SEQ ID NO: 219)
TTTPAPRPPTPAPTIASQPLSLRPEACRPAAGGAVHTRGLDFACD.
```

In some embodiments, the CD8α hinge is encoded by a nucleotide sequence having at least 80% identity, at least 90% identity, at least 95% identity, at least 99% identity or is identical to a sequence of

```
                                         (SEQ ID NO: 220)
accacgacgccagcgccgcgaccaccaacaccggcgccaccatcgcgtc gcagccctgtccctgcgcccagaggcgtgccggccagcggcggggggcg cagtgcacacgaggggctggacttcgcctgtgat.
```

In some embodiments, the CD28 hinge comprises an amino acid sequence having at least 80% identity, at least 90% identity, at least 95% identity, at least 99% identity or is identical to a sequence of CTIEVMYPPPYLD-NEKSNGTIIHVKGKHLCPSPLFPGPSKP (SEQ ID NO: 221). In some embodiments, the CD28 hinge comprises or consists essentially of CTIEVMYPPPYLD-NEKSNGTIIHVKGKHLCPSPLFPGPSKP (SEQ ID NO: 221). In some embodiments, the CD28 hinge is encoded by a nucleotide sequence having at least 80% identity, at least 90% identity, at least 95% identity, at least 99% identity or is identical to a sequence of

```
                                         (SEQ ID NO: 222)
tgtaccattgaagttatgtatcctcctccttacctagacaatgagaagag caatggaaccattatccatgtgaaagggaaacacctttgtccaagtcccc tatttcccggaccttctaagccc.
```

Combinations of LILRB1 Domains

In some embodiments, the inhibitory receptors of the disclosure comprise a polypeptide comprising more than one LILRB1 domain or functional equivalent thereof. For example, in some embodiments, the polypeptide comprises an LILRB1 transmembrane domain and intracellular domain, or an LILRB1 hinge domain, transmembrane domain and intracellular domain.

In particular embodiments, the polypeptide comprises an LILRB1 hinge domain or functional fragment or variant thereof, and the LILRB1 transmembrane domain or a functional variant thereof. In some embodiments, the polypeptide comprises a sequence at least 95% identical, at least 96% identical, at least 97% identical, at least 98% identical, at least 99% identical or identical to SEQ ID NO: 277. In some embodiments, the polypeptide comprises a sequence at least 95% identical to SEQ ID NO: 277. In some embodiments, the polypeptide comprises a sequence identical to SEQ ID NO: 277.

In further embodiments, the polypeptide comprises: the LILRB1 transmembrane domain or a functional variant thereof, and an LILRB1 intracellular domain and/or an intracellular domain comprising at least one immunoreceptor tyrosine-based inhibitory motif (ITIM), wherein the ITIM is selected from NLYAAV (SEQ ID NO: 256), VTY-AEV (SEQ ID NO: 257), VTYAQL (SEQ ID NO: 258), and SIYATL (SEQ ID NO: 259). In some embodiments, the polypeptide comprises the LILRB1 transmembrane domain or a functional variant thereof, and an LILRB1 intracellular domain and/or an intracellular domain comprising at least two ITIM, wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In some embodiments, the polypeptide comprises a LILRB1 transmembrane domain and intracellular domain. In some embodiments, the polypeptide comprises a sequence at least 95% identical, at least 96% identical, at least 97% identical, at least 98% identical, at least 99% identical or identical to SEQ ID NO: 278. In some embodiments, the polypeptide comprises a sequence at least 95% identical to SEQ ID NO: 278. In some embodiments, the polypeptide comprises a sequence identical to SEQ ID NO: 278.

In preferred embodiments, the polypeptide comprises: an LILRB1 hinge domain or functional fragment or variant thereof; an LILRB1 transmembrane domain or a functional variant thereof; and an LILRB1 intracellular domain and/or an intracellular domain comprising at least two immunoreceptor tyrosine-based inhibitory motifs (ITIMs), wherein each ITIM is independently selected from NLYAAV (SEQ ID NO: 256), VTYAEV (SEQ ID NO: 257), VTYAQL (SEQ ID NO: 258), and SIYATL (SEQ ID NO: 259).

In some embodiments, the polypeptide comprises a sequence at least 95% identical to SEQ ID NO: 254 or SEQ ID NO: 279, or at least 99% identical to SEQ ID NO: 254 or SEQ ID NO: 279, or identical to SEQ ID NO: 254 or SEQ ID NO: 279.

In some embodiments, the polypeptide comprises a sequence at least 99% identical to SEQ ID NO: 277, or at least 99% identical to SEQ ID NO: 277, or identical to SEQ ID NO: 277.

In some embodiments, the polypeptide comprises a sequence at least 99% identical to SEQ ID NO: 278, or at least 99% identical to SEQ ID NO: 278, or identical to SEQ ID NO: 278.

In some embodiments, the inhibitory receptor comprises a LIRLRB1 hinge, transmembrane and intracellular domain. In some embodiments, the LIRLRB1 hinge, transmembrane and intracellular domain comprises a sequence of SEQ ID NO: 254, or a sequence at 90%, at least 95% identical, at least 96% identical, at least 97% identical, at least 98% identical, at least 99% identical or identical thereto.

TABLE 16

Inhibitory receptor Hinge, Transmembrane and Intracellular Domains

| Construct | Protein Sequence | DNA Sequence |
|---|---|---|
| C-1765, C2162, C2163 | YGSQSSKPYLLT HPSDPLELVVSG PSGGPSSPTTGP TSTSGPEDQPLT PTGSDPQSGLGR HLGVVIGILVAV ILLLLLLLLLFL ILRHRRQGKHWT STQRKADFQHPA GAVGPEPTDRGL QWRSSPAADAQE ENLYAAVKHTQP EDGVEMDTRSPH DEDPQAVTYAEV KHSRPRREMASP PSPLSGEFLDTK DRQAEEDRQMDT EAAASEAPQDVT YAQLHSLTLRRE ATEPPPSQEGPS PAVPSIYATLAI H (SEQ ID NO: 254) | TACGGCTCACAGAGCTCCAAACCCTA CCTGCTGACTCACCCCAGTGACCCCC TGGAGCTCGTGGTCTCAGGACCGTCT GGGGGGCCCCAGCTCCCCGACAACAGG CCCCACCTCCACATCTGGCCCTGAGG ACCAGCCCCTCACCCCCACCGGGTCG GATCCCCAGAGTGGTCTGGGAAGGCA CCTGGGGGTTGTGATCGGCATCTTGG TGGCCGTCATCCTACTGCTCCTCCTC CTCCTCCTCCTCTTCCTCATCCTCCG ACATCGACGTCAGGGCAAACACTGGA CATCGACCCAGAGAAAGGCTGATTTC CAACATCCTGCAGGGGCTGTGGGGCC AGAGCCCACAGACAGAGGCCTGCAGT GGAGGTCCAGCCCAGCTGCCGATGCC CAGGAAGAAAACCTCTATGCTGCCGT CAGGAAGAAAACCTCTATGCTGCCGT GAAGCACACACAGCCTGAGGATGGGG TGGAGATGGACACTCGGAGCCCACAC GATGAAGACCCCCAGGCAGTGACGTA TGCCGAGGTGAAACACTCCAGACCTA GGAGAGAAATGGCCTCTCCTCCTTCC CCACTGTCTGGGGAATTCCTGGACAC AAAGGACAGACAGGCGGAAGAGGACA GGCAGATGGACACTGAGGCTGCTGCA TCTGAAGCCCCCAGGATGTGACCTA CGCCCAGCTGCACAGCTTGACCCTCA GACGGGAGGCAACTGAGCCTCCTCCA TCCCAGGAAGGGCCCTCTCCAGCTGT GCCCAGCATCTACGCCACTCTGGCCA TCCACTAG (SEQ ID NO: 255) |

Additional sequences for the LILRB1 based inhibitory receptors of the disclosure are shown in Table 17 below.

TABLE 17

Polypeptide Sequences for Elements of Illustrative Inhibitory Receptors

| Name | Sequence |
|---|---|
| LILRB1 | MTPILTVLICLGLSLGPRTHVQAGHLPKPTLWAEPGSVIT QGSPVTLRCQGGQETQEYRLYREKKTALWITRIPQELVKK GQFPIPSITWEHAGRYRCYYGSDTAGRSESSDPLELVVTG AYIKPTLSAQPSPVVNSGGNVILQCDSQVAFDGFSLCKEG EDEHPQCLNSQPHARGSSRAIFSVGPVSPSRRWWYRCYAY DSNSPYEWSLPSDLLELLVLGVSKKPSLSVQPGPIVAPEE TLTLQCGSDAGYNRFVLYKDGERDFLQLAGAQPQAGLSQA NFTLGPVSRSYGGQYRCYGAHNLSSEWSAPSDPLDILIAG QFYDRVSLSVQPGPTVASGENVTLLCQSQGWMQTFLLTKE GAADDPWRLRSTYQSQKYQAEFPMGPVTSAHAGTYRCYGS QSSKPYLLTHPSDPLELVVSGPSGGPSSPTTGPTSTSGPE DQPLTPTGSDPQSGLGRHLGVVIGILVAVILLLLLLLLF LILRHRRQGKHWTSTQRKADFQHPAGAVGPEPTDRGLQWR SSPAADAQEENLYAAVKHTQPEDGVEMDTRSPHDEDPQAV TYAEVKHSRPRREMASPPSPLSGEFLDTKDRQAEEDRQMD TEAAASEAPQDVTYAQLHSLTLRREATEPPPSQEGPSPAV PSIYATLAIH SEQ ID NO: 280 |
| LILRB1 hinge-trans-membrane-intra-cellular domain | YGSQSSKPYLLTHPSDPLELVVSGPSGGPSSPTTGPTSTS GPEDQPLTPTGSDPQSGLGRHLGVVIGILVAVILLLLLLL LLFLILRHRRQGKHWTSTQRKADFQHPAGAVGPEPTDRGL QWRSSPAADAQEENLYAAVKHTQPEDGVEMDTRSPHDEDP QAVTYAEVKHSRPRREMASPPSPLSGEFLDTKDRQAEEDR QMDTEAAASEAPQDVTYAQLHSLTLRREATEPPPSQEGPS PAVPSIYATLAIH SEQ ID NO: 254 |
| LILRB1 hinge-trans-membrane-intra- | VVSGPSGGPSSPTTGPTSTSGPEDQPLTPTGSDPQSGLGR HLGVVIGILVAVILLLLLLLLFLILRHRRQGKHWTSTQR KADFQHPAGAVGPEPTDRGLQWRSSPAADAQEENLYAAVK HTQPEDGVEMDTRSPHDEDPQAVTYAEVKHSRPRREMASP PSPLSGEFLDTKDRQAEEDRQMDTEAAASEAPQDVTYAQL |

TABLE 17-continued

Polypeptide Sequences for Elements of Illustrative Inhibitory Receptors

| Name | Sequence |
|---|---|
| cellular domain (w/o YGSQSSKPY LLTHPSDPL EL, SEQ ID NO: 18) | HSLTLRREATEPPPSQEGPSPAVPSIYATLAIH SEQ ID NO: 279 |
| LILRB1 hinge domain | YGSQSSKPYLLTHPSDPLELVVSGPSGGPSSPTTGPTSTS GPEDQPLTPTGSDPQSGLGRHLG SEQ ID NO: 275 |
| LILRB1 trans-membrane domain | VVIGILVAVILLLLLLLLFLIL SEQ ID NO: 269 |
| LILRB1 intra-cellular domain | RHRRQGKHWTSTQRKADFQHPAGAVGPEPTDRGLQWRSSP AADAQEENLYAAVKHTQPEDGVEMDTRSPHDEDPQAVTYA EVKHSRPRREMASPPSPLSGEFLDTKDRQAEEDRQMDTEA AASEAPQDVTYAQLHSLTLRREATEPPPSQEGPSPAVPSI YATLAIH SEQ ID NO: 266 |
| ITIM1 | NLYAAV SEQ ID NO: 256 |
| ITIM2 | VTYAEV SEQ ID NO: 257 |
| ITIM3 | VTYAQL SEQ ID NO: 258 |
| ITIM4 | SIYATL SEQ ID NO: 259 |
| ITIM1-2 | NLYAAVKHTQPEDGVEMDTRSPHDEDPQAVTYAEV SEQ ID NO: 281 |
| ITIM2-3 | VTYAEVKHSRPRREMASPPSPLSGEFLDTKDRQAEEDRQM DTEAAASEAPQDVTYAQL SEQ ID NO: 261 |
| ITIM3-4 | VTYAQLHSLTLRREATEPPPSQEGPSPAVPSIYATL SEQ ID NO: 262 |
| ITIM1-3 | NLYAAVKHTQPEDGVEMDTRSPHDEDPQAVTYAEVKHSRP RREMASPPSPLSGEFLDTKDRQAEEDRQMDTEAAASEAPQ DVTYAQL SEQ ID NO: 263 |
| ITIM2-4 | VTYAEVKHSRPRREMASPPSPLSGEFLDTKDRQAEEDRQM DTEAAASEAPQDVTYAQLHSLTLRREATEPPPSQEGPSPA VPSIYATL SEQ ID NO: 264 |
| ITIM1-4 | NLYAAVKHTQPEDGVEMDTRSPHDEDPQAVTYAEVKHSRP RREMASPPSPLSGEFLDTKDRQAEEDRQMDTEAAASEAPQ DVTYAQLHSLTLRREATEPPPSQEGPSPAVPSIYATL SEQ ID NO: 265 |
| D3D4 domain | YGSQSSKPYLLTHPSDPLEL SEQ ID NO: 274 |
| Short hinge | VVSGPSGGPSSPTTGPTSTSGPEDQPLTPTGSDPQSGLGR HLG SEQ ID NO: 276 |
| Hinge (iTIM hinge) | YGSQSSKPYLLTHPSDPLELVVSGPSGGPSSPTTGPTSTS GPEDQPLTPTGSDPQSGLGRHLGV (SEQ ID NO: 282) |
| Short hinge 2 | VVSGPSGGPSSPTTGPTSTSGPEDQPLTPTGSDPQSGLGR HLGV (SEQ ID NO: 283) |
| Long hinge 1 | AGSGGSGGSGGSPVPSTPPTPSPSTPPTPSPSGGSGNSSG SGGSPVPSTPPTPSPSTPPTPSPSASV (SEQ ID NO: 284) |
| Long hinge 2 | AGSGGSGGSGGSPVPSTPPTNSSTPPTPSPSPVPSTPPT NSSTPPTPSPSPVPSTPPTNSSTPPTPSPSASV (SEQ ID NO: 285) |

TABLE 17-continued

Polypeptide Sequences for Elements of
Illustrative Inhibitory Receptors

| Name | Sequence |
|---|---|
| 2X short hinge | VVSGPSGGPSSPTTGPTSTSGPEDQPLTPTGSDPQSGLGR HVVSGPSGGPSSPTTGPTSTSGPEDQPLTPTGSDPQSGLG RHLGV (SEQ ID NO: 286) |
| Hinge (truncated) | TTGPTSTSGPEDQPLTPTGSDPQSGLGRHLGV (SEQ ID NO: 287) |
| Hinge-transmembrane | YGSQSSKPYLLTHPSDPLELVVSGPSGGPSSPTTGPTSTS GPEDQPLTPTGSDPQSGLGRHLGVVIGILVAVILLLLLL LLFLIL SEQ ID NO: 277 |
| Transmembrane-intracellular domain | VVIGILVAVILLLLLLLLLFLILRHRRQGKHWTSTQRKAD FQHPAGAVGPEPTDRGLQWRSSPAADAQEENLYAAVKHTQ PEDGVEMDTRSPHDEDPQAVTYAEVKHSRPRREMASPPSP LSGEFLDTKDRQAEEDRQMDTEAAASEAPQDVTYAQLHSL TLRREATEPPPSQEGPSPAVPSIYATLAIH SEQ ID NO: 278 |

Assays

Provided herein are assays that can be used to measure the activity of the engineered receptors of the disclosure.

The activity of engineered receptors can be assayed using a cell line engineered to express a reporter of receptor activity such as a luciferase reporter. Exemplary cell lines include Jurkat T cells, although any suitable cell line known in the art may be used. For example, Jurkat cells expressing a luciferase reporter under the control of an NFAT promoter can be used as effector cells. Expression of luciferase by this cell line reflects TCR-mediated signaling.

The reporter cells can be transfected with each of the various fusion protein constructs, combinations of fusion protein constructs or controls described herein.

Expression of the fusion proteins in reporter cells can be confirmed by using fluorescently labeled MHC tetramers, for example Alexa Fluor 647-labeled HER2-MHC tetramer, to detect expression of the fusion protein.

To assay the activity of engineered receptors, target cells are loaded with antigen prior to exposure to the effector cells comprising the reporter and the engineered receptor. For example, target cells can be loaded with antigen at least 12, 14, 16, 18, 20, 22 or 24 hours prior to exposure to effector cells. Exemplary target cells include A375 cells, although any suitable cells known in the art may be used. In some cases, target cells can be loaded with serially diluted concentrations of an antigen, such as a HER2 antigen. The effector cells can then be co-cultured with target cells for a suitable period of time, for example 6 hours. Luciferase is then measured by luminescence reading after co-culture. Luciferase luminescence can be normalized to maximum and minimum intensity to allow comparison of activating peptide concentrations for each engineered receptor construct.

Provided herein are methods of determining the relative EC50 of engineered receptors of the disclosure. As used herein, "EC50" refers to the concentration of an inhibitor or agent where the response (or binding) is reduced by half. EC50s of engineered receptors of the disclosure refer to concentration of antigen where binding of the engineered receptor to the antigen is reduced by half. Binding of the antigen, or probe to the engineered receptor can be measured by staining with labeled peptide or labeled peptide-MHC complex, for example MHC:HER2 pMHC complex conjugated with fluorophore. EC50 can be obtained by nonlinear regression curve fitting of reporter signal with peptide titration. Probe binding and EC50 can be normalized to the levels of benchmark TCR without a fusion protein, e.g. HER2.

Polynucleotides

The disclosure provides a polynucleotide system, comprising one or more polynucleotides comprising polynucleotide sequences encoding: an activator receptor comprising an extracellular ligand binding domain specific to an erb-b2 receptor tyrosine kinase 2 (HER2) antigen; and an inhibitory receptor comprising an extracellular ligand binding domain specific to a non-target antigen that is not expressed by the cancer cell due to a loss of heterozygosity in the cancer cell.

The disclosure provides vectors comprising the polynucleotide system described herein. The disclosure provides vectors comprising the polynucleotides described herein.

The disclosure provides polynucleotides encoding the sequence(s) of the activator and inhibitory receptors described herein. In some embodiments, the sequence of the activating and/or inhibitory receptor, or a fusion protein of the activator and/or inhibitory receptor is operably linked to a promoter. In some embodiments, the sequence encoding the activator receptor, or a polypeptide thereof, is operably linked to a first promoter, and the sequence encoding an inhibitory receptor, or a fusion protein thereof, is operably linked to a second promoter.

In some embodiments, the polynucleotide or polynucleotide system comprises SEQ ID NO: 52, or a sequence that shares at least 80%, at least 85%, at least 90%, at least 95%, or at least 98% identity thereto. In some embodiments, the polynucleotide or polynucleotide system comprises SEQ ID NO: 54, or a sequence that shares at least 80%, at least 85%, at least 90%, at least 95%, or at least 98% identity thereto. In some embodiments, the polynucleotide or polynucleotide system comprises SEQ ID NO: 56, or a sequence that shares at least 80%, at least 85%, at least 90%, at least 95%, or at least 98% identity thereto.

In some embodiments, the polynucleotide or polynucleotide system comprises SEQ ID NO: 58, or a sequence that shares at least 80%, at least 85%, at least 90%, at least 95%, or at least 98% identity thereto. In some embodiments, the polynucleotide or polynucleotide system comprises SEQ ID NO: 60, or a sequence that shares at least 80%, at least 85%, at least 90%, at least 95%, or at least 98% identity thereto. In some embodiments, the polynucleotide or polynucleotide system comprises SEQ ID NO: 62, or a sequence that shares at least 80%, at least 85%, at least 90%, at least 95%, or at least 98% identity thereto. In some embodiments, the polynucleotide or polynucleotide system comprises SEQ ID NO: 21803, or a sequence that shares at least 80%, at least 85%, at least 90%, at least 95%, or at least 98% identity thereto.

In some embodiments, the polynucleotide or polynucleotide system comprises anyone of SEQ ID NOs: 75-86, or a sequence that shares at least 80%, at least 85%, at least 90%, at least 95%, or at least 98% identity thereto. In some embodiments, the polynucleotide or polynucleotide system comprises SEQ ID NO: 76, or a sequence that shares at least 80%, at least 85%, at least 90%, at least 95%, or at least 98% identity thereto. In some embodiments, the polynucleotide or polynucleotide system comprises SEQ ID NO: 77, or a sequence that shares at least 80%, at least 85%, at least 90%, at least 95%, or at least 98% identity thereto. In some embodiments, the polynucleotide or polynucleotide system comprises SEQ ID NO: 78, or a sequence that shares at least 80%, at least 85%, at least 90%, at least 95%, or at least 98% identity thereto. In some embodiments, the polynucleotide or polynucleotide system comprises SEQ ID NO: 79, or a sequence that shares at least 80%, at least 85%, at least 90%, at least 95%, or at least 98% identity thereto. In some embodiments, the polynucleotide or polynucleotide system comprises SEQ ID NO: 80, or a sequence that shares at least 80%, at least 85%, at least 90%, at least 95%, or at least 98% identity thereto. In some embodiments, the polynucleotide or polynucleotide system comprises SEQ ID NO: 81, or a sequence that shares at least 80%, at least 85%, at least 90%, at least 95%, or at least 98% identity thereto. In some embodiments, the polynucleotide or polynucleotide system comprises SEQ ID NO: 82, or a sequence that shares at least 80%, at least 85%, at least 90%, at least 95%, or at least 98% identity thereto. In some embodiments, the polynucleotide or polynucleotide system comprises SEQ ID NO: 83, or a sequence that shares at least 80%, at least 85%, at least 90%, at least 95%, or at least 98% identity thereto. In some embodiments, the polynucleotide or polynucleotide system comprises SEQ ID NO: 84, or a sequence that shares at least 80%, at least 85%, at least 90%, at least 95%, or at least 98% identity thereto. In some embodiments, the polynucleotide or polynucleotide system comprises SEQ ID NO: 85, or a sequence that shares at least 80%, at least 85%, at least 90%, at least 95%, or at least 98% identity thereto. In some embodiments, the polynucleotide or polynucleotide system comprises SEQ ID NO: 86, or a sequence that shares at least 80%, at least 85%, at least 90%, at least 95%, or at least 98% identity thereto. In some embodiments, the polynucleotide or polynucleotide system comprises SEQ ID NO: 208, or a sequence that shares at least 80%, at least 85%, at least 90%, at least 95%, or at least 98% identity thereto. In some embodiments, the polynucleotide or polynucleotide system comprises SEQ ID NO: 210, or a sequence that shares at least 80%, at least 85%, at least 90%, at least 95%, or at least 98% identity thereto. In some embodiments, the polynucleotide or polynucleotide system comprises SEQ ID NO: 212, or a sequence that shares at least 80%, at least 85%, at least 90%, at least 95%, or at least 98% identity thereto.

In some embodiments, the polynucleotide or polynucleotide system comprises any one of SEQ ID NOs: 224, 226, 227, 229, or 231, or a sequence that shares at least 80%, at least 85%, at least 90%, at least 95%, or at least 98% identity thereto.

In some embodiments, the polynucleotide or polynucleotide system comprises any one of SEQ ID NOs: 292, 294, 296, 298, 300, 302 304, 306, or 308, or a sequence that shares at least 80%, at least 85%, at least 90%, at least 95%, or at least 98% identity thereto.

The disclosure provides vectors encoding the coding sequence or sequences of any of the engineered receptors described herein. In some embodiments, the sequence of the activating and/or inhibitory receptor is operably linked to a promoter. In some embodiments, the sequence encoding the activating receptor is operably linked to a first promoter, and the sequence encoding an inhibitory receptor is operably linked to a second promoter.

In some embodiments, the activating receptor is encoded by a first vector and the inhibitory receptor is encoded by second vector. In some embodiments, both engineered receptors are encoded by a single vector.

In some embodiments, the activator and inhibitory receptors are encoded by a single vector. Methods of encoding multiple polypeptides using a single vector will be known to persons of ordinary skill in the art, and include, inter alia, encoding multiple polypeptides under control of different promoters, or, if a single promoter is used to control transcription of multiple polypeptides, use of sequences encoding internal ribosome entry sites (IRES) and/or self-cleaving peptides. Exemplary self-cleaving peptides include T2A, P2A, E2A and F2A self-cleaving peptides. In some embodiments, the T2A self-cleaving peptide comprises a sequence of EGRGSLLTCGDVEENPGP (SEQ ID NO: 288). In some embodiments, the P2A self-cleaving peptide comprises a sequence of ATNFSLLKQAGDVEENPGP (SEQ ID NO: 196). In some embodiments, the E2A self-cleaving peptide comprises a sequence of QCTNYALLKLAGDVESNPGP (SEQ ID NO: 289). In some embodiments, the F2A self-cleaving peptide comprises a sequence of VKQTLNFDLLKLAGDVESNPGP (SEQ ID NO: 290). Any of the foregoing can also include an N terminal GSG linker. For example, a T2A self-cleaving peptide can also comprise a sequence of GSGEGRGSLLTCGDVEENPGP (SEQ ID NO: 557), which can be encoded by a sequence of

```
                                              (SEQ ID NO: 558)
GGATCCGGAGAGGGCAGAGGCAGCCTGCTGACATGTGGCGACGTGGAAGA

GAACCCTGGCCCC.
```

In some embodiments, the vector comprises SEQ ID NO: 52, or a sequence that shares at least 80%, at least 85%, at least 90%, at least 95%, or at least 98% identity thereto. In some embodiments, the vector comprises SEQ ID NO: 54, or a sequence that shares at least 80%, at least 85%, at least 90%, at least 95%, or at least 98% identity thereto. In some embodiments, the vector comprises SEQ ID NO: 56, or a sequence that shares at least 80%, at least 85%, at least 90%, at least 95%, or at least 98% identity thereto. In some embodiments, the vector comprises SEQ ID NO: 58, or a sequence that shares at least 80%, at least 85%, at least 90%, at least 95%, or at least 98% identity thereto. In some embodiments, the vector comprises SEQ ID NO: 60, or a sequence that shares at least 80%, at least 85%, at least 90%, at least 95%, or at least 98% identity thereto. In some embodiments, the vector comprises SEQ ID NO: 62, or a sequence that shares at least 80%, at least 85%, at least 90%, at least 95%, or at least 98% identity thereto. In some embodiments, the vector comprises SEQ ID NO: 21803, or a sequence that shares at least 80%, at least 85%, at least 90%, at least 95%, or at least 98% identity thereto.

In some embodiments, the vector comprises SEQ ID NO: 75, or a sequence that shares at least 80%, at least 85%, at least 90%, at least 95%, or at least 98% identity thereto. In some embodiments, the vector comprises SEQ ID NO: 76, or a sequence that shares at least 80%, at least 85%, at least 90%, at least 95%, or at least 98% identity thereto. In some embodiments, the vector comprises SEQ ID NO: 77, or a sequence that shares at least 80%, at least 85%, at least 90%, at least 95%, or at least 98% identity thereto. In some embodiments, the vector comprises SEQ ID NO: 78, or a sequence that shares at least 80%, at least 85%, at least 90%, at least 95%, or at least 98% identity thereto. In some embodiments, the vector comprises SEQ ID NO: 79, or a sequence that shares at least 80%, at least 85%, at least 90%, at least 95%, or at least 98% identity thereto. In some embodiments, the vector comprises SEQ ID NO: 80, or a sequence that shares at least 80%, at least 85%, at least 90%, at least 95%, or at least 98% identity thereto. In some embodiments, the vector comprises SEQ ID NO: 81, or a sequence that shares at least 80%, at least 85%, at least 90%, at least 95%, or at least 98% identity thereto. In some embodiments, the vector comprises SEQ ID NO: 82, or a sequence that shares at least 80%, at least 85%, at least 90%, at least 95%, or at least 98% identity thereto. In some embodiments, the vector comprises SEQ ID NO: 83, or a sequence that shares at least 80%, at least 85%, at least 90%, at least 95%, or at least 98% identity thereto. In some embodiments, the vector comprises SEQ ID NO: 84, or a sequence that shares at least 80%, at least 85%, at least 90%, at least 95%, or at least 98% identity thereto. In some embodiments, the vector comprises SEQ ID NO: 85, or a sequence that shares at least 80%, at least 85%, at least 90%, at least 95%, or at least 98% identity thereto. In some embodiments, the vector comprises SEQ ID NO: 86, or a sequence that shares at least 80%, at least 85%, at least 90%, at least 95%, or at least 98% identity thereto. In some embodiments, the vector comprises SEQ ID NO: 208, or a sequence that shares at least 80%, at least 85%, at least 90%, at least 95%, or at least 98% identity thereto. In some embodiments, the vector comprises SEQ ID NO: 210, or a sequence that shares at least 80%, at least 85%, at least 90%, at least 95%, or at least 98% identity thereto. In some embodiments, the vector comprises SEQ ID NO: 212, or a sequence that shares at least 80%, at least 85%, at least 90%, at least 95%, or at least 98% identity thereto.

In some embodiments, the vector comprises SEQ ID NO: 224, 226, 227, 229, or 231, or a sequence that shares at least 80%, at least 85%, at least 90%, at least 95%, or at least 98% identity thereto. In some embodiments, the vector comprises SEQ ID NO: 292, 294, 296, 298, 300, 302, 304, 306, or 308, or a sequence that shares at least 80%, at least 85%, at least 90%, at least 95%, or at least 98% identity thereto.

In some embodiments, the vector encodes a polypeptide sequence comprising SEQ ID NO: 51, or a sequence that shares at least 80%, at least 85%, at least 90%, at least 95%, or at least 98% identity thereto. In some embodiments, the vector encodes a polypeptide sequence comprising SEQ ID NO: 53, or a sequence that shares at least 80%, at least 85%, at least 90%, at least 95%, or at least 98% identity thereto. In some embodiments, the vector encodes a polypeptide sequence comprising SEQ ID NO: 55, or a sequence that shares at least 80%, at least 85%, at least 90%, at least 95%, or at least 98% identity thereto. In some embodiments, the vector encodes a polypeptide sequence comprising SEQ ID NO: 57, or a sequence that shares at least 80%, at least 85%, at least 90%, at least 95%, or at least 98% identity thereto. In some embodiments, the vector encodes a polypeptide sequence comprising SEQ ID NO: 59, or a sequence that shares at least 80%, at least 85%, at least 90%, at least 95%, or at least 98% identity thereto. In some embodiments, the vector encodes a polypeptide sequence comprising SEQ ID NO: 61, or a sequence that shares at least 80%, at least 85%, at least 90%, at least 95%, or at least 98% identity thereto. In some embodiments, the vector encodes a polypeptide sequence comprising SEQ ID NO: 63, or a sequence that shares at least 80%, at least 85%, at least 90%, at least 95%, or at least 98% identity thereto. In some embodiments, the vector encodes a polypeptide sequence comprising SEQ ID NO: 64, or a sequence that shares at least 80%, at least 85%, at least 90%, at least 95%, or at least 98% identity thereto. In some embodiments, the vector encodes a polypeptide sequence comprising SEQ ID NO: 65, or a sequence that shares at least 80%, at least 85%, at least 90%, at least 95%, or at least 98% identity thereto. In some embodiments, the vector encodes a polypeptide sequence comprising SEQ ID NO: 66, or a sequence that shares at least 80%, at least 85%, at least 90%, at least 95%, or at least 98% identity thereto. In some embodiments, the vector encodes a polypeptide sequence comprising SEQ ID NO: 67, or a sequence that shares at least 80%, at least 85%, at least 90%, at least 95%, or at least 98% identity thereto. In some embodiments, the vector encodes a polypeptide sequence comprising SEQ ID NO: 68, or a sequence that shares at least 80%, at least 85%, at least 90%, at least 95%, or at least 98% identity thereto. In some embodiments, the vector encodes a polypeptide sequence comprising SEQ ID NO: 69, or a sequence that shares at least 80%, at least 85%, at least 90%, at least 95%, or at least 98% identity thereto. In some embodiments, the vector encodes a polypeptide sequence comprising SEQ ID NO: 70, or a sequence that shares at least 80%, at least 85%, at least 90%, at least 95%, or at least 98% identity thereto. In some embodiments, the vector encodes a polypeptide sequence comprising SEQ ID NO: 72, or a sequence that shares at least 80%, at least 85%, at least 90%, at least 95%, or at least 98% identity thereto. In some embodiments, the vector encodes a polypeptide sequence comprising SEQ ID NO: 73, or a sequence that shares at least 80%, at least 85%, at least 90%, at least 95%, or at least 98% identity thereto. In some embodiments, the vector encodes a polypeptide sequence comprising SEQ ID NO: 74, or a sequence that shares at least 80%, at least 85%, at least 90%, at least 95%, or at least 98% identity thereto.

In some embodiments, the vector encodes a polypeptide sequence comprising SEQ ID NO: 207, 209, or 211, or a sequence that shares at least 80%, at least 85%, at least 90%, at least 95%, or at least 98% identity thereto. In some embodiments, the vector encodes a polypeptide sequence comprising SEQ ID NO: 291, 293, 295, 297, 299, 301, 303, 305, 307, 21805, or a sequence that shares at least 80%, at least 85%, at least 90%, at least 95%, or at least 98% identity thereto.

In some embodiments, a polynucleotide sequence provided herein is codon-optimized. Codon-optimization is the process of introducing silent nucleotide changes into a nucleic acid sequence which increase the production of the protein encoded by the nucleic acid sequence without changing the amino acid sequence of the protein.

In some embodiments, the vector is an expression vector, i.e. for the expression of the engineered receptors of the disclosure in a suitable cell.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding engineered receptors is typically achieved by operably linking a nucleic acid encoding the fusion protein or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The polynucleotides encoding the fusion proteins can be cloned into a number of types of vectors. For example, the polynucleotides can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to cells, such as immune cells, in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). Another example of a suitable promoter is the U6 promoter. Another example of a suitable promoter is the H1 promoter. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. An exemplary sequence of the U6 promoter is set forth in SEQ ID NO: 21800. An exemplary sequence of the H1 promoter is set forth in SEQ ID NO: 21801.

In certain aspect, a vector comprises a termination sequence, for example, a T6 or T7 termination sequence.

In order to assess the expression of an engineered receptor, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected or transduced cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). One method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Immune Cells

Provided herein are immune cells comprising the polynucleotides, vectors, fusion proteins and engineered receptors described herein.

The disclosure provides an immune cell responsive to loss of heterozygosity in a cancer cell, comprising: an activator receptor comprising an extracellular ligand binding domain specific to an erb-b2 receptor tyrosine kinase 2 (HER2) antigen; and an inhibitory receptor comprising an extracellular ligand binding domain specific to a non-target antigen that is not expressed by the cancer cell due to a loss of heterozygosity in the cancer cell. In some embodiments, the non-target antigen is an HLA class I allele or a minor histocompatibility antigen (MiHA). In some embodiments, the HLA class I allele comprises HLA-A, HLA-B, HLA-C or HLA-E. In some embodiments, the non-target antigen is selected from CXCL16, COLEC12 and APCDD1, HLA-A*01, HLA-A*02, HLA-A*03, HLA-A*11, HLA-B*07, HLA-C*07, or an antigen peptide thereof. In some embodiments, the HLA class I allele is HLA-A*02. In some embodiments, the target antigen is HER2. In some embodiments, the target antigen is a peptide antigen of HER2 in a complex with a major histocompatibility class I complex (MHC I) or MHC II. In some embodiments, the cancer cell expresses HER2. In some embodiments, the cancer cell is a breast cancer cell, bladder cancer cell, ovarian cancer cell, gastric cancer cell, a salivary duct carcinoma cell, a non-small cell lung cancer cell, a pancreatic cancer cell, or a colon cancer cell. In some embodiments, the cancer cell is a breast cancer cell or gastric cancer cell.

In some embodiments, the HLA-A*02 non-target antigen is expressed by healthy cells of a subject. In some embodiments, the healthy cells of the subject express both the target antigen and the HLA-A*02 non-target antigen. In some embodiments, the activator receptor and the inhibitory receptor together specifically activate the immune cell in the presence of the cancer cell.

In some embodiments, the immune cell is a T cell. In some embodiments, the T cell is a CD8+ CD4− T cell. In some embodiments, the immune cell is autologous. In some embodiments, the immune cell is allogeneic.

As used herein, the term "immune cell" refers to a cell involved in the innate or adaptive (acquired) immune systems. Exemplary innate immune cells include phagocytic cells such as neutrophils, monocytes and macrophages, Natural Killer (NK) cells, polymorphonuclear leukocytes such as neutrophils eosinophils and basophils and mononuclear cells such as monocytes, macrophages and mast cells. Immune cells with roles in acquired immunity include lymphocytes such as T-cells and B-cells.

As used herein, a "T-cell" refers to a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells and stem memory T-cells. Different types of T-cells can be distinguished by the ordinarily skilled artisan based on their expression of markers. Methods of distinguishing between T-cell types will be readily apparent to the ordinarily skilled artisan.

In some embodiments, the engineered immune cell expresses the first and second receptors at a ratio of about 100:1 to 1:100 of first receptor to second receptor. In some embodiments, the engineered immune cell expresses the first and second receptors at a ratio of about 50:1 to 1:50 of first receptor to second receptor. In some embodiments, the engineered immune cell expresses the first and second receptors at a ratio of about 10:1 to 1:10 of first receptor to second receptor. In some embodiments, the engineered immune cell expresses the first and second receptors at a ratio of about 5:1 to 1:5 of first receptor to second receptor. In some embodiments, the engineered immune cell expresses the first and second receptors at a ratio of about 3:1 to 1:3 of first receptor to second receptor. In some embodiments, the engineered immune cell expresses the first and second receptors at a ratio of about 2:1 to 1:2 of first receptor to second receptor. In some embodiments, the engineered immune cell expresses the first and second receptors at a ratio of about 1:1.

In some embodiments, the first receptor comprises SEQ ID NO: 291, or a sequence sharing at least 75%, at least 80%, at least 85%, at least 90%, at least 95%, or at least 98% identity thereto; and the second receptor comprises SEQ ID NO: 303 or a sequence sharing at least 75%, at least 80%, at least 85%, at least 90%, at least 95%, or at least 98% identity thereto. In some embodiments, the first receptor comprises SEQ ID NO: 291, or a sequence sharing at least 75%, at least 80%, at least 85%, at least 90%, at least 95%, or at least 98% identity thereto; and the second receptor comprises SEQ ID NO: 305, or a sequence sharing at least 75%, at least 80%, at least 85%, at least 90%, at least 95%, or at least 98% identity thereto. In some embodiments, the first receptor comprises SEQ ID NO: 291, or a sequence sharing at least 75%, at least 80%, at least 85%, at least 90%, at least 95%, or at least 98% identity thereto; and the second receptor comprises SEQ ID NO: 307, or a sequence sharing at least 75%, at least 80%, at least 85%, at least 90%, at least 95%, or at least 98% identity thereto. In some embodiments, the first receptor comprises SEQ ID NO: 291, or a sequence sharing at least 75%, at least 80%, at least 85%, at least 90%, at least 95%, or at least 98% identity thereto; and the second receptor comprises SEQ ID NO: 21805, or a sequence sharing at least 75%, at least 80%, at least 85%, at least 90%, at least 95%, or at least 98% identity thereto.

In some embodiments, the first receptor comprises SEQ ID NO: 295, or a sequence sharing at least 75%, at least 80%, at least 85%, at least 90%, at least 95%, or at least 98% identity thereto; and the second receptor comprises SEQ ID NO: 303, or a sequence sharing at least 75%, at least 80%, at least 85%, at least 90%, at least 95%, or at least 98% identity thereto. In some embodiments, the first receptor comprises SEQ ID NO: 295, or a sequence sharing at least 75%, at least 80%, at least 85%, at least 90%, at least 95%, or at least 98% identity thereto; and the second receptor comprises SEQ ID NO: 305, or a sequence sharing at least 75%, at least 80%, at least 85%, at least 90%, at least 95%, or at least 98% identity thereto. In some embodiments, the first receptor comprises SEQ ID NO: 295, or a sequence sharing at least 75%, at least 80%, at least 85%, at least 90%, at least 95%, or at least 98% identity thereto; and the second receptor comprises SEQ ID NO: 307, or a sequence sharing at least 75%, at least 80%, at least 85%, at least 90%, at least 95%, or at least 98% identity thereto. In some embodiments, the first receptor comprises SEQ ID NO: 295, or a sequence sharing at least 75%, at least 80%, at least 85%, at least 90%, at least 95%, or at least 98% identity thereto; and the second receptor comprises SEQ ID NO: 21805, or a sequence sharing at least 75%, at least 80%, at least 85%, at least 90%, at least 95%, or at least 98% identity thereto.

In some embodiments, the first receptor comprises SEQ ID NO: 299, or a sequence sharing at least 75%, at least 80%, at least 85%, at least 90%, at least 95%, or at least 98% identity thereto; and the second receptor comprises SEQ ID NO: 303, or a sequence sharing at least 75%, at least 80%, at least 85%, at least 90%, at least 95%, or at least 98% identity thereto. In some embodiments, the first receptor comprises SEQ ID NO: 299, or a sequence sharing at least 75%, at least 80%, at least 85%, at least 90%, at least 95%, or at least 98% identity thereto; and the second receptor comprises SEQ ID NO: 305, or a sequence sharing at least 75%, at least 80%, at least 85%, at least 90%, at least 95%, or at least 98% identity thereto. In some embodiments, the first receptor comprises SEQ ID NO: 299, or a sequence sharing at least 75%, at least 80%, at least 85%, at least 90%, at least 95%, or at least 98% identity thereto; and the second receptor comprises SEQ ID NO: 307, or a sequence sharing at least 75%, at least 80%, at least 85%, at least 90%, at least 95%, or at least 98% identity thereto. In some embodiments, the first receptor comprises SEQ ID NO: 299, or a sequence sharing at least 75%, at least 80%, at least 85%, at least 90%, at least 95%, or at least 98% identity thereto; and the second receptor comprises SEQ ID NO: 21805, or a sequence sharing at least 75%, at least 80%, at least 85%, at least 90%, at least 95%, or at least 98% identity thereto.

In some embodiments, the immune cell further comprises a T2A self-cleaving peptide, wherein the T2A self-cleaving peptide comprises SEQ ID NO: 288 or 557, or a sequence sharing at least 75%, at least 80%, at least 85%, at least 90%, at least 95%, or at least 98% identity thereto.

In some embodiments, the engineered immune cell comprising the engineered receptors of the disclosure is a T cell. In some embodiments, the T cell is an effector T cell or a regulatory T cell. As used herein, a "T-cell" refers to a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells, NK T cells, γδ T cells, Mucosal-associated invariant T (MAIT) cells, and stem memory T-cells. Different types of T-cells can be distinguished by the ordinarily skilled artisan based on their expression of markers. Methods of distinguishing between T-cell types will be readily apparent to the ordinarily skilled artisan.

In some embodiments, the immune cell is selected form the group consisting of T cells, B cells and Natural Killer (NK) cells. In some embodiments, the immune cell is a T cell. In some embodiments, the immune cell is a B cell. In some embodiments, the immune cell is a Natural Killer (NK) cell. In some embodiments, the immune cell is CD8−. In some embodiments, the immune cell is CD8+. In some embodiments, the immune cell is CD4+. In some embodiments, the immune cell is CD4−. In some embodiments, the immune cell is CD8−/CD4+. In some embodiments, the immune cell is CD8+ CD4− T cell.

In some embodiments, the immune cell is a gamma delta (γδ) T cell. In some embodiments, the immune cell is an invariant T cell. In some embodiments, the immune cell is an invariant natural killer T cell (iNKT cell).

In some embodiments, the immune cell comprises a modification to an MHC Class I gene or a B2M gene. In some embodiments, the MHC Class I gene is HLA-A*02, or an allelic variant thereof. In some embodiments, the modification reduces or eliminates expression of the MHC Class I gene or the B2M gene.

In some embodiments, the immune cell comprises a polynucleotide or polynucleotide system described herein. In some embodiments, the polynucleotide or polynucleotide system comprises a sequence encoding a first receptor described herein. In some embodiments, the polynucleotide or polynucleotide system comprises a sequence encoding a second receptor described herein. In some embodiments, the polynucleotide or polynucleotide systems encodes an shRNA described herein. In some embodiments, the polynucleotide or polynucleotide system comprises a sequence encoding a first receptor described herein and a second receptor described herein. In some embodiments, the polynucleotide or polynucleotide system comprises a sequence encoding a first receptor described herein, a second receptor described herein, and an shRNA described herein.

Methods transforming populations of immune cells, such as T cells, with the vectors of the instant disclosure will be readily apparent to the person of ordinary skill in the art. For example, CD3+ T cells can be isolated from PBMCs using a CD3+ T cell negative isolation kit (Miltenyi), according to manufacturer's instructions. T cells can be cultured at a density of 1×10^6 cells/mL in X-Vivo 15 media supplemented with 5% human A/B serum and 1% Pen/strep in the presence of CD3/28 Dynabeads (1:1 cell to bead ratio) and 300 Units/mL of IL-2 (Miltenyi). After 2 days, T cells can be transduced with viral vectors, such as lentiviral vectors using methods known in the art. In some embodiments, the viral vector is transduced at a multiplicity of infection (MOI) of 5. Cells can then be cultured in IL-2 or other cytokines such as combinations of IL-7/15/21 for an additional 5 days prior to enrichment. Methods of isolating and culturing other populations of immune cells, such as B cells, or other populations of T cells, will be readily apparent to the person of ordinary skill in the art. Although this method outlines a potential approach it should be noted that these methodologies are rapidly evolving. For example excellent viral transduction of peripheral blood mononuclear cells can be achieved after 5 days of growth to generate a >99% CD3+ highly transduced cell population.

Methods of activating and culturing populations of T cells comprising the engineered TCRs, CARs, fusion proteins or vectors encoding the fusion proteins of the instant disclosure, will be readily apparent to the person of ordinary skill in the art.

Whether prior to or after genetic modification of T cells to express an engineered TCR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, 10,040,846; and U.S. Pat. Appl. Pub. No. 2006/0121005.

In some embodiments, T cells of the instant disclosure are expanded and activated in vitro. Generally, the T cells of the instant disclosure are expanded in vitro by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In some embodiments, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. In some embodiments, a ratio of 1:1 cells to beads is used. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the T cells. In one embodiment the cells (for example, CD4+ T cells) and beads (for example, DYNABEADS CD3/CD28 T paramagnetic beads at a ratio of 1:1) are combined in a buffer. Again, those of ordinary skill in the art can readily appreciate any cell concentration may be used. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. In some embodiments, cells that are cultured at a density of 1×106 cells/mL are used.

In some embodiments, the mixture may be cultured for several hours (about 3 hours) to about 14 days or any hourly integer value in between. In another embodiment, the beads and T cells are cultured together for 2-3 days. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In some embodiments, the media comprises X-VIVO-15 media supplemented with 5% human A/B serum, 1% penicillin/streptomycin (pen/strep) and 300 Units/ml of IL-2 (Miltenyi).

The T cells are maintained under conditions necessary to support growth, for example, an appropriate temperature (e.g., 37° C.) and atmosphere (e.g., air plus 5% CO2).

In some embodiments, the T cells comprising engineered TCRs, CARs, and/or inhibitory receptors of the disclosure are autologous. Prior to expansion and genetic modification, a source of T cells is obtained from a subject. Immune cells such as T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation.

In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In alternative embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In some embodiments, immune cells such as T cells are isolated from peripheral blood lymphocytes by lysing the red blood cells and depleting the monocytes, for example, by centrifugation through a PERCOLL™ gradient or by counterflow centrifugal elutriation. Specific subpopulations of immune cells, such as T cells, B cells, or CD4+ T cells can be further isolated by positive or negative selection techniques. For example, in one embodiment, T cells are isolated by incubation with anti-CD4-conjugated beads, for a time period sufficient for positive selection of the desired T cells.

Enrichment of an immune cell population, such as a T cell population, by negative selection can be accomplished with a combination of antibodies directed to surface markers unique to the negatively selected cells. One method is cell sorting and/or selection via negative magnetic immune-adherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD 11b, CD 16, HLA-DR, and CD8.

For isolation of a desired population of immune cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

In some embodiments, the cells may be incubated on a rotator for varying lengths of time at varying speeds at either 2-10° C. or at room temperature.

T cells for stimulation, or PBMCs from which immune cells such as T cells are isolated, can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

The disclosure provides an immune cell expressing the activator and/or inhibitory receptors described herein, wherein the immune cell has reduced expression and/or function the major histocompatibility (MHC) class I complex.

In some embodiments, the immune cell is autologous. For example, the immune cells is isolated or derived from same subject who will receive the cell as part of a therapeutic regimen. It can be advantageous to modify autologous immune cells to have reduced expression and/or function of MHC class I with the inhibitory receptor is specific to an MHC class I antigen. Without wishing to be bound by theory, modification of autologous immune cells to have reduced expression and/or function of MHC class I reduces binding of the inhibitory receptor by MHC class I expressed by the immune cells, either in cis or in trans.

In some embodiments, the immune cell is all allogeneic. Allogeneic immune cells can be derived from a donor other than the subject to which the immune cells will be administered. Allogeneic immune cells have been commonly referred to in cell therapy as "off-the-shelf" or "universal" because of the possibility for allogeneic cells to be prepared and stored for use in subjects of a variety of genotypes.

Any suitable methods of reducing expression and/or function the MHC class I complex are envisaged as within the scope of the instant disclosure, and include, inter alia, expression of interfering RNAs that knock down one or more RNAs encoding MHC class I components, or modifications of genes encoding MHC class I components.

The major histocompatibility complex (MHC) is a locus on the vertebrate genome that encodes a set of polypeptides required for the adaptive immune system. Among these are MHC class I polypeptides that include HLA-A, HLA-B, and HLA-C and alleles thereof. MHC class I alleles are highly polymorphic and expressed in all nucleated cells. MHC class I polypeptides encoded by HLA-A, HLA-B, and HLA-C and alleles thereof form heterodimers with (32 microglobulin (B2M) and present in complex with antigens on the surface of cells. As referred to herein, an MHC class I gene or polypeptide may refer to any polypeptide found in the MHC or the corresponding gene encoding said polypeptide. In some embodiments, the immune cells of the disclosure are inactivated by an inhibitor ligand comprising an MHC class I polypeptide, e.g. HLA-A, HLA-B, and HLA-C and alleles thereof. HLA-A alleles can be, for example and without limitation, HLA-A*02, HLA-A*02:01, HLA-A*02:01:01, HLA-A*02:01:01:01, and/or any gene that encodes protein identical or similar to HLA-A*02 protein. Thus, to prevent autocrine signaling/binding as described herein, it is desirable to eliminate or reduce expression of polypeptides encoded by HLA-A, HLA-B, and HLA-C and alleles thereof in the immune cells.

Immune Cells with Reduced MHC Class I Polypeptide Expression

In some embodiments, the immune cells described herein are modified to inactivate, or reduce or eliminate expression or function of an endogenous gene encoding an allele of an endogenous MHC class I polypeptide. In some embodiments, the gene encoding the MHC class I polypeptide is HLA-A, HLA-B, and/or HLA-C. HLA-A, HLA-B and HLA-C are encoded by the HLA-A, HLA-B and HLA-C loci. Each of HLA-A, HLA-B and HLA-C includes many variant alleles, all of which are envisaged as within the scope of the instant disclosure. In some embodiments, the gene encoding the MHC class I polypeptide is HLA-A. In some embodiments, the gene encoding the MHC class I polypeptide is HLA-A*02. In some embodiments, the gene encoding the MHC class I polypeptide is HLA-A*02:01. In some embodiments, the gene encoding the MHC class I polypeptide is HLA-A*02:01:01. In some embodiments, the gene encoding the MHC class I polypeptide is HLA-A*02:01:01:01.

In some embodiments, the genetically engineered immune cells described herein are modified to reduce or eliminate expression of the B2M gene product. The beta-2 microglobulin (B2M) gene encodes a protein that associates with the major histocompatibility complex (MHC) class I, i.e. MHC-I complex. The MHC-I complex is required for presentation of antigens on the cell surface. The MHC-I complex is disrupted and non-functional when the B2M is deleted (Wang D et al. Stem Cells Transl Med. 4:1234-1245 (2015)). Furthermore, the B2M gene can be disrupted with high efficiency using gene editing techniques known in the art (Ren et al. Clin. Cancer Res. 23:2255-2266 (2017)). Reducing or eliminating B2M can reduce, or eliminate functional MHC I on the surface of the immune cell.

The disclosure provides gene editing systems for editing an endogenous target gene in an immune cell. The disclosure provides interfering RNAs specific to sequences of target genes. Gene editing systems such as CRISPR/Cas systems, TALENs and zinc fingers can be used to generate double strand breaks, which, through gene repair mechanisms such as homology directed repair or non-homologous end joining (NHEJ), can be used to introduce mutations. NHEJ after resection of the ends of the break, or improper end joining, can be used to introduce deletions. In some embodiments, the target gene comprises a gene encoding a subunit of the MHC-I complex.

Target gene sequences include, but are not limited to, promoters, enhancers, introns, exons, intron/exon junctions, transcription products (pre-mRNA, mRNA, and splice variants), and/or 3' and 5' untranslated regions (UTRs). Any gene element or combination of gene elements may be targeted for the purpose of genetic editing in the immune cells described herein. Modifications to the target genes can be accomplished using any method known in the art to edit the target gene that results in altered or disrupted expression or function the target gene or gene product.

In some embodiments, modifying the gene encoding the MHC class I polypeptide comprises deleting all or a portion of the gene. In some embodiments, modifying the gene encoding the MHC class I polypeptide comprises introducing a mutation in the gene. In some embodiments, the mutation comprises a deletion, insertion, substitution, or frameshift mutation. In some embodiments, modifying the gene comprises using a nucleic acid guided endonuclease.

Gene sequences for the target genes described herein are known in the art. The sequences can be found at public databases, such as NCBI GenBank or the NCBI nucleotide database. Sequences may be found using gene identifiers, for example, the HLA-A gene has NCBI Gene ID: 3105, the HLA-B gene has NCBI Gene ID: 3106, the HLA-C gene has NCBI Gene ID: 3107, and the B2M gene has NCBI Gene ID: 567 and NCBI Reference Sequence: NC_000015.10. Gene sequences may also be found by searching public databases using keywords. For example, HLA-A alleles may be found in the NCBI nucleotide database by searching keywords, "HLA-A*02", "HLA-A*02:01", "HLA-A*02:01:01", or "HLA-A*02:01:01:01." These sequences can be used for targeting in various gene editing techniques known in the art. Table 18 provides non-limiting illustrative sequences of HLA-A allele and B2M gene sequences targeted for modification as described herein.

TABLE 18

Exemplary Target Gene Sequences

| Target | Sequence |
|---|---|
| B2M mRNA | AUUCCUGAAGCUGACAGCAUUCGGGCCGAGAUGUCUCGCUCCGUGG<br>CCUUAGCUGUGCUCGCGCUACUCUCUCUUUCUGGCCUGGAGGCUAU<br>CCAGCGUACUCCAAAGAUUCAGGUUUACUCACGUCAUCCAGCAGAG<br>AAUGGAAAGUCAAAUUUCCUGAAUUGCUAUGUGUCUGGGUUUCAUC<br>CAUCCGACAUUGAAGUUGACUUACUGAAGAAUGGAGAGAGAAUUGA<br>AAAAGUGGAGCAUUCAGACUUGUCUUUCAGCAAGGACUGGUCUUUC<br>UAUCUCUUGUACUACACUGAAUUCACCCCCACUGAAAAAGAUGAGU<br>AUGCCUGCCGUGUGAACCAUGUGACUUUGUCACAGCCCAAGAUAGU<br>UAAGUGGGAUCGAGACAUGUAAGCAGCAUCAUGGAGGUUUGAAGAU<br>GCCGCAUUUGGAUUGGAUGAAUUCCAAAUUCUGCUUGCUUGCUUUU<br>UAAUAUUGAUAUGCUUAUACACUUACACUUUAUGCACAAAAUGUAG<br>GGUUAUAAUAAUGUUAACAUGGACAUGAUCUUCUUUAUAAUUCUAC<br>UUUGAGUGCUGUCUCCAUGUUUGAUGUAUCUGAGCAGGUUGCUCCA<br>CAGGUAGCUCUAGGAGGGCUGGCAACUUAGAGGUGGGGAGCAGAGA<br>AUUCUCUUAUCCAACAUCAACAUCUUGGUCAGAUUUGAACUCUUCA<br>AUCUCUUGCACUCAAAGCUUGUUAAGAUAGUUAAGCGUGCAUAAGU<br>UAACUUCCAAUUUACAUACUCUGCUUAGAAUUUGGGGGAAAAUUUA<br>GAAAUAUAAUUGACAGGAUUAUUGGAAAUUUGUUAUAAUGAAUGAA<br>ACAUUUUGUCAUAUAAGAUUCAUAUUUACUUCUUAUACAUUUGAUA<br>AAGUAAGGCAUGGUUGUGGUUAAUCUGGUUUAUUUUUGUUCCACAA<br>GUUAAAUAAAUCAUAAAACUUGA (SEQ ID NO: 571) |
| B2M Gene<br>(GenBank: 567) | AAGTGGAGGCGTCGCGCTGGCGGGCATTCCTGAAGCTGACAGCATT<br>CGGGCCGAGATGTCTCGCTCCGTGGCCTTAGCTGTGCTCGCGCTAC<br>TCTCTCTTTCTGGCCTGGAGGCTATCCAGCGTGAGTCTCTCCTACC<br>CTCCCGCTCTGGTCCTTCCTCTCCCGCTCTGCACCCTCTGTGGCCC<br>TCGCTGTGCTCTCTCGCTCCGTGACTTCCCTTCTCCAAGTTCTCCT<br>TGGTGGCCCGCCGTGGGGCTAGTCCAGGGCTGGATCTCGGGGAAGC<br>GGCGGGGTGGCCTGGGAGTGGGGAAGGGGGTGCGCACCCGGGACGC |

TABLE 18-continued

Exemplary Target Gene Sequences

| Target | Sequence |
|---|---|
| | GCGCTACTTGCCCCTTTCGGCGGGGAGCAGGGGAGACCTTTGGCCT |
| | ACGGCGACGGGAGGGTCGGGACAAAGTTTAGGGCGTCGATAAGCGT |
| | CAGAGCGCCGAGGTTGGGGGAGGGTTTCTCTTCCGCTCTTTCGCGG |
| | GGCCTCTGGCTCCCCCAGCGCAGCTGGAGTGGGGGACGGGTAGGCT |
| | CGTCCCAAAGGCGCGGCGCTGAGGTTTGTGAACGCGTGGAGGGGCG |
| | CTTGGGGTCTGGGGGAGGCGTCGCCCGGGTAAGCCTGTCTGCTGCG |
| | GCTCTGCTTCCCTTAGACTGGAGAGCTGTGGACTTCGTCTAGGCGC |
| | CCGCTAAGTTCGCATGTCCTAGCACCTCTGGGTCTATGTGGGGCCA |
| | CACCGTGGGGAGGAAACAGCACGCGACGTTTGTAGAATGCTTGGCT |
| | GTGATACAAAGCGGTTTCGAATAATTAACTTATTTGTTCCCATCAC |
| | ATGTCACTTTTAAAAAATTATAAGAACTACCCGTTATTGACATCTT |
| | TCTGTGTGCCAAGGACTTTATGTGCTTTGCGTCATTTAATTTTGAA |
| | AACAGTTATCTTCCGCCATAGATAACTACTATGGTTATCTTCTGCC |
| | TCTCACAGATGAAGAAACTAAGGCACCGAGATTTTAAGAAACTTAA |
| | TTACACAGGGGATAAATGGCAGCAATCGAGATTGAAGTCAAGCCTA |
| | ACCAGGGCTTTTGCGGGAGCGCATGCCTTTTGGCTGTAATTCGTGC |
| | ATTTTTTTTTAAGAAAAACGCCTGCCTTCTGCGTGAGATTCTCCAG |
| | AGCAAACTGGGCGGCATGGGCCCTGTGGTCTTTTCGTACAGAGGGC |
| | TTCCTCTTTGGCTCTTTGCCTGGTTGTTTCCAAGATGTACTGTGCC |
| | TCTTACTTTCGGTTTTGAAAACATGAGGGGGTTGGGCGTGGTAGCT |
| | TACGCCTGTAATCCCAGCACTTAGGGAGGCCGAGGCGGGAGGATGG |
| | CTTGAGGTCCGTAGTTGAGACCAGCCTGGCCAACATGGTGAAGCCT |
| | GGTCTCTACAAAAAATAATAACAAAAATTAGCCGGGTGTGGTGGCT |
| | CGTGCCTGTGGTCCCAGCTGCTCCGGTGGCTGAGGCGGGAGGATCT |
| | CTTGAGCTTAGGCTTTTGAGCTATCATGGCGCCAGTGCACTCCAGC |
| | GTGGGCAACAGAGCGAGACCCTGTCTCTCAAAAAAGAAAAAAAAAA |
| | AAAAGAAAGAGAAAGAAAAGAAAGAAAGAAGTGAAGGTTTGTCA |
| | GTCAGGGGAGCTGTAAAACCATTAATAAAGATAATCCAAGATGGTT |
| | ACCAAGACTGTTGAGGACGCCAGAGATCTTGAGCACTTTCTAAGTA |
| | CCTGGCAATACACTAAGCGCGCTCACCTTTTCCTCTGGCAAAACAT |
| | GATCGAAAGCAGAATGTTTGATCATGAGAAAATTGCATTTAATTT |
| | GAATACAATTTATTTACAACATAAAGGATAATGTATATATCACCAC |
| | CATTACTGGTATTTGCTGGTTATGTTAGATGTCATTTTAAAAAATA |
| | ACAATCTGATATTTAAAAAAAAATCTTATTTTGAAAATTTCCAAAG |
| | TAATACATGCCATGCATAGACCATTTCTGGAAGATACCACAAGAAA |
| | CATGTAATGATGATTGCCTCTGAAGGTCTATTTTCCTCCTCTGACC |
| | TGTGTGTGGGTTTTGTTTTTGTTTTACTGTGGGCATAAATTAATTT |
| | TTCAGTTAAGTTTTGGAAGCTTAAATAACTCTCCAAAAGTCATAAA |
| | GCCAGTAACTGGTTGAGCCCAAATTCAAACCCAGCCTGTCTGATAC |
| | TTGTCCTCTTCTTAGAAAAGATTACAGTGATGCTCTCACAAAATCT |
| | TGCCGCCTTCCCTCAAACAGAGAGTTCCAGGCAGGATGAATCTGTG |
| | CTCTGATCCCTGAGGCATTTAATATGTTCTTATTATTAGAAGCTCA |
| | GATGCAAAGAGCTCTCTTAGCTTTTAATGTTATGAAAAAAATCAGG |
| | TCTTCATTAGATTCCCCAATCCACCTCTTGATGGGGCTAGTAGCCT |
| | TTCCTTAATGATAGGGTGTTTCTAGAGAGATATATCTGGTCAAGGT |
| | GGCCTGGTACTCCTCCTTCTCCCCACAGCCTCCCAGACAAGGAGGA |
| | GTAGCTGCCTTTTAGTGATCATGTACCCTGAATATAAGTGTATTTA |
| | AAAGAATTTTATACACATATATTTAGTGTCAATCTGTATATTTAGT |
| | AGCACTAACACTTCTCTTCATTTTCAATGAAAAATATAGAGTTTAT |
| | AATATTTTCTTCCCACTTCCCCATGGATGGTCTAGTCATGCCTCTC |
| | ATTTTGGAAAGTACTGTTTCTGAAACATTAGGCAATATATTCCCAA |
| | CCTGGCTAGTTTACAGCAATCACCTGTGGATGCTAATTAAAACGCA |
| | AATCCCACTGTCACATGCATTACTCCATTTGATCATAATGGAAAGT |
| | ATGTTCTGTCCCATTTGCCATAGTCCTCACCTATCCCTGTTGTATT |
| | TTATCGGGTCCAACTCAACCATTTAAGGTATTTGCCAGCTCTTGTA |
| | TGCATTTAGGTTTTGTTTCTTTGTTTTTTAGCTCATGAAATTAGGT |
| | ACAAAGTCAGAGAGGGGTCTGGCATATAAAACCTCAGCAGAAATAA |
| | AGAGGTTTTGTTGTTTGGTAAGAACATACCTTGGGTTGGTTGGGCA |
| | CGGTGGCTCGTGCCTGTAATCCCAACACTTTGGGAGGCCAAGGCAG |
| | GCTGATCACTTGAAGTTGGGAGTTCAAGACCAGCCTGGCCAACATG |
| | GTGAAATCCCGTCTCTACTGAAAATACAAAAATTAACCAGGCATGG |
| | TGGTGTGTGCCTGTAGTCCCAGGAATCACTTGAACCCAGGAGGCGG |
| | AGGTTGCAGTGAGCTGAGATCTCACCACTGCACTCCAGC |
| | CTGGGCAATGGAATGAGATTCCATCCCAAAAAATAAAAAAATAAAA |
| | AAATAAAGAACATACCTTGGGTTGATCCACTTAGGAACCTCAGATA |
| | ATAACATCTGCCACGTATAGAGCAATTGCTATGTCCCAGGCACTCT |
| | ACTAGACACTTCATACAGTTTAGAAAATCAGATGGGTGTAGATCAA |
| | GGCAGGAGCAGGAACCAAAAAGAAAGGCATAAACATAAGAAAAAAA |
| | ATGGAAGGGGTGGAAACAGAGTACAATAACATGAGTAATTTGATGG |
| | GGGCTATTATGAACTGAGAAATGAACTTTGAAAAGTATCTTGGGGC |
| | CAAATCATGTAGACTCTTGAGTGATGTGTTAAGGAATGCTATGAGT |
| | GCTGAGAGGGCATCAGAAGTCCTTGAGAGCCTCCAGAGAAAGGCTC |
| | TTAAAAATGCAGCGCAATCTCCAGTGACAGAAGATACTGCTAGAAA |
| | TCTGCTAGAAAAAAAACAAAAAAGGCATGTATAGAGGAATTATGAG |
| | GGAAAGATACCAAGTCACGGTTTATTCTTCAAAATGGAGGTGGCTT |
| | GTTGGGAAGGTGGAAGCTCATTTGGCCAGAGTGGAAATGGAATTGG |

TABLE 18-continued

Exemplary Target Gene Sequences

| Target | Sequence |
|---|---|
| | GAGAAATCGATGACCAAATGTAAACACTTGGTGCCTGATATAGCTT<br>GACACCAAGTTAGCCCCAAGTGAAATACCCTGGCAATATTAATGTG<br>TCTTTTCCCGATATTCCTCAGGTACTCCAAAGATTCAGGTTTACTC<br>ACGTCATCCAGCAGAGAATGGAAAGTCAAATTTCCTGAATTGCTAT<br>GTGTCTGGGTTTCATCCATCCGACATTGAAGTTGACTTACTGAAGA<br>ATGGAGAGAGAATTGAAAAAGTGGAGCATTCAGACTTGTCTTTCAG<br>CAAGGACTGGTCTTTCTATCTCTTGTACTACACTGAATTCACCCCC<br>ACTGAAAAAGATGAGTATGCCTGCCGTGTGAACCATGTGACTTTGT<br>CACAGCCCAAGATAGTTAAGTGGGGTAAGTCTTACATTCTTTTGTA<br>AGCTGCTGAAAGTTGTGTATGAGTAGTCATATCATAAAGCTGCTTT<br>GATATAAAAAGGTCTATGGCCATACTACCCTGAATGAGTCCCATC<br>CCATCTGATATAAACAATCTGCATATTGGGATTGTCAGGGAATGTT<br>CTTAAAGATCAGATTAGTGGCACCTGCTGAGATACTGATGCACAGC<br>ATGGTTTCTGAACCAGTAGTTTCCCTGCAGTTGAGCAGGGAGCAGC<br>AGCAGCACTTGCACAAATACATATACACTCTTAACACTTCTTACCT<br>ACTGGCTTCCTCTAGCTTTTGTGGCAGCTTCAGGTATATTTAGCAC<br>TGAACGAACATCTCAAGAAGGTATAGGCCTTTGTTTGTAAGTCCTG<br>CTGTCCTAGCATCCTATAATCCTGGACTTCTCCAGTACTTTCTGGC<br>TGGATTGGTATCTGAGGCTAGTAGGAAGGGCTTGTTCCTGCTGGGT<br>AGCTCTAAACAATGTATTCATGGGTAGGAACAGCAGCCTATTCTGC<br>CAGCCTTATTTCTAACCATTTTAGACATTTGTTAGTACATGGTATT<br>TTAAAAGTAAAACTTAATGTCTTCCTTTTTTTTCTCCACTGTCTTT<br>TTCATAGATCGAGACATGTAAGCAGCATCATGGAGGTAAGTTTTTG<br>ACCTTGAGAAAATGTTTTTGTTTCACTGTCCTGAGGACTATTTATA<br>GACAGCTCTAACATGATAACCCTCACTATGTGGAGAACATTGACAG<br>AGTAACATTTTAGCAGGGAAAGAAGAATCCTACAGGGTCATGTTCC<br>CTTCTCCTGTGGAGTGGCATGAAGAAGGTGTATGGCCCCAGGTATG<br>GCCATATTACTGACCCTCTACAGAGAGGGCAAAGGAACTGCCAGTA<br>TGGTATTGCAGGATAAAGGCAGGTGGTTACCCACATTACCTGCAAG<br>GCTTTGATCTTTCTTCTGCCATTTCCACATTGGACATCTCTGCTGA<br>GGAGAGAAAATGAACCACTCTTTTCCTTTGTATAATGTTGTTTTAT<br>TCTTCAGACAGAAGAGAGGAGTTATACAGCTCTGCAGACATCCCAT<br>TCCTGTATGGGACTGTGTTTGCCTCTTAGAGGTTCCCAGGCCACT<br>AGAGGAGATAAAGGGAAACAGATTGTTATAACTTGATATAATGATA<br>CTATAATAGATGTAACTACAAGGAGCTCCAGAAGCAAGAGAGAGGG<br>AGGAACTTGGACTTCTCTGCATCTTTAGTTGGAGTCCAAAGGCTTT<br>TCAATGAAATTCTACTGCCCAGGGTACATTGATGCTGAAACCCCAT<br>TCAAATCTCCTGTTATATTCTAGAACAGGGAATTGATTTGGGAGAG<br>CATCAGGAAGGTGGATGATCTGCCCAGTCACACTGTTAGTAAATTG<br>TAGAGCCAGGACCTGAACTCTAATATAGTCATGTGTTACTTAATGA<br>CGGGGACATGTTCTGAGAAATGCTTACACAAACCTAGGTGTTGTAG<br>CCTACTACACGCATAGGCTACATGGTATAGCCTATTGCTCCTAGAC<br>TACAAACCTGTACAGCCTGTTACTGTACTGAATACTGTGGGCAGTT<br>GTAACACAATGGTAAGTATTTGTGTATCTAAACATAGAAGTTGCAG<br>TAAAAATATGCTATTTTAATCTTATGAGACCACTGTCATATATACA<br>GTCCATCATTGACCAAAACATCATATCAGCATTTTTTCTTCTAAGA<br>TTTTGGGAGCACCAAAGGGATACACTAACAGGATATACTCTTTATA<br>ATGGGTTTGGAGAACTGTCTGCAGCTACTTCTTTTAAAAAGGTGAT<br>CTACACAGTAGAAATTAGACAAGTTTGGTAATGAGATCTGCAATCC<br>AAATAAAATAAATTCATTGCTAACCTTTTTCTTTTCTTTTCAGGTT<br>TGAAGATGCCGCATTTGGATTGGATGAATTCCAAATTCTGCTTGCT<br>TGCTTTTTAATATTGATATGCTTATACACTTACACTTTATGCACAA<br>AATGTAGGGTTATAATAATGTTAACATGGACATGATCTTCTTTATA<br>ATTCTACTTTGAGTGCTGTCTCCATGTTTGATGTATCTGAGCAGGT<br>TGCTCCACAGGTAGCTCTAGGAGGGCTGGCAACTTAGAGGTGGGGA<br>GCAGAGAATTCTCTTATCCAACATCAACATCTTGGTCAGATTTGAA<br>CTCTTCAATCTCTTGCACTCAAAGCTTGTTAAGATAGTTAAGCGTG<br>CATAAGTTAACTTCCAATTTACATACTCTGCTTAGAATTTGGGGGA<br>AAATTTAGAAATATAATTGACAGGATTATTGGAAATTTGTTATAAT<br>GAATGAAACATTTTGTCATATAAGATTCATATTTACTTCTTATACA<br>TTTGATAAAGTAAGGCATGGTTGTGGTTAATCTGGTTTATTTTTGT<br>TCCACAAGTTAAATAAATCATAAAACTTGA (SEQ ID NO: 572) |
| HLA-<br>A*02:01:01:01<br>sequence<br>encoding mRNA | CAGAAGCAGAGGGGTCAGGGCGAAGTCCCAGGGCCCCAGGCGTGGC<br>TCTCAGGGTCTCAGGCCCCGAAGGCGGTGTATGGATTGGGGAGTCC<br>CAGCCTTGGGGATTCCCCAACTCCGCAGTTTCTTTTCTCCCTCTCC<br>CAACCTATGTAGGGTCCTTCTTCCTGGATACTCACGACGCGGACCC<br>AGTTCTCACTCCCATTGGGTGTCGGGTTTCCAGAGAAGCCAATCAG<br>TGTCGTCGCGGTCGCGGTTCTAAAGTCCGCACGCACCCACCGGGAC<br>TCAGATTCTCCCCAGACGCCGAGGATGGCCGTCATGGCGCCCCGAA<br>CCCTCGTCCTGCTACTCTCGGGGGCTCTGGCCCTGACCCAGACCTG<br>GGCGGGCTCTCACTCCATGAGGTATTTCTTCACATCCGTGTCCCGG<br>CCCGGCCGCGGGGAGCCCCGCTTCATCGCAGTGGGCTACGTGGACG<br>ACACGCAGTTCGTGCGGTTCGACAGCGACGCCGCGAGCCAGAGGAT<br>GGAGCCGCGGGCGCCGTGGATAGAGCAGGAGGGTCCGGAGTATTGG |

TABLE 18-continued

Exemplary Target Gene Sequences

| Target | Sequence |
|---|---|
| | GACGGGGAGACACGGAAAGTGAAGGCCCACTCACAGACTCACCGAG<br>TGGACCTGGGGACCCTGCGCGGCTACTACAACCAGAGCGAGGCCGG<br>TTCTCACACCGTCCAGAGGATGTATGGCTGCGACGTGGGGTCGGAC<br>TGGCGCTTCCTCCGCGGGTACCACCAGTACGCCTACGACGGCAAGG<br>ATTACATCGCCCTGAAAGAGGACCTGCGCTCTTGGACCGCGGCGGA<br>CATGGCAGCTCAGACCACCAAGCACAAGTGGGAGGCGGCCCATGTG<br>GCGGAGCAGTTGAGAGCCTACCTGGAGGGCACGTGCGTGGAGTGGC<br>TCCGCAGATACCTGGAGAACGGGAAGGAGACGCTGCAGCGCACGGA<br>CGCCCCCAAAACGCATATGACTCACCACGCTGTCTCTGACCATGAA<br>GCCACCCTGAGGTGCTGGGCCCTGAGCTTCTACCCTGCGGAGATCA<br>CACTGACCTGGCAGCGGGATGGGGAGGACCAGACCCAGGACACGGA<br>GCTCGTGGAGACCAGGCCTGCAGGGGATGGAACCTTCCAGAAGTGG<br>GCGGCTGTGGTGGTGCCTTCTGGACAGGAGCAGAGATACACCTGCC<br>ATGTGCAGCATGAGGGTTTGCCCAAGCCCCTCACCCTGAGATGGGA<br>GCCGTCTTCCCAGCCCACCATCCCCATCGTGGGCATCATTGCTGGC<br>CTGGTTCTCTTTGGAGCTGTGATCACTGGAGCTGTGGTCGCTGCTG<br>TGATGTGGAGGAGGAAGAGCTCAGATAGAAAAGGAGGGAGCTACTC<br>TCAGGCTGCAAGCAGTGACAGTGCCCAGGGCTCTGATGTGTCTCTC<br>ACAGCTTGTAAAGTGTGAGACAGCTGCCTTGTGTGGGACTGAGAGG<br>CAAGAGTTGTTCCTGCCCTTCCCTTTGTGACTTGAAGAACCCTGAC<br>TTTGTTTCTGCAAAGGCACCTGCATGTGTCTGTGTTCGTGTAGGCA<br>TAATGTGAGGAGGTGGGGAGACCACCCCACCCCCATGTCCACCATG<br>ACCCTCTTCCCACGCTGACCTGTGCTCCCTCCCCAATCATCTTTCC<br>TGTTCCAGAGAGGTGGGGCTGAGGTGTCTCCATCTCTGTCTCAACT<br>TCATGGTGCACTGAGCTGTAACTTCTTCCTTCCCTATTAAAA<br>(SEQ ID NO: 573) |
| HLA-A*02<br>(GenBank:<br>LK021978.1) | ATGGCCGTCATGGCGCCCCGAACCCTCGTCCTGCTACTCTCGGGGG<br>CTCTGGCCCTGACCCAGACCTGGGCGGGTGAGTGCGGGGTCGGGAG<br>GGAAACGGCCTCTGTGGGGAGAAGCAACGGGCCCGCCTGGCGGGGG<br>CGCAGGACCCGGGAAGCCGCGCCGGGAGGAGGGTCGGGCGGGTCTC<br>AGCCACTCCTCGTCCCCAGGCTCTCACTCCATGAGGTATTTCTTCA<br>CATCCGTGTCCCGGCCCGGCCGCGGGGAGCCCCGCTTCATCGCAGT<br>GGGCTACGTGGACGACACGCAGTTCGTGCGGTTCGACAGCGACGCC<br>GCGAGCCAGAGGATGGAGCCGCGGGCGCCGTGGATAGAGCAGGAGG<br>GTCCGGAGTATTGGGACGGGGAGACACGGAAAGTGAAGGCCCACTC<br>ACAGACTCACCGAGTGGACCTGGGGACCCTGCGCGGCTACTACAAC<br>CAGAGCGAGGCCGGTGAGTGACCCCGGCCCGGGGCGCAGGTCACGA<br>CCTCTCATCCCCCACGGACGGGCCAGGTCGCCCACAGTCTCCGGGT<br>CCGAGATCCGCCCCGAAGCCGCGGGACCCCGAGACCCTTGCCCCGG<br>GAGAGGCCCAGGCGCCTTTACCCGGTTTCATTTTCAGTTTAGGCCA<br>AAAATCCCCCCAGGTTGGTCGGGGCGGGGCGGGGCTCGGGGGACCG<br>GGCTGACCGCGGGGTCCGGGCCAGGTTCTCACACCGTCCAGAGGAT<br>GTATGGCTGCGACGTGGGGTCGGACTGGCGCTTCCTCCGCGGGTAC<br>CACCAGTACGCCTACGACGGCAAGGATTACATCGCCCTGAAAGAGG<br>ACCTGCGCTCTTTGACCGCGGCGGACATGGCAGCTCAGACCACCAA<br>GCACAAGTGGGAGGCGGCCCATGTGGCGGAGCAGTTGAGAGCCTAC<br>CTGGAGGGCACGTGCGTGGAGTGGCTCCGCAGATACCTGGAGAACG<br>GGAAGGAGACGCTGCAGCGCACGGGTACCAGGGGCACGGGGCGCC<br>TCCCTGATCGCCTGTAGATCTCCCGGGCTGGCCTCCCACAAGGAGG<br>GGAGACAATTGGGACCAACACTAGAATATCGCCCTCCCTCTGGTCC<br>TGAGGGAGAGGAATCCTCCTGGGTTTCCAGATCCTGTACCAGAGAG<br>TGACTCTGAGGTTCCGCCCTGCTCTCTGACACAATTAAGGGATAAA<br>ATCTCTGAAGGAATGACGGGAAGACGATCCCTCGAATACTGATGAG<br>TGGTTCCCTTTGACACACACAGGCAGCAGCCTTGGGCCCGTGACTT<br>TTCCTCTCAGGCCTTGTTCTCTGCTTCACACTCAATGTGTGTGGGG<br>GTCTGAGTCCAGCACTTCTGAGTCCTTCAGCCTCCACTCAGGTCAG<br>GACCAGAAGTCGCTGTTCCCTCTTCAGGGACTAGAATTTTCCACGG<br>AATAGGAGATTATCCCAGGTGCCTGTGTCCAGGCTGGTGTCTGGGT<br>TCTGTGCTCCCTTCCCCATCCCAGGTGTCCTGTCCATTCTCAAGAT<br>AGCCACATGTGTGCTGGAGGAGTGTCCCATGACAGATGCAAAATGC<br>CTGAATGATCTGACTCTTCCTGACAGAGCCCCCAAAACGCATATG<br>ACTCACCACGCTGTCTCTGACCATGAAGCCACCCTGAGGTGCTGGG<br>CCCTGAGCTTCTACCCTGCGGAGATCACACTGACCTGGCAGCGGGA<br>TGGGGAGGACCAGACCCAGGACACGGAGCTCGTGGAGACCAGGCCT<br>GCAGGGGATGGAACCTTCCAGAAGTGGGCGGCTGTGGTGGTGCCTT<br>CTGGACAGGAGCAGAGATACACCTGCCATGTGCAGCATGAGGGTTT<br>GCCCAAGCCCCTCACCCTGAGATGGGTAAGGAGGGAGACGGGGGT<br>GTCATGTCTTTTAGGGAAAGCAGGAGCCTCTCTGACCTTTAGCAGG<br>GTCAGGGCCCCTCACCTTCCCCTCTTTTCCCAGAGCCGTCTTCCCA<br>GCCCACCATCCCCATCGTGGGCATCATTGCTGGCCTGGTTCTCTTT<br>GGAGCTGTGATCACTGGAGCTGTGGTCGCTGCTGTGATGTGGAGGA<br>GGAAGAGCTCAGGTGGGAAGGGGTGAAGGGTGGGTCTGAGATTTC<br>TTGTCTCACTGAGGGTTCCAAGACCCAGGTAGAAGTGTGCCCTGCC<br>TCGTTACTGGGAAGCACCACCCACAATTATGGGCCTACCCAGCCTG<br>GGCCCTGTGTGCCAGCACTTACTCTTTTGTAAAGCACCTGTTAAAA |

TABLE 18-continued

Exemplary Target Gene Sequences

| Target | Sequence |
|---|---|
| | TGAAGGACAGATTTATCACCTTGATTACAGCGGTGATGGGACCTGA<br>TCCCAGCAGTCACAAGTCACAGGGGAAGGTCCCTGAGGACCTTCAG<br>GAGGGCGGTTGGTCCAGGACCCACACCTGCTTTCTTCATGTTTCCT<br>GATCCCGCCCTGGGTCTGCAGTCACACATTTCTGGAAACTTCTCTG<br>AGGTCCAAGACTTGGAGGTTCCTCTAGGACCTTAAGGCCCTGACTC<br>CTTTCTGGTATCTCACAGGACATTTTCTTCCCACAGATAGAAAAGG<br>AGGGAGCTACTCTCAGGCTGCAAGTAAGTATGAAGGAGGCTGATGC<br>CTGAGGTCCTTGGGATATTGTGTTTGGGAGCCCATGGGGGAGCTCA<br>CCCACCCCACAATTCCTCCTCTAGCCACATCTTCTGTGGGATCTGA<br>CCAGGTTCTGTTTTTGTTCTACCCCAGGCAGTGACAGTGCCCAGGG<br>CTCTGATGTGTCTCTCACAGCTTGTAAAGGTGAGAGCCTGGAGGGC<br>CTGATGTGTGTTGGGTGTTGGGCGGAACAGTGGACACAGCTGTGCT<br>ATGGGGTTTCTTTCCATTGGATGTATTGAGCATGCGATGGGCTGTT<br>TAAAGTGTGACCCCTCACTGTGACAGATACGAATTTGTTCATGAAT<br>ATTTTTTTCTATAGTGTGAGACAGCTGCCTTGTGTGGGACTGAGAG<br>GCAAGAGTTGTTCCTGCCCTTCCCTTTGTGACTTGAAGAACCCTGA<br>CTTTGTTTCTGCAAAGGCACCTGCATGTGTCTGTGTTCGTGTAGGC<br>ATAATGTGAGGAGGTGGGGAGACCACCCCACCCCCATGTCCACCAT<br>GACCCTCTTCCCACGCTGACCTGTGCTCCCTCCCCAATCATCTTTC<br>CTGTTCCAGAGAGGTGGGGCTGAGGTGTCTCCATCTCTGTCTCAAC<br>TTCATGGTGCACTGAGCTGTAACTTCTTCCTTCCCTATTAAAA<br>(SEQ ID NO: 574) |

The person of ordinary skill in the art will appreciate that T can be substituted for U to convert an RNA sequence to a DNA sequence and vice versa, and both are envisaged as target gene sequences of the disclosure.

In some embodiments, a target gene is edited in the immune cells described herein using a nucleic acid guided endonuclease. Exemplary nucleic acid guided endonucleases include Class II endonucleases, such as CRISPR/Cas9.

"CRISPR" or "CRISPR gene editing" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence, knock out, or mutate a target gene. This system is a type of prokaryotic immune system that confers resistance to foreign genetic elements such as plasmids and phages and provides a form of acquired immunity. The CRISPR/Cas system has been modified for use in gene editing. This is accomplished by introducing into the eukaryotic cell a one or more specifically designed guide nucleic acids (gNAs), typically guide RNAs (gRNAs), and an appropriate Cas endonuclease which forms a ribonucleoprotein complex with the gNA. The gNA guides the gNA-endonuclease protein complex to a target genomic location, and the endonuclease introduces a strand break at the target genomic location. This double strand break can be repaired by cellular mechanisms such non-homologous end joining (leading to deletions) or homologous repair (which can generate insertions), thereby introducing genetic modifications into the host cell genome.

CRISPR/Cas systems are classified by class and by type. Class 2 systems currently represent a single interference protein that is categorized into three distinct types (types II, V and VI). Any class 2 CRISPR/Cas system suitable for gene editing, for example a type II, a type V or a type VI system, is envisaged as within the scope of the instant disclosure. Exemplary Class 2 type II CRISPR systems include Cas9, Csn2 and Cas4. Exemplary Class 2, type V CRISPR systems include, Cas12, Cas12a (Cpf1), Cas12b (C2c1), Cas12c (C2c3), Cas12d (CasY), Cas12e (CasX), Cas12f, Cas12g, Cas12h, Cas12i and Cas12k (C2c5). Exemplary Class 2 Type VI systems include Cas13, Cas13a (C2c2) Cas13b, Cas13c and Cas13d.

The CRISPR sequence, sometimes called a CRISPR locus, comprises alternating repeats and spacers. In a naturally-occurring CRISPR, the spacers usually comprise sequences foreign to the bacterium such as a plasmid or phage sequence. As described herein, spacer sequences may also be referred to as "targeting sequences." In CRISPR/Cas systems for a genetic engineering, the spacers are derived from the target gene sequence (the gNA).

An exemplary Class 2 type II CRISPR system relies on the protein Cas9, which is a nuclease with two active cutting sites, one for each strand of the double helix. Combining Cas9 and modified CRISPR locus RNA can be used in a system for gene editing. Pennisi (2013) Science 341: 833-836. In some embodiments, the Cas protein used to modify the immune cells is Cas9.

The CRISPR/Cas system can thus be used to edit a target gene, such as a gene targeted for editing in the immune cells described herein, by adding or deleting a base pair, or introducing a premature stop which thus decreases expression of the target. The CRISPR/Cas system can alternatively be used like RNA interference, turning off a target gene in a reversible fashion. In a mammalian cell, for example, the RNA can guide the Cas protein to a target gene promoter, sterically blocking RNA polymerases.

A Cas protein may be derived from any bacterial or archaeal Cas protein. Any suitable CRISPR/Cas system is envisaged as within the scope of the instant disclosure. In other aspects, Cas protein comprises one or more of Cas1, Cas1B, Cas2, Cas3, Cas4, Cas5, Cas6, Cas7, Cas8, Cas9, Cas10, Cas12a (Cpf1), Cas13, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, CasY, homologs thereof, or modified versions thereof. In some embodiments, the Cas protein is a Cas9 protein, a Cpf1 protein, a C2c1 protein, a C2c2 protein, a C2c3 protein, Cas3, Cas3-HD, Cas 5, Cas7, Cas8, Cas10, or combinations or complexes of these. In some embodiments, the Cas protein is a Cas9 protein.

Artificial CRISPR/Cas systems can be generated which inhibit a target gene, using technology known in the art, e.g., that described in U.S. Publication No. 20140068797, and Cong (2013) Science 339: 819-823. Other artificial CRISPR/Cas systems that are known in the art may also be generated which inhibit a target gene, e.g., that described in Tsai (2014) Nature Biotechnol., 32:6 569-576, U.S. Pat. Nos. 8,871,445; 8,865,406; 8,795,965; 8,771,945; and 8,697,359. Methods of designing suitable gNAs for a particular Cas protein will be known by persons of ordinary skill in the art.

The present disclosure provides gene-targeting guide nucleic acids (gNAs) that can direct the activities of an associated polypeptide (e.g., nucleic acid guided endonuclease) to a specific target gene sequence within a target nucleic acid genome. The genome-targeting nucleic acid can be an RNA. A genome-targeting RNA is referred to as a "guide RNA" or "gRNA" herein. A guide RNA can comprise at least a targeting sequence that hybridizes to a target nucleic acid sequence of interest, and a CRISPR repeat sequence. In some Type II systems, the gRNA also comprises a second RNA called the tracrRNA sequence, also referred to herein as a "scaffold" sequence. In the Type II guide RNA (gRNA), the CRISPR repeat sequence and scaffold sequence hybridize to each other to form a duplex. In the Type V guide RNA (gRNA), the crRNA forms a duplex. In both systems, the duplex can bind a site-directed polypeptide, such that the guide RNA and site-directed polypeptide form a complex. The gene-targeting nucleic acid can provide target specificity to the complex by virtue of its association with the site-directed polypeptide. The gene-targeting nucleic acid thus can direct the activity of the site-directed polypeptide.

In some embodiments, the disclosure provides a guide RNA comprising a targeting sequence and a guide RNA scaffold sequence, wherein the targeting sequence is complementary to the sequence of a target gene.

Exemplary guide RNAs include targeting sequences of about 15-20 bases. As is understood by the person of ordinary skill in the art, each gRNA can be designed to include a targeting sequence complementary to its genomic target sequence. For example, each of the targeting sequences, e.g., the RNA version of the DNA sequences presented in Table 19, minus the three 3' nucleotides which represent that PAM site, can be put into a single RNA chimera or a crRNA.

The gene targeting nucleic acid can be a double-molecule guide RNA. The gene targeting nucleic acid can be a single-molecule guide RNA. The gene targeting nucleic acid can be any known configuration of guide RNA known in the art, such as, for example, including paired gRNA, or multiple gRNAs used in a single step. Although it is clear from genomic sequences where the coding sequences and splice junctions are, other features required for gene expression may be idiosyncratic and unclear.

A double-molecule guide RNA can comprise two strands of RNA. The first strand comprises a sequence in the 5' to 3' direction, an optional spacer extension sequence, a targeting sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a targeting sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, guide RNA or single-molecule guide RNA (sgRNA) can comprise a targeting sequence and a scaffold sequence. In some embodiments, the scaffold sequence is a Cas9 gRNA sequence. In some embodiments, the scaffold sequence is encoded by a DNA sequence that comprises a sequence that shares at least 90%, at least 95%, at least 96%, at least 97%, at least 98%, or at least 99% identity to GTTTTAGAGCTAGAAATAGCAAGT-TAAAATAAGGCTAGTCCGTTATCAACTTGAA AAAGTGGCACCGAGTCGGTGCTTTTTTT (SEQ ID NO: 575). In some embodiments, the scaffold sequence is encoded by a DNA sequence that comprises (SEQ ID NO: 575)
GTTTTAGAGCTAGAAATAGCAAGTTAAAATAAGGCTAGTCCGTTATCAAC

TTGAAAAAGTGGCACCGAGTCGGTGCTTTTTTT.

In some embodiments, for example those embodiments where the CRISPR/Cas system is a Cas9 system, the sgRNA can comprise a 20 nucleotide targeting sequence at the 5' end of the sgRNA sequence. The sgRNA can comprise a less than a 20 nucleotide targeting sequence at the 5' end of the sgRNA sequence. The sgRNA can comprise a more than 20 nucleotide targeting sequence at the 5' end of the sgRNA sequence. The sgRNA can comprise a variable length targeting sequence with 17-30 nucleotides at the 5' end of the sgRNA sequence.

Suitable scaffold sequences, and arrangement of scaffold targeting sequences, will depend on choice of endonuclease, and will be known to persons of skill in the art.

A single-molecule guide RNA (sgRNA) in a Type II system, e.g. Cas9, can comprise, in the 5' to 3' direction, a minimum CRISPR repeat sequence and a targeting sequence.

By way of illustration, guide RNAs used in the CRISPR/Cas9 or CRISPR/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

The targeting sequence of a gRNA hybridizes to a sequence in a target nucleic acid of interest. The targeting sequence of a genome-targeting nucleic acid can interact with a target nucleic acid in a sequence-specific manner via hybridization (i.e., base pairing). The nucleotide sequence of the targeting sequence can vary depending on the sequence of the target nucleic acid of interest.

In a Cas9 system described herein, the targeting sequence can be designed to hybridize to a target nucleic acid that is located 5' of the reverse complement of a PAM of the Cas9 enzyme used in the system. The targeting sequence may perfectly match the target sequence or may have mismatches. Each CRISPR/Cas system protein may have a particular PAM sequence, in a particular orientation and position, that it recognizes in a target DNA. For example, S. pyogenes Cas9 recognizes in a target nucleic acid a PAM that comprises the sequence 5'-NRG-3', where R comprises either A or G, where N is any nucleotide and N is immediately 3' of the target nucleic acid sequence targeted by the targeting sequence. Selection of appropriate PAM sequences will be apparent to the person of ordinary skill in the art.

The target sequence is complementary to, and hybridizes with, the targeting sequence of the gRNA. The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. In some embodiments, for example those embodiments where the CRISPR/Cas system is a Cas9 system, the target nucleic acid sequence can comprise 20 nucleotides immediately 5' of the first nucleotide of the reverse complement of the PAM sequence. This target nucleic acid sequence is often referred to as the PAM strand or a target strand, and the complementary nucleic acid sequence is often referred to the non-PAM strand or non-target strand. One of skill in the art would recognize that the targeting sequence hybridizes to the non-PAM strand of the target nucleic acid, see e.g., US20190185849A1.

In some examples, the percent complementarity between the targeting sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the targeting sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the targeting sequence and the target nucleic acid is 100% over the six contiguous 5'-most nucleotides of the target sequence of the complementary strand of the target nucleic acid. The percent complementarity between the targeting sequence and the target nucleic acid can be at least 60% over about 20 contiguous nucleotides. The length of the targeting sequence and the target nucleic acid can differ by 1 to 6 nucleotides, which may be thought of as a bulge or bulges.

The targeting sequence can be designed or chosen using computer programs known to persons of ordinary skill in the art. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like. Available computer programs can take as input NCBI gene IDs, official gene symbols, Ensembl Gene IDs, genomic coordinates, or DNA sequences, and create an output file containing sgRNAs targeting the appropriate genomic regions designated as input. The computer program may also provide a summary of statistics and scores indicating on- and off-target binding of the sgRNA for the target gene (Doench et al. Nat Biotechnol. 34:184-191 (2016)). The disclosure provides guide RNAs comprising a targeting sequence. In some embodiments, the guide RNA further comprises a guide RNA scaffold sequence. In some embodiments, the targeting sequence is complementary to the sequence of a target gene selected from the group consisting of HLA-A, HLA-B, HLA-C, B2M or an allele thereof. In some embodiments, the target gene is an HLA-A gene. In some embodiments, the target gene is an HLA-B gene. In some embodiments, the target gene is an HLA-C gene. In some embodiments the target gene is HLA-A, HLA-B, HLA-C, or a combination thereof. In some embodiments, targeting sequence comprises a sequence that shares about 90%, about 95%, about 96%, about 97%, about 98%, about 99% identity to or is identical to a sequence disclosed in Table 18

Table 19.

In some embodiments, the gNAs specifically target the sequence of an endogenous HLA-A. In some embodiments, the gNAs that specifically target the sequence of an HLA-A locus comprise a sequence that shares about 90%, about 95%, about 96%, about 97%, about 98%, or about 99% identity to a sequence selected from the sequences disclosed in Table 19. In some embodiments, the gNAs that specifically target the sequence of an HLA-A locus comprise a sequence selected from the sequences disclosed in Table 19. In some embodiments, the gNAs that specifically target the sequence of an HLA-A locus comprise a sequence set forth in any one of SEQ ID NO: 576-8650.

In some embodiments, the gNAs specifically target a sequence of HLA-A*02 alleles. For example, the gRNAs specifically target, and hybridize to, a sequence shared by all HLA-A*02 alleles, but that is not shared by HLA-A*02 and HLA-A*03. In some embodiments, the gNAs specifically target a sequence of HLA-A*02:01 alleles. In some embodiments, the gNAs specifically target a sequence of HLA-A*02:01:01 alleles. In some embodiments, the gNAs specifically target a sequence of HLA-A*02:01:01:01 alleles. In some embodiments, the gNAs specifically target a sequence of HLA-A*02:01:01:01 alleles. In some embodiments, the gNAs specifically target a coding DNA sequence of HLA-A*02.

In some embodiments, the gNAs specifically target a coding DNA sequence that is shared by more than 1000 HLA-A*02 alleles.

TABLE 19

Illustrative Sequences Targeting HLA-A and HLA-Alleles

| SEQ ID NO | Guide Nucleic Acid Targeting Sequences |
|---|---|
| 576 | TGGACGACACGCAGTTCGTG |
| 577 | CAGATACCTGGAGAACGGGA |
| 578 | TCCCGTTCTCCAGGTATCTG |

TABLE 19-continued

Illustrative Sequences Targeting HLA-A and HLA-Alleles

| SEQ ID NO | Guide Nucleic Acid Targeting Sequences |
|---|---|
| 579 | CCGCCGCGGTCCAAGAGCGC |
| 580 | CCTGCGCTCTTGGACCGCGG |
| 581 | GGACCTGCGCTCTTGGACCGC |
| 582 | AAGGAGACGCTGCAGCGCACGGG |
| 583 | GAAGGAGACGCTGCAGCGCACGG |
| 584 | GCGGGCGCCGTGGATAGAGCAGG |
| 585 | TGCTCTATCCACGGCGCCCGCGG |
| 586 | CGATGAAGCGGGGCTCCCCGCGG |
| 587 | CGTGTCCCGGCCCGGCCGCGGGG |
| 588 | CGGCTCCATCCTCTGGCTCGCGG |
| 589 | GATGTAATCCTTGCCGTCGTAGG |
| 590 | ACAGCGACGCCGCGAGCCAGAGG |
| 591 | GGATGGAGCCGCGGGCGCCGTGG |
| 592 | GGCGCCGTGGATAGAGCAGGAGG |
| 593 | GCGCCGTGGATAGAGCAGGAGGG |
| 594 | CGGCTACTACAACCAGAGCGAGG |
| 595 | CTGGTTGTAGTAGCCGCGCAGGG |
| 596 | TACTACAACCAGAGCGAGGCCGG |
| 597 | CTACCTGGAGGGCACGTGCGTGG |
| 598 | CACGCACGTGCCCTCCAGGTAGG |
| 599 | GCAGGGTCCCCAGGTCCACTCGG |
| 600 | GTGGACCTGGGGACCCTGCGCGG |
| 601 | TGGAGGGCACGTGCGTGGAGTGG |
| 602 | GTATGGCTGCGACGTGGGGTCGG |
| 603 | CTGAGCTGCCATGTCCGCCGCGG |
| 604 | GGATTACATCGCCCTGAAAGAGG |
| 605 | CAAGTGGGAGGCGGCCCATGTGG |
| 606 | GTGGGAGGCGGCCCATGTGGCGG |
| 607 | CAGTTGAGAGCCTACCTGGAGGG |
| 608 | GCAGTTGAGAGCCTACCTGGAGG |
| 609 | TACCACCAGTACGCCTACGACGG |
| 610 | TGCCGTCGTAGGCGTACTGGTGG |
| 611 | CCAGTACGCCTACGACGGCAAGG |
| 612 | GGATGTGAAGAAATACCTCATGG |
| 613 | ATTTCTTCACATCCGTGTCCCGG |
| 614 | AGGCGTACTGGTGGTACCCGCGG |
| 615 | CGTACTGGTGGTACCCGCGGAGG |
| 616 | GAGGATGTATGGCTGCGACGTGG |
| 617 | GGATGTATGGCTGCGACGTGGGG |
| 618 | CTCAGACCACCAAGCACAAGTGG |
| 619 | TCAGACCACCAAGCACAAGTGGG |
| 620 | CACCAAGCACAAGTGGGAGGCGG |
| 621 | GACCACCAAGCACAAGTGGGAGG |
| 622 | GAGCCCCGCTTCATCGCAGTGGG |
| 623 | GTAGCCCACTGCGATGAAGCGGG |
| 624 | TAGCCCACTGCGATGAAGCGGGG |
| 625 | CGTAGCCCACTGCGATGAAGCGG |
| 626 | CTTCATCGCAGTGGGCTACGTGG |
| 627 | GGAGCCCCGCTTCATCGCAGTGG |
| 628 | CGGGGAGACACGGAAAGTGAAGG |
| 629 | AGTATTGGGACGGGGAGACACGG |
| 630 | AGGGTCCGGAGTATTGGGACGGG |
| 631 | GAGGGTCCGGAGTATTGGGACGG |
| 632 | GGACCCTCCTGCTCTATCCACGG |
| 633 | GTGGATAGAGCAGGAGGGTCCGG |
| 634 | AGACTCACCGAGTGGACCTGGGG |
| 635 | CACTCGGTGAGTCTGTGAGTGGG |
| 636 | CAGACTCACCGAGTGGACCTGGG |
| 637 | CCACTCACAGACTCACCGAGTGG |
| 638 | CCACTCGGTGAGTCTGTGAGTGG |
| 639 | TCGGACTGGCGCTTCCTCCGCGG |
| 640 | GCAGCCATACATCCTCTGGACGG |
| 641 | TCTCAACTGCTCCGCCACATGGG |
| 642 | ACCCTCATGCTGCACATGGCAGG |
| 643 | ACCTGCCATGTGCAGCATGAGGG |
| 644 | CACCTGCCATGTGCAGCATGAGG |
| 645 | GGAGGACCAGACCCAGGACACGG |
| 646 | GGATGGGAGGACCAGACCCAGG |
| 647 | GACCTGGCAGCGGGATGGGGAGG |
| 648 | AGATCACACTGACCTGGCAGCGG |
| 649 | GATCACACTGACCTGGCAGCGGG |
| 650 | AGGTCAGTGTGATCTCCGCAGGG |
| 651 | AAGCCCCTCACCCTGAGATGGGG |

TABLE 19-continued

Illustrative Sequences Targeting HLA-A and HLA-Alleles

| SEQ ID NO | Guide Nucleic Acid Targeting Sequences |
|---|---|
| 652 | CTGCGGAGATCACACTGACCTGG |
| 653 | CAGCAATGATGCCCACGATGGGG |
| 654 | CCAGCAATGATGCCCACGATGGG |
| 655 | GCCAGCAATGATGCCCACGATGG |
| 656 | GGATGGAACCTTCCAGAAGTGGG |
| 657 | GGGATGGAACCTTCCAGAAGTGG |
| 658 | ATGCCCACGATGGGGATGGTGGG |
| 659 | CAGCCCACCATCCCCATCGTGGG |
| 660 | CCAGCCCACCATCCCCATCGTGG |
| 661 | GATGCCCACGATGGGGATGGTGG |
| 662 | CAGGGCCCAGCACCTCAGGGTGG |
| 663 | AATGATGCCCACGATGGGGATGG |
| 664 | GGCCCTGACCCAGACCTGGGCGG |
| 665 | GACCCAGGACACGGAGCTCGTGG |
| 666 | ACACGGAGCTCGTGGAGACCAGG |
| 667 | CGTGGAGACCAGGCCTGCAGGGG |
| 668 | TCGTGGAGACCAGGCCTGCAGGG |
| 669 | AGCTGTGATCACTGGAGCTGTGG |
| 670 | AAAAGGAGGGAGCTACTCTCAGG |
| 671 | ATGTGGAGGAGGAAGAGCTCAGG |
| 672 | GTGTCTCTCACAGCTTGTAAAGG |
| 673 | GAGAGACACATCAGAGCCCTGGG |
| 674 | CTCCGCAGGGTAGAAGCTCAGGG |
| 675 | GGCCCTGAGCTTCTACCCTGCGG |
| 676 | GCTCAGGGCCCAGCACCTCAGGG |
| 677 | TATCTCTGCTCCTGTCCAGAAGG |
| 678 | AGTAGCAGGACGAGGGTTCGGGG |
| 679 | CCCCGAGAGTAGCAGGACGAGGG |
| 680 | CCCTCGTCCTGCTACTCTCGGGG |
| 681 | CCTCGTCCTGCTACTCTCGGGGG |
| 682 | CTGTGGTCGCTGCTGTGATGTGG |
| 683 | TCGCTGCTGTGATGTGGAGGAGG |
| 684 | TGGTCGCTGCTGTGATGTGGAGG |
| 685 | CACAGCCGCCCACTTCTGGAAGG |
| 686 | CCAGAAGTGGGCGGCTGTGGTGG |
| 687 | TGGAACCTTCCAGAAGTGGGCGG |
| 688 | TCACAGCTCCAAAGAGAACCAGG |
| 689 | CTGACCATGAAGCCACCCTGAGG |
| 690 | GCAAACCCTCATGCTGCACATGG |
| 691 | TGAAGCCACCCTGAGGTGCTGGG |
| 692 | GGTGAGTCATATGCGTTTTGGGG |
| 693 | GTGAGTCATATGCGTTTTGGGGG |
| 694 | CTTCATGGTCAGAGACAGCGTGG |
| 695 | TCTGGCCCTGACCCAGACCTGGG |

The sequences disclosed in Table 19 include the corresponding genomic sequences, inclusive of the PAM sequence. The skilled artisan will understand that the targeting sequence of the gRNA does not include three 3' terminal nucleotides of the sequences in Table 19, which represent the corresponding PAM site for the gRNA.

The disclosure provides gRNAs comprising a targeting sequence specific to the B2M gene. In some embodiments, the gRNAs specifically target the coding sequence (CDS) sequence of the B2M gene. In some embodiments, the gRNA comprises a sequence that targets the B2M gene promoter sequence.

In some embodiments the gRNA comprise a targeting sequence and a gRNA scaffold sequence. In some embodiments, the targeting sequence comprises a sequence set forth in Table 20, or a sequence shares about 90%, about 95%, about 96%, about 97%, about 98%, about 99% identity thereto.

In some embodiments, the targeting sequence is complementary to a sequence of the B2M gene. In some embodiments, the B2M gene comprises a sequence that shares about 90%, about 95%, about 96%, about 97%, about 98%, about 99% identity to the B2M sequence set forth in Table 18.

TABLE 20

Illustrative Sequences Targeting B2M

| SEQ ID NO | Sequence |
|---|---|
| 8657 | CGCGAGCACAGCTAAGGCCA |
| 8658 | GAGTAGCGCGAGCACAGCTA |
| 8659 | AGGGTAGGAGAGACTCACGC |
| 8660 | CTGAATCTTTGGAGTACCTG |
| 8661 | TCACGTCATCCAGCAGAGAA |
| 8662 | TCCTGAATTGCTATGTGTCT |
| 8663 | AAGTCAACTTCAATGTCGGA |
| 8664 | GTCTTTTCCCGATATTCCTC |
| 8665 | TGGAGTACCTGAGGAATATC |

TABLE 20-continued

Illustrative Sequences Targeting B2M

| SEQ ID NO | Sequence |
|---|---|
| 8666 | CAGCCCAAGATAGTTAAGTG |
| 8667 | ACAAAGTCACATGGTTCACA |
| 8668 | ACTCTCTCTTTCTGGCCTGG |
| 8669 | TGGGCTGTGACAAAGTCACA |
| 8670 | GGCCGAGATGTCTCGCTCCG |
| 8671 | CAGTAAGTCAACTTCAATGT |
| 8672 | ACTCACGCTGGATAGCCTCC |
| 8673 | CATACTCATCTTTTTCAGTG |
| 8674 | CACAGCCCAAGATAGTTAAG |
| 8675 | TTCAGACTTGTCTTTCAGCA |
| 8676 | AGTCACATGGTTCACACGGC |
| 8677 | ATACTCATCTTTTTCAGTGG |
| 8678 | GGCATACTCATCTTTTTCAG |
| 8679 | ACAGCCCAAGATAGTTAAGT |
| 8680 | GCTACTCTCTCTTTCTGGCC |
| 8681 | TGGAGAGAGAATTGAAAAAG |
| 8682 | ACTTGTCTTTCAGCAAGGAC |
| 8683 | GAAGTTGACTTACTGAAGAA |
| 8684 | GGCCACGGAGCGAGACATCT |
| 8685 | GCATACTCATCTTTTTCAGT |
| 8686 | CGTGAGTAAACCTGAATCTT |
| 8687 | TTACCCCACTTAACTATCTT |
| 8688 | TTGGAGTACCTGAGGAATAT |
| 8689 | ACCCAGACACATAGCAATTC |
| 8690 | TTTGACTTTCCATTCTCTGC |
| 8691 | TTCCTGAATTGCTATGTGTC |
| 8692 | CTCAGGTACTCCAAAGATTC |
| 8693 | CTTACCCCACTTAACTATCT |
| 8694 | CTCGCGCTACTCTCTCTTTC |
| 8695 | TCGATCTATGAAAAGACAG |
| 8696 | GAGACATGTAAGCAGCATCA |
| 8697 | ACATGTAAGCAGCATCATGG |
| 8698 | GAAGTCCTAGAATGAGCGCC |
| 8699 | GAGCGCCGGTGTCCCAAGC |
| 8700 | AGCGCCGGTGTCCCAAGCT |
| 8701 | GCGCCGGTGTCCCAAGCTG |
| 8702 | CTGGGGCGCGCACCCCAGAT |
| 8703 | GGGCGCGCACCCCAGATCGG |
| 8704 | GGCGCGCACCCCAGATCGGA |
| 8705 | CATCACGAGACTCTAAGAAA |
| 8706 | TAAGAAAAGGAAACTGAAAA |
| 8707 | AAGAAAAGGAAACTGAAAAC |
| 8708 | GAAAGTCCCTCTCTCTAACC |
| 8709 | CTAACCTGGCACTGCGTCGC |
| 8710 | CTGGCACTGCGTCGCTGGCT |
| 8711 | TGCGTCGCTGGCTTGGAGAC |
| 8712 | GCTGGCTTGGAGACAGGTGA |
| 8713 | GAGACAGGTGACGGTCCCTG |
| 8714 | AGACAGGTGACGGTCCCTGC |
| 8715 | CCTGCGGGCCTTGTCCTGAT |
| 8716 | CGGGCCTTGTCCTGATTGGC |
| 8717 | GGGCCTTGTCCTGATTGGCT |
| 8718 | GGGCACGCGTTTAATATAAG |
| 8719 | CACGCGTTTAATATAAGTGG |
| 8720 | TATAAGTGGAGGCGTCGCGC |
| 8721 | AAGTGGAGGCGTCGCGCTGG |
| 8722 | AGTGGAGGCGTCGCGCTGGC |
| 8723 | TTCCTGAAGCTGACAGCATT |
| 8724 | TCCTGAAGCTGACAGCATTC |
| 8725 | GCCCGAATGCTGTCAGCTTC |
| 8726 | AAACGCGTGCCCAGCCAATC |
| 8727 | GTGCCCAGCCAATCAGGACA |
| 8728 | CCAATCAGGACAAGGCCCGC |
| 8729 | CAATCAGGACAAGGCCCGCA |
| 8730 | CAAGCCAGCGACGCAGTGCC |
| 8731 | CGCAGTGCCAGGTTAGAGAG |
| 8732 | GCAGTGCCAGGTTAGAGAGA |
| 8733 | GAGTCTCGTGATGTTTAAGA |
| 8734 | TAAGAAGGCATGCACTAGAC |
| 8735 | AAGAAGGCATGCACTAGACT |
| 8736 | TGAGTTTGCTGTCTGTACAT |
| 8737 | TACATCGGCGCCCTCCGATC |
| 8738 | ACATCGGCGCCCTCCGATCT |
| 8739 | CATCGGCGCCCTCCGATCTG |

TABLE 20-continued

Illustrative Sequences Targeting B2M

| SEQ ID NO | Sequence |
|---|---|
| 8740 | CTGGGGTGCGCGCCCCAGCT |
| 8741 | TGGGGTGCGCGCCCCAGCTT |
| 8742 | CGCGCCCCAGCTTGGGACAC |
| 8743 | GCGCCCCAGCTTGGGACACC |
| 8744 | CAAGTCACTTAGCATCTCTG |
| 8745 | ACAGAAGTTCTCCTTCTGCT |
| 8746 | ATTCAAAGATCTTAATCTTC |
| 8747 | TTCAAAGATCTTAATCTTCT |
| 8748 | TTTTCTCGAATGAAAAATGC |
| 8749 | TGCAGGTCCGAGCAGTTAAC |
| 8750 | GGTCCGAGCAGTTAACTGGC |
| 8751 | GTCCGAGCAGTTAACTGGCT |
| 8752 | TCCGAGCAGTTAACTGGCTG |
| 8753 | AGCAAGTCACTTAGCATCTC |
| 8754 | GCAAGTCACTTAGCATCTCT |
| 8755 | TGGGGCCAGTCTGCAAAGCG |
| 8756 | GGGGCCAGTCTGCAAAGCGA |
| 8757 | GGGCCAGTCTGCAAAGCGAG |
| 8758 | GGCCAGTCTGCAAAGCGAGG |
| 8759 | GGACACCGGGCGCTCATTCT |
| 8760 | GGCGCTCATTCTAGGACTTC |
| 8761 | CTCATTCTAGGACTTCAGGC |
| 8762 | ATTCTAGGACTTCAGGCTGG |
| 8763 | TTCAGGCTGGAGGCACATTA |
| 8764 | TGCCCCCTCGCTTTGCAGAC |
| 8765 | GATGCTAAGTGACTTGCTAA |
| 8766 | GCCCCAGCCAGTTAACTGCT |
| 8767 | GCATTTTCATTCGAGAAAA |
| 8768 | TTTGAATGCTACCTAGCAGA |
| 8769 | TTCTGTTTATAACTACAGCT |
| 8770 | TCTGTTTATAACTACAGCTT |

In some embodiments, the immune cells described herein are edited using TALEN gene editing.

"TALEN" or "TALEN gene editing" refers to a transcription activator-like effector nuclease, which is an artificial nuclease used to edit a target gene.

TALENs are produced artificially by fusing a TAL effector DNA binding domain to a DNA cleavage domain. Transcription activator-like effectors (TALEs) derived from Xanthomonas bacteria can be engineered to bind any desired DNA sequence, including a portion of target genes such as TCR subunits, MHC class I complex components, or CD52. By combining an engineered TALE with a DNA cleavage domain, a restriction enzyme can be produced which is specific to any desired DNA sequence, including a target gene sequence. These can then be introduced into a cell, wherein they can be used for genome editing.

To produce a TALEN, a TALE protein is fused to a nuclease (N), which is a wild-type or mutated FokI endonuclease. Several mutations to FokI have been made for its use in TALENs; these, for example, improve cleavage specificity or activity.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity.

TALENs specific to sequences in a target gene can be constructed using any method known in the art, including various schemes using modular components.

In some embodiments, a target gene is edited in the immune cells described herein using ZFN gene editing.

"ZFN" or "Zinc Finger Nuclease" or "ZFN gene editing" refer to a zinc finger nuclease, an artificial nuclease which can be used to edit a target gene.

Like a TALEN, a ZFN comprises a FokI nuclease domain (or derivative thereof) fused to a DNA-binding domain. In the case of a ZFN, the DNA-binding domain comprises one or more zinc fingers.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart.

Also like a TALEN, a ZFN can create a double-stranded break in the DNA, which can create a frame-shift mutation if improperly repaired, leading to a decrease in the expression and amount of a target gene or gene product in a cell. ZFNs can also be used with homologous recombination to mutate in a target gene.

ZFNs specific to sequences in a target gene can be constructed using any method known in the art.

In some embodiments, the expression and of function of one or more MCH-I components are reduced using RNA interference. "RNAi" or "RNA interference" refers to the process of sequence-specific post-transcriptional gene silencing, mediated by double-stranded RNA (dsRNA). Duplex RNAs such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof are all capable of mediating RNA interference. These dsRNA molecules may be commercially available or may be designed and prepared based on known sequence information. The anti-sense strand of these molecules can include RNA, DNA, PNA, or a combination thereof.

DNA/RNA chimeric polynucleotides include, but are not limited to, a double-strand polynucleotide composed of DNA and RNA that inhibits the expression of a target gene. dsRNA molecules can also include one or more modified nucleotides, as described herein, which can be incorporated on either or both strands.

In RNAi gene silencing or knockdown, dsRNA comprising a first (anti-sense) strand that is complementary to a portion of a target gene and a second (sense) strand that is fully or partially complementary to the first anti-sense strand is introduced into an organism. After introduction into the organism, the target gene-specific dsRNA is processed into relatively small fragments (siRNAs) and can subsequently become distributed throughout the organism, decrease messenger RNA of target gene, leading to a phenotype that may come to closely resemble the phenotype arising from a complete or partial deletion of the target gene.

Certain dsRNAs in cells can undergo the action of Dicer enzyme, a ribonuclease III enzyme. Dicer can process the dsRNA into shorter pieces of dsRNA, i.e. siRNAs. RNAi also involves an endonuclease complex known as the RNA induced silencing complex (RISC). Following cleavage by Dicer, siRNAs enter the RISC complex and direct cleavage of a single stranded RNA target having a sequence complementary to the anti-sense strand of the siRNA duplex. The other strand of the siRNA is the passenger strand. Cleavage of the target RNA takes place in the middle of the region complementary to the anti-sense strand of the siRNA duplex. siRNAs can thus down regulate or knock down gene expression by mediating RNA interference in a sequence-specific manner.

As used herein with respect to RNA interference, "target gene" or "target sequence" refers to a gene or gene sequence whose corresponding RNA is targeted for degradation through the RNAi pathway using dsRNAs or siRNAs as described herein. Exemplary target gene sequences are shown in Table 18. To target a gene, for example using an siRNA, the siRNA comprises an anti-sense region complementary to, or substantially complementary to, at least a portion of the target gene or sequence, and sense strand complementary to the anti-sense strand. Once introduced into a cell, the siRNA directs the RISC complex to cleave an RNA comprising a target sequence, thereby degrading the RNA. The disclosure provides interfering RNAs. The double stranded RNA molecule of the disclosure may be in the form of any type of RNA interference molecule known in the art. In some embodiments, the double stranded RNA molecule is a small interfering RNA (siRNA). In other embodiments, the double stranded RNA molecule is a short hairpin RNA (shRNA) molecule. In other embodiments, the double stranded RNA molecule is a Dicer substrate that is processed in a cell to produce an siRNA. In other embodiments the double stranded RNA molecule is part of a microRNA precursor molecule.

In some embodiments, the shRNA is a length to be suitable as a Dicer substrate, which can be processed to produce a RISC active siRNA molecule. See, e.g., Rossi et al., US2005/0244858.

A Dicer substrate double stranded RNA (e.g. a shRNA) can be of a length sufficient that it is processed by Dicer to produce an active siRNA, and may further include one or more of the following properties: (i) the Dicer substrate shRNA can be asymmetric, for example, having a 3' overhang on the anti-sense strand, (ii) the Dicer substrate shRNA can have a modified 3' end on the sense strand to direct orientation of Dicer binding and processing of the dsRNA to an active siRNA, for example the incorporation of one or more DNA nucleotides, and (iii) the first and second strands of the Dicer substrate ds RNA can be from 21-30 bp in length.

In some embodiments, the interfering RNAs comprise a sequence complementary to a sequence of a B2M mRNA. In some embodiments, the interfering RNA is capable of inducing RNAi-mediated degradation of the B2M mRNA. In some embodiments, the B2M mRNA sequence comprises a coding sequence. In some embodiments, the B2M mRNA sequence comprises an untranslated region In some embodiments, the interfering RNAs comprise a sequence complementary to a sequence of an HLA-A*02 mRNA. In some embodiments, the interfering RNA is capable of inducing RNAi-mediated degradation of the HLA-A*02 mRNA. In some embodiments, the HLA-A*02 mRNA sequence comprises a coding sequence. In some embodiments, the HLA-A*02 mRNA sequence comprises an untranslated region.

In some embodiments, the interfering RNA is a short hairpin RNA (shRNA). In some embodiments, the shRNA comprises a first sequence, having from 5' to 3' end a sequence complementary to the B2M mRNA; and a second sequence, having from 5' to 3' end a sequence complementary to the first sequence, wherein the first sequence and second sequence form the shRNA.

In some embodiments, the first sequence is 18, 19, 20, 21, or 22 nucleotides. In some embodiments, the first sequence is complementary to a sequence selected from the sequences set forth in Table 21 and Table 22. In some embodiments, the first sequence has GC content greater than or equal to 25% and less than 60%. In some embodiments, the first sequence is complementary to a sequence selected from the sequences set forth in Table 21 and Table 22. In some embodiments, the first sequence does not comprise four nucleotides of the same base or a run of seven C or G nucleotide bases. In some embodiments, the first sequence is 21 nucleotides.

In some embodiments, the first sequence is complementary to a sequence selected from SEQ ID NOs 8771-13382. In some embodiments, the first sequence has GC content greater than or equal to 25% and less than 60%. In some embodiments, the first sequence is complementary to a sequence selected from SEQ ID NOs: 8771-13382. In some embodiments, the first sequence does not comprise four nucleotides of the same base or a run of seven C or G nucleotide bases. In some embodiments, the first sequence is complementary to a sequence selected from SEQ ID NOs: 8771-13382. In some embodiments, the first sequence is 21 nucleotides. In some embodiments, the first sequence is complementary to a sequence selected from SEQ ID NOs: 8771-9352. In some embodiments, the first sequence is complementary to a sequence selected from SEQ ID NOs: 8771-9052. In some embodiments, the first sequence is complementary to a sequence selected from SEQ ID NOs: 8771-8908. Illustrative target B2M sequences complementary to the first sequence are set forth in SEQ ID NOs: 8771-8908.

Illustrative target B2M sequences complementary to the first sequence are shown in Table 21. In some embodiments, the first sequence targeting B2M comprises a sequence set forth in any one of SEQ ID NOs: 8771-13382.

In some cases, the first sequence may have 100% identity, i.e. complete identity, homology, complementarity to the target nucleic acid sequence. In other cases, there may be one or more mismatches between the first sequence and the target nucleic acid sequence. For example, there may be 1, 2, 3, 4, 5, 6, or 7 mismatches between the sense region and the target nucleic acid sequence.

The sequences set forth in Table 21 are presented as DNA sequences. In all sequences set forth in Table 21, thymine (T) may be replaced by uracil (U) to arrive at the sequence of the target mRNA sequence.

TABLE 21

Illustrative target B2M sequences complementary to first sequence.

| SEQ ID NO | Sequence |
|---|---|
| 8771 | AGAGAATGGAAAGTCAAATTT |
| 8772 | ATGGACATGATCTTCTTTATA |
| 8773 | TGGACATGATCTTCTTTATAA |
| 8774 | GGACATGATCTTCTTTATAAT |
| 8775 | TGACAGGATTATTGGAAATTT |
| 8776 | TTGTGGTTAATCTGGTTTATT |
| 8777 | TGTGGTTAATCTGGTTTATTT |
| 8778 | GCAGAGAATGGAAAGTCAAAT |
| 8779 | CAGAGAATGGAAAGTCAAATT |
| 8780 | GAGAATGGAAAGTCAAATTTC |
| 8781 | GTCACAGCCCAAGATAGTTAA |
| 8782 | TGCTTATACACTTACACTTTA |
| 8783 | GCTTATACACTTACACTTTAT |
| 8784 | CTTTATACACTTACACTTTATG |
| 8785 | ACATGGACATGATCTTCTTTA |
| 8786 | CATGGACATGATCTTCTTTAT |
| 8787 | ATCAACATCTTGGTCAGATTT |
| 8788 | CTTGCACTCAAAGCTTGTTAA |
| 8789 | AGTTAAGCGTGCATAAGTAA |
| 8790 | GCATAAGTTAACTTCCAATTT |
| 8791 | TACATACTCTGCTTAGAATTT |
| 8792 | ACATACTCTGCTTAGAATTTG |
| 8793 | TTGACAGGATTATTGGAAATT |
| 8794 | GACAGGATTATTGGAAATTTG |
| 8795 | TAAGGCATGGTTGTGGTTAAT |
| 8796 | GTTGTGGTTAATCTGGTTTAT |
| 8797 | GTTCCACAAGTTAAATAAATC |
| 8798 | TCCAGCGTACTCCAAAGATTC |
| 8799 | TACTCCAAAGATTCAGGTTTA |
| 8800 | ACTCCAAAGATTCAGGTTTAC |
| 8801 | CACGTCATCCAGCAGAGAATG |
| 8802 | GGTTTCATCCATCCGACATTG |

TABLE 21-continued

Illustrative target B2M sequences complementary to first sequence.

| SEQ ID NO | Sequence |
|---|---|
| 8803 | CCGACATTGAAGTTGACTTAC |
| 8804 | TGAAGAATGGAGAGAGAATTG |
| 8805 | GAGCATTCAGACTTGTCTTTC |
| 8806 | TTCAGCAAGGACTGGTCTTTC |
| 8807 | GCAAGGACTGGTCTTTCTATC |
| 8808 | CGTGTGAACCATGTGACTTTG |
| 8809 | CTTTGTCACAGCCCAAGATAG |
| 8810 | TCACAGCCCAAGATAGTTAAG |
| 8811 | AGTGGGATCGAGACATGTAAG |
| 8812 | AGGTTTGAAGATGCCGCATTT |
| 8813 | GGTTTGAAGATGCCGCATTTG |
| 8814 | TTGATATGCTTATACACTTAC |
| 8815 | TGAGTGCTGTCTCCATGTTTG |
| 8816 | TGTCTCCATGTTTGATGTATC |
| 8817 | TCAACATCTTGGTCAGATTTG |
| 8818 | TCAGATTTGAACTCTTCAATC |
| 8819 | TTCAATCTCTTGCACTCAAAG |
| 8820 | TTGCACTCAAAGCTTGTTAAG |
| 8821 | ACTCAAAGCTTGTTAAGATAG |
| 8822 | AGATAGTTAAGCGTGCATAAG |
| 8823 | TGCATAAGTTAACTTCCAATT |
| 8824 | GTTAACTTCCAATTTACATAC |
| 8825 | ATTGACAGGATTATTGGAAAT |
| 8826 | GTAAGGCATGGTTGTGGTTAA |
| 8827 | GGTTGTGGTTAATCTGGTTTA |
| 8828 | TTCCTGAAGCTGACAGCATTC |
| 8829 | GCTATCCAGCGTACTCCAAAG |
| 8830 | CATCCAGCAGAGAATGGAAAG |
| 8831 | CAAATTTCCTGAATTGCTATG |
| 8832 | ATTGCTATGTGTCTGGGTTTC |
| 8833 | GAAGATGCCGCATTTGGATTG |
| 8834 | CAATTTACATACTCTGCTTAG |
| 8835 | TATCCAGCGTACTCCAAAGAT |
| 8836 | ATCCAGCGTACTCCAAAGATT |
| 8837 | CTCCAAAGATTCAGGTTTACT |
| 8838 | TGCTATGTGTCTGGGTTTCAT |
| 8839 | TTTCATCCATCCGACATTGAA |

TABLE 21-continued

Illustrative target B2M sequences complementary to first sequence.

| SEQ ID NO | Sequence |
|---|---|
| 8840 | GAAGTTGACTTACTGAAGAAT |
| 8841 | GAAGAATGGAGAGAGAATTGA |
| 8842 | AGAATGGAGAGAGAATTGAAA |
| 8843 | CAGCAAGGACTGGTCTTTCTA |
| 8844 | AGCAAGGACTGGTCTTTCTAT |
| 8845 | ACTTTGTCACAGCCCAAGATA |
| 8846 | TTGTCACAGCCCAAGATAGTT |
| 8847 | TGTCACAGCCCAAGATAGTTA |
| 8848 | CACAGCCCAAGATAGTTAACT |
| 8849 | GCAGCATCATGGAGGTTTGAA |
| 8850 | CCGCATTTGGATTGGATGAAT |
| 8851 | TTGAGTGCTGTCTCCATGTTT |
| 8852 | AGTGCTGTCTCCATGTTTGAT |
| 8853 | CTGTCTCCATGTTTGATGTAT |
| 8854 | TCTAGGAGGGCTGGCAACTTA |
| 8855 | CAACATCTTGGTCAGATTTGA |
| 8856 | GTCAGATTTGAACTCTTCAAT |
| 8857 | TCTTGCACTCAAAGCTTGTTA |
| 8858 | TGCACTCAAAGCTTGTTAAGA |
| 8859 | GCACTCAAAGCTTGTTAAGAT |
| 8860 | CACTCAAAGCTTGTTAAGATA |
| 8861 | TCAAAGCTTGTTAAGATAGTT |
| 8862 | CAAAGCTTGTTAAGATAGTTA |
| 8863 | GATAGTTAAGCGTGCATAAGT |
| 8864 | ATAGTTAAGCGTGCATAAGTT |
| 8865 | TAGTTAAGCGTGCATAAGTTA |
| 8866 | TTAAGCGTGCATAAGTTAACT |
| 8867 | TAAGCGTGCATAAGTTAACTT |
| 8868 | ATTTACATACTCTGCTTAGAA |
| 8869 | TTTACATACTCTGCTTAGAAT |
| 8870 | ACAGGATTATTGGAAATTTGT |
| 8871 | CAGGATTATTGGAAATTTGTT |
| 8872 | AGGCATGGTTGTGGTTAATCT |
| 8873 | CAGCAGAGAATGGAAAGTCAA |
| 8874 | TCCGACATTGAAGTTGACTTA |
| 8875 | CTGGTCTTTCTATCTCTTGTA |

TABLE 21-continued

Illustrative target B2M sequences complementary to first sequence.

| SEQ ID NO | Sequence |
|---|---|
| 8876 | CCGTGTGAACCATGTGACTTT |
| 8877 | CCCAAGATAGTTAAGTGGGAT |
| 8878 | GGTTGCTCCACAGGTAGCTCT |
| 8879 | GCTCCACAGGTAGCTCTAGGA |
| 8880 | GGGAGCAGAGAATTCTCTTAT |
| 8881 | GGAGCAGAGAATTCTCTTATC |
| 8882 | GAGCAGAGAATTCTCTTATCC |
| 8883 | GAGAATTCTCTTATCCAACAT |
| 8884 | GAATTCTCTTATCCAACATCA |
| 8885 | AAGTGGAGCATTCAGACTTGT |
| 8886 | AAGGACTGGTCTTTCTATCTC |
| 8887 | AAGCTTGTTAAGATAGTTAAG |
| 8888 | AAGCGTGCATAAGTTAACTTC |
| 8889 | AAGATGCCGCATTTGGATTGG |
| 8890 | AAGAATGGAGAGAGAATTGAA |
| 8891 | AACATCAACATCTTGGTCAGA |
| 8892 | AAGGCATGGTTGTGGTTAATC |
| 8893 | AAGCAGCATCATGGAGGTTTG |
| 8894 | AAGATGAGTATGCCTGCCGTG |
| 8895 | AAGTTGACTTACTGAAGAATG |
| 8896 | AAGATAGTTAAGCGTGCATAA |
| 8897 | AACTTCCAATTTACATACTCT |
| 8898 | AACATCTTGGTCAGATTTGAA |
| 8899 | AACTCTTCAATCTCTTGCACT |
| 8900 | AATTTCCTGAATTGCTATGTG |
| 8901 | AATGGAAAGTCAAATTTCCTG |
| 8902 | AACCATGTGACTTTGTCACAG |
| 8903 | AATTGACAGGATTATTGGAAA |
| 8904 | AATTCTCTTATCCAACATCAA |
| 8905 | AAAGTGGAGCATTCAGACTTG |
| 8906 | AAAGTCAAATTTCCTGAATTG |
| 8907 | GTTGCTCCACAGGTAGCTCTA |
| 8908 | AATTTACATACTCTGCTTAGA |

An exemplary sequence encoding a B2M shRNA comprises a sequence of GCACTCAAAGCTTGTTAA-GATCGAAATCTTAACAAGCTTTGAGTGC (SEQ ID NO: 13383), or a sequence having at least 90%, at least 95%, at least 97% or at least 99% identity thereto. A further exemplary sequence encoding a B2M shRNA comprises a sequence of GTTAACTTCCAATTTACAT-
ACCGAAGTATGTAAATTGGAAGTTAAC (SEQ ID NO:
13384), or a sequence having at least 90%, at least 95%, at
least 97% or at least 99% identity thereto.

In some embodiments, the shRNA comprises a first sequence, having from 5' end to 3' end a sequence complementary to an HLA-A*02 mRNA; and a second sequence, having from 5' end to 3' end a sequence complementary to the first sequence. In some embodiments, the HLA-A*02 mRNA sequence comprises a coding sequence. In some embodiments, the HLA-A*02 mRNA sequence comprises an untranslated region. In some embodiments, the first and second sequence are present on a polynucleotide, wherein the first sequence and the second sequence are separated by 4, 5, 6, 7, 8, 9, 10, 11, 12, 13, 14, or 15 nucleotides, wherein the 4, 5, 6, 7, 8, 9, 10, 11, 12, 13, 14, or 15 nucleotides form a loop region in the shRNA. In some embodiments, the shRNA further comprises a 5' flank sequence and a 3' flank sequence, wherein the 5' flank sequence is joined to the 5' end of the first sequence, and wherein the 3' flank sequence is joined to the 3' end of the second sequence.

In some embodiments, the polynucleotide encoding an shRNA has from 5' end to 3' end, a 5' flank sequence, a first sequence, a loop sequence, a second sequence, a 3' flank sequence. In some embodiments, the polynucleotide encoding an shRNA has from 5' end to 3' end, a 5' flank sequence, a second sequence, a loop sequence, a first sequence, and a 3' flank sequence.

In some embodiments, the first sequences is 18, 19, 20, 21, or 22 nucleotides. In some embodiments, the first sequence is complementary to a sequence selected from SEQ ID NOs: 13385-21779. In some embodiments, the first sequence has GC content greater than or equal to 25% and less than 60%. In some embodiments, the first sequence is complementary to a sequence selected from SEQ ID NOs: 13385-16975. In some embodiments, the first sequence does not comprise four nucleotides of the same base or a run of seven C or G nucleotide bases. In some embodiments, the first sequence is complementary to a sequence selected from SEQ ID NOs: 13385-16493. In some embodiments, the first sequence is complementary to a sequence selected from SEQ ID NOs: 13385-13663. In some embodiments, the first sequence is complementary to a sequence selected from SEQ ID NOs: 13385-13470.

Illustrative target HLA sequences complementary to the first sequence are shown in Table 22.

TABLE 22

Illustrative target HLA sequences complementary to first sequence

| SEQ ID NO | Sequence |
|---|---|
| 13385 | CTTCTTCCTTCCCTATTAAAA |
| 13386 | TCTCACTCCATGAGGTATTTC |
| 13387 | CTCTCACTCCATGAGGTATTT |
| 13388 | GAGGAGGAAGAGCTCAGATAG |
| 13389 | GCTCTCACTCCATGAGGTATT |
| 13390 | AGGATTACATCGCCCTGAAAG |
| 13391 | ACACCGTCCAGAGGATGTATG |
| 13392 | AGGGTCCTTCTTCCTGGATAC |

TABLE 22-continued

Illustrative target HLA sequences complementary to first sequence

| SEQ ID NO | Sequence |
|---|---|
| 13393 | CCTACGACGGCAAGGATTACA |
| 13394 | TCACTCCATGAGGTATTTCTT |
| 13395 | CTACGACGGCAAGGATTACAT |
| 13396 | CTCACTCCATGAGGTATTTCT |
| 13397 | GGAGGAAGAGCTCAGATAGAA |
| 13398 | CACACCGTCCAGAGGATGTAT |
| 13399 | CACGCTGTCTCTGACCATGAA |
| 13400 | CTGGACAGGAGCAGAGATACA |
| 13401 | TGGAGGAGGAAGAGCTCAGAT |
| 13402 | GGCTCTCACTCCATGAGGTAT |
| 13403 | CATCTCTGTCTCAACTTCATG |
| 13404 | TACGACGGCAAGGATTACATC |
| 13405 | GGATTACATCGCCCTGAAAGA |
| 13406 | GATTACATCGCCCTGAAAGAG |
| 13407 | CTCAGACCACCAAGCACAAGT |
| 13408 | TCACACCGTCCAGAGGATGTA |
| 13409 | ACTCCATGAGGTATTTCTTCA |
| 13410 | CACTCCATGAGGTATTTCTTC |
| 13411 | CCATGAGGTATTTCTTCACAT |
| 13412 | ACTTCTTCCTTCCCTATTAAA |
| 13413 | GTGTCTCTCACAGCTTGTAAA |
| 13414 | CTGTGTTCGTGTAGGCATAAT |
| 13415 | TGTGTTCGTGTAGGCATAATG |
| 13416 | TAACTTCTTCCTTCCCTATTA |
| 13417 | TCTGGACAGGAGCAGAGATAC |
| 13418 | TTGCTGGCCTGGTTCTCTTTG |
| 13419 | TGTCTCTCACAGCTTGTAAAG |
| 13420 | ACTTGAAGAACCCTGACTTTG |
| 13421 | GAAGAACCCTGACTTTGTTTC |
| 13422 | TCTGTGTTCGTGTAGGCATAA |
| 13423 | CATGGTGCACTGAGCTGTAAC |
| 13424 | GTAACTTCTTCCTTCCCTATT |
| 13425 | CATGTGCAGCATGAGGGTTTG |
| 13426 | TTGTTCCTGCCCTTCCCTTTG |
| 13427 | ACCCAGTTCTCACTCCCATTG |
| 13428 | GGGTTTCCAGAGAAGCCAATC |
| 13429 | TTCTCCCTCTCCCAACCTATG |

TABLE 22-continued

Illustrative target HLA sequences complementary to first sequence

| SEQ ID NO | Sequence |
|---|---|
| 13430 | GTCTCTCACAGCTTGTAAAGT |
| 13431 | TGTGTCTCACAGCTTGTAA |
| 13432 | GAGGAAGAGCTCAGATAGAAA |
| 13433 | TGAAGAACCCTGACTTTGTTT |
| 13434 | TTGAAGAACCCTGACTTTGTT |
| 13435 | GTGTTCGTGTAGGCATAATGT |
| 13436 | TGGTGCACTGAGCTGTAACTT |
| 13437 | CTCCCTCTCCCAACCTATGTA |
| 13438 | AGGAGGAAGAGCTCAGATAGA |
| 13439 | ACCTATGTAGGGTCCTTCTTC |
| 13440 | GGGTCCTTCTTCCTGGATACT |
| 13441 | GGTCCTTCTTCCTGGATACTC |
| 13442 | GTCCTTCTTCCTGGATACTCA |
| 13443 | AAGCCAATCAGTGTCGTCGCG |
| 13444 | AAGAGGACCTGCGCTCTTGGA |
| 13445 | AAGTGTGAGACAGCTGCCTTG |
| 13446 | AAGGCACCTGCATGTGTCTGT |
| 13447 | AATCATCTTTCCTGTTCCAGA |
| 13448 | AAAGGCACCTGCATGTGTCTG |
| 13449 | AAAGAGGACCTGCGCTCTTGG |
| 13450 | AAACGCATATGACTCACCACG |
| 13451 | GGAAGAGCTCAGATAGAAA |
| 13452 | GGGAGACACGGAAAGTGAA |
| 13453 | CACCTGCCATGTGCAGCATGA |
| 13454 | GGAGATCACACTGACCTGGCA |
| 13455 | GGATTACATCGCCCTGAAAG |
| 13456 | GCAGGAGGGTCCGGAGTATT |
| 13457 | GGACGGGGAGACACGGAAAG |
| 13458 | GAAAGTGAAGGCCCACTCA |
| 13459 | GATACCTGGAGAACGGGAAG |
| 13460 | GCTGTGGTGGTGCCTTCTGG |
| 13461 | GCTACTACAACCAGAGCGAG |
| 13462 | GTGGCTCCGCAGATACCTG |
| 13463 | GCCAATCAGTGTCGTCGCG |
| 13464 | GAGGACCTGCGCTCTTGGA |
| 13465 | GTGTGAGACAGCTGCCTTG |
| 13466 | GGCACCTGCATGTGTCTGT |
| 13467 | TCATCTTTCCTGTTCCAGA |
| 13468 | AGGCACCTGCATGTGTCTG |
| 13469 | AGAGGACCTGCGCTCTTGG |
| 13470 | ACGCATATGACTCACCACG |

In some embodiments, the first sequence and second sequence are separated by a linker, sometimes referred to as a loop. In some embodiments, both the first sequence and the second sequence are encoded by one single-stranded RNA or DNA vector. In some embodiments, the loop is between the first and second sequences. In these embodiments, and the first sequence and the second sequence hybridize to form a duplex region. The first sequence and second sequence are joined by a linker sequence, forming a "hairpin" or "stem-loop" structure. The shRNA can have complementary first sequences and second sequences at opposing ends of a single stranded molecule, so that the molecule can form a duplex region with the complementary sequence portions, and the strands are linked at one end of the duplex region by a linker (i.e. loop sequence). The linker, or loop sequence, can be either a nucleotide or non-nucleotide linker. The linker can interact with the first sequence, and optionally, second sequence through covalent bonds or non-covalent interactions.

Any suitable nucleotide loop sequence is envisaged as within the scope of the disclosure. An shRNA of this disclosure may include a nucleotide, non-nucleotide, or mixed nucleotide/non-nucleotide linker that joins the first sequence of the shRNA to the second sequence of the shRNA. A nucleotide loop sequence can be ≥2 nucleotides in length, for example about 4, 5, 6, 7, 8, 9, 10, 11, 12, 13, 14, or 15 nucleotides in length. Illustrative loop sequences are disclosed in Table 23.

In some embodiments, the shRNA further comprises a 5' flank sequence and a 3' flank sequence. In some embodiments, wherein the 5' flank sequence is joined to the 5' end of the first sequence, and wherein the 3' flank sequence is joined to the 3' end of the second sequence.

Without wishing to be bound by theory, it is thought that flanking shRNA stem loop sequence with 5' and 3' sequences similar to those found in microRNAs can target the shRNA for processing by the endogenous microRNA processing machinery, increasing the effectiveness of shRNA processing. Alternatively, or in addition, flanking sequences may increase shRNA compatibility with polymerase II or polymerase III promoters, leading to more effective regulation of shRNA expression.

In some embodiments, the 5' flank sequence is selected from the sequences set forth in Table 23. Illustrative flank sequence are shown in Table 23.

TABLE 23

Illustrative flank sequences

| SEQ ID NO | 5' Flank Sequence |
|---|---|
| 21780 | GG |
| 21781 | ACACCAUGUUGCCAGUCUCUAGG |
| 21782 | UGAUAGCAAUGUCAGCAGUGCCU |
| 21783 | UAUUGCUGUUGACAGUGAGCGAC |

| SEQ ID NO | 3' Flank Sequence |
|---|---|
| 21784 | UGGCGUCUGGCCCAACCACAC |
| 21785 | GUAAGGUUGACCAUACUCUAC |

In some embodiments, the first and second sequence are present on a single stranded polynucleotide, wherein the first sequence and second sequence are separated by 4, 5, 6, 7, 8, 9, 10, 11, 12, 13, 14, or 15 nucleotides, wherein the 4, 5, 6, 7, 8, 9, 10, 11, 12, 13, 14, or 15 nucleotides form a loop region in the shRNA. In some embodiments, the loop region comprises a sequence selected from the sequences set forth in Table 24.

TABLE 24

Illustrative loop region sequences

| SEQ ID NO | Loop Region Sequence |
|---|---|
| 21786 | CGAA |
| 21787 | UUCAAGA |
| 21788 | AUAUUCA |
| 21789 | UGUGCUGUC |
| 21790 | CUCGAG |
| 21791 | CUUCCUGUCAGA |
| 21792 | CUUCCCUUUGUCAGA |
| 21793 | GUGUUAUUCUUG |
| 21794 | GUGUCUUAAUUG |
| 21795 | GUGUUAGUCUUG |
| 21796 | UCAAGAG |
| 21797 | GGACAUCCAGGG |
| 21798 | GUGAAGCCACAGAUG |
| 21799 | GAUUCUAAAA | shRNAs of the disclosure may be generated exogenously by chemical synthesis, by in vitro transcription, or by cleavage of longer double-stranded RNA with Dicer or another appropriate nuclease with similar activity. Chemically synthesized siRNAs, produced from protected ribonucleoside phosphoramidites using a conventional DNA/RNA synthesizer, may be obtained from commercial suppliers such as Millipore Sigma (Houston, Tex.), Ambion Inc. (Austin, Tex.). Invitrogen (Carlsbad, Calif.), or Dharmacon (Lafayette, Colo.). siRNAs can be purified by extraction with a solvent or resin, precipitation, electrophoresis, chromatography, or a combination thereof, for example. Alternatively, siRNAs may be used with little if any purification to avoid losses due to sample processing. In some embodiments, shRNAs of the disclosure can be produced using an expression vector into which a nucleic acid encoding the double stranded RNA has been cloned, for example under control of a suitable promoter.

Pharmaceutical Compositions

The disclosure provides pharmaceutical compositions comprising immune cells expressing the engineered receptors of the disclosure and a pharmaceutically acceptable diluent, carrier or excipient. In some embodiments, the pharmaceutical composition is for use as a medicament in the treatment of cancer. In some embodiments, the cancer is breast cancer, bladder cancer, ovarian cancer, gastric cancer, salivary duct carcinoma, non-small cell lung cancer, pancreatic cancer, or colon cancer. In some embodiments, the cancer is breast cancer. In some embodiments, the cancer is gastric cancer.

Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; and preservatives.

In some embodiments, the immune cell expresses both the first receptor and the second receptor. In some embodiments, at least about 50%, about 55%, about 60%, about 65%, about 70%, about 75%, about 80%, about 85%, about 90%, or about 95% of the immune cells express both the first receptor and the second receptor. In some embodiments, at least 90% of the immune cells express both the first receptor and the second receptor.

The disclosure provides pharmaceutical compositions comprising a plurality of immune cells of the disclosure, and a pharmaceutically acceptable carrier, diluent or excipient.

Formulations of a pharmaceutical composition suitable for parenteral administration typically generally comprise of immune cells combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. Parenteral formulations also include aqueous solutions which may contain excipients such as salts, carbohydrates and buffering agents. Exemplary parenteral administration forms include solutions or suspensions in sterile aqueous solutions, for example, aqueous propylene glycol or dextrose solutions. Such dosage forms can be suitably buffered, if desired. Formulations for parenteral administration may be formulated to be immediate and/or modified release. Modified release formulations include delayed-, sustained-, pulsed-, controlled-, targeted and programmed release.

In some embodiments, the formulated composition comprising the immune cells is suitable for administration via injection. In some embodiments, the formulated composition comprising the immune cells is suitable for administration via infusion.

The pharmaceutical compositions of the present disclosure, which may conveniently be presented in unit dosage form, may be prepared according to conventional techniques well known in the pharmaceutical industry. Such techniques include the step of bringing into association the immune cells with the pharmaceutical carrier(s) or excipient(s), such as liquid carriers.

Aqueous suspensions may further contain substances that increase the viscosity of the suspension including, for example, sodium carboxymethylcellulose, sorbitol and/or dextran. The suspension may also contain stabilizers.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, preservatives, antioxidants, opacifiers, thickening agents and stabilizers. However, such materials, when added, should not unduly interfere with the biological activities of the immune cells of the compositions of the present disclosure.

The formulation or composition may also contain more than one active ingredient useful for the particular indication, disease, or condition being treated with the immune cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

Administration can be effected in one dose, continuously or intermittently throughout the course of treatment. Single or multiple administrations can be carried out with the dose level and pattern being selected by the treating physician.

The pharmaceutical composition in some embodiments contains the immune cells in amounts effective to treat or prevent a cancer, such as a therapeutically effective or prophylactically effective amount. Therapeutic or prophylactic efficacy in some embodiments is monitored by periodic assessment of treated subjects. For repeated administrations over days, weeks or months, depending on the condition, the treatment can be repeated until a desired suppression of cancer signs or symptoms occurs. However, other dosage regimens may be useful and can be determined. The desired dosage can be delivered by a single bolus administration or infusion of the composition or by multiple bolus administrations or infusions of the composition.

Methods of Use

Provided herein are methods for selectively killing HER2-positive tumor cells having loss of heterozygosity at an allele encoding a non-target antigen in the HER2-positive cancer, comprising contacting the HER2-positive tumor cells with an immune cell comprising the engineered receptors of the disclosure. The cells may be, for example, in a tissue (e.g., in vivo) or in a mixed culture. In some embodiments, the non-target antigen is an HLA class I allele or a minor histocompatibility antigen (MiHA). In some embodiments, the HLA class I allele comprises HLA-A, HLA-B, HLA-C or HLA-E. In some embodiments, the HLA class I allele is HLA-A*02. In some embodiments, the non-target antigen is selected from the group consisting of HLA-A*02, HLA-A*01, HLA-A*03, HLA-A*11, HLA-B*07, and HLA-C*07.

Provided herein are methods of treating a subject in need thereof, comprising administering to the subject a therapeutically effective amount of a composition comprising immune cells comprising the engineered receptors of the disclosure.

In some embodiments, the method comprises treating a HER2+ cancer in a subject identified as having or suspected of having a loss of heterozygosity at an allele encoding a non-target antigen in the HER2+ cancer, comprising administering to the subject the immune cells described herein. In some embodiments, the immune cells are autologous. In some embodiments, the immune cells are allogeneic. In some embodiments, the non-target antigen is an HLA class I allele or a minor histocompatibility antigen (MiHA). In some embodiments, the HLA class I allele comprises HLA-A, HLA-B, HLA-C or HLA-E. In some embodiments, the HLA class I allele is HLA-A*02. In some embodiments, the non-target antigen is selected from the group consisting of HLA-A*02, HLA-A*01, HLA-A*03, HLA-A*11, HLA-B*07, and HLA-C*07.

The disclosure provides methods of making an immune cell therapy. In some embodiments, the method comprises transforming immune cells with the polynucleotide system described herein. In some embodiments, the polynucleotide system comprises one or more polynucleotides comprising polynucleotide sequences encoding: an activator receptor comprising an extracellular ligand binding domain specific to an erb-b2 receptor tyrosine kinase 2 (HER2) antigen; and an inhibitory receptor comprising an extracellular ligand binding domain specific to a non-target antigen that is not expressed by the cancer cell due to a loss of heterozygosity in the cancer cell.

In some embodiments, the method of treating a subject comprises providing immune cells from a subject suffering from or at risk for a HER2 positive (HER2+) cancer. In some embodiments, the method comprises transducing the immune cell with the polynucleotide system described herein.

The current method for adoptive cell therapy using autologous cells includes isolating immune cells from patient blood, performing a series of modifications on the isolated cells, and administering the cells to a patient (Papathanasiou et al. Cancer Gene Therapy. 27:799-809 (2020)). Providing immune cells from a subject suffering from or at risk for cancer or a hematological malignancy requires isolation of immune cell from the patient's blood, and can be accomplished through methods known in the art, for example, by leukapheresis. During leukapheresis, blood from a subject is extracted and the peripheral blood mononuclear cells (PBMCs) are separated, and the remainder of the blood is returned to the subject's circulation. The PBMCs are stored either frozen or cryopreserved as a sample of immune cells and provided for further processing steps, such as, e.g. the modifications described herein.

In some embodiments, the method of treating a subject described herein comprises modifications to immune cells from the subject comprising a series of modifications comprising enrichment, activation, genetic modification, expansion, formulation, and cryopreservation.

The disclosure provides enrichment steps that can be, for example, washing and fractionating methods known in the art for preparation of subject PBMCs for downstream procedures, e.g. the modifications described herein. For example, without limitation, methods can include devices to remove gross red blood cells and platelet contaminants, systems for size-based cell fractionation for the depletion of monocytes and the isolation of lymphocytes, and/or systems that allow the enrichment of specific subsets of T cells, such as, e.g. CD4+, CD8+, CD25+, or CD62L+ T cells. Following the enrichment steps, a target sub-population of immune cells will be isolated from the subject PMBCs for further processing. Those skilled in the art will appreciate that enrichment steps, as provided herein, may also encompass any newly discovered method, device, reagent or combination thereof.

The disclosure provides activation steps that can be any method known in the art to induce activation of immune cells, e.g. T cells, required for their ex vivo expansion. Immune cell activation can be achieved, for example, by culturing the subject immune cells in the presence of dendritic cells, culturing the subject immune cells in the presence of artificial antigen-presenting cells (AAPCs), or culturing the immune cells in the presence of irradiated K562-derived AAPCs. Other methods for activating subject immune cells can be, for example, culturing the immune cells in the presence of isolated activating factors and compositions, e.g. beads, surfaces, or particles functionalized with activating factors. Activating factors can include, for example, antibodies, e.g. anti-CD3 and/or anti-CD28 antibodies. Activating factors can also be, for example, cytokines, e.g. interleukin (IL)-2 or IL-21. Activating factors can also be costimulatory molecules, such as, for example, CD40, CD40L, CD70, CD80, CD83, CD86, CD137L, ICOSL, GITRL, and CD134L. Those skilled in the art will appreciate that activating factors, as provided herein, may also encompass any newly discovered activating factor, reagent, composition, or combination thereof that can activate immune cells.

The disclosure provides genetic modification steps for modifying the subject immune cells. In some embodiments, the genetic modification comprises transducing the immune cell with an engineered receptor. In some embodiments, the method comprises transducing the immune cell with a first vector comprising a sequence encoding the activator receptor and a second vector comprising a sequence encoding the inhibitory receptor, thereby producing an immune cell expressing the activator and inhibitory receptors.

The disclosure provides expansion steps for the genetically modified subject immune cells. Genetically modified subject immune cells can be expanded in any immune cell expansion system known in the art to generate therapeutic doses of immune cells for administration. For example, bioreactor bags for use in a system comprising controller pumps, and probes that allow for automatic feeding and waste removal can be used for immune cell expansion. Cell culture flasks with gas-permeable membranes at the base may be used for immune cell expansion. Any such system known in the art that enables expansion of immune cells for clinical use is encompassed by the expansion step provided herein. Immune cells are expanded in culture systems in media formulated specifically for expansion. Expansion can also be facilitated by culturing the immune cell of the disclosure in the presence of activation factors as described herein. Those skilled in the art will appreciate that expansion steps, as provided herein, may also encompass any newly discovered culture systems, media, or activating factors that can be used to expand immune cells.

The disclosure provides formulation and cryopreservation steps for the expanded genetically modified subject immune cells. Formulation steps provided include, for example, washing away excess components used in the preparation and expansion of immune cells of the methods of treatment described herein. Any pharmaceutically acceptable formulation medium or wash buffer compatible with immune cell known in the art may be used to wash, dilute/concentration immune cells, and prepare doses for administration. Formulation medium can be acceptable for administration of the immune cells, such as, for example crystalloid solutions for intravenous infusion. Cryopreservation can optionally be used to store immune cells long-term. Cryopreservation can be achieved using known methods in the art, including for example, storing cells in a cryopreservation medium containing cryopreservation components. Cryopreservation components can include, for example, dimethyl sulfoxide or glycerol. Immune cells stored in cryopreservation medium can be cryopreserved by reducing the storage temperature to −80° C. to −180° C.

In some embodiments, the method comprises administering immune cells described herein. In some embodiments, the method comprises administering a conditioning regimen prior to administering the immune cells described herein. In some embodiments, the conditioning regimen is lymphodepletion. A lymphodepletion regimen can include, for example, administration of alemtuzumab, cyclophosphamide, benduamustin, rituximab, pentostatin, and/or fludarabine. Lymphodepletion regimen can be administered in one or more cycles until the desired outcome of reduced circulating immune cells.

In some embodiments, the conditioning regimen comprises administering an agent that specifically targets, and reduces or eliminates CD52+ cells in the subject, and the immune cells are modified to reduce or eliminate CD52 expression.

In some embodiments, the method of treatment comprises determining the HLA germline type of the subject. In some embodiments, determining the HLA germline type comprises determining the presence of HLA-A*02:01 heterozygosity. In some embodiments, the HLA germline type is determined in bone marrow.

In some embodiments, the method of treatment comprises determining the level of expression of an activator ligand, e.g. a HER2 antigen. In some embodiments, the level of expression of an activator ligand is determined in tumor tissue samples from the subject. In some embodiments, the expression level of an activator ligand is determined using next generation sequencing. In some embodiments, the expression level of an activator ligand is determined using RNA sequencing. In some embodiments, the level of an activator ligand is determined using immunohistochemistry.

In some embodiments, the method of treatment comprises administering a therapeutically effective dose of immune cells in a subject in need thereof, wherein the subject is determined to be HLA germline HLA-A*02:01 heterozygous and have tumor tissue with activator expression and loss of HLA-A*02:01.

In some embodiments, a therapeutically effective dose of the immune cells described herein are administered. In some embodiments, the immune cells of the disclosure are administered by intravenous injection. In some embodiments, the immune cells of the disclosure are administered by intraperitoneal injection. In some embodiments, a therapeutically effective dose comprises about $0.5 \times 10^6$ cells, about $1 \times 10^6$ cells, about $2 \times 10^6$ cells, about $3 \times 10^6$ cells, $4 \times 10^6$ cells, about $5 \times 10^6$ cells, about $6 \times 10^6$ cells, about $7 \times 10^6$ cells, about $8 \times 10^6$ cells, about $9 \times 10^6$ cells, about $1 \times 10^7$, about $2 \times 10^7$, about $3 \times 10^7$, about $4 \times 10^7$, about $5 \times 10^7$, about $6 \times 10^7$, about $7 \times 10^7$, about $8 \times 10^7$, about $9 \times 10^7$, $1 \times 10^8$ cells, about $2 \times 10^8$ cells, about $3 \times 10^8$ cells, about $4 \times 10^8$ cells, about $5 \times 10^8$ cells, or about $6 \times 10^8$ cells. In some embodiments, a therapeutically effective dose comprises about $0.5 \times 10^6$ cells to about $6 \times 10^8$ cells, about $1 \times 10^6$ cells to about $5 \times 10^8$ cells, about $2 \times 10^6$ cells to about $5 \times 10^8$ cells, about $3 \times 10^6$ cells to about $4 \times 10^8$ cells, about $4 \times 10^6$ cells to about $3 \times 10^8$ cells, about $5 \times 10^6$ cells to about $2 \times 10^8$ cells, about $6 \times 10^6$ cells to about $1 \times 10^8$ cells, about $7 \times 10^6$ cells to about $9 \times 10^7$ cells, about $8 \times 10^6$ cells to about $8 \times 10^7$ cells, about $9 \times 10^6$ cells to about $7 \times 10^7$ cells, about $1 \times 10^7$ cells to about $6 \times 10^7$ cells, or about $2 \times 10^7$ cells to about $5 \times 10^7$ cells. In some embodiments, a therapeutically effective dose comprises about $0.5 \times 10^6$ cells to about $6 \times 10^8$ cells. The term "about" as referred to in a therapeutically dose, can be, for example, $\pm 0.5 \times 10^6$ cells, $\pm 0.5 \times 10^7$ cells, or $\pm 0.5 \times 10^8$ cells.

In some embodiments, the subject in need thereof has cancer. In some embodiments, the cancer is a HER2 positive (HER2+) cancer. Cancer is a disease in which abnormal cells divide without control and spread to nearby tissue. In some embodiments, the cancer comprises a liquid tumor or a solid tumor. Exemplary liquid tumors include leukemias and lymphomas. Exemplary solid tumors include sarcomas and carcinomas. Cancers can arise in virtually an organ in the body, including blood, bone marrow, lung, breast, colon, bone, central nervous system, pancreas, prostate and ovary. Further cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

Any cancer wherein a plurality of the cancer cells express the first, activator ligand and do not express the second, inhibitor ligand is envisaged as within the scope of the instant disclosure. For example, HER2 positive cancers that can be treated using the methods described herein include breast cancer cell, bladder cancer cell, ovarian cancer cell, gastric cancer cell, a salivary duct carcinoma cell, a non-small cell lung cancer cell, a pancreatic cancer cell, or a colon cancer cell.

In some embodiments, a plurality of cancer cells do not express a polymorphic allele of COLEC12, APCDD1 or CXCL16. In some embodiments, a plurality of cancer cells do not express a non-target antigen. In some embodiments, a plurality of cancer cells do not express HLA-A*02. In some embodiments, the plurality of cancer cells do not express an allelic variant of HLA-A*02. In some embodiments, the plurality of cancer cells do not express HLA-A*01. In some embodiments, the plurality of cancer cells do not express HLA-A*03. In some embodiments, the plurality of cancer cells do not expression HLA-A*11. In some embodiments, the plurality of cancer cells do not express HLA-B*07. In some embodiments, the plurality of cancer cells do not expression HLA-C*07. For example, the cancer cells have lost an allele of COLEC12, APCDD1 or CXCL16, or HLA-A*02 through loss of heterozygosity at that locus.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleomorphism.

The disclosure provides methods of treating a cancer in a subject comprising: (a) determining the genotype of normal cells and a plurality of cancer cells of the subject at a polymorphic locus selected from the group consisting of a polymorphic locus of COLEC12, a polymorphic locus of APCDD1 and a polymorphic locus of CXCL16, or the HLA-A*02 locus; (b) determining the expression of HER2 in a plurality of cancer cells; and (c) administering a plurality of immune cells to the subject if the normal cells are heterozygous for the polymorphic locus and the plurality of cancer cells are hemizygous for the polymorphic locus or have lost HLA-A*02, and the plurality of cancer cells are HER2-positive, wherein the plurality of immune cells comprise: (i) a first receptor, optionally a chimeric antigen receptor (CAR) or T cell receptor (TCR), comprising an extracellular ligand binding domain specific to HER2, or a peptide antigen thereof in a complex with a major histocompatibility complex class I (MHC-I); and (ii) a second receptor, optionally an inhibitory chimeric antigen receptor (i.e. inhibitory receptors), comprising an extracellular ligand binding specific to a non-target antigen selected from COLEC12, APCDD1, and CXCL16, or an antigen peptide thereof in a complex with an a major histocompatibility complex class I (MHC-I), or HLA-A*02, wherein the non-target antigen comprises a polymorphism.

Methods of genotyping cancer cells and normal cells from a subject for the presence or absence of SNPs will be readily apparent to persons of ordinary skill in the art. SNP genotyping methods include, inter alia, PCR based methods such as dual-probe TaqMan assays, array based hybridization methods and sequencing.

Methods of measuring the expression of the target antigen in cancer or normal cells from a subject will be readily apparent to persons of ordinary skill in the art. These include, inter alia, methods of measuring RNA expression such as RNA sequencing and reverse transcription polymerase chain reaction (RT-PCR), as well as methods of measuring protein expression such as immunohistochemistry based methods. Methods of measuring loss of heterozygosity in a plurality of cancer cells, include, inter alia, high throughput sequencing of genomic DNA extracted from cancer cells using methods known in the art.

Methods of measuring the expression of the target antigen in cancer or normal cells from a subject will be readily apparent to persons of ordinary skill in the art. These include, inter alia, methods of measuring RNA expression such as RNA sequencing and reverse transcription polymerase chain reaction (RT-PCR), as well as methods of measuring protein expression such as immunohistochemistry based methods.

In some embodiments, the immune cells are T cells.

In some embodiments, the immune cells are allogeneic or autologous.

In some embodiments, the second receptor increases the specificity of the immune cells for the HER2-positive cancer cells compared to immune cells that express the first receptor but do not express the second receptor. In some embodiments, the immune cells have reduced side effects compared to immune cells that express the first receptor but do not express the second receptor.

Dosage and Administration

The immune cells and of the present disclosure may be administered in a number of ways depending upon whether local or systemic treatment is desired.

In general, administration may be parenteral.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al and U.S. Pat. No. 4,690,915 to Rosenberg.

The compositions of the disclosure are suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques. In some embodiments, parenteral administration of the compositions of the present disclosure comprises intravenous or intraarterial administration.

The cells or population of cells can be administrated in one or more doses. In some embodiments, an effective amount of cells can be administrated as a single dose. In some embodiments, an effective amount of cells can be administrated as more than one doses over a period time. Timing of administration is within the judgment of a managing physician and depends on the clinical condition of the patient.

The cells or population of cells may be obtained from any source, such as a blood bank or a donor, or the patient themselves.

An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

For purposes of the disclosure, an assay, which comprises, for example, comparing the extent to which target cells are lysed or one or more cytokines are secreted by immune cells expressing the receptors, upon administration of a given dose of such immune cells to a mammal, among a set of mammals of which is each given a different dose of the immune cells, can be used to determine a starting dose to be administered to a mammal.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The immune cells of the disclosure are in some embodiments are co-administered with one or more additional therapeutic agents or in connection with another therapeutic intervention, either simultaneously or sequentially in any order. In some contexts, the immune cells are co-administered with another therapy sufficiently close in time such that the immune cell populations enhance the effect of one or more additional therapeutic agents, or vice versa. In some embodiments, the immune cells are administered prior to the one or more additional therapeutic agents. In some embodiments, the immune cells are administered after to the one or more additional therapeutic agents.

In embodiments, a lymphodepleting chemotherapy is administered to the subject prior to, concurrently with, or after administration (e.g., infusion) of adoptive immune cells. In an example, the lymphodepleting chemotherapy is administered to the subject prior to administration of the immune cells. For example, the lymphodepleting chemotherapy ends 1-4 days (e.g., 1, 2, 3, or 4 days) prior to adoptive cell infusion. In embodiments, multiple doses of adoptive cells are administered, e.g., as described herein. In embodiments, a lymphodepleting chemotherapy is administered to the subject prior to, concurrently with, or after administration (e.g., infusion) of the immune cells described herein. Examples of lymphodepletion include, but may not be limited to, nonmyeloablative lymphodepleting chemotherapy, myeloablative lymphodepleting chemotherapy, total body irradiation, etc. Examples of lymphodepleting agents include, but are not limited to, antithymocyte globulin, anti-CD3 antibodies, anti-CD4 antibodies, anti-CD8 antibodies, anti-CD52 antibodies, anti-CD2 antibodies, TCRαβ blockers, anti-CD20 antibodies, anti-CD19 antibodies, Bortezomib, rituximab, anti-CD 154 antibodies, rapamycin, CD3 immunotoxin, fludarabine, cyclophosphamide, busulfan, melphalan, Mabthera, Tacrolimus, alefacept, alemtuzumab, OKT3, OKT4, OKT8, OKT11, fingolimod, anti-CD40 antibodies, anti-BR3 antibodies, Campath-1H, anti-CD25 antibodies, calcineurin inhibitors, mycophenolate, and steroids, which may be used alone or in combination. As a further example, a lymphodepletion regimen can include, administration of alemtuzumab, cyclophosphamide, benduamustin, rituximab, pentostatin, and/or fludarabine. Lymphodepletion regimen can be administered in one or more cycles until the desired outcome of reduced circulating immune cells. In some embodiments, the lymphodepletion comprises administering an agent that specifically targets, and reduces or eliminates CD52+ cells in the subject, and the immune cells are modified to reduce or eliminate CD52 expression.

In some embodiments, an immune stimulating therapy is administered to the subject prior to, concurrently with, or after administration (e.g. infusion) of adoptive immune cells. In some embodiments, the immune stimulating therapy comprises homeostatic cytokines. In some embodiments, the immune stimulating therapy comprises immune-stimulatory molecules. In some embodiments, the immune stimulating therapy comprises IL-2, IL-7, IL-12, IL-15, IL-21, IL-9, or a functional fragment thereof. In some embodiments, the immune stimulating therapy comprises IL-2, IL-7, IL-12, IL-15, IL-21, IL-9, or combinations thereof. In some embodiments, the immune stimulating therapy comprises IL-2, or a functional fragment thereof.

Methods for adoptive cell therapy using autologous cells includes isolating immune cells from patient blood, performing a series of modifications on the isolated cells including transducing the cells with one or more vectors encoding the dual receptor system described herein, and administering the cells to a patient. Providing immune cells from a subject suffering from or at risk for cancer or a hematological malignancy requires isolation of immune cell from the patient's blood, and can be accomplished through methods known in the art, for example, by leukapheresis. During leukapheresis, blood from a subject is extracted and the peripheral blood mononuclear cells (PBMCs) are separated, and the remainder of the blood is returned to the subject's circulation. The PBMCs are stored either frozen or cryopreserved as a sample of immune cells and provided for further processing steps, such as, e.g. the modifications described herein.

In some embodiments, the method of treating a subject described herein comprises modifications to immune cells from the subject comprising a series of modifications comprising enrichment and/or depletion, activation, genetic modification, expansion, formulation, and cryopreservation.

The disclosure provides enrichment and/or depletion steps that can be, for example, washing and fractionating methods known in the art for preparation of subject PBMCs for downstream procedures, e.g. the modifications described herein. For example, without limitation, methods can include devices to remove gross red blood cells and platelet contaminants, systems for size-based cell fractionation for the depletion of monocytes and the isolation of lymphocytes, and/or systems that allow the enrichment or depletion of specific subsets of T cells, such as, e.g. CD4+, CD8+, CD25+, or CD62L+ T cells. Following the enrichment steps, a target sub-population of immune cells will be isolated from the subject PMBCs for further processing. Those skilled in the art will appreciate that enrichment steps, as provided herein, may also encompass any newly discovered method, device, reagent or combination thereof.

The disclosure provides activation steps that can be any method known in the art to induce activation of immune cells, e.g. T cells, required for their ex vivo expansion. Immune cell activation can be achieved, for example, by culturing the subject immune cells in the presence of dendritic cells, culturing the subject immune cells in the presence of artificial antigen-presenting cells (AAPCs), or culturing the immune cells in the presence of irradiated K562-derived AAPCs. Other methods for activating subject immune cells can be, for example, culturing the immune cells in the presence of isolated activating factors and compositions, e.g. beads, surfaces, or particles functionalized with activating factors. Activating factors can include, for example, antibodies, e.g. anti-CD3 and/or anti-CD28 antibodies. Activating factors can also be, for example, cytokines, e.g. interleukin (IL)-2 or IL-21. Activating factors can also be costimulatory molecules, such as, for example, CD40, CD40L, CD70, CD80, CD83, CD86, CD137L, ICOSL, GITRL, and CD134L. Those skilled in the art will appreciate that activating factors, as provided herein, may also encompass any newly discovered activating factor, reagent, composition, or combination thereof that can activate immune cells.

The disclosure provides genetic modification steps for modifying the subject immune cells. In some embodiments, the genetic modification comprises transducing the immune cell with a vector comprising a shRNA described herein complementary to B2M or HLA-A. In some embodiments, the genetic modification comprises modifying the genome of the immune cells to induce mutations in B2M or HLA-A using CRISPR/Cas mediated genome engineering. In some embodiments, the method comprises transducing the immune cell with one or more vectors encoding the activator and inhibitory receptors, thereby producing immune cells expressing the activator and inhibitory receptors.

The disclosure provides expansion steps for the genetically modified subject immune cells. Genetically modified subject immune cells can be expanded in any immune cell expansion system known in the art to generate therapeutic doses of immune cells for administration. For example, bioreactor bags for use in a system comprising controller pumps, and probes that allow for automatic feeding and waste removal can be used for immune cell expansion. Cell culture flasks with gas-permeable membranes at the base may be used for immune cell expansion. Any such system known in the art that enables expansion of immune cells for clinical use is encompassed by the expansion step provided herein. Immune cells are expanded in culture systems in media formulated specifically for expansion. Expansion can also be facilitated by culturing the immune cell of the disclosure in the presence of activation factors as described herein. Those skilled in the art will appreciate that expansion steps, as provided herein, may also encompass any newly discovered culture systems, media, or activating factors that can be used to expand immune cells.

The disclosure provides formulation and cryopreservation steps for the expanded genetically modified subject immune cells. Formulation steps provided include, for example, washing away excess components used in the preparation and expansion of immune cells of the methods of treatment described herein. Any pharmaceutically acceptable formulation medium or wash buffer compatible with immune cell known in the art may be used to wash, dilute/concentration immune cells, and prepare doses for administration. Formulation medium can be acceptable for administration of the immune cells, such as, for example crystalloid solutions for intravenous infusion.

Cryopreservation can optionally be used to store immune cells long-term. Cryopreservation can be achieved using known methods in the art, including for example, storing cells in a cryopreservation medium containing cryopreservation components. Cryopreservation components can include, for example, dimethyl sulfoxide or glycerol. Immune cells stored in cryopreservation medium can be cryopreserved by reducing the storage temperature to −80° C. to −196° C.

In some embodiments, the method of treatment comprises determining the HLA germline type of the subject. In some embodiments, the HLA germline type is determined in bone marrow.

In some embodiments, the method of treatment comprises determining the level of expression of HER2. In some embodiments, the level of expression of HER2 is determined in tumor tissue samples from the subject. In some embodiments, the expression level of HER2 is determined using next generation sequencing. In some embodiments, the expression level of HER2 is determined using RNA sequencing. In some embodiments, the level of HER2 is determined using immunohistochemistry.

In some embodiments, the method of treatment comprises administering a therapeutically effective dose of immune cells comprising an HLA-A*02 inhibitory receptor to a subject in need thereof, wherein the subject is determined to be HLA germline HLA-A*02 heterozygous and have cancer cells with loss of HLA-A*02. In some embodiments, the method of treatment comprises administering a therapeutically effective dose of immune cells comprising an HLA-A*01 inhibitory receptor to a subject in need thereof, wherein the subject is determined to be HLA germline HLA-A*01 heterozygous and have cancer cells with loss of HLA-A*01. In some embodiments, the method of treatment comprises administering a therapeutically effective dose of immune cells comprising an HLA-A*03 to a subject in need thereof, wherein the subject is determined to be HLA germline HLA-A*03 heterozygous and have cancer cells with loss of HLA-A*03. In some embodiments, the method of treatment comprises administering a therapeutically effective dose of immune cells comprising an HLA-A*07 inhibitory receptor to a subject in need thereof, wherein the subject is determined to be HLA germline HLA-A*07 heterozygous and have cancer cells with loss of HLA-A*07. In some embodiments, the method of treatment comprises administering a therapeutically effective dose of immune cells comprising an HLA-C*07 inhibitory receptor to a subject in need thereof, wherein the subject is determined to be HLA germline HLA-C*07 heterozygous and have cancer cells with and loss of HLA-C*07. In some embodiments, the method of treatment comprises administering a therapeutically effective dose of immune cells comprising an HLA-B*07 inhibitory receptor in a subject in need thereof, wherein the subject is determined to be HLA germline HLA-B*07 heterozygous and have cancer cells with loss of HLA-B*07.

In various embodiments, the disclosure provides method of treatment of heterozygous HLA-A*02 patients with malignancies that express HER2 and have lost HLA-A*02 expression; and/or of treatment of heterozygous HLA-A*02 adult patients with recurrent unresectable or metastatic solid tumors that express HER2 and have lost HLA-A*02 expression.

In some embodiments, a therapeutically effective dose of the immune cells described herein are administered. In some embodiments, the immune cells of the disclosure are administered by intravenous injection. In some embodiments, the immune cells of the disclosure are administered by intraperitoneal injection. In some embodiments, a therapeutically effective dose comprises about $0.5 \times 10^6$ cells, about $1 \times 10^6$ cells, about $2 \times 10^6$ cells, about $3 \times 10^6$ cells, $4 \times 10^6$ cells, about $5 \times 10^6$ cells, about $6 \times 10^6$ cells, about $7 \times 10^6$ cells, about $8 \times 10^6$ cells, about $9 \times 10^6$ cells, about $1 \times 10^7$, about $2 \times 10^7$, about $3 \times 10^7$, about $4 \times 10^7$, about $5 \times 10^7$, about $6 \times 10^7$, about $7 \times 10^7$, about $8 \times 10^7$, about $9 \times 10^7$, about $1 \times 10^8$ cells, about $2 \times 10^8$ cells, about $3 \times 10^8$ cells, about $4 \times 10^8$ cells, about $5 \times 10^8$ cells, about $6 \times 10^8$ cells, about $7 \times 10^8$ cells, about $8 \times 10^8$ cells, about $9 \times 10^8$ cells, about $1 \times 10^9$ cells, about $2 \times 10^9$ cells, about $3 \times 10^9$ cells, about $3 \times 10^9$ cells, about $4 \times 10^9$ cells, about $5 \times 10^9$ cells, about $5 \times 10^9$ cells, about $6 \times 10^9$ cells, about $7 \times 10^9$ cells, about $8 \times 10^9$ cells, about $9 \times 10^9$ cells, about $1 \times 10^{10}$ cells, about $2 \times 10^{10}$ cells, about $3 \times 10^{10}$ cells, about $4 \times 10^{10}$ cells, about $5 \times 10^{10}$ cells, about $6 \times 10^{10}$ cells, about $7 \times 10^{10}$ cells, about $8 \times 10^{10}$ cells, or about $9 \times 10^{10}$ cells.

In some embodiments, a therapeutically effective dose comprises about $0.5 \times 106$ cells to about $9 \times 10^{10}$ cells, about $1 \times 10^6$ cells to about $5 \times 10^{10}$ cells, about $2 \times 10^6$ cells to about $5 \times 10^9$ cells, about $3 \times 10^6$ cells to about $5 \times 10^9$ cells, $4 \times 10^6$ cells to about $3 \times 10^9$ cells, about $5 \times 10^6$ cells to about $2 \times 10^9$ cells, about $6 \times 10^6$ cells to about $1 \times 10^9$ cells, $0.5 \times 10^6$ cells to about $6 \times 10^9$ cells, about $1 \times 10^6$ cells to about $5 \times 10^9$ cells, about $2 \times 10^6$ cells to about $5 \times 10^9$ cells, about $3 \times 10^6$ cells to about $4 \times 10^9$ cells, about $4 \times 10^6$ cells to about $3 \times 10^9$ cells, about $5 \times 10^6$ cells to about $2 \times 10^9$ cells, about $6 \times 10^6$ cells to about $1 \times 10^9$ cells, $0.5 \times 10^6$ cells to about $6 \times 10^8$ cells, about $1 \times 10^6$ cells to about $5 \times 10^8$ cells, about $2 \times 10^6$ cells to about $5 \times 10^8$ cells, about $3 \times 10^6$ cells to about $4 \times 10^8$ cells, about $4 \times 10^6$ cells to about $3 \times 10^8$ cells, about $5 \times 10^6$ cells to about $2 \times 10^8$ cells, about $6 \times 10^6$ cells to about $1 \times 10^8$ cells, about $7 \times 10^6$ cells to about $9 \times 10^8$ cells, about $8 \times 10^6$ cells to about $8 \times 10^8$ cells, about $9 \times 10^6$ cells to about $7 \times 10^8$ cells, about $1 \times 10^7$ cells to about $6 \times 10^8$ cells, about $2 \times 10^7$ cells to about $5 \times 10^8$ cells, about $7 \times 10^6$ cells to about $9 \times 10^7$ cells, about $8 \times 10^6$ cells to about $8 \times 10^7$ cells, about $9 \times 10^6$ cells to about $7 \times 10^7$ cells, about $1 \times 10^7$ cells to about $6 \times 10^7$ cells, or about $2 \times 10^7$ cells to about $5 \times 10^7$ cells.

In some embodiments, a therapeutically effective dose comprises about $0.5 \times 10^5$ cells to about $9 \times 10^{10}$ cells. In some embodiments, a therapeutically effective dose comprises about $0.5 \times 10^6$ cells to about $1 \times 10^{10}$ cells. In some embodiments, a therapeutically effective dose comprises about $0.5 \times 10^6$ cells to about $5 \times 10^9$ cells. In some embodiments, a therapeutically effective dose comprises about $0.5 \times 10^6$ cells to about $1 \times 10^9$ cells. In some embodiments, a therapeutically effective dose comprises about $0.5 \times 10^6$ cells to about $6 \times 10^8$ cells. In some embodiments, a therapeutically effective dose comprises about $0.5 \times 10^6$ cells to about $9 \times 10^{10}$ cells. In some embodiments, a therapeutically effective dose comprises about $0.5 \times 10^7$ cells to about $1 \times 10^{10}$ cells. In some embodiments, a therapeutically effective dose comprises about $0.5 \times 10^7$ cells to about $5 \times 10^9$ cells. In some embodiments, a therapeutically effective dose comprises about $0.5 \times 10^7$ cells to about $1 \times 10^9$ cells. In some embodiments, a therapeutically effective dose comprises about $0.5 \times 10^7$ cells to about $6 \times 10^8$ cells. In some embodiments, a therapeutically effective dose comprises about $0.5 \times 10^8$ cells to about $9 \times 10^{10}$ cells. In some embodiments, a therapeutically effective dose comprises about $0.5 \times 10^8$ cells to about $1 \times 10^{10}$ cells. In some embodiments, a therapeutically effective dose comprises about $0.5 \times 10^8$ cells to about $5 \times 10^9$ cells. In some embodiments, a therapeutically effective dose comprises about $0.5 \times 10^8$ cells to about $1 \times 10^9$ cells. The term "about" as referred to in a therapeutically dose, can be, for example, $\pm 0.5 \times 10^6$ cells, $\pm 0.5 \times 10^7$ cells, or $\pm 0.5 \times 10^8$ cells.

Kits and Articles of Manufacture

The disclosure provides kits and articles of manufacture comprising the polynucleotides and vectors encoding the engineered receptors described herein, and immune cells edited using gene editing systems described herein and comprising the engineered receptors described herein. In some embodiments, the kit comprises articles such as vials, syringes and instructions for use.

In some embodiments, the kit comprises a polynucleotide or vector comprising a sequence encoding one or more engineered receptors of the disclosure.

In some embodiments, the kit comprises a plurality of immune cells comprising an engineered receptor as described herein. In some embodiments, the plurality of immune cells comprises a plurality of T cells.

EXAMPLES

Example 1: Methods of Assaying HER2 CAR Activity in Jurkat and Primary T Cells

Cell Culture

Jurkat cells encoding an NFAT luciferase reporter were obtained from BPS Bioscience. In culture, Jurkat cells were maintained in RPMI media supplemented with 10% FBS, 1% Pen/Strep and 0.4 mg/mL G418/Geneticin. HCT.116 and HeLa cells were maintained as suggested by ATCC.

Jurkat Cell Transfection

Jurkat cells were transiently transfected via 100 uL or 20 ul format 4D Nucleofactor (Lonza) according to manufacturer's protocol. Cotransfection was performed with 1-3 ug of activator receptor construct and 1-3 ug of inhibitory receptor constructs or empty vector per 1e6 cells and recovered in RPMI media supplemented with 20% heat-inactivated FBS and 0.1% Pen/Strep. To confirm inhibitory receptor surface expression, Jurkat cells were stained 18-24 hours post-transfection with 10 ug/mL streptavidin-PE-HLA-A*02-pMHC tetramer for 60 minutes at 4° C. in PBS with 1% BSA and characterized by flow cytometry (BD FACSCanto II).

Jurkat-NFAT-Luciferase Activation Studies

Briefly, Jurkat NFAT-Firefly-Luciferase cells were transfected with activator and inhibitory (blocker) receptor constructs using Lonza 4D Nucleofector™ (AAF-1002B) or Neon™ transfection systems (ThermoFisher, MPK5000). mRNA transfected target cells (10,000 cells/well), activator only or activator/blocker expressing target cells at different densities, were added to transfected Jurkat-NFAT-Firefly-Luciferase cells (12,000 cells/well) to a final volume of 20 mL in 384-well plates (Corning 3570). After a 6-hour incubation at 37° C., the One-Step™ Luciferase firefly assay system (BPS Bioscience, 60690) was used to determine luminescence intensity on a Tecan Infinite® M1000.

Solid Substrate Antigen Titration

Biotinylated pMHCs were added to streptavidin-coated plates with and without biotinylated recombinant CD28 agonist, biotinylated recombinant PD-L1, or both at concentrations equimolar to the highest pMHC molarity. Mouse IgG1 was used as a control to ensure the binding capacity of the well was not exceeded. The unbound molecules were washed off and transduced T-cells were added. Half of the T-cells were recovered and stained with anti-CD69 at 24 hours and the rest were stained with anti-CD25 at 48 hours.

Activator mRNA Titration

HER2 or HLA-A2 mRNA were synthesized as described below and were diluted two fold 12 times. Each dilution of mRNA was mixed with two million Her2 knock-out HeLa cells (Her2−/HLA-A2−) and electroporated using 4D Nucleofactor. mRNA transfected target cells were then co-cultured with Jurkat cells transfected with HER2 CAR or blocker receptor for 6 hours before the degree of activation was measured as described above.

In Vitro Transcription of mRNA

HER2 sequence was synthesized by Genscript with T7 promoter in the 5' end together with 5' and 3' synthetic UTR sequences. In vitro transcription was done in 1×IVT buffer (40 mM Tris, 10 mM DTT, 2 mM Spermidine, 0.002% Triton X-100, and 27 mM $MgCl_2$) with T7 RNA polymerase (NEB, M0251S), Inorganic pyrophosphatase (NEB, M2403S) and murine RNase inhibitor (NEB, M0314S). In addition, 500 ng PCR purified template, 5 mM CleanCap Cap1 AG trimer, 5 mM each of ATP, CTP, GTP and pseudo-uridine triphosphate (pseudo-UTP) were added, and the transcription reaction was incubated at 37° C. for 2 hours, followed by addition of DNase I (NEB, M0303S) for additional 15 minutes incubation at 37° C.

In vitro transcription reaction was finalized by the addition of poly A tailing with poly A enzyme (NEB, M0276S) and incubation at 37° C. for 30 minutes. The mRNA was then cleaned using the NEB Monarch kit. The purified mRNA was treated with Antarctic phosphatase (NEB, M0289S) for 1 hour at 37° C. in 1× Antarctic phosphatase buffer (NEB). mRNA was then purified again using the NEB Monarch kit. mRNA concentrations were measured by Nanodrop. The quality of mRNA was accessed by gel electrophoresis. The final in vitro transcribed mRNA was aliquoted and stored at −80° C. until shortly before use.

Primary T Cell Transduction, Expansion, and Enrichment

Human PBMCs were purified from Leukopaks purchased from Allcells® according to methods described previously (Garcia et al., 2014). Collection protocols and donor informed consent were approved by an Institutional Review Board (IRB) at Allcells®. Allcells® also followed HIPAA compliance and approved protocols with strict oversight (https://www.allcells.com/cell-tissue-procurement/donor-facilities/). Unless otherwise specified, all LymphoONE media (Takara WK552) was supplemented with 1% human AB Serum (GeminiBio 100-512). Human PBMCs were grown in LymphoONE plus TransAct™ (Miltenyi 130-111-160) following the manufacturers guidelines (1:100 dilution) for 24 hours before transduction with lentivirus encoding the activator (CAR) and/or the blocker. 24 hours after transduction, additional LymphoONE plus IL-2 (300 IU/ml) was added to transduced cells, grown for 3 days before transfer to a 24-well G-Rex plate (Wilson Wolf 80192M). Fresh IL-2 (300 IU/ml) was added every 48 hours with media change every 7 days when the cells were expanded in G-Rex plates. Expression and antigen binding of transduced activator or activator and blocker in primary T cells were confirmed by flow cytometry using protein L for the activator and HLA-A2 pMHC or LIL-RB1 antibody for the blocker. If needed, CAR- or blocker-expressing cells were labeled with protein L-biotin/streptavidin-PE or pMHC/streptavidin-PE, followed by anti-PE microbeads (Miltenyi 130-048-801) according to the manufacturer's instructions, and subsequently enriched using AutoMACS® Pro Separator (Miltenyi). Enriched cells were grown in G-Rex plates until use.

Primary T Cell In Vitro Cytotoxicity Studies

For cytotoxicity studies, enriched primary T cells were incubated with HeLa and HCT.116 cells expressing renilla luciferase (Biosettia). Live luciferase-expressing target cells were quantified using a renilla Luciferase Reporter Assay System (Promega). Target cells stably expressing GFP and renilla luciferase (Biosettia) or stably expressing RFP and firefly luciferase (Biosettia) were imaged together with unlabeled primary T cells using an IncuCyte live cell imager. Fluorescence intensity of live target cells over time was quantified using IncuCyte imaging software after 40 hours. For reversibility studies, enriched primary T cells were similarly cocultured with "normal" or "tumor" target cells for 3 days and imaged. After 3 days, T cells were separated from remaining target cells by pipetting, FACS or magnetic beads. In separate wells, live luciferase-expressing target cells were quantified using a Dual-Luciferase Reporter Assay System (Promega) at 72 hours.

Mouse Xenograft Study

Activator and blocker expressing T cells were generated as described in above.

Five to six week old female NSG (NOD.Cg-Prkdc$^{scid}$Il2rg$^{tm1Wjl}$/SzJ), JAX stock No. 005557 mice were purchased from The Jackson Labs. Animals were acclimated to the housing environment for at least 3 days prior to the initiation of the study. Animals were injected with 5e6 HER2+ HCT.116 cells that were HLA-A*02 positive in one flank and HLA-A*02 negative cells, in the other flank. When total volume of tumors in both flanks reached an average of 100 mm3 (V=L×W×W/2), animals were randomized into groups, and 2e6, 5e6, or 10e6 total T cells were administered via the tail vein. Post T cell injection, tumor measurements on both flanks were performed 3 times per week for 4 weeks.

Statistical Analysis

Statistical analyses were performed using GraphPad Prism software. All peptide and cell titration studies are shown as mean±standard deviation (SD), while in vitro and in vivo studies using primary T cells are shown as mean±standard error of the mean (SEM), unless otherwise noted. Peptide and cell titration curves were fit using a four-parameter non-linear regression analysis. EC50 values were calculated directly from the curves. All other groups of data were analyzed using an ordinary two-way ANOVA followed by a Tukey's multiple-comparisons test, unless otherwise noted.

Example 2: Activity of HER2 Chimeric Antigen Receptors in Jurkat Cells

The sensitivity of different HER2 chimeric antigen receptors (CARs) was determined in Jurkat cells and rank ordered. The formats of the different HER2 CARs assayed, and the HER2 antigen binding domains for these CARs, are shown in FIG. 1. Sequences of the HER2 CARs assayed are shown in Table 25 below.

Figure 2B:
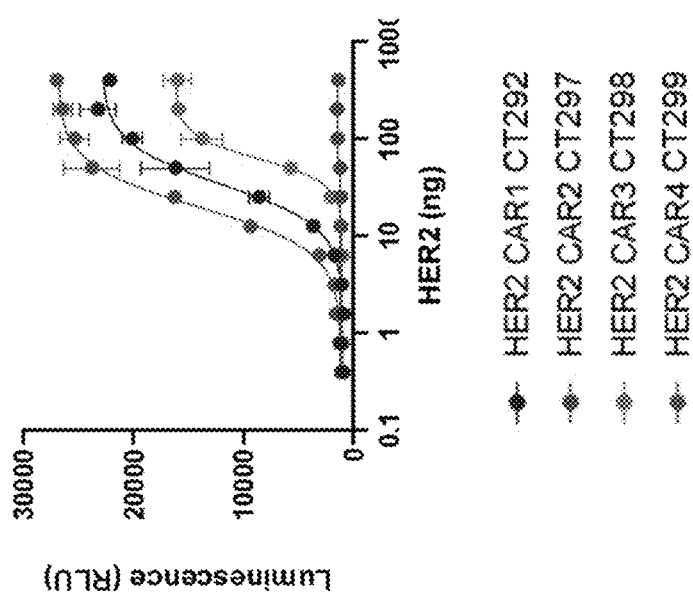
FIG. 2B is a plot showing HER2 activator EC50 in Jurkat cells, as measured by HCT.116 target cell number titration. HER2 CAR2 and HER2 CAR3 showed no activity.
Figure 2C:
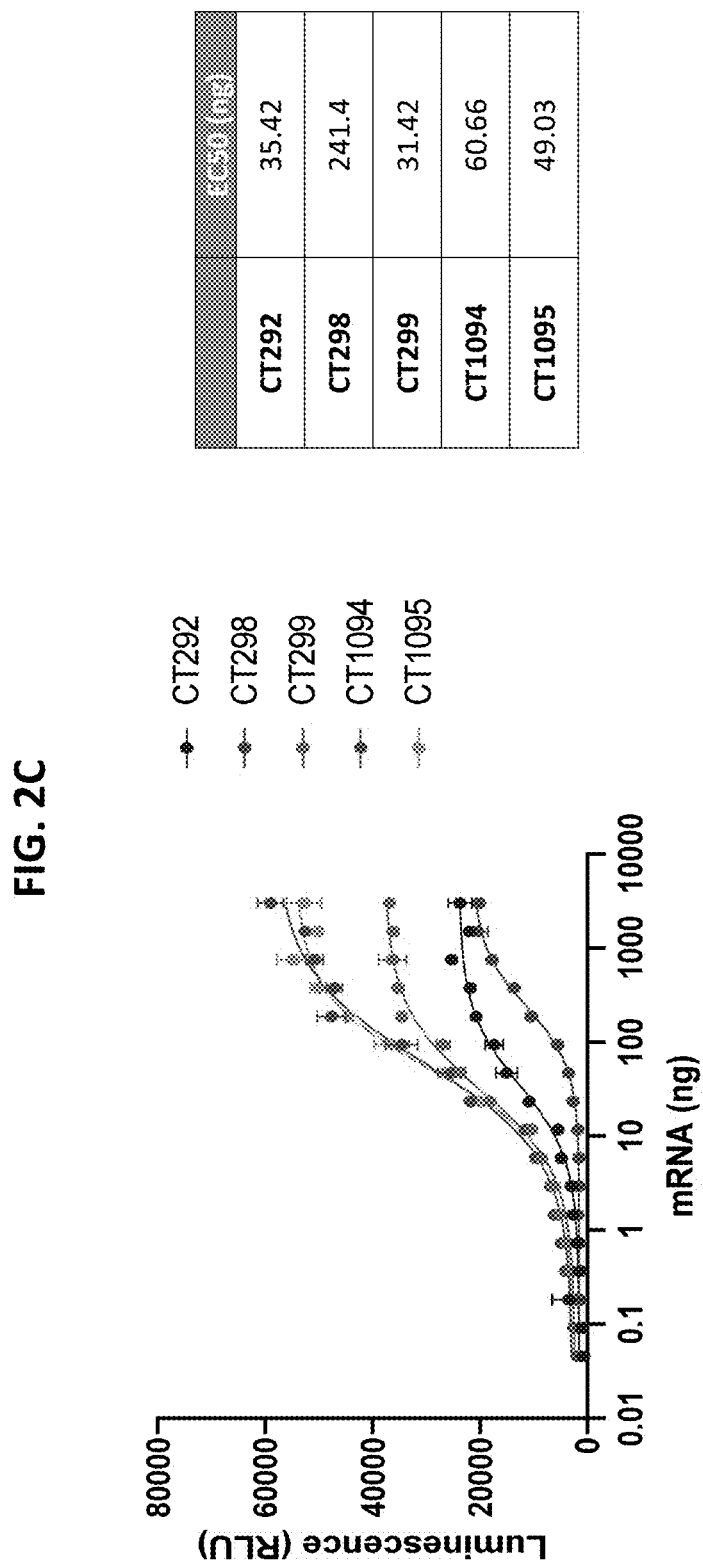
FIG. 2C as a plot and a table showing HER2 activator EC50 in Jurkat cells, as measured by titration of target HER2 mRNA. HER2 CAR2 (C297) showed no activity with antigen titration on a solid substrate (FIG. 2A) or target cell number titration (FIG. 2B) and was further engineered with different hinges (CT1094, CT1095).

The activity of Jurkat cells expressing HER2 CARS 1-4 (CT292, CT297, CT298 and CT299, respectively) was assayed using a titration of HER2 antigen on a solid substrate (FIG. 2A), and by titrating the number of HCT.116 HER2 positive target cells (FIG. 2B). In both cases, the HER2 CAR2, which had an FRP5 antigen binding domain, showed little to no activity. The FRP5 antigen binding domain, and a variant of FRP5, were assayed in a different CAR format that used an IgG1 hinge domain (CT1094 and CT1095). As shown in FIG. 2C, FRP5 antigen binding domain in combination with an IgG1 hinge shows detectable activity.

TABLE 25

| Construct | Amino Acid Sequence | DNA Sequence |
|---|---|---|
| CT292 | MDFQVQIFSFLLI | ATGGATTTTCAGGTGCAGATTTTCAGCTTCCTGCT |
|  | SASVIMSRGDIQM | AATCAGTGCCTCAGTCATAATGTCCAGAGGAGATA |
|  | TQSPSSLSASVGD | TCCAGATGACCCAGTCCCCGAGCTCCCTGTCCGCC |
|  | RVTITCRASQDVN | TCTGTGGGCGATAGGGTCACCATCACCTGCCGTGC |
|  | TAVAWYQQKPGKA | CAGTCAGGATGTGAATACTGCTGTAGCCTGGTATC |
|  | PKLLIYSASFLYS | AACAGAAACCAGGAAAAGCTCCGAAACTACTGATT |
|  | GVPSRFSGSRSGT | TACTCGGCATCCTTCCTTTATTCTGGAGTCCCTTC |
|  | DFTLTISSLQPED | TCGCTTCTCTGGATCTAGATCTGGGACGGATTTCA |
|  | FATYYCQQHYTTP | CTCTGACCATCAGCAGTCTGCAGCCGGAAGACTTC |
|  | PTFGQGTKVEIKR | GCAACTTATTACTGTCAGCAACATTATACTACTCC |
|  | TGSTSGSGKPGSG | TCCCACGTTCGGACAGGGTACCAAGGTGGAGATCA |

TABLE 25-continued

| Construct | Amino Acid Sequence | DNA Sequence |
| --- | --- | --- |
| | EGSEVQLVESGGG LVQPGGSLRLSCA ASGFNIKDTYIHW VRQAPGKGLEWVA RIYPTNGYTRYAD SVKGRFTISADTS KNTAYLQMNSLRA EDTAVYYCSRWGG DGFYAMDVWGQGT LVTVSSAAAFVPV FLPAKPTTTPAPR PPTPAPTIASQPL SLRPEACRPAAGG AVHTRGLDFACDI YIWAPLAGTCGVL LLSLVITLYCNHR NRSKRSRLLHSDY MNMTPRRPGPTRK HYQPYAPPRDFAA YRSRFSVVKRGRK KLLYIFKQPFMRP VQTTQEEDGCSCR FPEEEEGGCELRV KFSRSADAPAYQQ GQNQLYNELNLGR REEYDVLDKRRGR DPEMGGKPRRKNP QEGLYNELQKDKM AEAYSEIGMKGER RRGKGHDGLYQGL STATKDTYDALHM QALPPR (SEQ ID NO: 291) | AACGCACTGGGTCTACATCTGGATCTGGGAAGCCG GGTTCTGGTGAGGGTTCTGAGGTTCAGCTGGTGGA GTCTGGCGGTGGCCTGGTGCAGCCAGGGGGCTCAC TCCGTTTGTCCTGTGCAGCTTCTGGCTTCAACATT AAAGACACCTATATACACTGGGTGCGTCAGGCCCC GGGTAAGGGCCTGGAATGGGTTGCAAGGATTTATC CTACGAATGGTTATACTAGATATGCCGATAGCGTC AAGGGCCGTTTCACTATAAGCGCAGACACATCCAA AAACACAGCCTACCTGCAGATGAACAGCCTGCGTG CTGAGGACACTGCCGTCTATTATTGTTCTAGATGG GGAGGGGACGGCTTCTATGCTATGGACGTGTGGGG TCAAGGAACCCTGGTCACCGTTTCCTCGGCGGCCG CATTCGTGCCGGTCTTCCTGCCAGCGAAGCCCACC ACGACGCCAGCGCCGCGACCACCAACACCGGCGCC CACCATCGCGTCGCAGCCCCTGTCCCTGCGCCCAG AGGCGTGCCGGCCAGCGGCGGGGGGCGCAGTGCAC ACGAGGGGCTGGACTTCGCCTGTGATATCTACAT CTGGGCGCCCTTGGCCGGGACTTGTGGGGTCCTTC TCCTGTCACTGGTTATCACCCTTTACTGCAACCAC AGGAACAGGAGTAAGAGGAGCAGGCTCCTGCACAG TGACTACATGAACATGACTCCCCGCCGCCCCGGGC CCACCCGCAAGCATTACCAGCCCTATGCCCCACCA CGCGACTTCGCAGCCTATCGCTCCCGTTTCTCTGT TGTTAAACGGGGCAGAAAGAAGCTCCTGTATATAT TCAAACAACCATTTATGAGACCAGTACAAACTACT CAAGAGGAAGATGGCTGTAGCTGCCGATTTCCAGA AGAAGAAGGAGGATGTGAACTGAGAGTGAAGT TCAGCAGGAGCGCAGACGCCCCCGCGTACCAGCAG GGCCAGAACCAGCTCTATAACGAGCTCAATCTAGG ACGAAGAGGAGTACGATGTTTTGGACAAGAGGC GTGGCCGGGACCCTGAGATGGGGGGAAAGCCGAGA AGGAAGAACCCTCAGGAAGGCCTGTACAATGAACT GCAGAAAGATAAGATGGCGGAGGCCTACAGTGAGA TTGGGATGAAAGGCGAGCGCCGGAGGGGCAAGCAC CAAGGACACCTACGACGCCCTTCACATGCAGGCCC TGCCCCCTCGCTAG(SEQ ID NO: 292) |
| CT298 | MLLLVTSLLLCEL PHPAFLLIPDIQM TQSPSSLSASVGD RVTITCRASQDVN TAVAWYQQKPGKA PKLLIYSASFLYS GVPSRFSGSRSGT DFTLTISSLQPED FATYYCQQHYTTP PTFGQGTKVEIKG STSGGGSGGGSGG GGSSEVQLVESGG GLVQPGGSLRLSC AASGFNIKDTYIH WVRQAPGKGLEWV ARIYPTNGYTRYA DSVKGRFTISADT SKNTAYLQMNSLR AEDTAVYYCSRWG GDGFYAMDYVVGQ GTLVTVSSGGGSS GGGSGIYIWAPLA GTCGVLLLSLVIT KRGRKKLLYIFKQ PFMRPVQTTQEED GCSCRFPEEEEGG CELGGGRVKFSRS ADAPAYQQGQNQL YNELNLGRREEYD VLDKRRGRDPEMG GKPRRKNPQEGLY NELQKDKMAEAYS EIGMKGERRRGKG HDGLYQGLSTATK DTYDALHMQALPP R (SEQ ID NO: 293) | ATGCTGCTACTGGTCACCAGTCTACTGCTGTGCGA ACTGCCACATCCGGCCTTCCTGCTAATACCGGATA TCCAGATGACCCAGTCCCCGAGCTCCCTGTCCGCC TCTGTGGGCGATAGGGTCACCATCACCTGCCGTGC CAGTCAGGATGTGAATACTGCTGTAGCCTGGTATC AACAGAAACCAGGAAAAGCTCCGAAACTACTGATT TACTCGGCATCCTTCCTTTATTCTGGAGTCCCTTC TCGCTTCTCTGGATCTAGATCTGGGACGGATTTCA CTCTGACCATCAGCAGTCTGCAGCCGGAAGACTTC GCAACTTATTACTGTCAGCAACATTATACTACTCC TCCCACGTTCGGACAGGGTACCAAGGTGGAGATCA AAGGGTCTACATCTGGCGGTGGCTCTGGTGGCGGT TCCGGCGGTGGCGGTTCTTCCGAGGTTCAGCTGGT GGAGTCTGGCGGTGGCCTGGTGCAGCCAGGGGGCT CACTCCGTTTGTCCTGTGCAGCTTCTGGCTTCAAC ATTAAAGACACCTATATACACTGGGTGCGTCAGGC CCCGGGTAAGGGCCTGGAATGGGTTGCAAGGATTT ATCCTACGAATGGTTATACTAGATATGCCGATAGC GTCAAGGGCCGTTTCACTATAAGCGCAGACACATC CAAAAACACAGCCTACCTGCAGATGAACAGCCTGC GTGCTGAGGACACTGCCGTCTATTATTGTTCTAGA TGGGGAGGGGACGGCTTCTATGCTATGGACTATTG GGGTCAAGGAACCCTGGTCACCGTCTCCTCGGGTG GCGGTTCTTCCGGCGGTGGCTCTGGTATCTACATC TGGGCGCCCTTGGCCGGGACTTGTGGGGTCCTTCT CCTGTCACTGGTTATCACCAAACGGGGCAGAAAGA AGCTCCTGTATATATTCAAACAACCATTTATGAGA CCAGTACAAACTACTCAAGAGGAAGATGGCTGTAG CTGCCGATTTCCAGAAGAAGAAGAAGGAGGATGTG AACTGGGCGGTGGCAGAGTGAAGTTCAGCAGGAGC GCAGACGCCCCCGCGTACCAGCAGGGCCAGAACCA GCTCTATAACGAGCTCAATCTAGGACGAAGAGAGG AGTACGATGTTTTGGACAAGAGACGTGGCCGGGAC CCTGAGATGGGGGGAAAGCCGAGAAGGAAGAACCC TCAGGAAGGCCTGTACAATGAACTGCAGAAAGATA AGATGGCGGAGGCCTACAGTGAGATTGGGATGAAA GGCGAGCGCCGGAGGGGCAAGGGGCACGATGGCCT TTACCAGGGTCTCAGTACAGCCACCAAGGACACCT ACGACGCCCTTCACATGCAGGCCCTGCCCCCTCGC TAG (SEQ ID NO: 294) |

TABLE 25-continued

| Construct | Amino Acid Sequence | DNA Sequence |
|---|---|---|
| CT299 | MLLLVTSLLLCEL PHPAFLLIPDIQM TQSPSSLSASVGD RVTITCRASQDVN TAVAWYQQKPGKA PKLLIYSASFLYS GVPSRFSGSRSGT DFTLTISSLQPED FATYYCQQHYTTP PTFGQGTKVEIKG STSGGGSGGGSGG GGSSEVQLVESGG GLVQPGGSLRLSC AASGFNIKDTYIH WVRQAPGKGLEWV ARIYPTNGYTRYA DSVKGRFTISADT SKNTAYLQMNSLR AEDTAVYYCSRWG GDGFYAMDYVVGQ GTLVTVSSESKYG PPCPSCPAPEFEG GPSVFLFPPKPKD TLMISRTPEVTCV VVDVSQEDPEVQF NWYVDGVEVHNAK TKPREEQFQSTYR VVSVLTVLHQDWL NGKEYKCKVSNKG LPSSIEKTISKAK GQPREPQVYTLPP SQEEMTKNQVSLT CLVKGFYPSDIAV EWESNGQPENNYK TTPPVLDSDGSFF LYSRLTVDKSRWQ EGNVFSCSVMHEA LHNHYTQKSLSLS LGKIYIWAPLAGT CGVLLLSLVITKR GRKKLLYIFKQPF MRPVQTTQEEDGC SCRFPEEEEGGCE LGGGRVKFSRSAD APAYQQGQNQLYN ELNLGRREEYDVL DKRRGRDPEMGGK PRRKNPQEGLYNE LQKDKMAEAYSEI GMKGERRRGKHD GLYQGLSTATKDT YDALHMQALPPR (SEQ ID NO: 295) | ATGCTGCTACTGGTCACCAGTCTACTGCTGTGCGA ACTGCCACATCCGGCCTTCCTGCTAATACCGGATA TCCAGATGACCCAGTCCCCGAGCTCCCTGTCCGCC TCTGTGGGCGATAGGGTCACCATCACCTGCCGTGC CAGTCAGGATGTGAATACTGCTGTAGCCTGGTATC AACAGAAACCAGGAAAAGCTCCGAAACTACTGATT TACTCGGCATCCTTCCTTTATTCTGGAGTCCCTTC TCGCTTCTCTGGATCTAGATCTGGGACGGATTTCA CTCTGACCATCAGCAGTCTGCAGCCGGAAGACTTC GCAACTTATTACTGTCAGCAACATTATACTACTCC TCCCACGTTCGGACAGGGTACCAAGGTGGAGATCA AAGGGTCTACATCTGGCGGTGGCTCTGGTGGCGGT TCCGGCGGTGGCGGTTCTTCCGAGGTTCAGCTGGT GGAGTCTGGCGGTGGCCTGGTGCAGCCAGGGGGCT CACTCCGTTTGTCCTGTGCAGCTTCTGGCTTCAAC ATTAAAGACACCTATATACACTGGGTGCGTCAGGC CCCCGGGTAAGGGCCTGGAATGGGTTGCAAGGATTT ATCCTACGAATGGTTATACTAGATATGCCGATAGC GTCAAGGGCCGTTTCACTATAAGCGCAGACACATC CAAAAACACAGCCTACCTGCAGATGAACAGCCTGC GTGCTGAGGACACTGCCGTCTATTATTGTTCTAGA TGGGGAGGGGACGGCTTCTATGCTATGGACTATTG GGGTCAAGGAACCCTGGTCACCGTCTCCTCGGAGT CCAAATATGGTCCCCCATGCCCATCATGCCCAGCA CCTGAGTTCGAGGGGGGACCATCAGTCTTCCTGTT CCCCCCAAAACCCAAGGACACTCTCATGATCTCCC GGACCCCTGAGGTCACGTGCGTGGTGGTGGACGTG AGCCAGGAAGACCCCGAGGTCCAGTTCAACTGGTA CGTGGATGGCGTGGAGGTGCATAATGCCAAGACAA AGCCGCGGGAGGAGCAGTTCCAGAGCACGTACCGT GTGGTCAGCGTCCTCACCGTCCTGCACCAGGACTG GCTGAACGGCAAGGAGTACAAGTGCAAGGTCTCCA ACAAAGGCCTCCCGTCCTCCATCGAGAAAACCATC TCCAAAGCCAAAGGGCAGCCCCGAGAGCCACAGGT GTACACCCTGCCCCCATCCCAGGAGGAGATGACCA AGAACCAGGTCAGCCTGACCTGCCTGGTCAAAGGC TTCTACCCCAGCGACATCGCCGTGGAGTGGGAGAG CAATGGGCAGCCGGAGAACAACTACAAGACCACGC CTCCCGTGCTGGACTCCGACGGCTCCTTCTTCCTC TACAGCAGGCTCACCGTGGACAAGAGCAGGTGGCA GGAGGGGAATGTCTTCTCATGCTCCGTGATGCATG AGGCTCTGCACAACCACTACACACAGAAGAGCCTC TCCCTGTCTCTGGGTAAAATCTACATCTGGGCGCC CTTGGCCGGGACTTGTGGGGTCCTTCTCCTGTCAC TGGTTATCACCAAACGGGGCAGAAAGAAGCTCCTG TATATATTCAAACAACCATTTATGAGACAGACACA AACTACTCAAGAGGAAGATGGCTGTAGCTGCCGAT TTCCAGAAGAAGAAGAAGGAGGATGTGAACGGGC GGTGGCAGAGTGAAGTTCAGCAGGAGCGCAGACGC CCCCGCGTACCAGCAGGGCCAGAACCAGCTCTATA ACGAGCTCAATCTAGGACGAAGAGAGGAGTACGAT GTTTTGGACAAGAGACGTGGCCGGGACCCTGAGAT GGGGGGAAAGCCGAGAAGGAAGAACCCTCAGGAAG GCCTGTACAATGAACTGCAGAAAGATAAGATGGCG GAGGCCTACAGTGAGATTGGGATGAAAGGCGAGCG CCGGAGGGGCAAGGGGCACGATGGCCTTTACCAGG GTCTCAGTACAGCCACCAAGGACACCTACGACGCC CTTCACATGCAGGCCCTGCCCCCTCGCTAG (SEQ ID NO: 296) |
| CT297 | MDMRVPAQLLGLL LLWLRGARCQVQL QQSGPELKKPGET VKISCKASGYPFT NYGMNWVKQAPGQ GLKWMGWINTSTG ESTFADDFKGRFD FSLETSANTAYLQ INNLKSEDSATYF CARWEVYHGYVPY VVGQGTTVTVSSG GGGSGGGGSGGGG SDIQLTQSHKFLS TSVGDRVSITCKA SQDVYNAVAWYQQ KPGQSPKLLIYSA | ATGGACATGAGGGTCCCCGCTCAGCTCCTGGGGCT CCTGCTACTCTGGCTCCGAGGTGCCAGATGTCAGG TACAACTGCAGCAGTCAGGACCTGAACTGAAGAAG CCTGGAGAGACAGTCAAGATCTCCTGCAAGGCCTC TGGGTATCCTTTCACAAACTATGGAATGAACTGGG TGAAGCAGGCTCCAGGACAGGGTTTAAAGTGGATG GGCTGGATTAACACCTCCACTGGAGAGTCAACATT TGCTGATGACTTCAAGGGACGGTTTGACTTCTCTT TGGAAACCTCTGCCAACACTGCCTATTTGCAGATC AACAACCTCAAAAGTGAAGACTCGGCTACATATTT CTGTGCAAGATGGGAGGTTTACCACGGCTACATTG CTTACTGGGCCAAGGGACCACGGTCACCGTTTCC TCTGGCGGTGGCGGTTCTGGTGGCGGTGGCTCCGG CGGTGGCGGTTCTGACATCCAGCTGACCCAGTCTC ACAAATTCCTGTCCACTTCAGTAGGAGACAGGGTC AGCATCACCTGCAAGGCCAGTCAGGATGTGTATAA |

TABLE 25-continued

| Construct | Amino Acid Sequence | DNA Sequence |
|---|---|---|
| | SSRYTGVPSRFTG SGSGPDFTFTISS VQAEDLAVYFCQQ HFRTPFTFGSGTK LEIKIEVMYPPPY LDNEKSNGTIIHV KGKHLCPSPLFPG PSKPFWVLVVVGG VLACYSLLVTVAF IIFWVRSKRSRLL HSDYMNMTPRRPG PTRKHYQPYAPPR DFAAYRSVKFSR SADAPAYKQGQNQ LYNELNLGRREEY DVLDKRRGRDPEM GGKPRRKNPQEGL YNELQKDKMAEAY ESIGMKGERRRGK GHDGLYQGLSTAT KDTYDALHMQALP PR (SEQ ID NO: 297) | TGCTGTTGCCTGGTATCAACAGAAACCAGGACAAT CTCCTAAACTTCTGATTTACTCGGCATCCTCCCGG TACACTGGAGTCCCTTCTCGCTTCACTGGCAGTGG CTCTGGGCCGGATTTCACTTTCACCATCAGCAGTG TGCAGGCTGAAGACCTGGCAGTTTATTTCTGTCAG CAACATTTTCGTACTCCATTCACGTTCGGCTCGGG GACAAAATTGGAGATCAAAATTGAAGTTATGTATC CTCCTCCTTACCTAGACAATGAGAAGAGCAATGGA ACCATTATCCATGTGAAAGGGAAACACCTTTGTCC AAGTCCCTATTTCCCGGACCTTCTAAGCCCTTCT GGGTGCTGGTCGTTGTGGGCGGCGTGCTGGCCTGC TACAGCCTGCTGGTGACAGTGGCCTTCATCATCTT TTGGGTGAGGAGCAAGCGGAGCAGACTGCTGCACA GCGACTACATGAACATGACCCCCCGGAGGCCTGGC CCCACCCGGAAGCACTACCAGCCCTACGCCCCTCC CAGGGATTTCGCCGCCTACCGGAGCAGAGTGAAGT TCAGCAGGAGCGCAGACGCCCCCGCGTACAAGCAG GGCCAGAACCAGCTCTATAACGAGCTCAATCTAGG ACGAAGAGAGGAGTACGATGTTTTGGACAAGCGTA GAGGCCGGGACCCTGAGATGGGGGGAAAGCCGAGA AGGAAGAACCCTCAGGAAGGCCTGTACAATGAACT GCAGAAAGATAAGATGGCGGAGGCCTACAGTGAGA TTGGGATGAAAGGCGAGCGCCGGAGGGGCAAGGGG CACGATGGCCTTTACCAGGGACTCAGTACAGCCAC CAAGGACACCTACGACGCCCTTCACATGCAGGCCC TGCCCCCTCGCTAG (SEQ ID NO: 298) |
| CT1094 | MDMRVPAQLLGLL LLWLRGARCQVQL QQSGPELKKPGET VKISCKASGYPFT NYGMNWVKQAPGQ GLKWMGWINTSTG ESTFADDFKGRFD FSLETSANTAYLQ INNLKSEDSATYF CARWEVYHGYVPY VVGQGTTVTVSSG GGGSGGGGSGGGG SDIQLTQSHKFLS TSVGDRVSITCKA SQDVYNAVAWYQQ KPGQSPKLLIYSA SSRYTGVPSRFTG SGSGPDFTFTISS VQAEDLAVYFCQQ HFRTPFTFGSGTK LEIKAEPKSPDKT HTCPPCPKDPKFW VLVVVGGVLACYS LLVTVAFIIFWVR SKRSRLLHSDYMN MTPRRPGPTRKHY QPYAPPRDFAAYR SRVKFSRSADAPA YKQGQNQLYNELN LGRREEYDVLDKR RGRDPEMGGKPRR KNPQEGLYNELQK DKMAEAYSEIGMK GERRRGKGHDGLY QGLSTATKDTYDA LHMQALPPR (SEQ ID NO: 299) | ATGGACATGAGGGTCCCCGCTCAGCTCCTGGGGCT CCTGCTACTCTGGCTCCGAGGTGCCAGATGTCAGG TACAACTGCAGCAGTCAGGACCTGAACTGAAGAAG CCTGGAGAGACAGTCAAGATCTCCTGCAAGGCCTC TGGGTATCCTTTCACAAACTATGGAATGAACTGGG TGAAGCAGGCTCCAGGACAGGGTTTAAAGTGGATG GGCTGGATTAACACCTCCACTGGAGAGTCAACATT TGCTGATGACTTCAAGGGACGGTTTGACTTCTCTT TGGAAACCTCTGCCAACACTGCCTATTTGCAGATC AACAACCTCAAAAGTGAAGACTCGGCTACATATTT CTGTGCAAGATGGGAGGTTTACCACGGCTACGTTC CTTACTGGGGCCAAGGGACCACGGTCACCGTTTCC TCTGGCGGTGGCGGTTCTGGTGGCGGTGGCTCCGG CGGTGGCGGTTCTGACATCCAGCTGACCCAGTCTC ACAAATTCCTGTCCACTTCAGTAGGAGACAGGGTC AGCATCACCTGCAAGGCCAGTCAGGATGTGTATAA TGCTGTTGCCTGGTATCAACAGAAACCAGGACAAT CTCCTAAACTTCTGATTTACTCGGCATCCTCCCGG TACACTGGAGTCCCTTCTCGCTTCACTGGCAGTGG CTCTGGGCCGGATTTCACTTTCACCATCAGCAGTG TGCAGGCTGAAGACCTGGCAGTTTATTTCTGTCAG CAACATTTTCGTACTCCATTCACGTTCGGCTCGGG GACAAAATTGGAGATCAAAGCCGAGCCCAAGTCCC CTGATAAAACTCACACCTGCCCACCCTGTCCTAAG GACCCGAAGTTCTGGGTGCTGGTCGTTGTGGGCGG CGTGCTGGCCTGCTACAGCCTGCTGGTGACAGTGG CCTTCATCATCTTTTGGGTGAGGAGCAAGCGGAGC AGACTGCTGCACAGCGACTACATGAACATGACCCC CCGGAGGCCTGGCCCCACCCGGAAGCACTACCAGC CCTACGCCCCTCCCAGGGATTTCGCCGCCTACCGG AGCAGAGTGAAGTTCAGCAGGAGCGCAGACGCCCC CGCGTACAAGCAGGGCCAGAACCAGCTCTATAACG AGCTCAATCTAGGACGAAGAGAGGAGTACGATGTT TTGGACAAGCGTAGAGGCCGGGACCCTGAGATGGG GGGAAAGCCGAGAAGGAAGAACCCTCAGGAAGGCC TGTACAATGAACTGCAGAAAGATAAGATGGCGGAG GCCTACAGTGAGATTGGGATGAAAGGCGAGCGCCG GAGGGGCAAGGGGCACGATGGCCTTTACCAGGGAC TCAGTACAGCCACCAAGGACACCTACGACGCCCTT CACATGCAGGCCCTGCCCCCTCGCTAG (SEQ ID NO: 300) |

TABLE 25-continued

| Construct | Amino Acid Sequence | DNA Sequence |
|---|---|---|
| CT1095 | MDMRVPAQLLGLL LLWLRGARCQVQL QQSGPELKKPGET VKISCKASGYPFT NYGMNWVKQAPGQ GLKWMGWINTSTG ESTFADDFKGRFD FSLETSANTAYLQ INNLKSEDMATYF CARWEVYHGYVPY VVGQGTTVTVSSG GGGSGGGGSGGGG SDIQLTQSHKFLS TSVGDRVSITCKA SQDVYNAVAWYQQ KPGQSPKLLIYSA SSRYTGVPSRFTG SGSGPDFTFTISS VQAEDLAVYFCQQ HFRTPFTFGSGTK LEIKAEPKSPDKT HTCPPCPKDPKFW VLVVVGGVLACYS LLVTVAFIIFWVR SKRSRLLHSDYMN MTPRRPGPTRKHY QPYAPPRDFAAYR SRVKFSRSADAPA YKQGQNQLYNELN LGRREEYDVLDKR RGRDPEMGGKPRR KNPQEGLYNELQK DKMAEAYSEIGMK GERRRGKGHDGLY QGLSTATKDTYDA LHMQALPPR (SEQ ID NO: 301) | ATGGACATGAGGGTCCCCGCTCAGCTCCTGGGGCT CCTGCTACTCTGGCTCCGAGGTGCCAGATGTCAGG TACAACTGCAGCAGTCAGGACCTGAACTGAAGAAG CCTGGAGAGACAGTCAAGATCTCCTGCAAGGCCTC TGGGTATCCTTTCACAAACTATGGAATGAACTGGG TGAAGCAGGCTCCAGGACAGGGTTTAAAGTGGATG GGCTGGATTAACACCTCCACTGGAGAGTCAACATT TGCTGATGACTTCAAGGGACGGTTTGACTTCTCTT TGGAAACCTCTGCCAACACTGCCTATTTGCAGATC AACAACCTCAAAAGTGAAGACATGGCTACATATTT CTGTGCAAGATGGGAGGTTTACCACGGCTACGTTC CTTACTGGGGCCAAGGGACCACGGTCACCGTTTCC TCTGGCGGTGGCGGTTCTGGTGGCGGTGGCTCCGG CGGTGGCGGTTCTGACATCCAGCTGACCCAGTCTC ACAAATTCCTGTCCACTTCAGTAGGAGACAGGGTC AGCATCACCTGCAAGGCCAGTCAGGATGTGTATAA TGCTGTTGCCTGGTATCAACAGAAACCAGGACAAT CTCCTAAACTTCTGATTTACTCGGCATCCTCCCGG TACACTGGAGTCCCTTCTCGCTTCACTGGCAGTGG CTCTGGGCCGGATTTCACTTTCACCATCAGCAGTG TGCAGGCTGAAGACCTGGCAGTTTATTTCTGTCAG CAACATTTTCGTACTCCATTCACGTTCGGCTCGGG GACAAAATTGGAGATCAAAGCCGAGCCCAAGTCCC CTGATAAAACTCACACCTGCCCACCCTGTCCTAAG GACCCGAAGTTCTGGGTGCTGGTCGTTGTGGGCGG CGTGCTGGCCTGCTACAGCCTGCTGGTGACAGTGG CCTTCATCATCTTTTGGGTGAGGAGCAAGCGGAGC AGACTGCTGCACAGCGACTACATGAACATGACCCC CCGGAGGCCTGGCCCCACCCGGAAGCACTACCAGC CCTACGCCCCTCCCAGGGATTTCGCCGCCTACCGG AGCAGAGTGAAGTTCAGCAGGAGCGCAGACGCCCC CGCGTACAAGCAGGGCCAGAACCAGCTCTATAACG AGCTCAATCTAGGACGAAGAGAGGAGTACGATGTT TTGGACAAGCGTAGAGGCCGGGACCCTGAGATGGG GGGAAAGCCGAGAAGGAAGAACCCTCAGGAAGGCC TGTACAATGAACTGCAGAAAGATAAGATGGCGGAG GCCTACAGTGAGATTGGGATGAAAGGCGAGCGCCG GAGGGGCAAGGGGCACGATGGCCTTTACCAGGGAC TCAGTACAGCCACCAAGGACACCTACGACGCCCTT CACATGCAGGCCCTGCCCCCTCGCTAG (SEQ ID NO: 302) |

Example 3: An HLA-A*02 Inhibitory Receptor can Inhibit HER2 CAR Mediated Activation of Jurkat Cells The ability of an HLA-A*-02 LIR1 based inhibitory receptor to inhibit HER2 mediated activation of Jurkat cells expressing both a HER2 CAR and the based inhibitory receptor was assayed.

Figure 3:
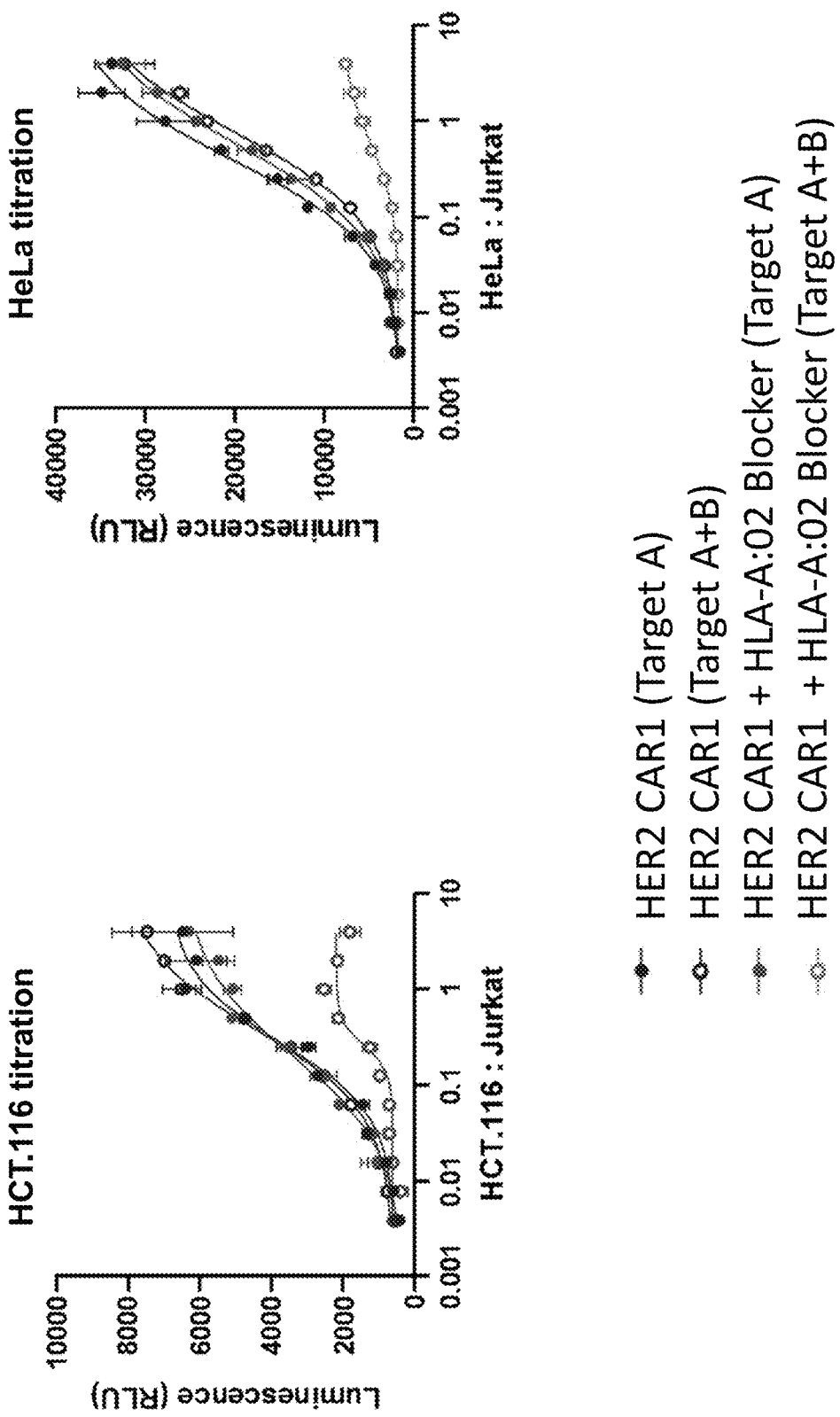
FIG. 3 is a pair of plots showing that activation of Jurkat cells that co-express an HLA-A*02 specific inhibitory receptor (HLA-A*02 Blocker) with the HER2 (CT292) CAR1 activator is blocked by target cells that express ligands for both the activator and blocker receptors. Target A: activator ligand (HER2); Target B: inhibitor ligand (HLA-A*02); left panel shows HCT.116 target cells; right panel: HeLa target cells.
Figure 4:
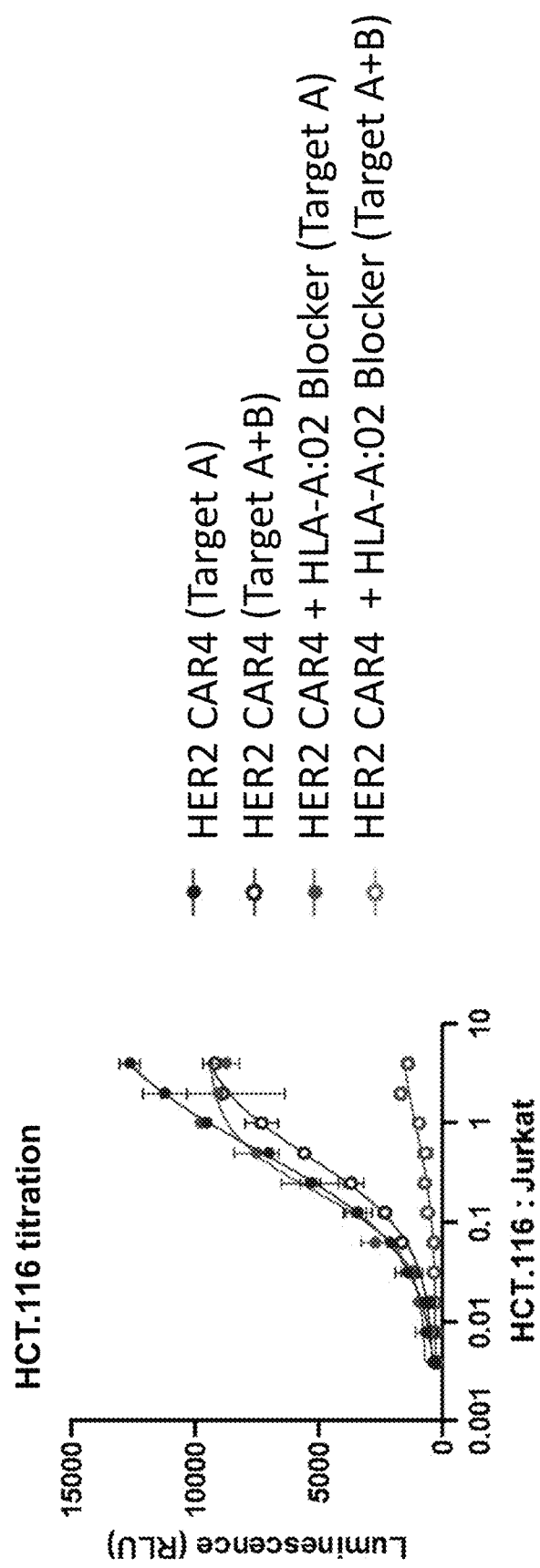
FIG. 4 is a plot showing that activation of Jurkat cells that co-express an HLA-A*02 specific inhibitory receptor (HLA-A*02 Blocker) with the HER2 (CT299) CAR1 activator is blocked by HCT.116 target cells that express ligands for both the activator and blocker receptors. Target A: activator ligand (HER2); Target B: inhibitor ligand (HLA-A*02).

Jurkat cells expressing either the HER2 CAR1 (FIG. 3) or HER2 CAR4 (FIG. 4), either alone or in combination with the CT1765 HLA-A*02 LIR1 inhibitory receptor, were co-cultured with HCT.116 or HeLa cells. HCT.116 Hela cells expressed HER2 (Target A), or HER2 and HLA-A*02 (Target AB). As can be seen from FIG. 3, activation Jurkat cells expressing the HLA-A*02 inhibitory receptor and HER2 CAR1 was inhibited by HCT.116 or HeLa target cells that expressed both HER2 and HLA-A*02. In contrast, activation Jurkat cells expressing only HER2 CAR1 was not inhibited in the presence of target cells expressing both HER2 and HLA-A*02. Similar results were observed for HER2 CAR4, as shown in FIG. 4.

Figure 5:
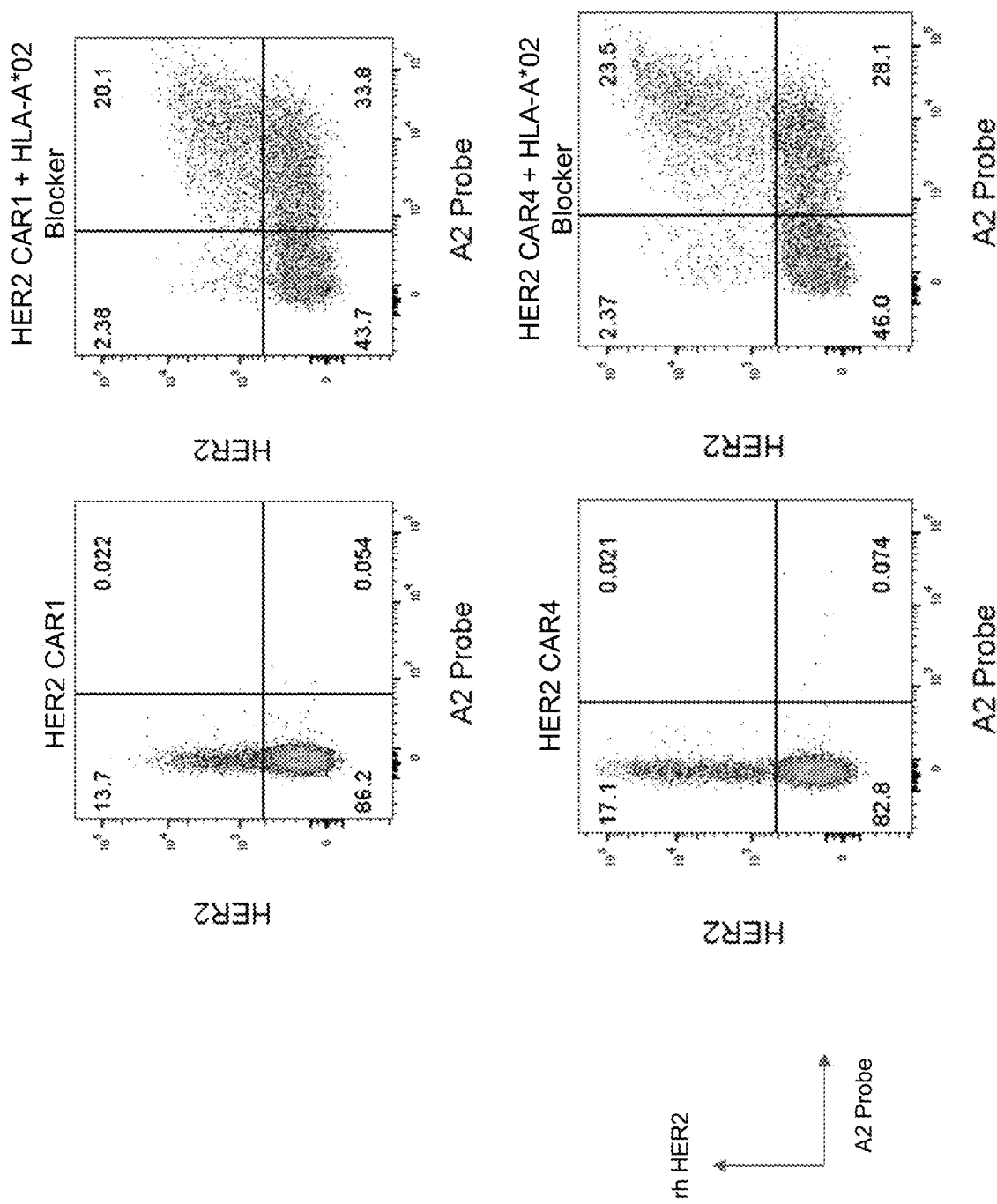
FIG. 5 is a series of fluorescence activated cell sorting (FACS) plots showing expression of the HER2 CAR1 or HER2 CAR4, alone or in combination with the HLA-A*02 Blocker, in Jurkat cells.

Surface expression of both the HER2 CAR, and the HLA-A*02 inhibitory receptor by Jurkat cells was validated by staining Jurkat cells using protein L for the activator receptor and pMHC or anti-LILRB1 antibody for the blocker receptor as shown in FIG. 5.

Example 4: An HLA-A*02 Inhibitory Receptor can Inhibit HER2 CAR Mediated Activation of Primary T Cells The efficacy, selectivity, and reversibility of HER2 CAR1 (CT292) in combination with an HLA-A*02 LIR1 inhibitory receptor was demonstrated in primary T cells. A murine version of the HLA-A*02 LIR1 inhibitory receptor (C1765), as well as two humanized versions (C2162 and C2163) were assayed in combination with HER2 CAR. The sequences of the HLA-A*02 inhibitory receptors are provided in Table 26 below.

Figure 6:
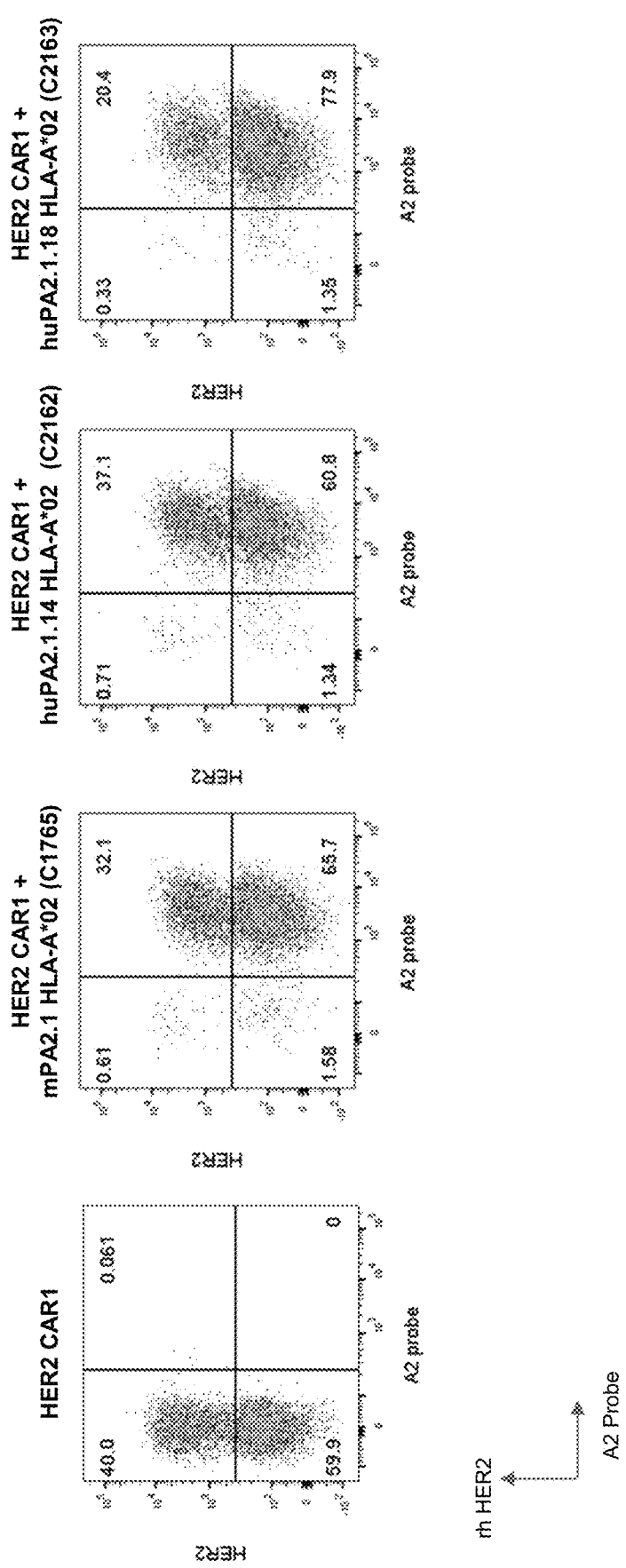
FIG. 6 is a series of FACS plots showing expression of HER2 CAR1 (CT292) in primary T cells, alone and in combination with HLA-A*02 blocker constructs mPA2.1 (C1765), humanized (hu) PA2.1.14 (C2162) and humanized PA2.1.18 (C2163). HER2 CAR1 and PA2.1 HLA-A*02 blockers can be expressed and enriched in primary T cells.
Figure 7:
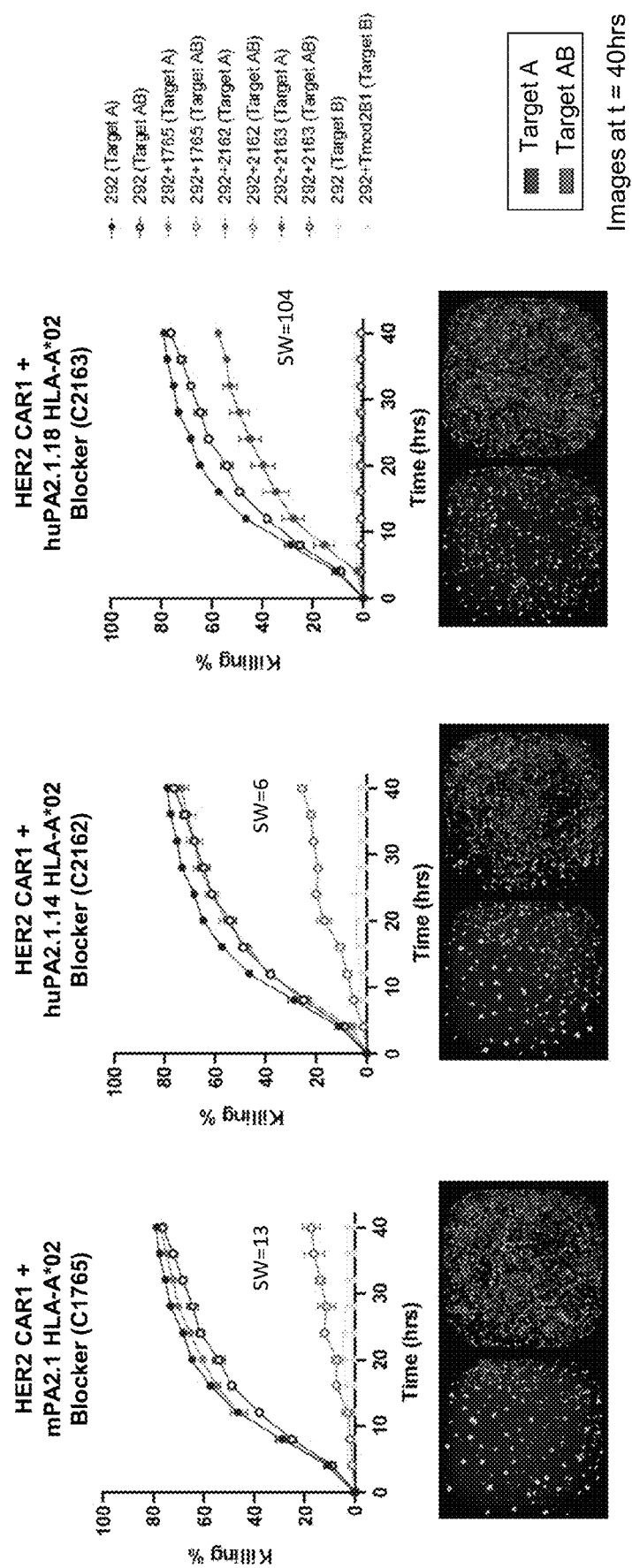
FIG. 7 is a series of plots and images showing that HER2 CAR1 (CT292) mediated primary T cell killing of HeLa target cells is inhibited when the T cells express an HLA-A*02 inhibitory receptors (as indicated), and the HeLa target cells co-express the HER2 activator ligand and HLA-A*02 blocker target ligand at a 1:40 ratio. Target A: activator ligand (HER2); Target B: inhibitor ligand (HLA-A*02); hu: humanized; SW: selectivity window. Images were taken at 40 hours, and show HeLa cells expression of activator (left image in each panel), or a combination of activator and inhibitor ligands (right panel in each image). Effector and target cells were at a ratio of 1:1.
Figure 8:
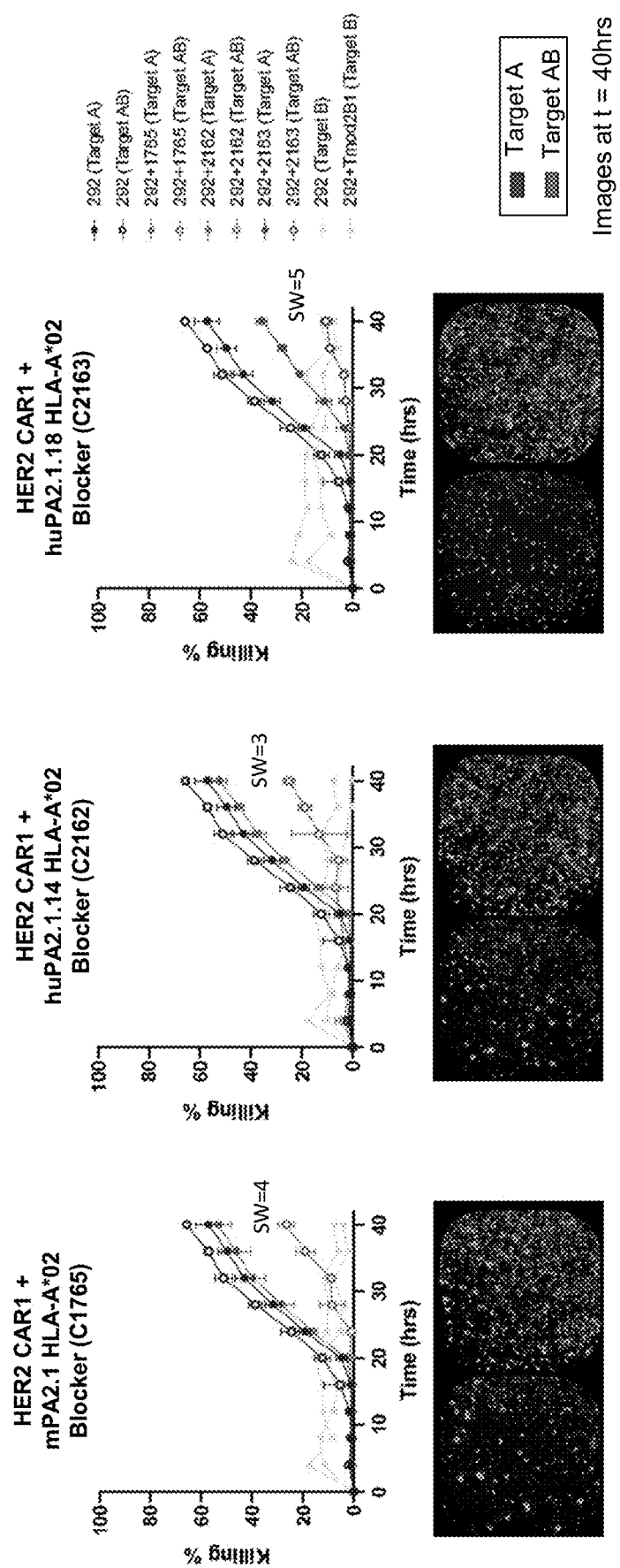
FIG. 8 is a series of plots and images showing that HER2 CAR1 (CT292) mediated primary T cell killing of HCT.116 target cells is inhibited when the T cells express an HLA-A*02 inhibitory receptors (as indicated), and the HCT.116 target cells co-express the HER2 activator ligand and HLA-A*02 blocker target ligand at a 1:4 ratio. Target A: activator ligand (HER2); Target B: inhibitor ligand (HLA-A*02); hu: humanized; SW: selectivity window. Images were taken at 40 hours, and show HCT.116 cells expression of activator (left image in each panel), or a combination of activator and inhibitor ligands (right panel in each image). Effector and target cells were at a ratio of 1:1.
Figure 12:
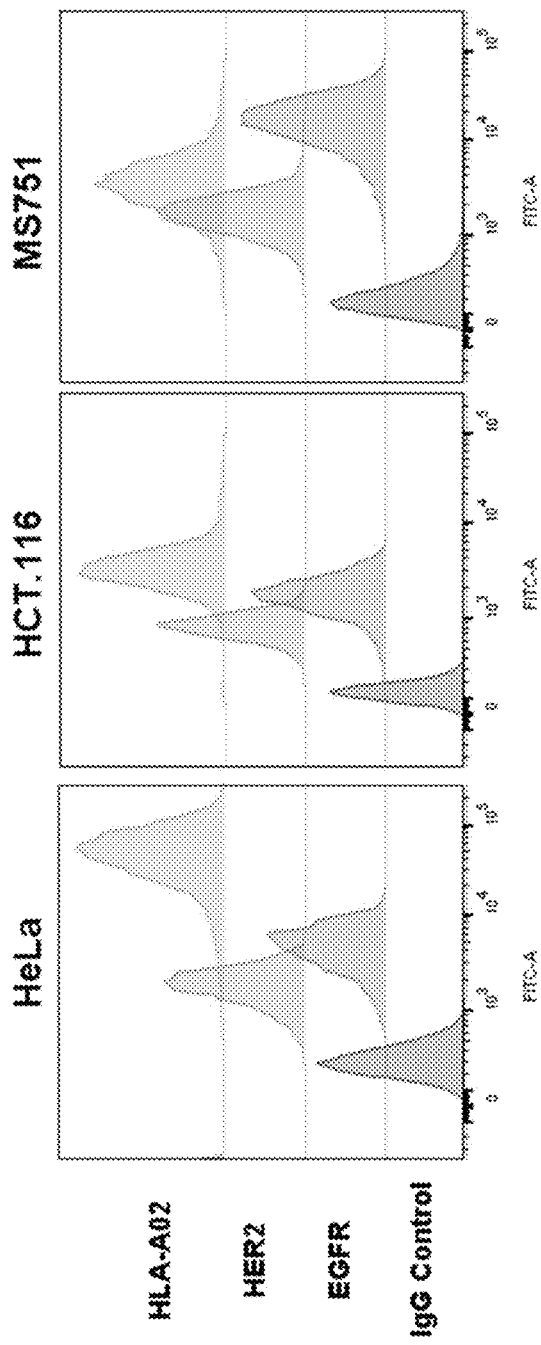
FIG. 12 is a series of FACS plots showing the expression of activator and inhibitor ligands by HeLa, HCT.116 and MS751 target cells. Cell surface antigens were quantified using the Agilent QIFI Kit.

As can be seen in FIG. 6, all of the HER2 CAR1, and the three inhibitory receptor constructs, were expressed by primary T cells following lentiviral transduction and enrichment. The activity of primary T cells expressing each of the three inhibitory receptors in combination with HER2 CAR1 was assayed using HeLa target cells expressing activator ligand to inhibitor ligand at a ratio of 1:40 (HER: HLA-A*-02). As shown in FIG. 7, all inhibitory receptors were able to inhibit HER2 mediated primary T cell activation. Similar results were obtained using HCT.116 target cells expressed activator to blocker antigen at a ratio of about 1:4 (FIG. 8). Antigen expression, and antigen densities, for HeLa and HCT.116 target cells are shown in FIGS. 12 and 13.

TABLE 26

HLA-A*02 Inhibitory receptors

| Construct | Amino Acid Sequence | DNA Sequence |
|---|---|---|
| C-1765 | MDMRVPAQLLGLLLLWLRGARCDVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPRTSGGGTKLEIKGGGGSGGGGSGGGGSGGQVQLQQSGPELVKPGASVRISCKASGYTFTSYHIHWVKQRPGQGLEWIGWIYPGNVNTEYNEKFKGKATLTADKSSSTAYMHLSSLTSEDSAVYFCAREEITYAMDYWGQGTSVTVSSYGSQSSKPYLLTHPSDPLEVVSGPSGGPSSPTTGPTSTSGPEDQPLTPTGSDPQSGLGRHLGVVIGILVAVILLLLLLLLLFLILRHRRQGKHWTSTQRKADFQHPAGAVGPEPTDRGLQWRSSPAADAQEENLYAAVKHTQPEDGVEMDTRSPHDEDPQAVTYAEVKHSRPRREMASPPSPLSGEFLDTKDRQAEEDRQMDTEAAASEAPQDVTYAQLHSLTLRREATEPPPSQEGPSPAVPSIYATLAIH (SEQ ID NO: 303) | ATGGACATGAGGGTCCCCGCTCAGCTCCTGGGGCTCCTGCTACTCTGGCTCCGAGGTGCCAGATGTGATGTTTTGATGACCCAAACTCCACTCTCCCTGCCTGTCAGTCTTGGAGATCAAGCCTCCATCTCTTGCAGATCTAGTCAGAGCATTGTACATAGTAATGGAAACACCTATTTAGAATGGTACCTGCAGAAACCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGTAGAGTGGAGGCTGAGGATCTGGGAGTTTATTACTGCTTTCAAGGTTCACATGTTCCTCGGACGTCCGGTGGAGGCACCAAGCTGGAAATCAAAGGCGGAGGTGGAAGCGGAGGGGGAGGATCTGGCGGCGGAGGAAGCGGAGGCCAGGTCCAGCTGCAGCAGTCTGGACCTGAGCTGGTGAAGCCTGGGGCTTCAGTGAGGATATCCTGCAAGGCTTCTGGCTACACCTTCACAAGTTACCATATACATTGGGTGAAGCAGAGGCCTGGACAGGGACTTGAGTGGATTGGATGGATTTATCCTGGAAATGTTAATACTGAGTACAATGAAGAAGTTCAAGGGCAAGGCCACACTGACTGCAGACAAATCGTCCAGCACAGCCTACATGCACCTCAGCAGCCTGACCTCTGAGGACTCTGCGGTCTATTTCTGTGCCAGAGAGGAGATTACCTATGCTATGGACTACTGGGGTCAAGGAACCTCAGTCACCGTGTCCTCATACGGCTCACAGAGCTCCAAACCCTACCTGCTGACTCACCCCAGTGACCCTGGAGCTCGTGGTCTCAGGACCGTCTGGGGCCCCAGCTCCCCGACAACAGGCCCCACCTCCACATCTGGCCCTGAGGACCAGCCCCTCACCCCCACCGGGTCGGATCCCCAGAGTGGTCTGGGAAGGCACCTGGGGGTTGTGATCGGCATCTTGGTGGCCGTCATCCTACTGCTCCTCCTCCTCCTCCTCCTCTTCCTCATCCTCCGACATCGACGTCAGGGCAAACACTGGACATCGACCCAGAGAAAGGCTGATTTCCAACATCCTGCAGGGGCTGTGGGGCCAGAGCCCACAGACAGAGGCCTGCAGTGGAGGTCCAGCCCAGCTGCCGATGCCCAGGAAGAAAACCTCTATGCTGCCGTGAAGCACACACAGCCTGAGGATGGGGTGGAGATGGACACTCGGAGCCCACACGATGAAGACCCCCAGGCAGTGACGTATGCCGAGGTGAAACACTCCAGACTTAGGAGAGAAATGGCCTCTCCTCCTTCCCCACTGTCTGGGGAATTCCTGGACACAAAGGACAGACAGGCGGAAGAGGACAGGCAGATGGACACTGAGGCTGCTGCATCTGAAGCCCCCCAGGATGTGACCTACGCCCAGCTGCACAGCTTGACCCTCAGAGGGAGGCAACTGAGCCTCCTCCATCCCAGGAAGGGCCCTCTCCAGCTGTGCCCAGCATCTACGCCACTCTGGCCATCCACTAG (SEQ ID NO: 304) |
| C-2162 | MDMRVPAQLLGLLLLWLRGARCQVQLVQSGAEVKKPGSSVKVSCKASGYTFTSYHIHWVRQAPGQGLEWIGWIYPGNVNTEYNEKFKGKATITADESTNTAYMELSSLRSEDTAVYYCAREEITYAMDYWGQGTLVTVSSGGGGSGGGGSGGGGSGDIQMTQSPSTLSASVGDRVTITCRSSQSIVHSNGNTYLEWYQQKPGKAPKLLIYKVSNRFSGVPARFSGSGSGTEFTLTISSLQPDDFATYYCFQGSHVPRTFGQGTKVEVKYGSQSSKPYLLTHPSDPLEVVSGPSGGPSSPTTGPTSTSGPEDQPLTPTGSDPQSGLGRHLGVVIGILVAVILLLLLLL | ATGGACATGAGGGTCCCCGCTCAGCTCCTGGGGCTCCTGCTACTCTGGCTCCGAGGTGCCAGATGTCAGGTGCAGCTGGTGCAGTCTGGGGCTGAGGTGAAGAAGCCTGGGTCCTCAGTGAAGGTTTCCTGCAAGGCTTCTGGATACACCTTCACTAGCTATCATATACATTGGGTGCGCCAGGCCCCCGGACAAGGGCTTGAGTGGATCGGATGGATCTACCCTGGCAATGTTAACACAGAATATAATGAGAAGTTCAAGGGCAAAGCCACCATTACCGCGGACGAATCCACGAACACAGCCTACATGGAGCTGAGCAGCCTGAGATCTGAAGACACGGCTGTGTATTACTGTGCGAGGGAGGAAATTACCTACGCTATGGACTACTGGGGCCAGGGAACCCTGGTCACCGTGTCCTCAGGCGGAGGTGGAAGCGGAGGGGGAGGATCTGGCGGCGGAGGAAGCGGAGGCGACATTCAAATGACCCAGAGCCCATCCACCCTGAGCGCATCTGTAGGTGACCGGGTCACCATCACTTGTAGATCCAGTCAGAGTATTGTACACAGTAATGGGAACACCTATTTGGAATGGTATCAGCAGAAACCAGGTAAAGCCCCAAAATTGCTCATCTACAAAGTCTCTAACAGATTTAGTGGTGTACCAGCCAGGTTCAGCGGTTCCGGAAGTGGTACTGAATTCACCCTCACGATTCCTCTCTCCAGCCAGATGATTTCGCCACTTATTACTGTTTTCAAGGTTCACATGTGCCGCGCACATTCGGTCAGGGTACTAAAGTAGAAGTCAAATACGGCTCACAGAGCTCCAAACCCTACCTGCTGACTCACCCCAGTGACCCTGGAGCTCGTGGTCTCAGGACCGTCTGGGGCCCCAGCTCCCCGACAACAGGCCCCACCTCCACATCTGGCCCTGAGGACCAGCCCCTCACCCCCACCGGGTCGGATCCCCAGAGTGGTCTGGGAAGGCACCTGGGGGTTGTGATCGGCATCTTGGTGGCCGTCATCCTACTGCTCCTCCTCCTC |

TABLE 26-continued

HLA-A*02 Inhibitory receptors

| Construct | Amino Acid Sequence | DNA Sequence |
|---|---|---|
| | LLLFLILRHRRQ GKHWTSTQRKAD FQHPAGAVGPEP TDRGLQWRSSPA ADAQEENLYAAV KHTQPEDGVEMD TRSPHDEDPQAV TYAEVKHSRPRR EMASPPSPLSGE FLDTKDRQAEED RQMDTEAAASEA PQDVTYAQLHSL TLRREATEPPPS QEGPSPAVPSIY ATLAIH (SEQ ID NO: 305) | CTCCTCCTCTTCCTCATCCTCCGACATCGACGTCAG GGCAAACACTGGACATCGACCCAGAGAAAGGCTGAT TTCCAACATCCTGCAGGGGCTGTGGGGCCAGAGCCC ACAGACAGAGGCCTGCAGTGGAGGTCCAGCCCAGCT GCCGATGCCCAGGAAGAAAACCTCTATGCTGCCGTG AAGCACACACAGCCTGAGGATGGGGTGGAGATGGAC ACTCGGAGCCCACACGATGAAGACCCCCAGGCAGTG ACGTATGCCGAGGTGAAACACTCCAGACCTAGGAGA GAAATGGCCTCTCCTCCTTCCCCACTGTCTGGGGAA TTCCTGGACACAAAGGACAGACAGGCGGAAGAGGAC AGGCAGATGGACACTGAGGCTGCTGCATCTGAAGCC CCCCAGGATGTGACCTACGCCCAGCTGCACAGCTTG ACCCTCAGACGGGAGGCAACTGAGCCTCCTCCATCC CAGGAAGGGCCCTCTCCAGCTGTGCCCAGCATCTAC GCCACTCTGGCCATCCACTAG (SEQ ID NO: 306) |
| C-2163 | MDMRVPAQLLGL LLLWLRGARCQV QLVQSGAEVKKP GSSVKVSCKASG YTFTSYHMHWVR QAPGQGLEWIGY IYPGNVNTEYNE KFKGKATLTADK STNTAYMELSSL RSEDTAVYFCAR EEITYAMDYWGQ GTLVTVSSGGGG SGGGGSGGGGSG GDVQMTQSPSTL SASVGDRVTITC SSSQSIVHSNGN TYMEWYQQKPGK APKLLIYKVSNR FSGVPDRFSGSG SGTEFTLTISSL QPDDFATYYCHQ GSHVPRTFGQGT KVEVKYGSQSSK PYLLTHPSDPLE LVVSGPSGGPSS PTTGPTSTSGPE DQPLTPTGSDPQ SGLGRHLGVVIG ILVAVILLLLLL LLLFLILRHRRQ GKHWTSTQRKAD FQHPAGAVGPEP TDRGLQWRSSPA ADAQEENLYAAV KHTQPEDGVEMD TRSPHDEDPQAV TYAEVKHSRPRR EMASPPSPLSGE FLDTKDRQAEED RQMDTEAAASEA PQDVTYAQLHSL TLRREATEPPPS QEGPSPAVPSIY ATLAIH (SEQ ID NO: 307) | ATGGACATGAGGGTCCCCGCTCAGCTCCTGGGGCTC CTGCTACTCTGGCTCCGAGGTGCCAGATGTCAGGTG CAGCTGGTGCAGTCTGGGGCTGAGGTGAAGAAGCCT GGGTCCTCAGTGAAGGTTTCCTGCAAGGCTTCTGGA TACACCTTCACTAGCTATCATATGCATTGGGTGCGC CAGGCCCCCGGACAAGGGCTTGAGTGGATCGGATAC ATCTACCCTGGCAATGTTAACACAGAATATAATGAG AAGTTCAAGGGCAAAGCCACCCTTACCGCGGACAAA TCCACGAACACAGCCTACATGGAGCTGAGCAGCCTG AGATCTGAAGACACGGCTGTGTATTTCTGTGCGAGG GAGGAAATTACCTACGCTATGGACTACTGGGGCCAG GGAACCCTGGTCACCGTGTCCTCAGGCGGAGGTGGA AGCGGAGGGGAGGATCTGGCGGCGGAGGAAGCGGA GGCGACGTTCAAATGACCCAGAGCCCATCCACCCTG AGCGCATCTGTAGGTGACCGGGTCACCATCACTTGT AGCTCCAGTCAGAGTATTGTACACAGTAATGGGAAC ACCTATATGGAATGGTATCAGCAGAAACCAGGTAAA GCCCCAAAATTGCTCATCTACAAAGTCTCTAACAGA TTTAGTGGTGTACCAGACAGGTTCAGCGGTTCCGGA AGTGGTACTGAATTCACCCTCACGATCTCCTCTCTC CAGCCAGATGATTTCGCCACTTATTACTGTCATCAA GGTTCACATGTGCCGCGCACATTCGGTCAGGGTACT AAAGTAGAAGTCAAATACGGCTCACAGAGCTCCAAA CCCTACCTGCTGACTCACCCCAGTGACCCCCTGGAG CTCGTGGTCTCAGGACCGTCTGGGGGCCCCAGCTCC CCGACAACAGGCCCCACCTCCACATCTGGCCCTGAG GACCAGCCCCTCACCCCCACCGGGTCGGATCCCCAG AGTGGTCTGGGAAGGCACCTGGGGGTTGGATCGGC ATCTTGGTGGCCGTCATCCTACTGCTCCTCCTCCTC CTCCTCCTCTTCCTCATCCTCCGACATCGACGTCAG GGCAAACACTGGACATCGACCCAGAGAAAGGCTGAT TTCCAACATCCTGCAGGGGCTGTGGGGCCAGAGCCC ACAGACAGAGGCCTGCAGTGGAGGTCCAGCCCAGCT GCCGATGCCCAGGAAGAAAACCTCTATGCTGCCGTG AAGCACACACAGCCTGAGGATGGGGTGGAGATGGAC ACTCGGAGCCCACACGATGAAGACCCCCAGGCAGTG ACGTATGCCGAGGTGAAACACTCCAGACCTAGGAGA GAAATGGCCTCTCCTCCTTCCCCACTGTCTGGGGAA TTCCTGGACACAAAGGACAGACAGGCGGAAGAGGAC AGGCAGATGGACACTGAGGCTGCTGCATCTGAAGCC CCCCAGGATGTGACCTACGCCCAGCTGCACAGCTTG ACCCTCAGACGGGAGGCAACTGAGCCTCCTCCATCC CAGGAAGGGCCCTCTCCAGCTGTGCCCAGCATCTAC GCCACTCTGGCCATCCACTAG (SEQ ID NO: 308) |

Figure 9:
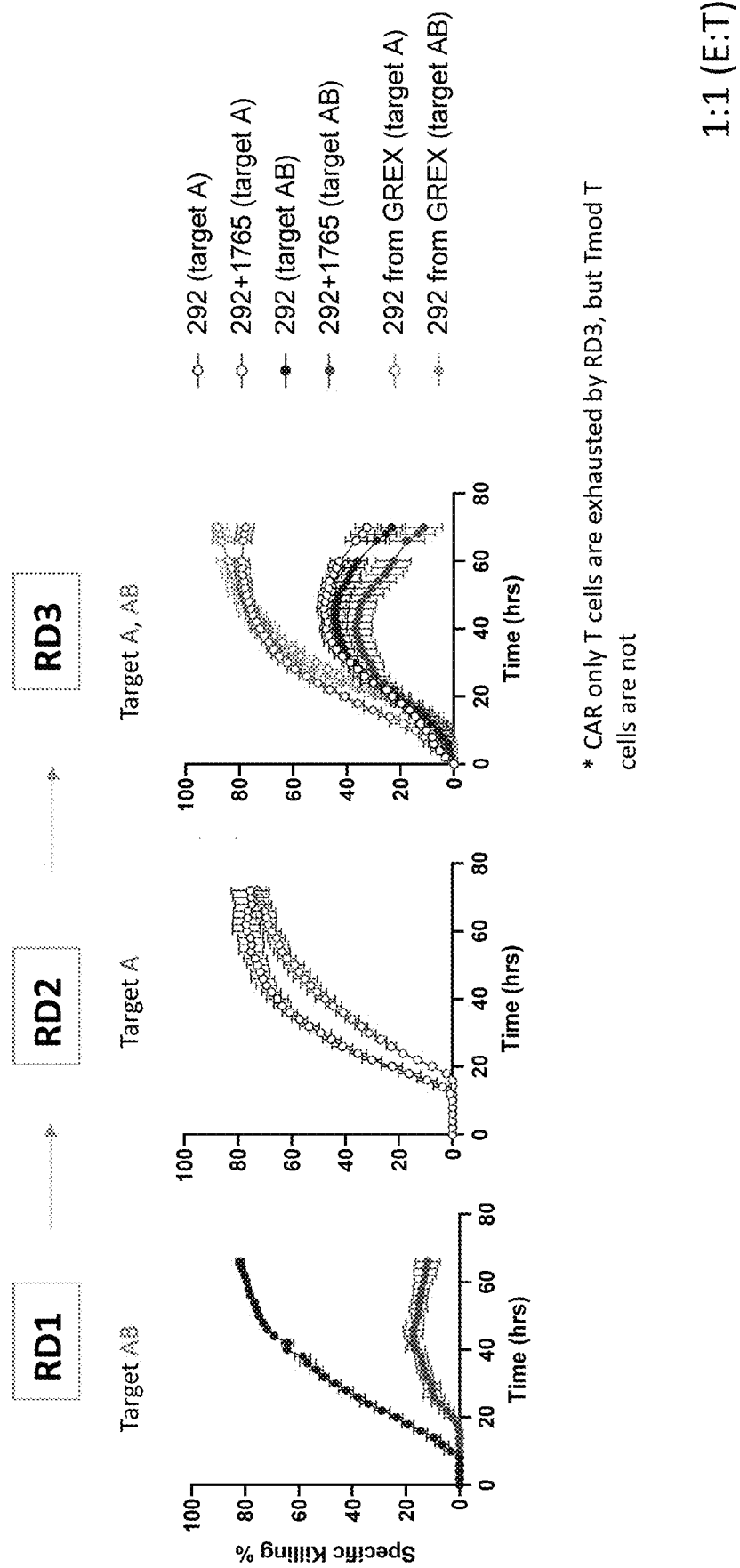
FIG. 9 is a series of plots showing that inhibition of primary T cell activation by the HER2 CAR1 (CT292) by HLA-A*02 inhibitory receptors is reversible. Activation of primary T cells was assayed using HCT.116 target cells. Target AB: HCT.116 cells expressing both activator (HER2) and inhibitor (HLA-A*02) ligands; Target A: HCT.116 cells expressing HER2; RD: round; E:T stands for Effector: Target. Primary T cells that expressed only the HER2 CAR, and not the HLA-A*02 inhibitory receptor were exhausted by Round 3, while Primary T cells that expressed both the HER2 CAR and the HLA-A*02 inhibitory receptor were not.
Figure 14:
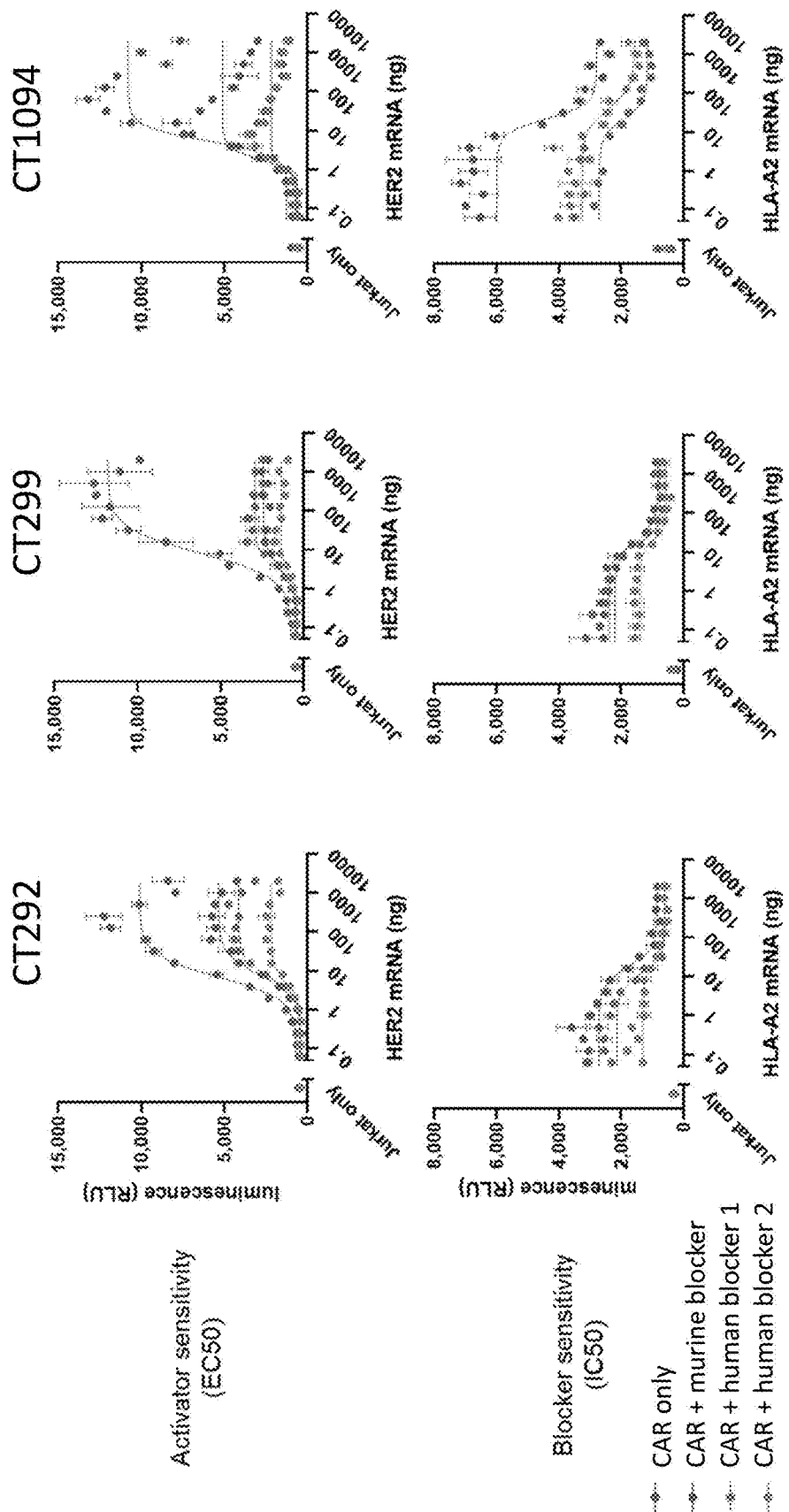
FIG. 14 is a series of plots showing sensitivity of nine receptor pairs comprising scFvs CT292 (left column), CT299 (middle column), or CT1094 (right column) paired with no modules (CAR only), murine blocker (C1765), humanized blocker 1 (C2162), or humanized blocker 2 (C2163). Activator (top row) and blocker (bottom row).

Example 5: Inhibition of HER CAR-Mediated Primary T Cell Activation by the HLA-A*02 Inhibitory Receptor is Reversible The ability of the HLA-A*02 LIR1 inhibitory receptor to inhibit HER2 mediated activation of primary T cells expressing a HER2 CAR was reversible. Primary T cells expressing HER2 CAR1 (CT292) alone or in combination with the CT1765 HLA-A*02 inhibitory receptor were co-cultured with HCT.116 cells expressing both HER2 and HLA-A*02 (FIG. 9, RD1, or round 1) at a ratio of 1:1. HCT.116 target cells were then removed, and the primary T cells were co-cultured with HCT.116 target cells expressing HER2 only (FIG. 9, RD2, or round 2) at a ratio of 1:1. Finally, primary T cells were again co-cultured with HCT.116 cells expressing both HER2 and HLA-A*02, or HER2 alone as a control (FIG. 9, RD3, or round 3) at a ratio of 1:1. As can be seen in FIG. 9, activation and inactivation of the T cells was reversible. In addition, T cells expressing only the HER2 CAR were exhausted by round 3 of co-culture, while T cells that expressed both the HER2 CAR and the HLA-A*02 LIR1 inhibitory receptor were not.

sity. Results are shown in FIG. 14 and summarized in Table 27. Blocker C2163 showed similar blocking activity to C2162 with lower level of activation and was not studied further.

TABLE 27

HER2 CARs and Inhibitory Receptors Screened

| Activator scFv | Blocker | Construct | EC50 (molecules/ cell) | IC50 (molecules/ cell) | T cell Expression | T cell Killing/ Blocking |
|---|---|---|---|---|---|---|
| CT292 | N/A | CT292 | 7,200 | N/A | +++ | ++ |
| | Murine | CT1110 | 7,600 | 28,000 | ++ | ++/++ |
| | Human-1 | CT1118 | 7,000 | 17,000 | + | ++/++ |
| | Human-2 | CT1184 | 6,400 | 44,800 | N/D | N/D |
| CT299 | N/A | CT299 | 7,800 | N/A | + | + |
| | Murine | CT1112 | 5,500 | 33,700 | + | +/+ |
| | Human-1 | CT1120 | 5,800 | 22,800 | + | +/++ |
| | Human-2 | CT1186 | 5,200 | 33,300 | N/D | N/D |
| CT1094 | N/A | CT1094 | 6,500 | N/A | +++ | ++ |
| | Murine | CT1113 | 4,900 | 38,800 | +++ | ++/++ |
| | Human-1 | CT1121 | 4,600 | 37,900 | ++ | ++/++ |
| | Human-2 | CT1187 | 4,500 | 87,400 | N/D | N/D |

Figure 10:
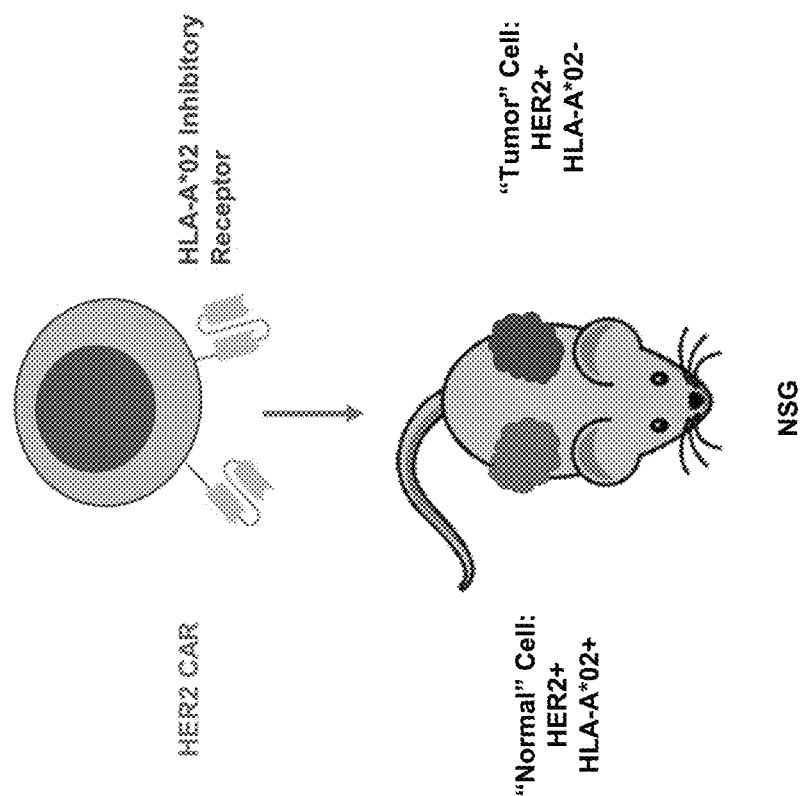
FIG. 10 is a diagram showing an experiment assaying the ability of primary T cells expressing the HER2 CAR and HLA-A*02 inhibitory receptor to kill target cells in a mouse xenograft model of a HER2 positive cancer that has lost expression of HLA-A*02.
Figure 11:
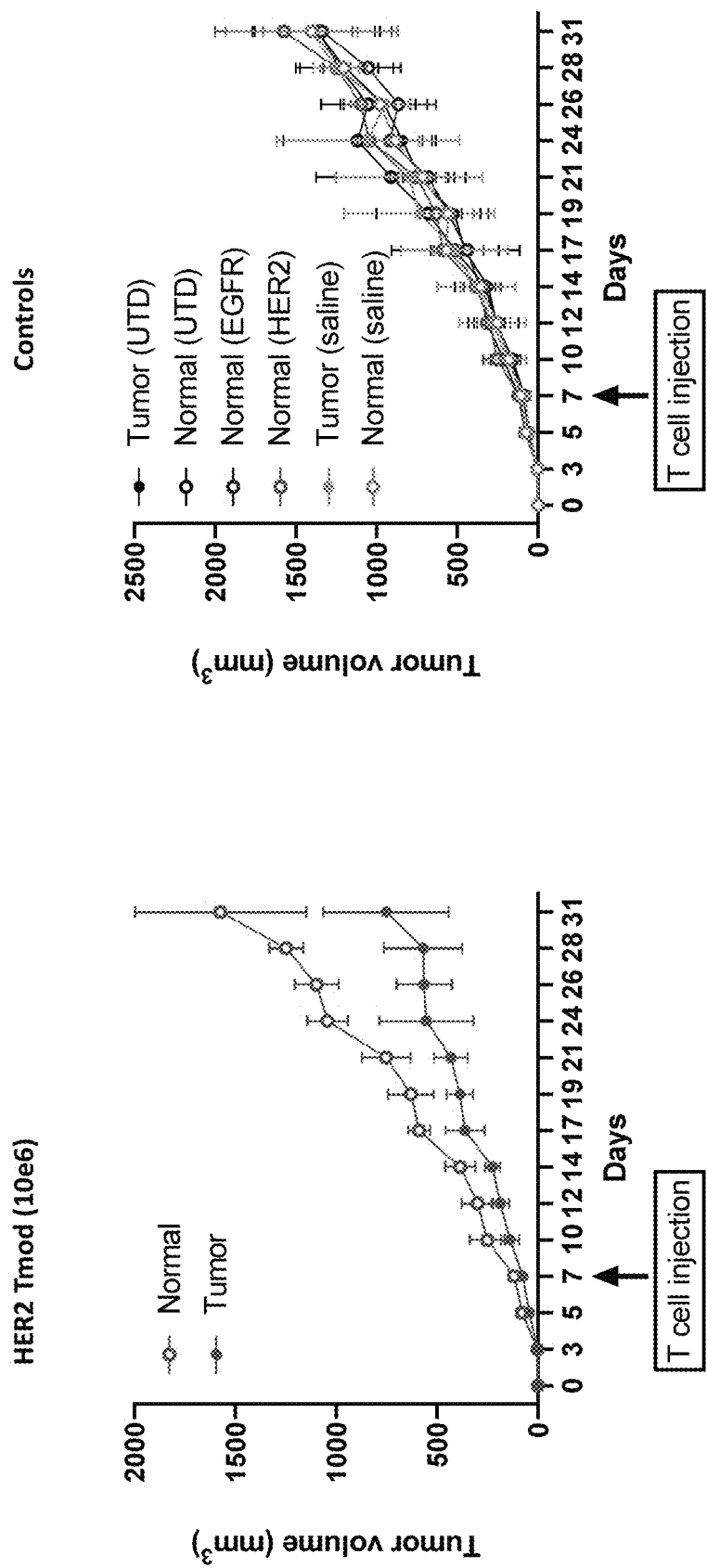
FIG. 11 is a pair of plots showing that primary T cells expressing the HER2 CAR and HLA-A*02 inhibitory receptor selectively kill tumor cells, and not normal cells, in a mouse xenograft model of a HER2 positive cancer that has lost expression of HLA-A*02.

Example 6: Activity of Primary T Cells Expressing HER2 CAR and HLA-A*02 Inhibitory Receptor in a Mouse Xenograft Model The optimal dose of T cells to be used for in vivo treatments and studies was assayed using a mouse xenograft model. Mice were implanted with 5e6 target cells in each flank. Target cells were HCT.116 wild type cells ("normal" cells) which are HER2+ and HLA-A*02 positive, or HCT.116 in which HLA-A*02 had been knocked out ("tumor" cells). The normal target cells were grafted in one flank and the tumor cells were grafted in the other flank. Mice were treated with T cells from HLA-A*02 negative donors which were either untransduced, or transduced with the HER2 CAR1 activator receptor (CT292) in combination with the C2162 HLA-A*02 LIR1 inhibitory receptor. Xenograft model mice were injected with 2e6, 5e6, or 10e6 total T cells, and tumor volume was monitored in the days following T cell injection. A diagram of the experiment is shown in FIG. 10. As seen in FIG. 11, T cells expressing the combination of the HER2 CAR and the HLA-A*02 LIR inhibitory receptor showed cytotoxicity and blocking effect in the xenograft in vivo model and a dose of 1e7 total T cells per mouse.

Example 7: Activity of HER2 CAR and HLA-A*02 Inhibitory Receptor Expressed in Jurkat Cells Nine candidates of receptor pairs were tested. scFvs CT292, CT299, or CT1094 were paired with no modules (CAR only), murine blocker (C1765), humanized blocker 1 (C2162), or humanized blocker 2 (C2163). The various combinations of blockers and inhibitors are shown in Table 27.

Figure 15:
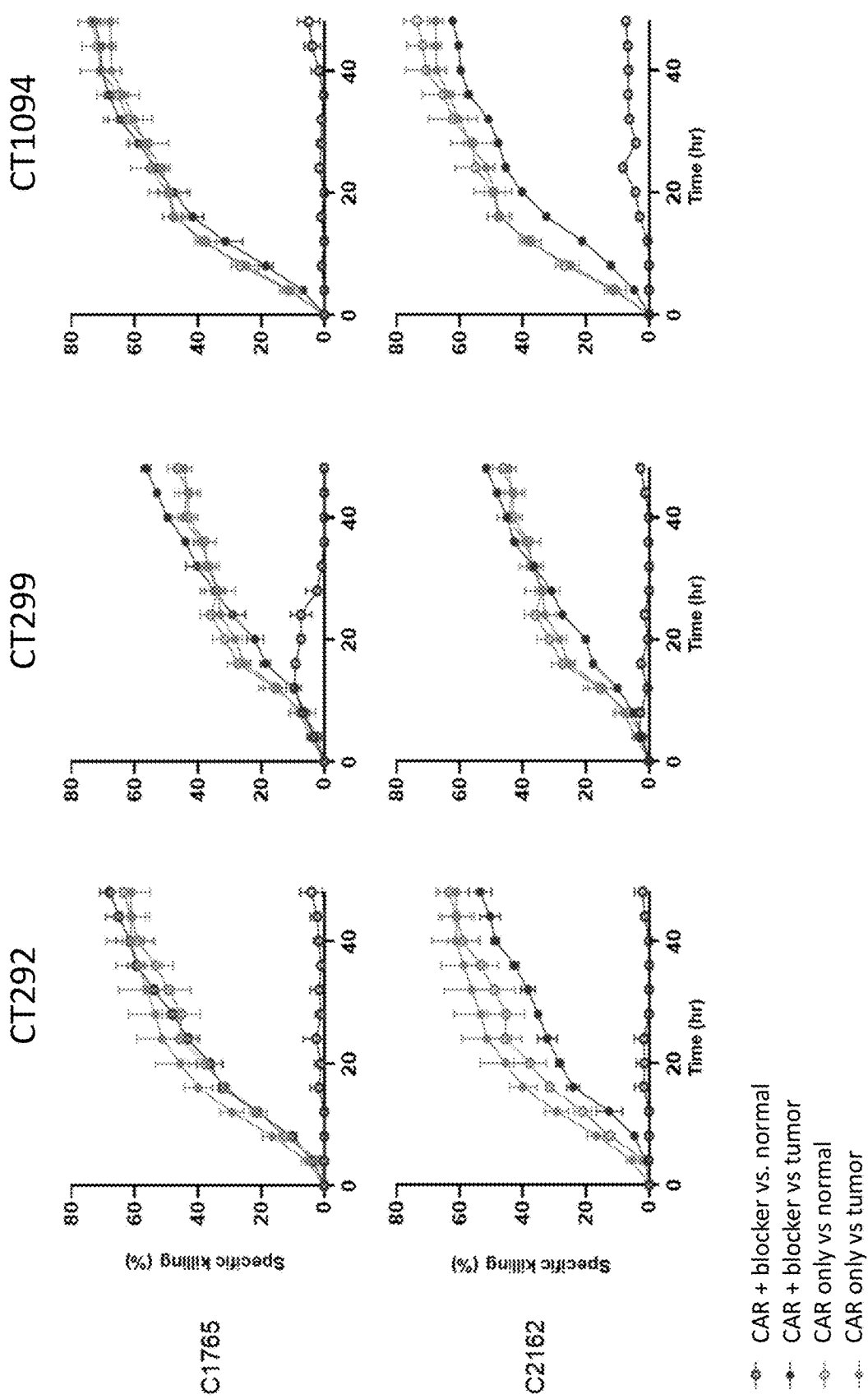
FIG. 15 is a series of plots showing killing of HeLa target cells by primary T cells transduced with 6 candidates of activator-blocker pairs at 1:1 E:T ratio. The activator-blocker pairs comprise scFvs of CT292 (left column), CT299 (middle column), or CT1094; right column) with blockers in murine form (C1765; top row) or humanized form (C2162; bottom row).

Activator and blocker sensitivity was measured using the mRNA titration assay. mRNA was titrated and used to transfect HER2− HeLa target cells, which was then cocultured with Jurkat cells expressing the appropriate HER2 constructs and NFAT luciferase. After 6 hours of coculture, Jurkat cell activation was measured by luminescence inten- Example 8: Selective Cell Killing by Primary T Cell Expressing HER2 CAR and HLA-A*02 Inhibitory Receptor Primary T cells were transduced with six activator-blocker receptor pairs and measured for acute cytotoxicity function on HeLa target cells at 1:1 E:T ratio. Cells were transfected with a HER2 CAR (CT292, CT299, or CT1094) only or with HER2 CAR and blockers in murine form (C1765) or humanized form (C2162). Results are shown in FIG. 15. Cell transfected with any one of the receptor pairs tested selectively killed tumor cells but spared normal cells, while cells transfected with CARs only killed both cell types.

Figure 16:
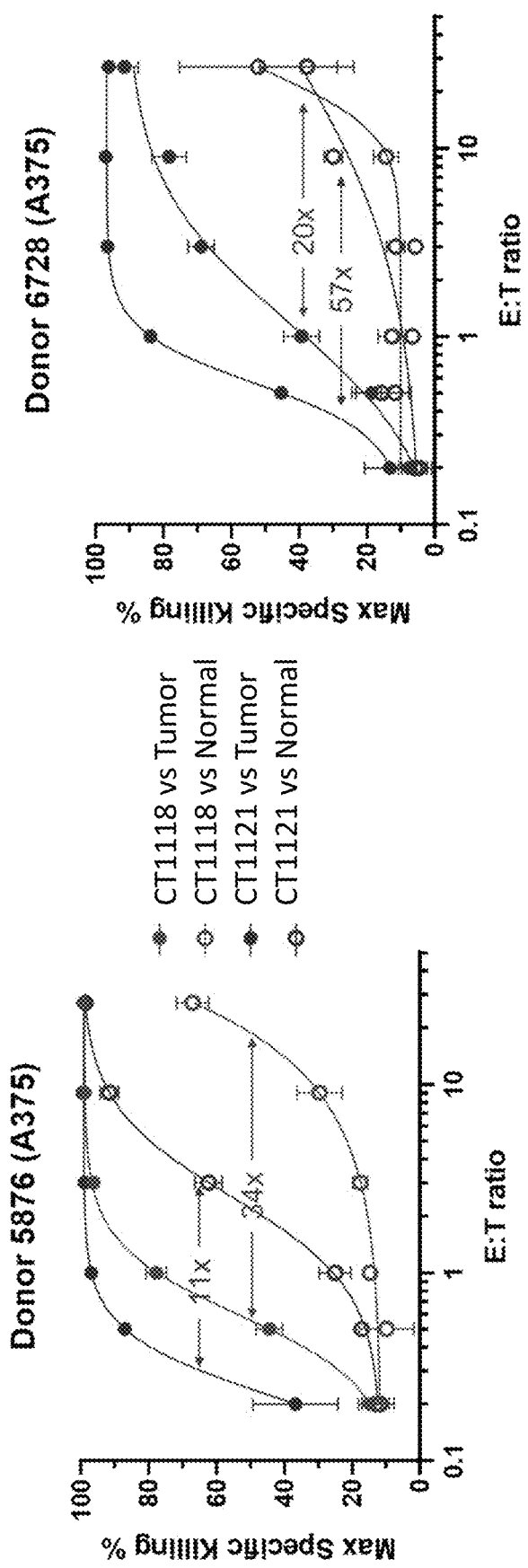
FIG. 16 is a pair of plots showing cell killing of tumor (solid circles) or normal (hollow circles) A375 target cells by CT1118 or CT1121 constructs. This analysis was conducted in two HLA-A*02− T cell donors (left vs right).

Primary T cells were transduced with HER2 CAR CT292 and human blocker 1 (CT1118 cells) or with HER2 CAR CT1094 and human blocker 1 (CT1121 cells) and co-cultured with A375 normal (HLA-A*02-proficient) or tumor (HLA-A*02-deficient) target cells over a wide range of E:T ratios for 48 hours, and the maximum specific killing at each E:T ratio was recorded. The data was fitted using nonlinear regression to derive the E:T ratio giving rise to 50% maximum cytotoxicity (EC50). Results are shown in FIG. 16, where the fold-change of EC50 from tumor to normal target cells is indicated as the selectivity ratio. This analysis was conducted in two individual HLA-A*02− T cell donors (left vs right). Overall, the CT1211 receptor combination is more potent than CT1118. Both constructs are selective, but the CT1118 receptor combination appears to protect normal A375 target cells better over the range of E:T ratios tested.

Example 9: Further Characterization of the CT1118 Receptor Combination

Figure 17:
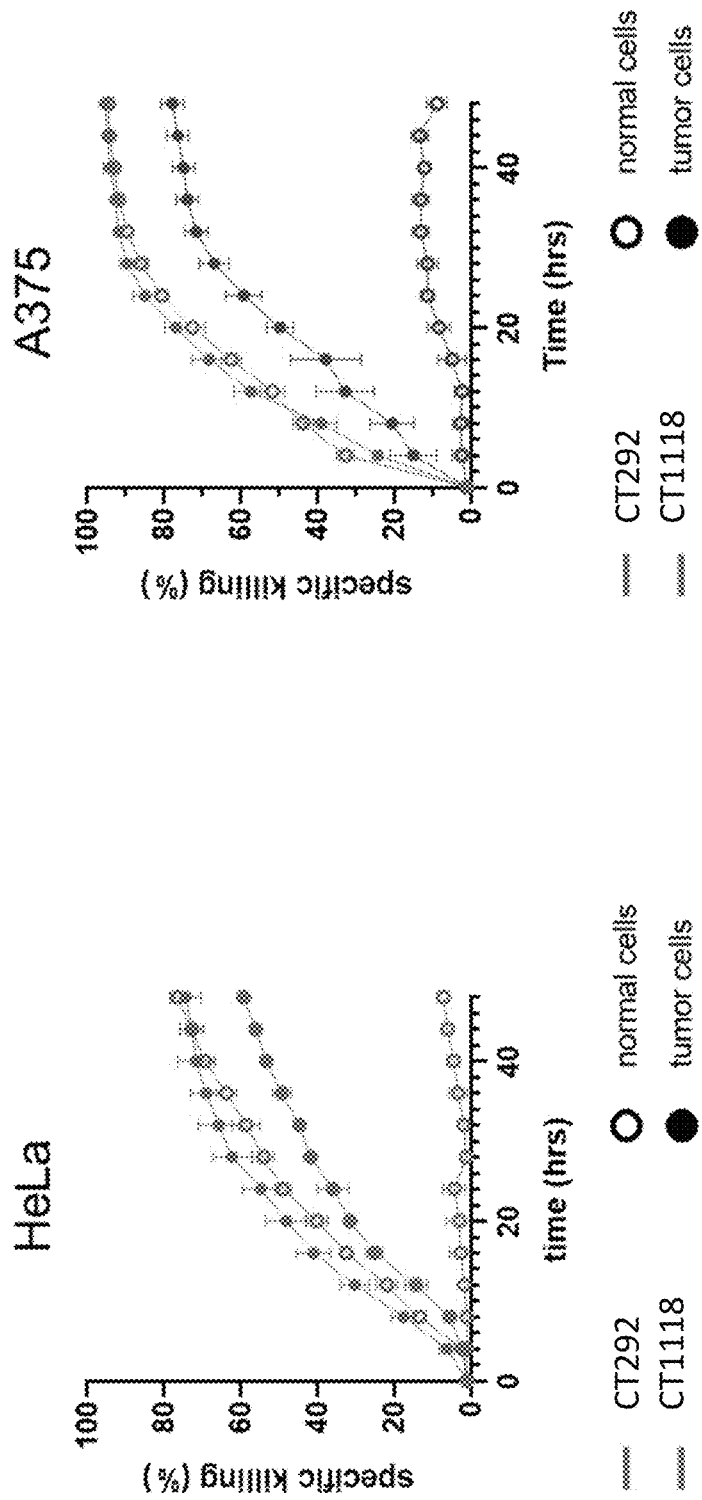
FIG. 17 is a pair of plots showing cell killing of HeLa target cells (left panel) or A375 target cells (right panel) by primary T cell transfected with HER2 CAR1 (CT292) and CAR/human blocker (CT2162) at 1:1 E:T ratio.

The CT1118 receptor combination (CT292 CAR and human blocker CT2162) was benchmarked against the CT292 CAR alone. Primary T cells were transduced with CT292 alone or in combination with CT2162 and acute cytotoxicity at 1:1 E:T ratio on HeLa target cells or A375 target cells was evaluated. Results are shown in FIG. 17. CT292 cells killed both tumor and normal cells than CT1118 cells. CT1118 cells killed tumor cells with similar efficiency as the CT292 cells while sparing normal cells, thus demonstrating improved selectivity of the receptor combination over the CAR alone.

Figure 18:
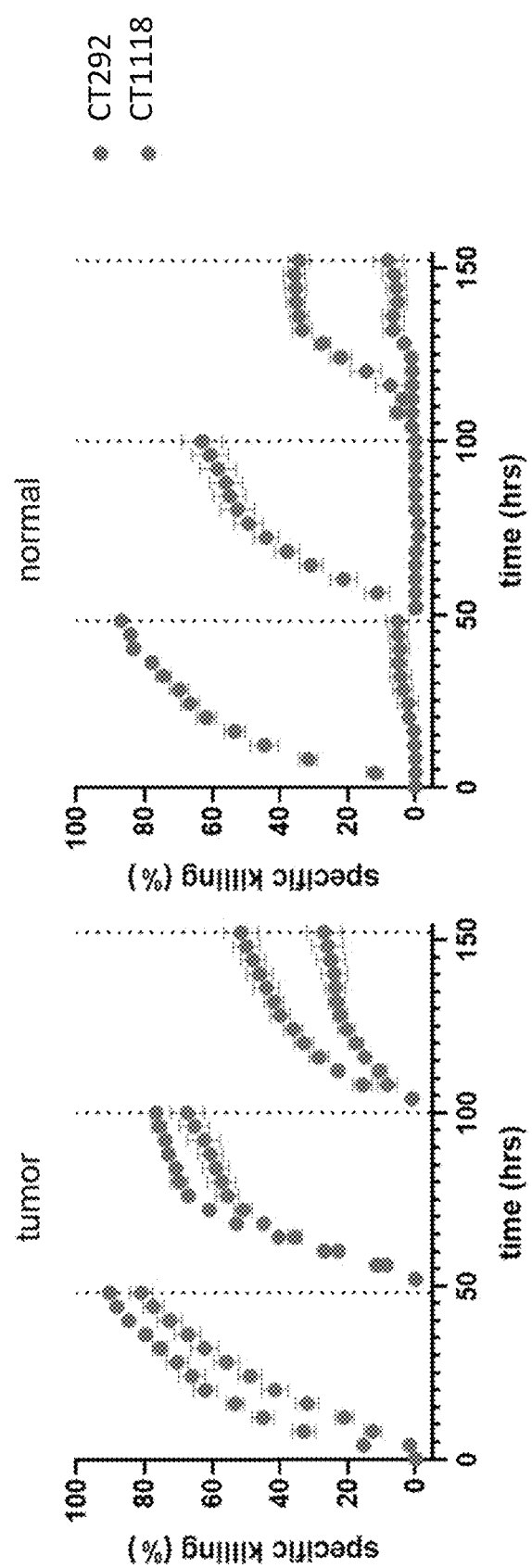
FIG. 18 is a pair of plots showing cell killing of HER2+/HLA-A*02− HeLa target cells (left panel) or normal HeLa target cells (right panel) by primary T cells transfected with HER2 CAR1 or CT2162 in three 48-hour rounds of tumor rechallenge on at 1:1 E:T ratio.

Next, the activity and selectivity of the CT1118 cells was evaluated after rechallenge. Results are shown in FIG. 18. Primary CT292 T cells and CT1118 T cells maintained similar potency for up to three 48-hour rounds of tumor rechallenge on HER2+/HLA-A*02− HeLa target cells at 1:1 E:T ratio. However, the CT1118 cells continuously spared HER2+/HLA-A*02+ HeLa target cells, while CT292 cells did not.

Example 10: Reversibility of CT1118 Function

Figure 19:
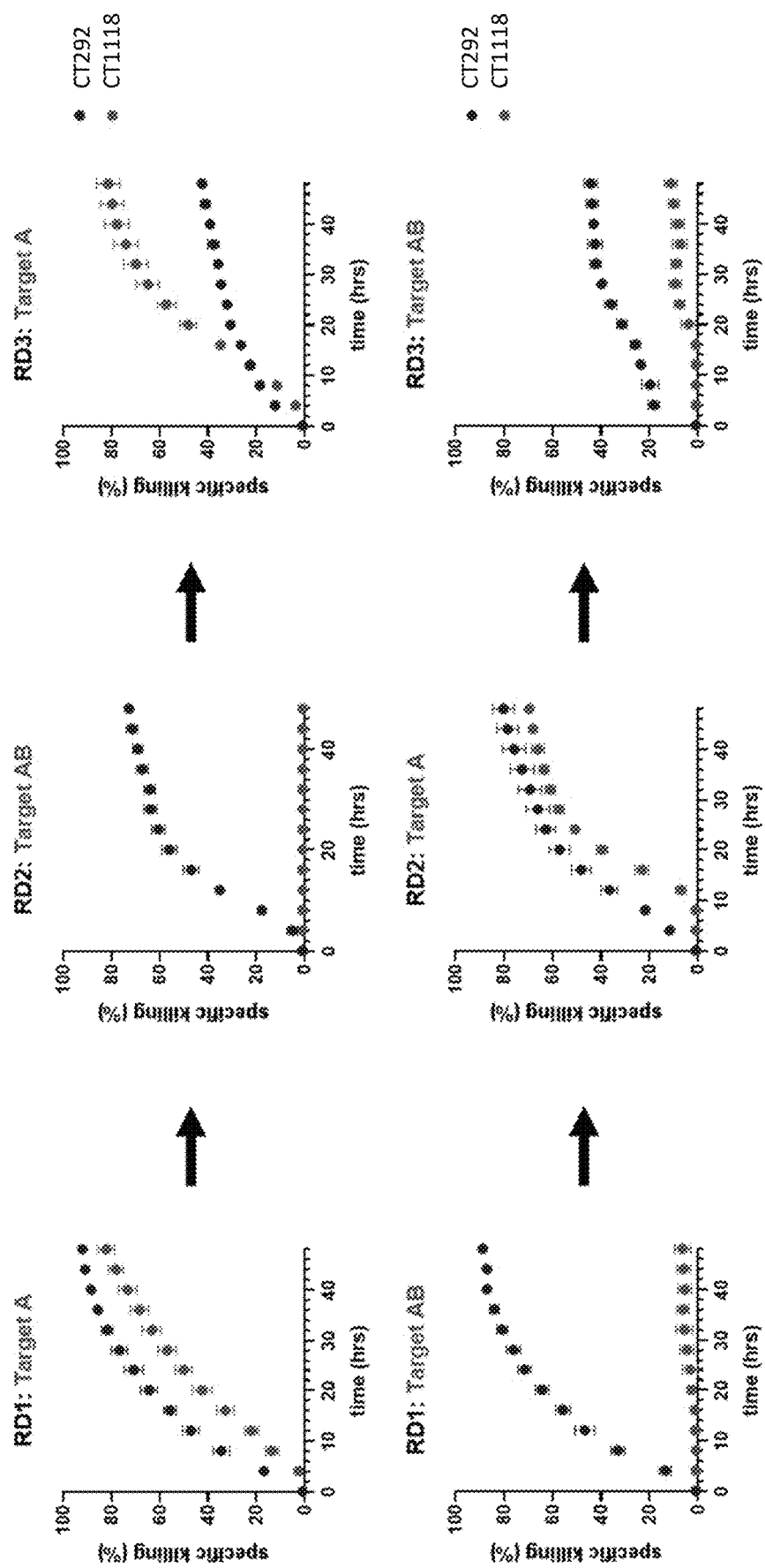
FIG. 19 is a series of plots showing reversibility of the ability of HER2 CAR1 and CT2162 to kill tumor (target A; HER2+/HLA-A*02−) or normal (target AB; HER2+/HLA-A*02+) HeLa cells in 48-hour rounds at 1:1 E:T ratio. Arrows indicate the sequence of exposure: tumor→normal-→tumor (top panel) vs normal→top→normal (bottom panel).
Figure 20:
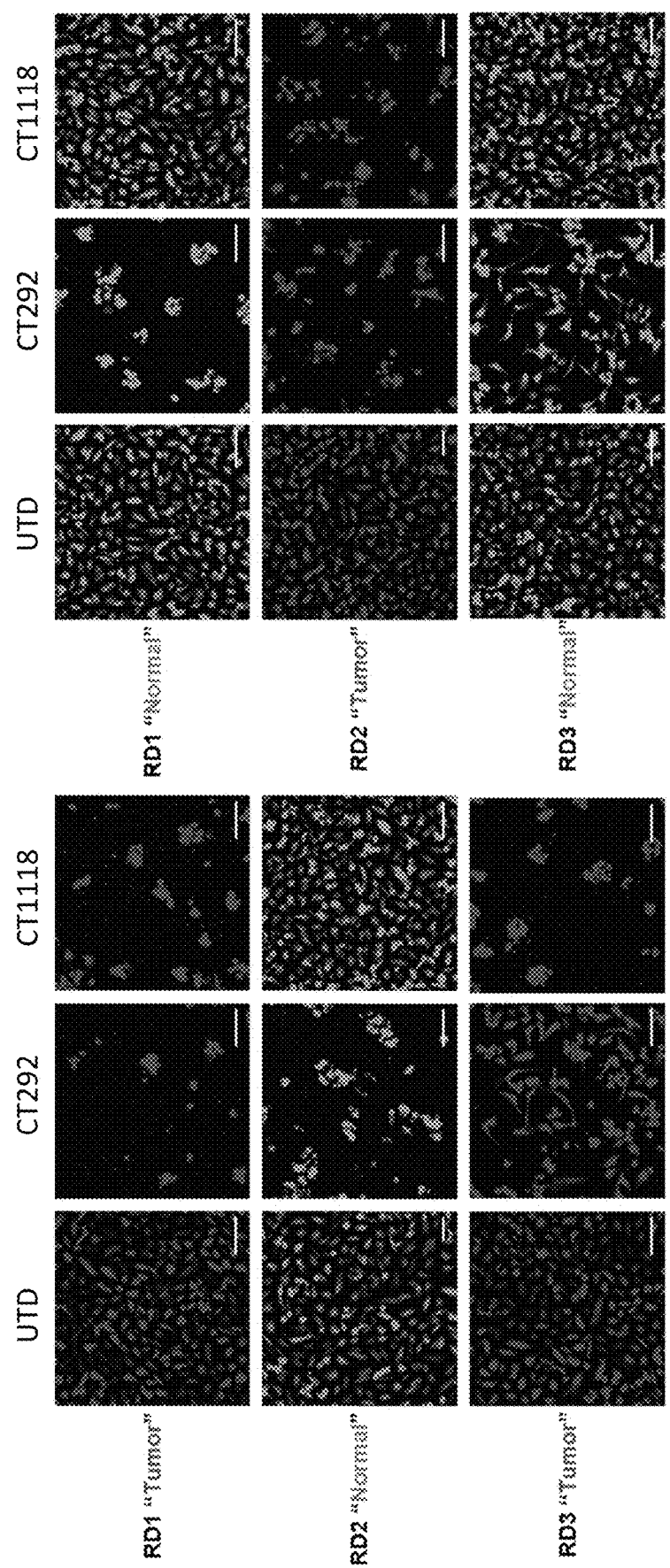
FIG. 20 is a series of images showing reversibility of the ability of untransduced T cells (UTD), HER2 CAR1 T cells, or CT2162 cells to kill HER2+/HLA-A*02− HeLa cells ("Tumor") or HER2+/HLA-A*02+ HeLa cells ("Normal") at 1:1 E:T ratio. Images of the target cells at t=48 hrs are shown for each sequence i.e. left panel: tumor→normal-→tumor vs right panel: normal→tumor→normal. Scale bar=50 μm.
Figure 21:
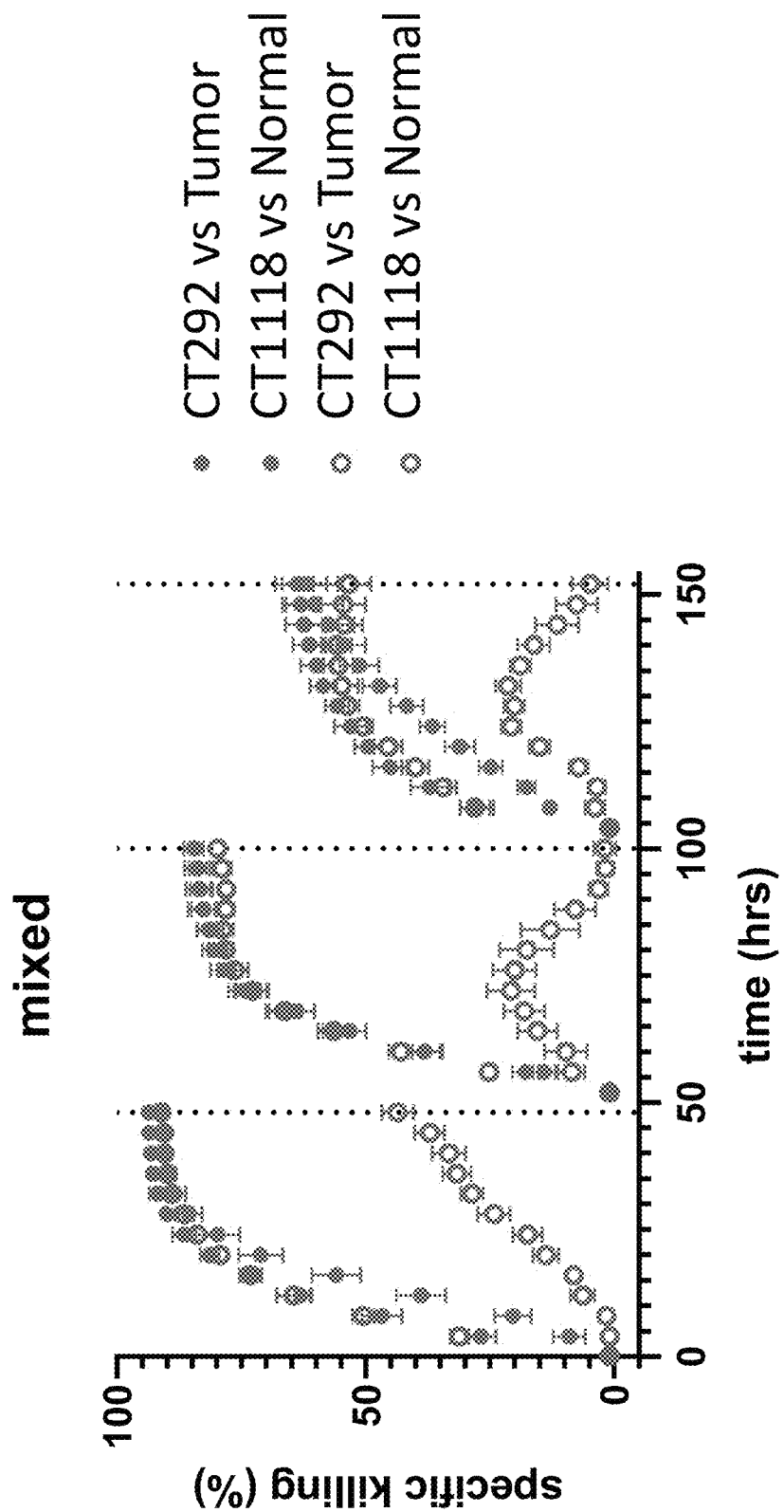
FIG. 21 is a plot showing selective killing of tumor (target A; solid circles) and normal (target AB; hollow circles) HeLa target cells by HER2 CAR1 and CT2162 cells at a 1:1 ratio over three rounds of 48-hours.
Figure 22:
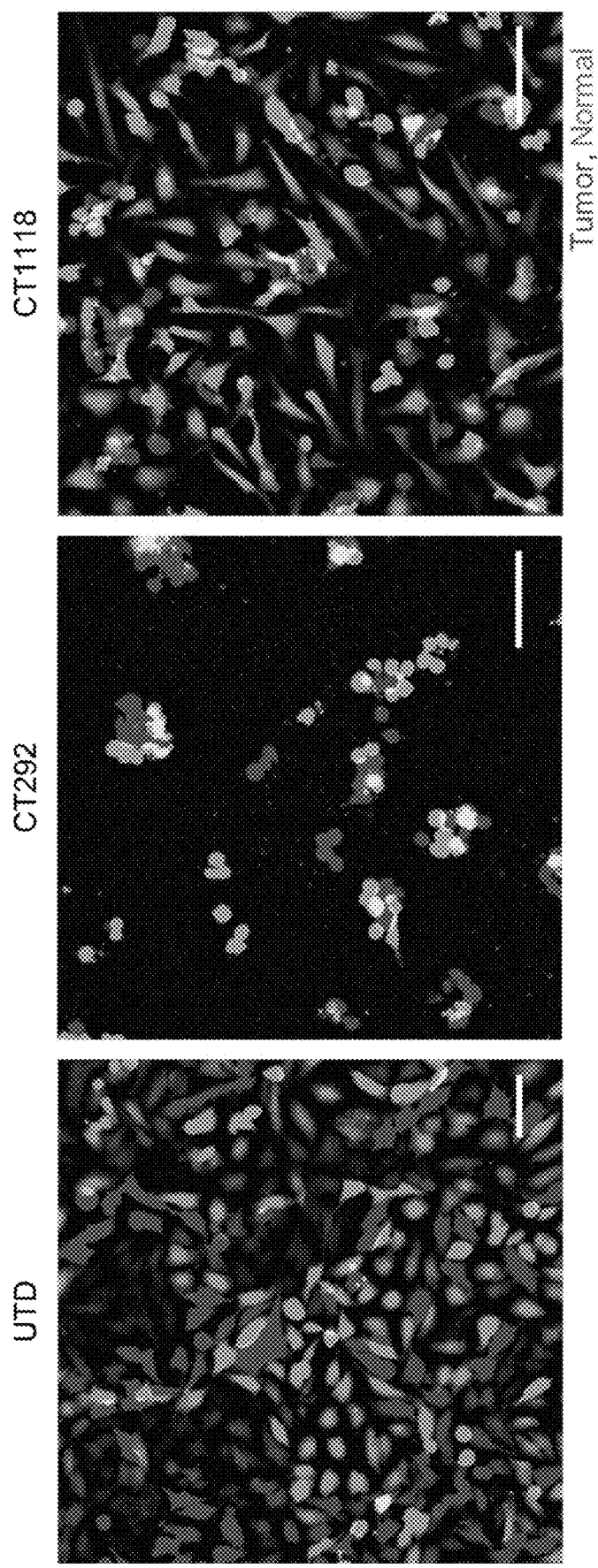
FIG. 22 is a series of images showing selective killing of tumor but not normal HeLa target cells in a mixed culture after 20 hours of coculture with untransduced (UTD; left), CT292 (middle), or CT118 (right) cells.
Figure 23:
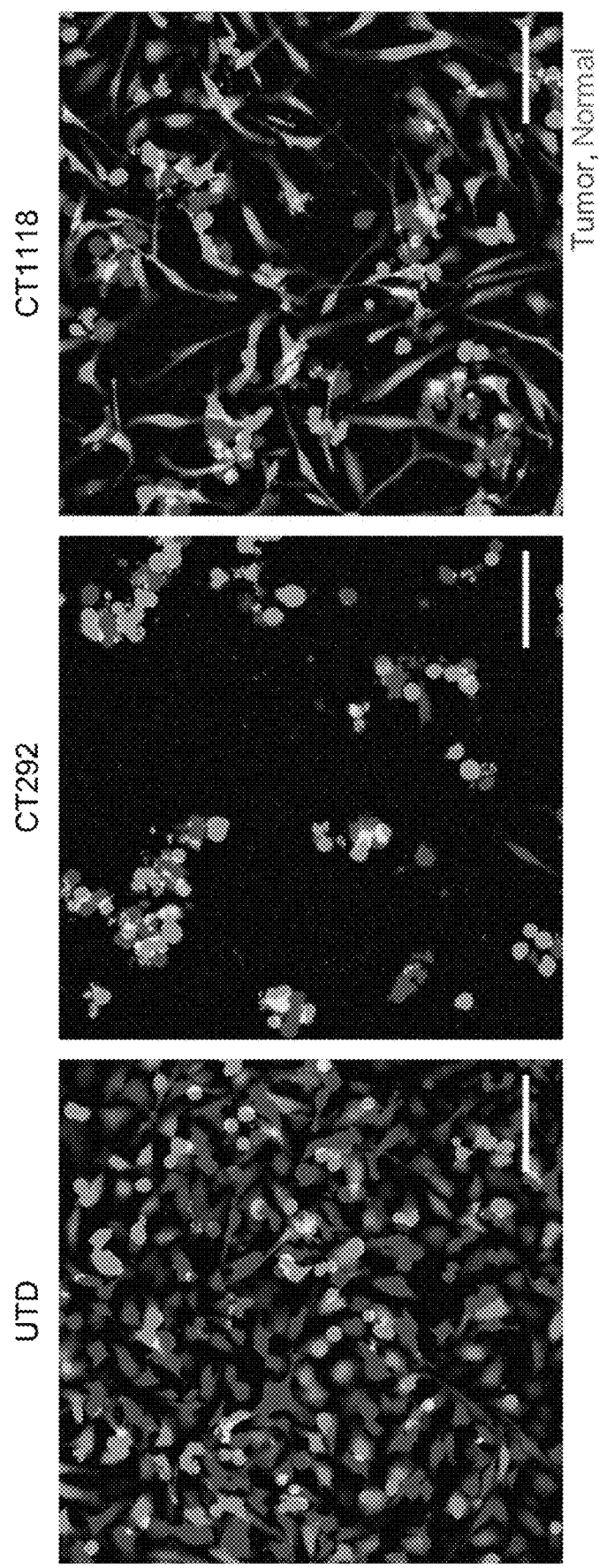
FIG. 23 is a series of images showing selective killing of tumor but not normal HeLa target cells in a rechallenge (i.e. round 2) of mixed culture after 24 hours of coculture with untransduced (UTD; left), CT292 (middle), or CT118 (right) cells.

The reversibility of the function of CT292 and CT1118 cells was evaluated by coculturing CT292 cells and CT1118 cells with HeLa isotypes of tumor (target A; HER2+/HLA-A*02−) or normal (target AB; HER2+/HLA-A*02+) for 48 hours per round at 1:1 E:T ratio. Results are shown in FIG. 19. CT292 T cells killed both cell types while CT1118 cells showed reversible activation. Moreover, CT1118 cells showed inactivation of cytotoxicity, which was dependent on the HLA-A*02 status. This reversibility of function was observed regardless of the sequence of exposure, tumor-→normal→tumor or normal→top→normal. FIG. 20 shows images of the target cells at t=48 hrs for each sequence (left panel: tumor→normal→tumor; right panel: normal→tumor-→normal). Regardless of the sequence, CT1118 cells exhibited reversible function. UTD treatment resulted in healthy, adherent target cells regardless of HLA-A*02 expression while CT292 cells killed both tumor and normal target cells. CT1118 cells selectively killed tumor cells but spared normal cells Example 11: Selectivity Toxicity of CT1118 in Mixed Culture Selective cytotoxicity was assessed by coculturing CT292 cells or CT1118 cells with tumor and normal HeLa target cells mixed at a 1:1 ratio for three 48-hour rounds. Results are shown in FIG. 21. CT1118 cells showed continuous selective killing of tumor cells, whereas CT292 cells killed both cell types. FIG. 22 shows images of tumor and normal HeLa target cells in a mixed culture after 20 hours of coculture with untransduced T cells, CT292 cells, or CT1118 cells. CT292 cells killed both normal and tumor cells, while CT1118 cells selectively killed tumor cells. FIG. 23 shows that the selectivity of CT1118 is maintained after a rechallenge for 24 hours.

Example 12: Effects of CT292 In Vivo

Figure 24:
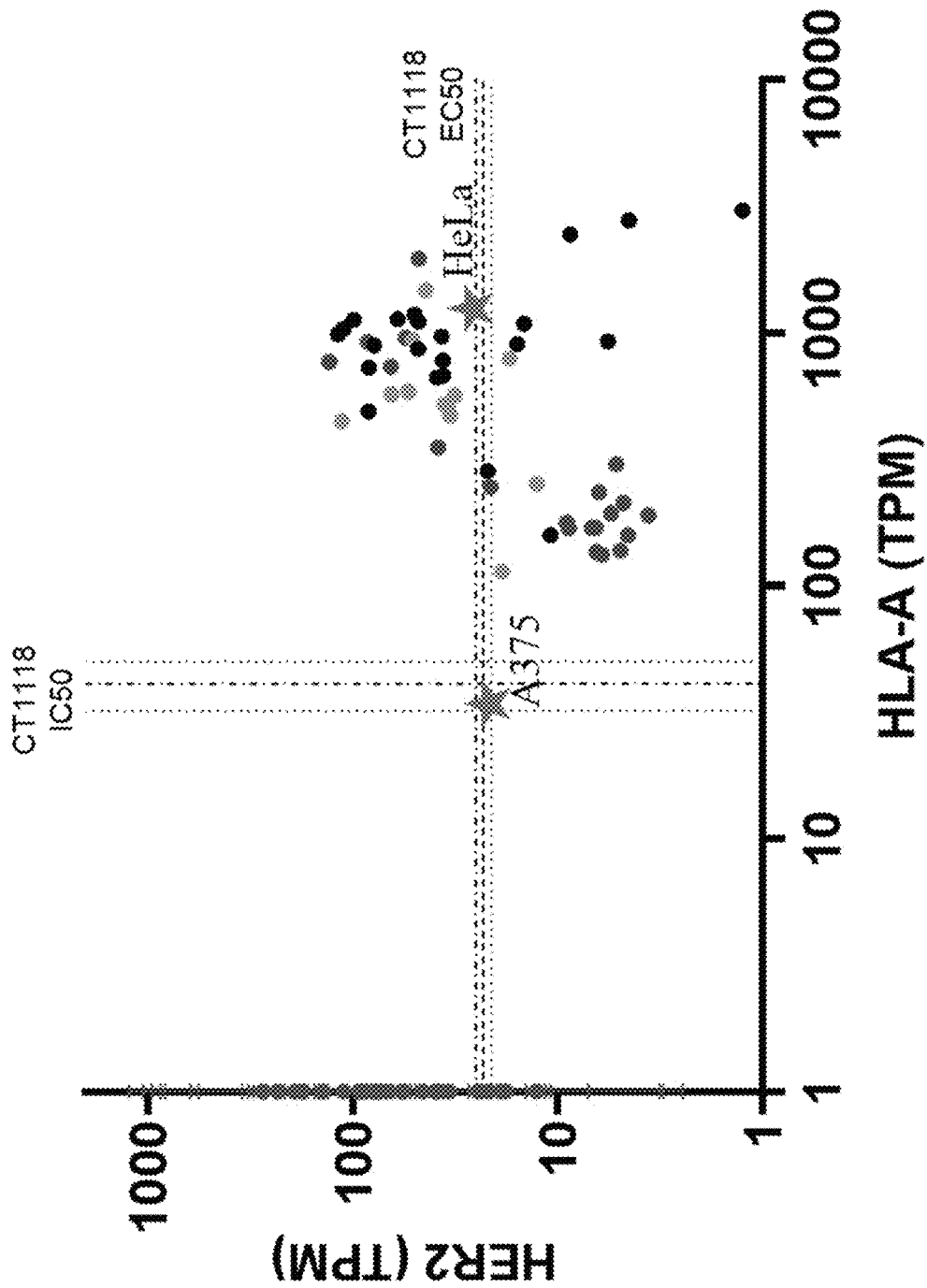
FIG. 24 shows a Quant Plot of HER2 and HLA-A2 expression in normal, tumors (assuming LOH of HLA-A2), and cell lines (stars). The EC50 and IC50 of CT1118 are marked by dashed lines. Lighter dashed lines show the range of measured EC50 and IC50s. A375, the cell line used in the in vivo study described in Example 12, has HER2 and HLA-A2 expression similar to the EC50 and IC50 of HER2 CT1118, respectively.

1E6 A375 A2+ (normal) and A2− (tumor) were grafted on each flank of the NSG mice on day 0. A375 cells have HER2 and HLA-A2 expression similar to the EC50 and IC50 of CT1118, respectively (FIG. 24). On day 8, untransduced ("UTD"), CT292 cells, and CT1118 cells were injected at 20 million cells per mouse. Tumor volumes were measured by caliper every 2-3 days after injection.

Figure 25:
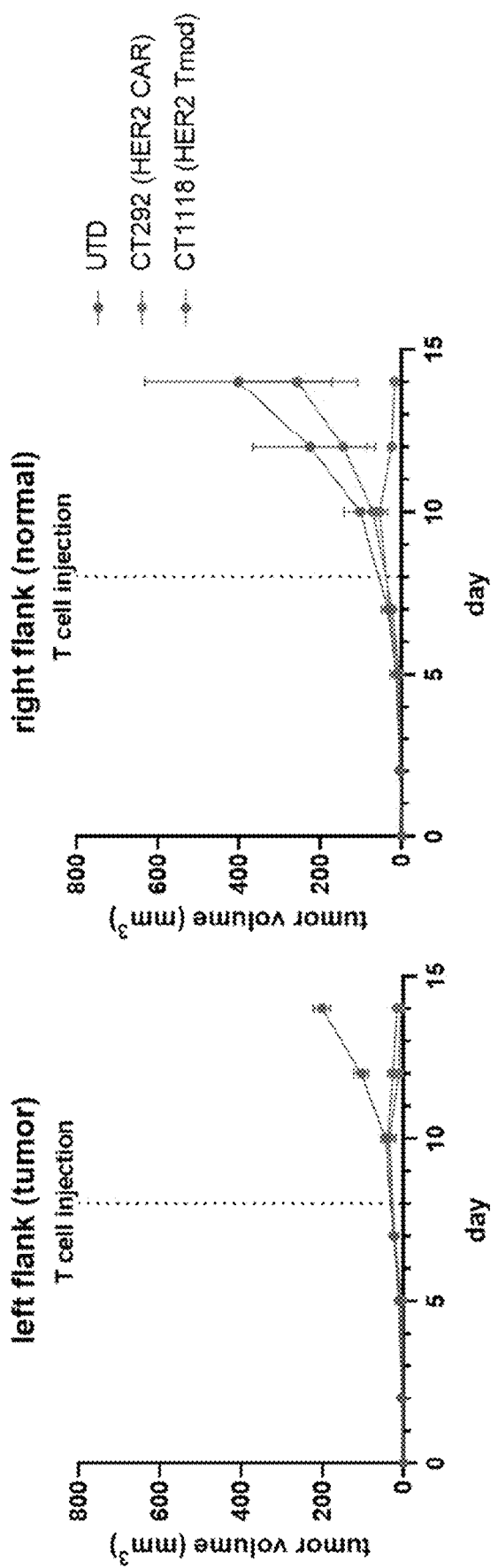
FIG. 25 shows tumor volume in mice bearing tumor (left panel) and normal (right panel) A375 xenografts after treatment with Untransduced ("UTD") cells, CT292 cells, and CT1118 cells.

Results are shown in FIG. 25. CT292 cells reduced both tumor and normal xenografts, while CT1118 cells selectively reduced the tumor xenograft but not the normal xenograft.

Example 13: In Vitro Efficacy of CT292 Paired With HLA-A03, HLA-A*11 or HLA-B807 Blockers Jurkat NFAT luciferase (JNL) cell inhibition with the CT292 paired with either HLA-A*03:01 blocker 26 (comprising an scFv of SEQ ID NO: 405), HLA-A*11:01 blocker 4 (comprising an scFv of SEQ ID NO: 345), or HLA-B*07:02 blocker BB7.1 (comprising an scFv of SEQ ID NO: 21806) was measured in an mRNA titration assay.

Figure 26A:
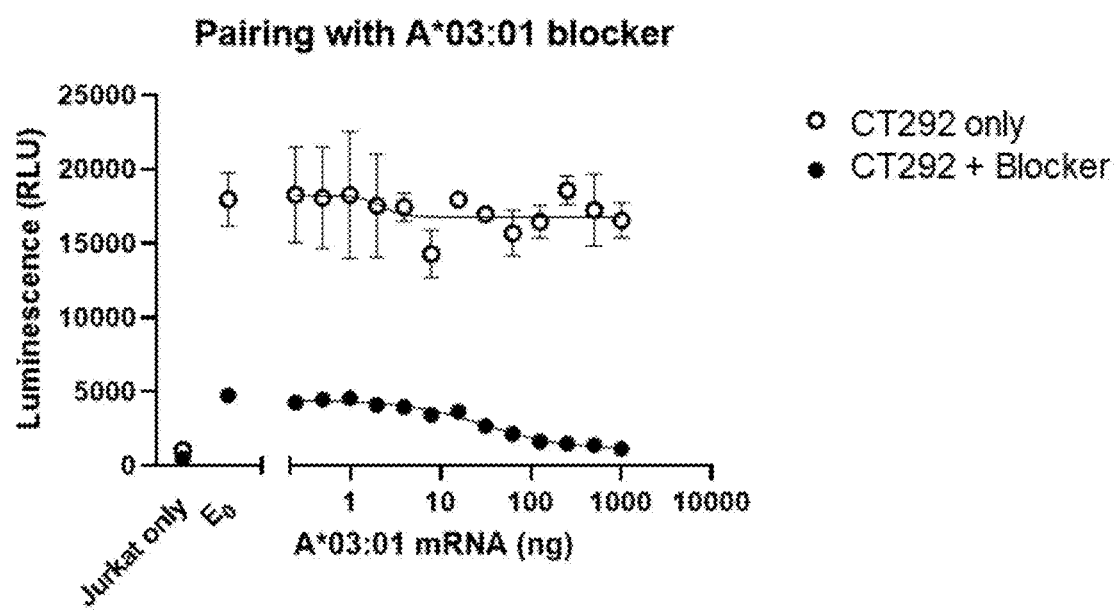
FIGS. 26A-26C show Jurkat NFAT luciferase (JNL) cell inhibition with CT292 paired with either a HLA-A*03 blocker, a HLA-A*11 blocker, or a HLA-B*07 blocker measured in an mRNA titration assay.
Figure 26B:
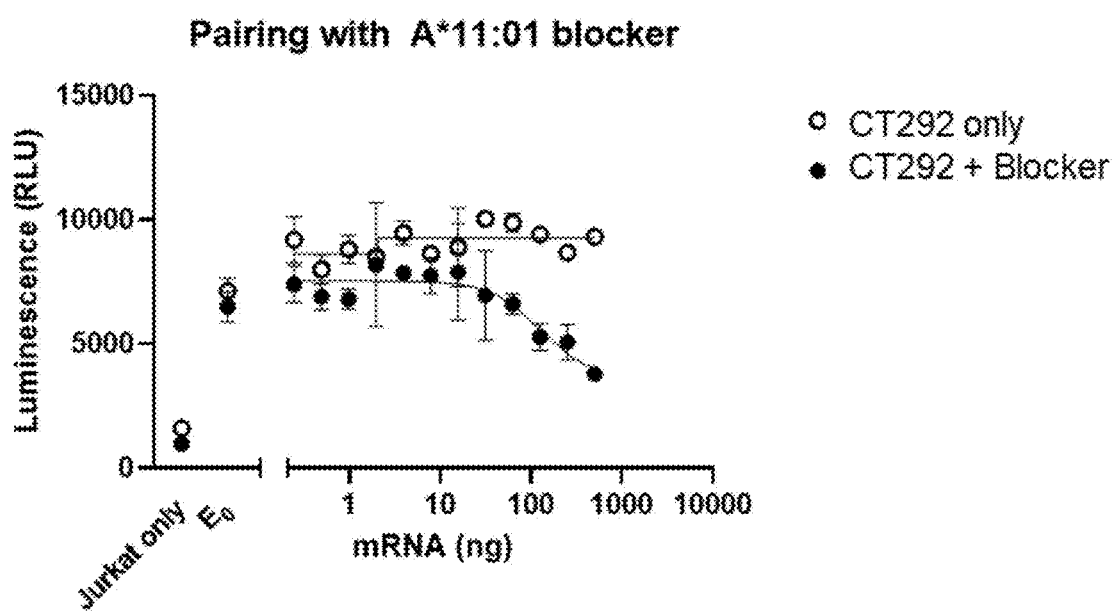
Figure 26C:
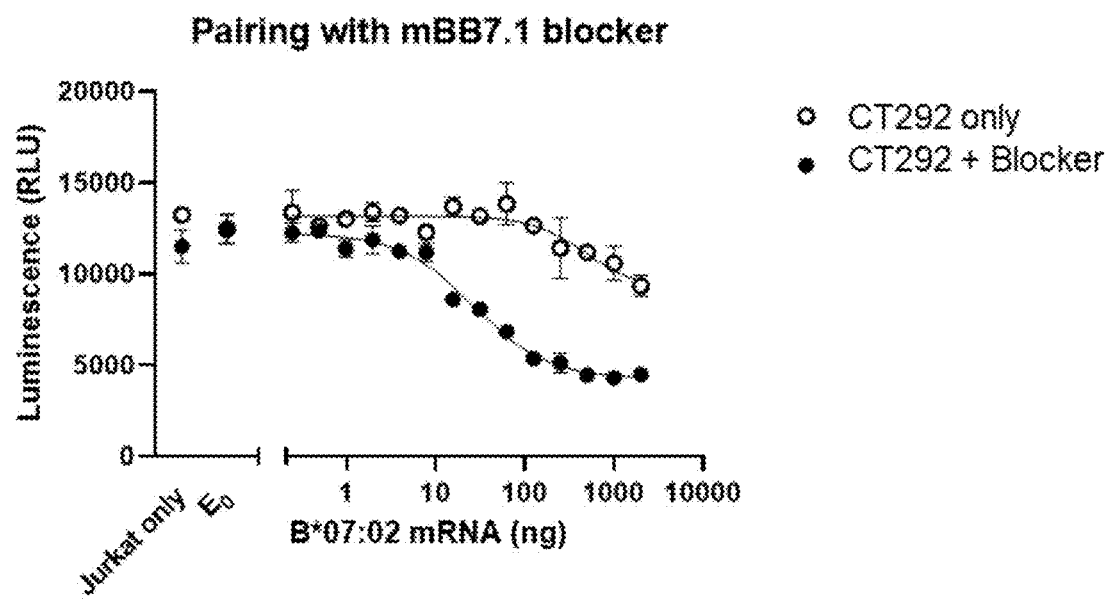

JNL cell activation was measured in an mRNA titration assay using HeLa cells transfected with mRNA. HeLa cells were transfected with serially-diluted mRNA encoding either the A*03:01, A*11:01, or B*07:02 blocker. JNL cells were transiently transfected with CT292 and negative control vector (open circle), or CT292 and either the HLA-A*03:01, HLA-A*11:01, or HLA-B*07:02 blocker (closed circle). The functional response was assessed after a 6-hour co-culture of 5,000 JNL cells and 5,000 HeLa cells. Data are shown in FIGS. 26A-26C. The results show that all blockers block activation of the HER2 CAR in the presence of titrated corresponding HLA mRNAs.

Figure 27:
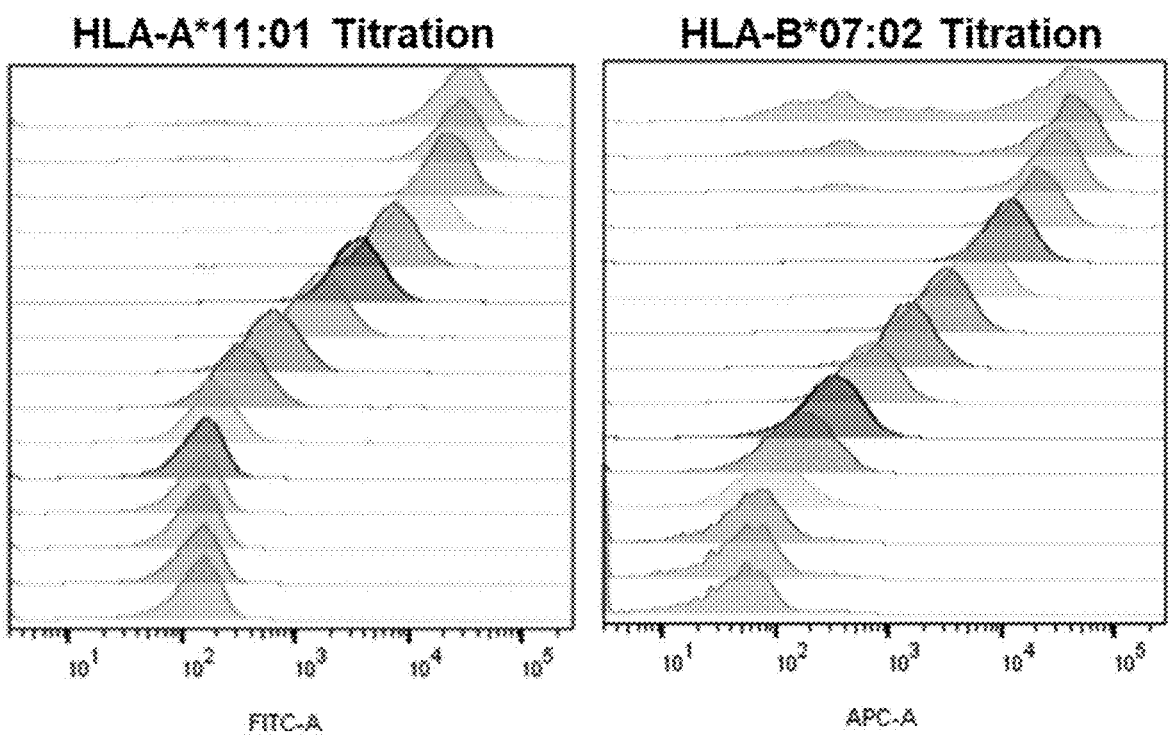
FIG. 27 shows titrated HLA-A*11:01 or HLA-B*07:02 protein on the surface of HeLa cells upon mRNA transfection. HeLa cells were transfected with 2× serially-diluted mRNA encoding either FLAG-tagged HLA-A*11:01 or FLAG-tagged HLA-B*07:02 with top dose of 2000 ng per 200,000 HeLa cells. The bottom panel contains 0 ng mRNA.

HLA-A*11:01 or HLA-B*07:02 protein on the surface of HeLa cells upon mRNA transfection was assessed by flow cytometer. HeLa cells were transfected with 2× serially-diluted mRNA encoding either FLAG-tagged HLA-A*11:01 or FLAG-tagged HLA-B*07:02 with top dose of 2000 ng per 200,000 HeLa cells. Cells were transfected using the 4D nucleofector X-Unit (Lonza) in the 20 uL format, according to manufacturer's instructions. Transfected cells were transferred to MEM media containing 10% FBS and 0.1% penicillin and streptomycin and incubated at 37° C., 5% CO2 for 16-24 hours. On the next day, cells were mechanically detached and washed twice with 100 uL FACS buffer (PBS+1% BSA), then stained with either anti-HLA*A11:01 (One Lambda 0284HA) or anti-B*07:02 mRNA (BB7.1) antibody for 30 minutes on ice. After 2× wash with 100 uL FACS buffer, cells were stained with either anti-mouse IgG FITC or APC secondary antibody for 30 minutes on ice. Cells were then washed twice with FACS buffer and fluorescence was measured. Results are shown in FIG. 27, where the bottom panel contains 0 ng mRNA.

SEQUENCE LISTING

The patent contains a lengthy sequence listing. A copy of the sequence listing is available in electronic form from the USPTO web site (https://seqdata.uspto.gov/?pageRequest=docDetail&DocID=US11730764B2). An electronic copy of the sequence listing will also be available from the USPTO upon request and payment of the fee set forth in 37 CFR 1.19(b)(3).

What is claimed is:

1. An immune cell responsive to loss of heterozygosity at an HLA-A*02 allele in a cancer cell, comprising:
   (a) an activator receptor comprising an extracellular ligand binding domain specific to an erb-b2 receptor tyrosine kinase 2 (HER2) antigen, wherein the activator receptor comprises a polypeptide sequence at least 95% identical to SEQ ID NO: 291, wherein the extracellular ligand binding domain of the activator receptor comprises an scFv comprising
      (i) a heavy chain variable (VH) region comprising complement determining regions (CDRs) CDR-H1 of SEQ ID NO: 36, CDR-H2 of SEQ ID NO: 38, and CDR-H3 of SEQ ID NO: 41; and
      (ii) a light chain variable region (VL) comprising CDRs CDR-L1 of SEQ ID NO: 30, CDR-L2 of SEQ ID NO: 32, and CDR-L3 of SEQ ID NO: 34,
   (b) an inhibitory receptor comprising an extracellular ligand binding domain specific to an HLA-A*02 allele of HLA-A, wherein the inhibitory receptor comprises a polypeptide sequence at least 95% identical to SEQ ID NO: 305, wherein the extracellular ligand binding domain of the inhibitory receptor comprises an scFv comprising:
      (i) VH region comprising CDRs CDR-H1 of SEQ ID NO: 95, CDR-H2 of SEQ ID NO: 98, and CDR-H3 of SEQ ID NO: 101; and
      (ii) a VL region comprising CDRs CDR-L1 of SEQ ID NO: 87, CDR-L2 of SEQ ID NO: 90 or SEQ ID NO: 91, and CDR-L3 of SEQ ID NO: 92.

2. The immune cell of claim 1, wherein the activator receptor and the inhibitory receptor together specifically activate the immune cell in the presence of the cancer cell.

3. The immune cell of claim 1, wherein the immune cell is a T cell.

4. The immune cell of claim 3, wherein the T cell is a CD8+ CD4− T cell.

5. The immune cell of claim 1, wherein the scFv comprises a sequence having at least 97% identity to a sequence selected from the group consisting of SEQ ID NO: 51.

6. The immune cell of claim 1, wherein the activator receptor is a chimeric antigen receptor (CAR) and wherein the CAR comprises a CD8 hinge.

7. The immune cell of claim 6, wherein the CAR comprises a transmembrane domain isolated or derived from CD8 or CD28.

8. The immune cell of claim 7, wherein the CAR comprises CD28, 4-1BB and CD3z intracellular domains.

9. The immune cell of claim 1, wherein the inhibitory receptor comprises LILRB1 hinge and transmembrane domain.

10. The immune cell of claim 1, wherein the immune cell is modified to inactivate, or reduce or eliminate expression or function of an endogenous gene encoding an allele of an endogenous WIC class I polypeptide.

11. The immune cell of claim 10, wherein the immune cell is modified to reduce or eliminate expression of the B2M gene product.

12. A pharmaceutical composition, comprising a therapeutically effective amount of the immune cells of claim 1.

13. The immune cell of claim 3, wherein the T cell is a CD8− CD4+ T cell.

14. A polynucleotide system, comprising one or more polynucleotides comprising polynucleotide sequences encoding:
   (a) an activator receptor comprising an extracellular ligand binding domain specific to an erb-b2 receptor tyrosine kinase 2 (HER2) antigen, wherein the activator receptor comprises a polypeptide sequence at least 95% identical to SEQ ID NO: 291, wherein the extracellular ligand binding domain of the activator receptor comprises an scFv comprising
      (i) a heavy chain variable (VH) region comprising complement determining regions (CDRs) CDR-H1 of SEQ ID NO: 36, CDR-H2 of SEQ ID NO: 38, and CDR-H3 of SEQ ID NO: 41; and
      (ii) a light chain variable region (VL) comprising CDRs CDR-L1 of SEQ ID NO: 30, CDR-L2 of SEQ ID NO: 32, and CDR-L3 of SEQ ID NO: 34; and
   (b) an inhibitory receptor comprising an extracellular ligand binding domain specific to an HLA-A*02 allele of HLA-A, wherein the inhibitory receptor comprises a polypeptide sequence at least 95% identical to SEQ ID NO: 305, wherein the extracellular ligand binding domain of the inhibitory receptor comprises an scFv comprising:
      (i) VH region comprising CDRs CDR-H1 of SEQ ID NO: 95, CDR-H2 of SEQ ID NO: 98, and CDR-H3 of SEQ ID NO: 101; and
      (ii) a VL region comprising CDRs CDR-L1 of SEQ ID NO: 87, CDR-L2 of SEQ ID NO: 90 or SEQ ID NO: 91, and CDR-L3 of SEQ ID NO: 92.

15. A vector, comprising the polynucleotide system of claim 14.

16. A method of treating a HER2+ cancer in a subject identified as having or suspected of having a loss of heterozygosity at an HLA-A*02 allele of HLA-A in the HER2-positive cancer, comprising administering to the subject the immune cells of claim 1.

17. A method of selectively killing HER2-positive tumor cells having loss of heterozygosity at an HLA-A*02 allele of HLA-A in the HER2-positive cancer, comprising contacting the HER2-positive tumor cells with the immune cells of claim 1.

18. An immune cell responsive to loss of heterozygosity at an HLA-A*02 allele in a cancer cell, comprising:
   (a) a polynucleotide comprising a polynucleotide sequence at least 90% identical to SEQ ID NO: 292, or encoding an activator receptor comprising an extracellular ligand binding domain specific to an erb-b2 receptor tyrosine kinase 2 (HER2) antigen, wherein the activator receptor comprises a polypeptide sequence at least 95% identical to SEQ ID NO: 291, wherein the extracellular ligand binding domain of the activator receptor comprises an scFv comprising
      (i) a heavy chain variable (VH) region comprising complement determining regions (CDRs) CDR-H1 of SEQ ID NO: 36, CDR-H2 of SEQ ID NO: 38, and CDR-H3 of SEQ ID NO: 41; and
      (ii) a light chain variable region (VL) comprising CDRs CDR-L1 of SEQ ID NO: 30, CDR-L2 of SEQ ID NO: 32, and CDR-L3 of SEQ ID NO: 34; and
   (b) a polynucleotide comprising a polynucleotide sequence at least 90% identical to SEQ ID NO: 306, or encoding an inhibitory receptor comprising an extracellular ligand binding domain specific to an HLA-A*02 allele of HLA-A, wherein the inhibitory receptor comprises a polypeptide sequence at least 95% identical to SEQ ID NO: 305, wherein the extracellular ligand binding domain of the inhibitory receptor comprises an scFv comprising:
      (i) VH region comprising CDRs CDR-H1 of SEQ ID NO: 95, CDR-H2 of SEQ ID NO: 98, and CDR-H3 of SEQ ID NO: 101; and (ii) a VL region comprising CDRs CDR-L1 of SEQ ID NO: 87, CDR-L2 of SEQ ID NO: 90 or SEQ ID NO: 91, and CDR-L3 of SEQ ID NO: 92.

19. The immune cell of claim 18, wherein the activator receptor and the inhibitory receptor together specifically activate the immune cell in the presence of the cancer cell.

20. The immune cell of claim 18, wherein the immune cell is a T cell.

21. The immune cell of claim 18, wherein the T cell is a CD8+ CD4− T cell.

22. The immune cell of claim 18, wherein the T cell is a CD8− CD4− T cell.

* * * * *

UNITED STATES PATENT AND TRADEMARK OFFICE
CERTIFICATE OF CORRECTION

PATENT NO. : 11,730,764 B2
APPLICATION NO. : 17/809409
DATED : August 22, 2023
INVENTOR(S) : Yuta Ando et al.

It is certified that error appears in the above-identified patent and that said Letters Patent is hereby corrected as shown below:

In the Claims

At Column 195, Claim number 10, Line number 4, delete "WIC" and replace with --MHC--

Signed and Sealed this
Twenty-third Day of January, 2024

*Katherine Kelly Vidal*

Katherine Kelly Vidal
*Director of the United States Patent and Trademark Office*